US010801050B2

(12) United States Patent
Corre et al.

(10) Patent No.: US 10,801,050 B2
(45) Date of Patent: Oct. 13, 2020

(54) MICROORGANISM MODIFIED FOR THE ASSIMILATION OF LEVULINIC ACID

(71) Applicant: METABOLIC EXPLORER, Saint Beauzire (FR)

(72) Inventors: Gwenaëlle Corre, Saint-Beauzire (FR); Laurence Dumon-Seignovert, Pont du Chateau (FR); Philippe Soucaille, Deyme (FR)

(73) Assignee: METABOLIC EXPLORER, Saint Beauzire (FR)

( * ) Notice: Subject to any disclaimer, the term of this patent is extended or adjusted under 35 U.S.C. 154(b) by 5 days.

(21) Appl. No.: 15/770,449

(22) PCT Filed: Oct. 23, 2015

(86) PCT No.: PCT/IB2015/002119
§ 371 (c)(1),
(2) Date: Apr. 23, 2018

(87) PCT Pub. No.: WO2017/068385
PCT Pub. Date: Apr. 27, 2017

(65) Prior Publication Data
US 2018/0312890 A1    Nov. 1, 2018

(51) Int. Cl.
| | |
|---|---|
| *C12P 17/18* | (2006.01) |
| *C12P 7/04* | (2006.01) |
| *C12N 9/00* | (2006.01) |
| *C12N 9/10* | (2006.01) |
| *C12P 7/06* | (2006.01) |
| *C12P 7/42* | (2006.01) |
| *C12P 7/18* | (2006.01) |
| *C12P 7/16* | (2006.01) |
| *C12P 7/46* | (2006.01) |
| *C12P 13/08* | (2006.01) |
| *C12P 13/12* | (2006.01) |
| *C12N 1/16* | (2006.01) |
| *C12N 1/20* | (2006.01) |
| *C12N 15/52* | (2006.01) |
| *C12N 15/70* | (2006.01) |
| *C12N 15/81* | (2006.01) |

(52) U.S. Cl.
CPC ............... *C12P 17/18* (2013.01); *C12N 1/16* (2013.01); *C12N 1/20* (2013.01); *C12N 9/1029* (2013.01); *C12N 9/13* (2013.01); *C12N 9/93* (2013.01); *C12P 7/065* (2013.01); *C12P 7/16* (2013.01); *C12P 7/18* (2013.01); *C12P 7/42* (2013.01); *C12P 7/46* (2013.01); *C12P 13/08* (2013.01); *C12P 13/12* (2013.01); *C12Y 203/01009* (2013.01); *C12Y 203/01016* (2013.01); *C12Y 208/03005* (2013.01); *C12Y 208/03008* (2013.01); *C12Y 602/01* (2013.01); C12N 15/52 (2013.01); C12N 15/70 (2013.01); C12N 15/81 (2013.01); Y02E 50/10 (2013.01); Y02E 50/17 (2013.01)

(58) Field of Classification Search
CPC ............... C12Y 208/03005; C12Y 208/03008
See application file for complete search history.

(56) References Cited

U.S. PATENT DOCUMENTS

| | | | |
|---|---|---|---|
| 8,956,835 B2 | 2/2015 | Nakas et al. | |
| 8,980,593 B1 | 3/2015 | Ashby et al. | |
| 9,109,242 B2 | 8/2015 | Park et al. | |
| 2007/0072279 A1 | 3/2007 | Meynial-Salles et al. | |
| 2008/0118948 A1 | 5/2008 | Kroger et al. | |
| 2015/0104822 A1 | 4/2015 | Desfougeres et al. | |
| 2017/0159031 A1* | 6/2017 | Botes ................... | C12Y 208/03 |

FOREIGN PATENT DOCUMENTS

| | | |
|---|---|---|
| EP | 2532751 A1 | 12/2012 |
| WO | WO 99/14313 A2 | 3/1999 |
| WO | WO 99/61624 A2 | 12/1999 |
| WO | WO 2005/059093 A2 | 6/2005 |
| WO | WO 2005/073364 A2 | 8/2005 |
| WO | WO 2008/040387 A1 | 4/2008 |
| WO | WO 2008/052973 A2 | 5/2008 |
| WO | WO 2008/116852 A1 | 10/2008 |
| WO | WO 2008/116853 A1 | 10/2008 |
| WO | WO 2010/003728 A1 | 1/2010 |
| WO | WO 2010/076324 A1 | 7/2010 |
| WO | WO 2010/141920 A2 | 12/2010 |
| WO | WO 2011/157728 A1 | 12/2011 |
| WO | WO 2012/055798 A1 | 5/2012 |
| WO | WO 2012/135731 A2 | 10/2012 |
| WO | WO 2012/172050 A1 | 12/2012 |
| WO | WO 2013/082542 A2 | 6/2013 |
| WO | WO 2013/188546 A2 | 12/2013 |
| WO | WO 2014/099707 A2 | 6/2014 |

OTHER PUBLICATIONS

Zhou et al., Cell Mol Life Sci 63:2260-2290, 2006 (Year: 2006).*
Kozak, M., Gene 234:187-208, 1999 (Year: 1999).*
Boronat et al., J. Bacteriol. 147:181-185, 1981 (Year: 1981).*
KEGG Database Entry for EC 2.8.3.5, 2 pages, last viewed on Feb. 24, 2020 (Year: 2020).*
KEGG Database Entry for EC 2.8.3.8, 2 pages, last viewed on Feb. 24, 2020 (Year: 2020).*
Agnew, "Metabolic Engineering of *Escherichia coli* for the Synthesis of Defined Polyhydroxyalkanoates from Unrelated Feedstocks," Ph.D. thesis, Madison, WI, USA, 2013, pp. i-xii, 1-132.
Altschul et al., "Basic local alignment search tool," Journal of Molecular Biology, vol. 215, No. 3, 1990, pp. 403-410.

(Continued)

*Primary Examiner* — David Steadman
(74) *Attorney, Agent, or Firm* — Birch, Stewart, Kolasch & Birch, LLP

(57) ABSTRACT

The present invention relates to a genetically modified microorganism for the fermentative conversion of levulinic acid into propionyl-CoA and acetyl-CoA, and to a fermentation process for performing said conversion.

13 Claims, 3 Drawing Sheets

Specification includes a Sequence Listing.

(56) References Cited

OTHER PUBLICATIONS

Babbitt et al., "Ancestry of the 4-chlorobenzoate dehalogenase: analysis of amino acid sequence identities among families of acyl:adenyl ligases, enoyl-CoA hydratases/isomerases, and acyl-CoA thioesterases," Biochemistry, vol. 31, No. 24, 1992, pp. 5594-5604.
Bantscheff et al., "Quantitative mass spectrometry in proteomics: a critical review," Analytical and Bioanalytical Chemistry, vol. 389, No. 4, 2007, pp. 1017-1031.
Brämer et al., "The methylcitric acid pathway in Ralstonia eutropha: new genes identified involved in propionate metabolism," Microbiology, vol. 147, No. 8, 2001, pp. 2203-2214.
Brosius et al., "Spacing of the −10 and −35 regions in the tac promoter. Effect on its in vivo activity," Journal of Biological Chemistry, vol. 260, No. 6, Mar. 25, 1985, pp. 3539-3541.
Burnette, "'Western blotting': electrophoretic transfer of proteins from sodium dodecyl sulfate-polyacrylamide gels to unmodified nitrocellulose and radiographic detection with antibody and radioiodinated protein A," Analytical Biochemistry, vol. 112, No. 2, 1981, pp. 195-203.
Carrier et al., "Library of synthetic 5' secondary structures to manipulate mRNA stability in Escherichia coli," Biotechnology Progress, vol. 15, No. 1, 1999, pp. 58-64.
Chambers et al., "The pMTL nic-cloning vectors. I. Improved pUC polylinker regions to facilitate the use of sonicated DNA for nucleotide sequencing," Gene, vol. 68, No. 1, 1988, pp. 139-149.
Chang et al., "Acyl-adenylate motif of the acyl-adenylate/thioester-forming enzyme superfamily: a site-directed mutagenesis study with the Pseudomonas sp. strain CBS3 4-chlorobenzoate: coenzyme A ligase," Biochemistry, vol. 36, No. 50, 1997, pp. 15650-15659.
Christianson et al., "Multifunctional yeast high-copy-number shuttle vectors," Gene, vol. 110, No. 1, 1992, pp. 119-122.
Curran et al., "Use of High Capacity Terminators in Saccharomyces cerevisiae to Increase mRNA half-life and Improve Gene Expression Control for Metabolic Engineering Applications," Metabolic Engineering, vol. 19, Sep. 2013, pp. 88-97 (pp. 1-24).
Database Uniprot, Q0KBG1, Oct. 3, 2006, 2 pages, XP-002758982.
Database Uniprot, Q0KC00, Oct. 3, 2006, 1 page, XP-002758986.
Database Uniprot, R7XEA9, Jul. 24, 2013, 1 page, XP-002758987.
Database Uniprot, R7XI66, Jul. 24, 2013, 1 page, XP-002758988.
Datsenko et al., "One-step inactivation of chromosomal genes in Escherichia coli K-12 using PCR products," Proceedings of the National Academy of Sciences, vol. 97, No. 12, Jun. 6, 2000, pp. 6640-6645.
Davis et al., "Characterizing the native codon usages of a genome: an axis projection approach," Molecular Biology and Evolution, vol. 28, No. 1, 2010 (advance access publication Aug. 2, 2010), pp. 211-221.
De Boer et al., "The tac promoter: a functional hybrid derived from the trp and lac promoters," Proceedings of the National Academy of Sciences, vol. 80, No. 1, Jan. 1983, pp. 21-25.
Deml et al., "Multiple effects of codon usage optimization on expression and immunogenicity of DNA candidate vaccines encoding the human immunodeficiency virus type 1 Gag protein," Journal of Virology, vol. 75, No. 22, Nov. 2001, pp. 10991-11001.
Dickson et al., "Genetic regulation: the Lac control region," Science, vol. 187, No. 4171, Jan. 10, 1975, pp. 27-35.
Eikmanns et al., "A family of Corynebacterium glutamicum/Escherichia coli shuttle vectors for cloning, controlled gene expression, and promoter probing," Gene, vol. 102, No. 1, 1991, pp. 93-98.
Engvall et al., "Enzyme-linked immunosorbent assay (ELISA) quantitative assay of immunoglobulin G," Immunochemistry, vol. 8, No. 9, 1971, pp. 871-874.
Ewering et al., "Metabolic engineering of strains of Ralstonia eutropha and Pseudomonas putida for biotechnological production of 2-methylcitric acid," Metabolic Engineering, vol. 8, No. 6, 2006 (available online Jun. 14, 2006), pp. 587-602.

Graf et al., "Concerted action of multiple cis-acting sequences is required for Rev dependence of late human immunodeficiency virus type 1 gene expression," Journal of Virology, vol. 74, No. 22, Nov. 2000, pp. 10822-10826.
Güldener et al., "A new efficient gene disruption cassette for repeated use in budding yeast," Nucleic Acids Research, vol. 24, No. 13, 1996, pp. 2519-2524.
Habe et al., "Bacterial production of short-chain organic acids and trehalose from levulinic acid: a potential cellulose-derived building block as a feedstock for microbial production," Bioresource Technology, vol. 177, 2015 (available online Nov. 18, 2014), pp. 381-386.
Hasunuma et al., "Efficient fermentation of xylose to ethanol at high formic acid concentrations by metabolically engineered Saccharomyces cerevisiae," Applied Microbiology and Biotechnology, vol. 90, No. 3, 2011 (published online Jan. 19, 2011), pp. 997-1004.
Holt et al., "Production of solvents by Clostridium acetobutylicum cultures maintained at neutral pH," Applied and Environmental Microbiology, vol. 48, No. 6, Dec. 1984, pp. 1166-1170.
International Search Report and Written Opinion of the International Searching Authority (Forms PCT/ISA/210 and PCT/ISA/237) for Application No. PCT/IB2015/002119, dated Jul. 12, 2016.
Jaremko et al., "The initial metabolic conversion of levulinic acid in Cupriavidus necator," Journal of Biotechnology, vol. 155, No. 3, 2011 (available online Jul. 30, 2011), pp. 293-298.
Jönsson et al., "Bioconversion of lignocellulose: inhibitors and detoxification," Biotechnology for Biofuels, vol. 6, No. 16, 2013, pp. 1-10.
Karan et al., "Molecular evolution of the AMP-forming acetyl-CoA synthetase," Gene, vol. 265, No. 1, 2001, pp. 95-101.
Keilhauer et al., "Isoleucine synthesis in Corynebacterium glutamicum: molecular analysis of the ilvB-ilvN-ilvC operon," Journal of Bacteriology, vol. 175, No. 17, Sep. 1993, pp. 5595-5603.
Kirchner et al., "Tools for genetic engineering in the amino acid-producing bacterium Corynebacterium glutamicum," Journal of Biotechnology, vol. 104, Nos. 1-3, 2003, pp. 287-299.
Kleinkauf et al., "A nonribosomal system of peptide biosynthesis," European Journal of Biochemistry, vol. 236, 1996, pp. 335-351.
Kovach et al., "Four new derivatives of the broad-host-range cloning vector pBBR1MCS, carrying different antibiotic-resistance cassettes," Gene, vol. 166, No. 1, 1995, pp. 175-176.
Larsson et al., "Effect of overexpression of Saccharomyces cerevisiae Pad1p on the resistance to phenylacrylic acids and lignocellulose hydrolysates under aerobic and oxygen-limited conditions," Applied Microbiology and Biotechnology, vol. 57, Nos. 1-2, 2001 (published online Aug. 2, 2001), pp. 167-174.
Lee et al., "Construction of Escherichia coli-Clostridium acetobutylicum shuttle vectors and transformation of Clostridium acetobutylicum strains," Biotechnology Letters, vol. 14, No. 5, May 1992, pp. 427-432.
Lee et al., "Diverse protein regulations on PHA formation in Ralstonia eutropha on short chain organic acids," International Journal of Biological Sciences, vol. 5, No. 3, Feb. 23, 2009, pp. 215-225.
Luzier, "Materials derived from biomass/biodegradable materials," Proceedings of the National Academy of Sciences, vol. 89, No. 3, Feb. 1992, pp. 839-842.
Marahiel et al., "Modular peptide synthetases involved in nonribosomal peptide synthesis," Chemical Reviews, vol. 97, No. 7, 1997, pp. 2651-2673.
Marchler-Bauer et al., "CDD: NCBI's conserved domain database," Nucleic Acids Research, vol. 43, 2015 (published online Nov. 20, 2014), pp. D222-D226.
Needleman et al., "A general method applicable to the search for similarities in the amino acid sequence of two proteins," Journal of Molecular Biology, vol. 48, No. 3, 1970, pp. 443-453.
Nevoigt et al., "Engineering of promoter replacement cassettes for fine-tuning of gene expression in Saccharomyces cerevisiae," Applied and Environmental Microbiology, vol. 72, No. 8, Aug. 2006, pp. 5266-5273.
Niu et al., "Stereospecific microbial conversion of lactic acid into 1, 2-propanediol," ACS Synthetic Biology, vol. 4, No. 4, 2014, 5 pages.

(56) References Cited

OTHER PUBLICATIONS

Partow et al., "Characterization of different promoters for designing a new expression vector in *Saccharomyces cerevisiae*," Yeast, vol. 27, No. 11, 2010, pp. 955-964.

Pátek et al., "Corynebacterium glutamicum promoters: a practical approach," Microbial Biotechnology, vol. 6, No. 2, 2013, pp. 103-117.

Pohlmann et al., "Genome sequence of the bioplastic-producing "Knallgas" bacterium *Ralstonia eutropha* H16," Nature Biotechnology, vol. 24, No. 10, 2006 (published online Sep. 10, 2006), pp. 1257-1262 (pp. 1-6).

Salis, "The ribosome binding site calculator," Chapter 2 of Methods in Enzymology, Academic Press, vol. 498, 2011, pp. 19-42.

Sánchez et al., "Trends in biotechnological production of fuel ethanol from different feedstocks," Bioresource Technology, vol. 99, No. 13, 2008 (available online Dec. 26, 2007), pp. 5270-5295.

Segel, "Enzyme kinetics," John Wiley & Sons, 1993, pp. 44-54 and 100-112.

Sikorski et al., "A system of shuttle vectors and yeast host strains designed for efficient manipulation of DNA in *Saccharomyces cerevisiae*," Genetics, vol. 122, No. 1, 1989, pp. 19-27.

Srirangan et al., "Manipulating the sleeping beauty mutase operon for the production of 1-propanol in engineered *Escherichia coli*," Biotechnology for Biofuels, vol. 6, No. 1, 2013, pp. 1-14.

Steinbüchel et al., "Biosynthetic and biodegradable polyesters from renewable resources: current state and prospects," Macromolecular Symposia, vol. 123, No. 1. 1997, pp. 61-66.

Steinbüchel et al., "Physiology and molecular genetics of poly(β-hydroxyalkanoic acid) synthesis in Alcaligenes eutrophus," Molecular Microbiology, vol. 5, No. 3, 1991, pp. 535-542.

Suzuki et al., "Large-scale engineering of the Corynebacterium glutamicum genome," Applied and Environmental Microbiology, vol. 71, No. 6, Jun. 2005, pp. 3369-3372.

Tummala et al., "Development and Characterization of a Gene Expression Reporter System for Clostridium acetobutylicum ATCC 824," Applied and Environmental Microbiology, vol. 65, No. 9, Sep. 1999, pp. 3793-3799.

Van Dijken et al., "An interlaboratory comparison of physiological and genetic properties of four *Saccharomyces cerevisiae* strains," Enzyme and Microbial Technology, vol. 26, Nos. 9-10, 2000, pp. 706-714.

Wang et al., "Biosynthesis and thermal properties of PHBV produced from levulinic acid by Ralstonia eutropha," PLoS One, vol. 8, No. 4, Apr. 4, 2013, e60318, pp. 1-8.

Watkins et al., "Evidence for 26 distinct acyl-coenzyme A synthetase genes in the human genome," Journal of Lipid Research, vol. 48, No. 12, Aug. 30, 2007, pp. 2736-2750.

Watkins, "Fatty acid activation," Progress in Lipid Research, vol. 36, No. 1, 1997, pp. 55-83.

Yu et al., "Metabolic carbon fluxes and biosynthesis of polyhydroxyalkanoates in Ralstonia eutropha on short chain fatty acids," Biotechnology Progress, vol. 20, No. 4, 2004 (published on web Jul. 1, 2004), pp. 1015-1024.

Zirrolli et al., "Analysis of long-chain fatty acyl coenzyme a thioesters by negative ion fast-atom bombardment mass spectrometry and tandem mass spectrometry," Journal of the American Society for Mass Spectrometry, vol. 5, No. 5, 1994, pp. 416-424.

De Boer et al., "The tac promoter: A functional hybrid derived from the trp and lac promoters," Proc. Natl. Acad. Sci. USA, vol. 80, Jan. 1983, pp. 21-25.

Hanai et al., "Engineered Synthetic Pathway for Isopropanol Production in *Escherichia coli*," Applied and Environmental Microbiology, vol. 73. No. 24, Dec. 2007, pp. 7814-7818.

Studier et al., "Use of T7 RNA Polymerase to Direct Expression of Cloned Genes," Methods in Enzymology, vol. 185, 1990, pp. 60-89.

\* cited by examiner

MICROORGANISM MODIFIED FOR THE ASSIMILATION OF LEVULINIC ACID

INTRODUCTION

The present invention relates to a genetically modified microorganism for the fermentative conversion of levulinic acid into propionyl-CoA and acetyl-CoA, and to a fermentation process for performing said conversion.

Lignocellulosic biomass is an abundant, renewable and low-cost raw material, which can be partly converted into a fermentable substrate through chemical, physical and/or enzymatic hydrolysis. The substrates that are obtained through such process can notably be used as a source of carbon to promote the growth of microorganisms, such as yeasts, bacteria, fungi etc.

However, contrary to sugarcane or starch-derived feedstocks, the use of lignocellulosic substrates can be limited by the fact that a wide variety of by-products are produced during hydrolysis, among which fermentation inhibitors. The presence of those inhibitors in the culture medium can negatively affect microbial growth and metabolism, thereby hindering the fermentation process and leading to a decrease in the productivity and yield of the compound of interest (such as alcohols, amino acids, carboxylic acids, vitamins etc) that is produced by the microorganism.

Lignocellulosic hydrolysates that act as inhibitors of microorganisms include more particularly phenolic compounds and other aromatics, aliphatic acids, furan aldehydes, and inorganic ions. Among these inhibitors, aliphatic acids resulting from such hydrolysis typically consist of acetic acid, formic acid and levulinic acid. Acetic acid is known to be primarily formed by hydrolysis of acetyl groups of hemicellulose, while formic acid and levulinic acid are known to arise as acid-catalyzed degradation products from polysaccharides. The toxic effects of these aliphatic acids are mainly attributed to their undissociated form, and likely to increase along with their concentration in the culture medium.

Countermeasures have thus been developed in order to limit the toxic effects of lignocellulosic substrates due to the presence of these inhibitors. One of the most effective strategy is the detoxification prior to fermentation, i.e. the removal of inhibitors, for example by overliming or ion exchange resin (Sanchez & Cardona 2008); such approach is however labor-intensive. Other strategies include, among others, the use of SSF (simultaneous saccharification and fermentation, not applicable with all microorganisms); fed-batch or continuous cultivation rather than batch processes (more expensive); the use of large inocula (not adapted to an industrial context); and the selection of microorganisms that exhibit resistance to inhibitors, for example by adaptation in culture or through genetic engineering.

Examples of the latter strategy include the development of *Saccharomyces cerevisiae* strains exhibiting a resistance to phenolics through overexpression of a laccase enzyme (Larsson et al., 2001), a resistance to phenylacrylic acid under aerobic and oxygen-limited conditions through overexpression of the decarboxylase Pad1p (Larsson et al., 2001), a resistance to acetic and formic acid through overexpression of a transaldolase or transketolase (Hasunuma et al., 2011), or the resistance to formic acid through overexpression of a FDH1 and FDH2 enzymes (Hasunuma et al., 2011).

However, while various genetic engineering approaches have been conducted to produce yeast strains that are highly tolerant to these inhibiting-by-products, no solution has yet been proposed with regard to levulinic acid, let alone in other microorganisms. This is notably due to the lack of current knowledge regarding the microbial levulinic acid metabolic pathway. Indeed, to this day, the detailed information on levulinic acid metabolic genes and enzymes, as well as levulinic acid metabolites, remain unknown.

The Inventors have herein surprisingly discovered that levulinic acid can be successfully metabolized into levulinyl-CoA, propionyl-CoA and acetyl-CoA, by microorganisms through microbial overexpression of specific types of enzymes, that have never been identified so far for such purpose. As demonstrated in the Examples hereafter, such overexpression increased not only the microbial growth but also greatly improved the overall productivity and yield of 1,2-propanediol, glycolic acid, and ethanol (to name a few) in bacteria and yeast strains capable of producing said compounds.

The present invention thus provides herein for the first time a microorganism genetically modified for the fermentative conversion of levulinic acid into propionyl-CoA and acetyl-CoA, by overexpression of:
  i) at least one enzyme converting levulinic acid into levulinyl-CoA; and
  ii) at least one enzyme converting said levulinyl-CoA into propionyl-CoA and acetyl-CoA.

The invention also relates to a method for the fermentative conversion of levulinic acid into propionyl-CoA and acetyl-CoA, comprising the step of culturing, under fermentation conditions, the genetically modified microorganism according to the invention, in a culture medium comprising as a source of carbon at least levulinic acid. The invention further relates to the use of the microorganism according to the invention for the production of a desired product chosen among alcohols, amino acids, carboxylic acids or polyhydroxyalkanoates.

DESCRIPTION OF THE INVENTION

It shall be understood that the following detailed description is not limitative and that various modifications, substitutions, omissions, and changes may be made without departing from the scope of the invention. It shall also be understood that the terminology used herein is for the purpose of describing particular embodiments of the invention, and is not intended to be limiting.

All publications, patents and patent applications cited herein, whether supra or infra, are hereby incorporated by reference in their entirety.

Furthermore, unless otherwise stated, all technical and scientific terms used herein have the same meanings as commonly understood by one of ordinary skill in the art. Conventional microbiological and molecular biological techniques are also those well-known and commonly used in the art. Such techniques are fully explained in the literature.

Nevertheless, with respect to the use of different terms throughout the current specification, the following definitions more particularly apply.

The singular forms "a", "an", and "the" include herein plural reference unless the context clearly dictates otherwise. Thus, for example, a reference to "a microorganism" includes a plurality of such microorganisms, and a reference to "an endogenous gene" is a reference to one or more endogenous genes, and so forth.

The terms "comprise", "contain", "involve" or "include" or variations such as "comprises", "comprising", "containing", "involved", "includes", "including" are used herein in an inclusive sense, i.e. to specify the presence of the stated features but not to preclude the presence or addition of further features in various embodiments of the invention.

The term "microorganism", as used herein, refers to a living microscopic organism, which may be a single cell or a multicellular organism and which can generally be found in nature. In the context of the present invention, the microorganism is preferably a bacterium, yeast or fungus. More preferably, the microorganism of the invention belongs to the family of the bacteria Enterobacteriaceae, Clostridiaceae, Bacillaceae, Streptomycetaceae or to the family of yeasts Saccharomycetaceae. Even more preferably, the microorganism according to the invention is the Enterobacteriaceae bacterium *Escherichia coli*, the Clostridiaceae bacterium *Clostridium acetobutylicum*, the Corynebacteriaceae bacterium *Corynebacterium glutamicum*, or the Saccharomycetaceae yeast *Saccharomyces cerevisiae*.

The terms "genetically modified microorganism" and "recombinant microorganism" are interchangeable and refer to a microorganism as defined above that is not found in nature and therefore genetically differs from its natural counterpart. In other words, it refers to a microorganism that is modified by introduction and/or by deletion and/or by modification of its genetic elements. Such modification can be performed for example by genetic engineering, or by forcing the development and evolution of new metabolic pathways by combining directed mutagenesis and evolution under specific selection pressure (see, for example, WO2005/073364 or WO2008/116852, incorporated herein by reference).

A microorganism genetically modified for the fermentative conversion of levulinic acid into propionyl-CoA and acetyl-CoA is thus a recombinant microorganism as defined above that is capable of converting levulinic acid into propionyl-CoA and acetyl-CoA in fermentative culture conditions. In other words, said microorganism has been genetically modified to allow fermentative conversion of levulinic acid into propionyl-CoA and acetyl-CoA. To do so, the microorganism according to the invention overexpresses at least two enzymes, which are further detailed below.

By "overexpressing", "overexpressed", or "overexpression" of a protein of interest, such as an enzyme, it is meant herein increasing the expression level of said protein in a microorganism, as compared to the unmodified microorganism. By contrast, "underexpressing", "underexpressed" or "underexpression" of a protein of interest means decreasing the expression level of said protein in a microorganism, as compared to the unmodified microorganism. The expression of a protein of interest can also be completely abolished, meaning that the expression level of said protein is null.

The term "expression level", as applied herein, refers to the amount (e.g. relative amount, concentration) of a protein of interest (or of the gene encoding said protein) expressed in a microorganism, which is measurable by methods well-known in the art, such as by Western Blot-Immunoblot (Burnette W N, 1981), Enzyme-linked immunosorbent assay (e.g. ELISA) (E. Engvall et P. Perlman, 1971), or quantitative proteomics (Bantscheff et al. 2007) approaches.

It is within the skill of the person in the art to modulate the expression level of a protein of interest in a microorganism.

For example, such modulation can be achieved by modulating the expression level of one or more endogenous genes that encode said protein within the microorganism. In other words, the expression level of said gene can be up-regulated, downregulated, or even completely abolished by comparison to its natural expression level. Such modulation can therefore result in an enhancement of the expression level and/or activity of the gene product (i.e. protein), or alternatively, in a lower or null expression level and/or activity of said product.

By "gene", it is meant herein a nucleotide sequence which comprises at least a region coding for a protein of interest. Said region may further be flanked on each 5' and/or 3' end by untranslated regions (UTRs, named 5'UTR and/or 3'UTR), which may contain regulatory elements that control protein synthesis.

The term "endogenous gene" thus refers herein to gene as defined above that is naturally present in a microorganism.

An endogenous gene can notably be overexpressed by introducing heterologous sequences which favour upregulation in addition to endogenous regulatory elements, or by substituting those endogenous regulatory elements with such heterologous sequences, or by introducing one or more supplementary copies of the endogenous gene chromosomally (i.e. into the chromosome) or extra-chromosomally (e.g. into a plasmid or vector) within the microorganism. In this regard, several copies of a gene can be introduced on a chromosome by methods well-known in the art such as by genetic recombination. By contrast, when a gene is expressed extra-chromosomally, it can be carried by different types of plasmid that may differ in respect to their origin of replication depending on the microorganism in which they can replicate, and by their copy number in the cell. For example, a microorganism transformed by a plasmid can contain 1 to 5 copies of the plasmid, or about 20 copies of it, or even up to 500 copies of it, depending on the nature of the selected plasmid. A variety of plasmids, which differ in respect of their origin of replication and of their copy number in a cell, are well known in the art and can be easily selected by the skilled practitioner for such purpose. Examples of low copy number plasmids which can replicate in *E. coli* include, without limitation, the pSC101 plasmid (tight replication), the RK2 plasmid (tight replication), as well as the pACYC and pRSF1010 plasmids, while an example of high copy number plasmid which can replicate in *E. coli* is pSK bluescript II.

Another way to modulate the expression of an endogenous gene is to exchange its promoter (i.e. wild-type promoter) with a stronger or weaker promoter to up or down-regulate its expression level. Promoters suitable for such purpose can be homologous (originating from the same species) or heterologous (originating from a different species), and are well-known in the art. It is within the skill of the person in the art to select appropriate promoters for modulating the expression of an endogenous gene. Promoters that are the most convenient for increasing gene expression level are well-known to the skilled person in the art: these include, among others, promoters Ptrc, Ptac, Plac, and the lambda promoter PR and PL. These promoters can be "inducible" by a particular compound or by specific external conditions such as temperature or light, and/or may be homologous or heterologous.

Endogenous gene expression level can also be increased or decreased by introducing mutations into their coding sequence. Mutations can be introduced by site-directed mutagenesis using for example Polymerase Chain Reaction (PCR), by random mutagenesis techniques for example via mutagenic agents (Ultra-Violet rays or chemical agents like nitrosoguanidine (NTG) or ethylmethanesulfonate (EMS)) or DNA shuffling or error-prone PCR. A deletion of all or a part of an endogenous gene can alternatively be performed to totally inhibit its expression within the microorganism.

In addition, or alternatively, a microorganism can be genetically modified to express one or more exogenous genes so as to overexpress its gene product (i.e. protein), provided that said genes are introduced into the microorganism with all the regulatory elements necessary for their expression in the host microorganism. The genetic modification or transformation of microorganisms with exogenous DNA is a routine task for those skilled in the art.

By "exogenous gene", it is meant herein a gene that is not naturally occurring in a microorganism. In order to express (i.e. overexpress) an exogenous gene in a microorganism, such gene can be directly integrated into the microorganism chromosome, or be expressed extra-chromosomally within the microorganism, as explained above. Exogenous genes according to the invention are advantageously homologous genes.

In the context of the invention, the term "homologous gene" or "homolog" not only refers to a gene inherited by two species (i.e. microorganism species) by a theoretical common genetic ancestor, but also includes genes which may be genetically unrelated that have, nonetheless, evolved to encode proteins which perform similar functions and/or have similar structure (i.e. functional homolog). Therefore, the term "functional homolog" refers herein to a gene that encodes a functionally homologous protein.

Using the information available in databases such as UniProt (for proteins), GenBank (for genes), or NCBI (for proteins or genes), the skilled practitioner can easily determine the sequence of a specific protein and/or gene of a microorganism, and identify based on this sequence the one of equivalent proteins or genes, or homologs thereof, in another microorganism. This routine work can be performed for example by alignment of a specific gene (or protein) sequence of a microorganism with gene (or protein) sequences or the genome (or proteome) of other microorganisms, which can be found in the above mentioned databases. Such sequence alignment can advantageously be performed using the BLAST algorithm developed by Altschul et al. (1990). Once a sequence homology has been established between those sequences, a consensus sequence can be derived and used to design degenerate probes in order to clone the corresponding homolog gene (and hence homolog protein) of the related microorganism. These routine methods of molecular biology are well known to those skilled in the art.

It shall be further understood that, in the context of the present invention, should an exogenous gene encoding a protein of interest be expressed in a specific microorganism, a synthetic version of this gene is preferably constructed by replacing non-preferred codons or less preferred codons with preferred codons of said microorganism which encode the same amino acid. It is indeed well-known in the art that codon usage varies between microorganism species, which may impact the recombinant expression level of the protein of interest. To overcome this issue, codon optimization methods have been developed, and are extensively described by Graf et al. (2000), Deml et al. (2001) and Davis & Olsen (2011). Several software have notably been developed for codon optimization determination such as the GeneOptimizer® software (Lifetechnologies) or the OptimumGene™ software of (GenScript). In other words, the exogenous gene encoding a protein of interest is preferably codon-optimized for expression in a specific microorganism.

A microorganism can also be genetically modified to increase or decrease the activity of one or more proteins which are naturally or not naturally expressed in the microorganism.

The term "activity" or "biological activity" of a protein of interest refers to the natural biological function(s) exerted by said protein. With regard to enzymes, the term "activity" can more particularly be referred as "catalytic activity" and designates the reaction that is catalyzed by an enzyme in order to convert its substrate into another molecule (product). It corresponds to the number of moles of substrate converted or moles of product formed per unit of time. Moles of substrate or product can be measured by methods well-known in the art, such as spectrophotometry or liquid or gas chromatography eventually coupled to mass spectrometry.

Increasing such activity can be achieved by improving the protein catalytic efficiency (if the protein is an enzyme).

Improving the protein catalytic efficiency means increasing the kcat and/or decreasing the Km for a given substrate and/or a given cofactor, and/or increasing the Ki for a given inhibitor. kcat, Km and Ki are Michaelis-Menten constants that the man skilled in the art is able to determine (Segel, 1993). Decreasing protein turnover means stabilizing the protein. Methods to improve protein catalytic efficiency and/or decrease protein turnover are well known from the man skilled in the art. Those include rational engineering with sequence and/or structural analysis and directed mutagenesis, as well as random mutagenesis and screening. Stabilizing the protein can also be achieved by adding a "tag" peptide sequence either at the N-terminus or the C-terminus of the protein. Such tags are well known in the art, and include, among others, the Glutathione-S-Transferase (GST).

Increasing a protein activity can also be achieved by improving the protein expression, through, for example, a decrease in protein turnover, a decrease in messenger RNA (mRNA) turnover, an increase in the transcription of the gene encoding said protein, or an increase in mRNA translation.

Decreasing mRNA turnover can be achieved by modifying the gene sequence of the 5'-untranslated region (5'-UTR) and/or the coding region, and/or the 3'-UTR (Carrier and Keasling, 1999).

Increasing the transcription of a gene, whether endogenous or exogenous, can be achieved by increasing the number of its copies within the microorganism and/or by placing said gene under the control of a stronger promoter, according to the methods described above.

Increasing translation of the mRNA can be achieved by modifying the Ribosome Binding Site (RBS). A RBS is a sequence on mRNA that is bound by the ribosome when initiating protein translation. It can be either the 5' cap of a mRNA in eukaryotes, a region 6-7 nucleotides upstream of the start codon AUG in prokaryotes (called the Shine-Dalgarno sequence), or an internal ribosome entry site (IRES) in viruses. By modifying this sequence, it is possible to change the protein translation initiation rate, to proportionally alter its production rate, and control its activity inside the cell. It is also possible to optimize the strength of a RBS sequence to achieve a targeted translation initiation rate by using the software RBS CALCULATOR (Salis, 2011). It is within the skill of the person in the art to select the RBS sequence based on the nature of the mRNA.

By contrast, decreasing the activity of a protein can mean either decreasing its specific catalytic activity by mutating the gene encoding said protein, or decreasing its expression by deleting the coding region of said gene.

By "fermentative conversion", it is meant herein that the conversion of levulinic acid into propionyl-CoA and acetyl-CoA occurs when the microorganism is cultured under appropriate fermentation conditions. The term "fermentation conditions" refers to the experimental conditions allowing the growth of a given microorganism. The growth of a microorganism is generally performed in fermenters with an appropriate growth medium adapted to the microorganism being used, and which can be easily determined by the skilled person in the art.

A "culture medium" means herein a medium (e.g., a sterile, liquid media) comprising nutrients essential or beneficial to the maintenance and/or growth of the microorganism such as carbon sources or carbon substrates; nitrogen sources, for example peptone, yeast extracts, meat extracts, malt extracts, urea, ammonium sulfate, ammonium chloride, ammonium nitrate and ammonium phosphate; phosphorus sources, for example monopotassium phosphate or dipotassium phosphate; trace elements (e.g., metal salts) for example magnesium salts, cobalt salts and/or manganese salts; as well as growth factors such as amino acids and vitamins.

The term "source of carbon", "carbon source" or "carbon substrate" according to the present invention refers to any molecule that a microorganism is capable to metabolize and which contains at least one carbon atom.

Examples of carbon sources are levulinic acid and carbohydrate substrates.

The term "levulinic acid" refers herein to 4-oxopentanoic acid as defined by IUPAC (International Union of Pure and Applied Chemistry) also registered under the CAS (Chemical Abstracts Service) number 123-76-2. Other names known for levulinic acid include without limitation laevulinic acid, β-acetylpropionic acid, 3-acetopropionic acid, and β-acetylpropionic acid.

The term "carbohydrate substrate" refers herein to any molecule that a microorganism is capable to metabolize and containing at least one carbon atom, two atoms of hydrogen and one atom of oxygen. In the context of the present invention, the carbohydrate substrate preferably is glucose or xylose.

Preferably, the carbon source according to the invention is levulinic acid and optionally at least one carbohydrate substrate.

More preferably, the carbon source according to the invention is a lignocellulosic substrate, as such substrate can contain levulinic acid and at least one carbohydrate substrate.

The term "lignocellulosic substrate" refers herein to a substrate obtained from lignocellulosic biomass or lignocellulosic feedstock, through chemical, physical and/or enzymatic hydrolysis. By "lignocellulosic biomass" or "lignocellulosic feedstock", it is meant herein a raw plant material which consists of carbohydrate polymers such as cellulose and hemicellulose, and lignin. Said carbohydrate polymers contain different sugar monomers which are tightly bound to lignin. Accordingly, when the lignocellulosic substrate is produced, the carbohydrate polymers lead to the formation of sugar monomers such as pentose (including xylose and arabinose) and hexose sugars (including glucose, mannose and galactose), sugar acids, aliphatic acids (including acetic acid, glycolic acid, formic acid and levulinic acid), and furan derivatives (including 5-hydroxymethylfurfural, furfural, 5-methylfurfural and furoic acid), while the lignin can remain as a solid residue which may be partly degraded into phenolics and other aromatic compounds. The products of degradation of carbohydrate polymers can then be used in a fermentation process as a source of carbon. Methods for producing a lignocellulosic substrate, so-called pre-treatment technologies, are well-known in the art and include, without limitation, acid hydrolysis and enzymatic hydrolysis (for example using cellulases) (Jonsson et al., 2013).

Examples of lignocellulosic biomass include, without limitation, herbaceous energy crops (e.g. switchgrass, miscanthus, canary grass, giant reed, alfalfa, Napier grass), wood (softwood such as pine, cedar, spruce, cypress, fir, hemlock; or hardwood such as poplar, willow, oak, cottonwood, or aspen), solid waste (e.g. paper, cardboard, kitchen waste and garden waste), agricultural crop residues (e.g. rice straw, wheat straw, corn stover, and sugarcane bagasse).

Additional definitions are provided throughout the specification.

The present invention may be understood more readily by reference to the following detailed description, including preferred embodiments of the invention, and examples included herein.

In a first aspect of the present invention, the present invention is directed to a microorganism genetically modified for the fermentative conversion of levulinic acid into propionyl-CoA and acetyl-CoA, by overexpression of:
i) at least one enzyme converting levulinic acid into levulinyl-CoA; and
ii) at least one enzyme converting said levulinyl-CoA into propionyl-CoA and acetyl-CoA.

Still preferably, the conversion i) of levulinic acid into levulinyl-CoA can be achieved by overexpression in said microorganism of:
at least one enzyme converting levulinic acid into levulinyl-phosphate; and
at least one enzyme converting levulinyl-phosphate into levulinyl-CoA.

The Inventors have indeed discovered that the overexpression of enzymes displaying the above activities greatly improves microbial growth in presence of levulinic acid, as well as fermentative production by the microorganism of a product of interest.

The Inventors more particularly identified specific enzymes that have the capacity to perform the above conversions, so as to generate propionyl-CoA and acetyl-CoA from levulinic acid.

According to a preferred embodiment, said enzyme converting levulinic acid into levulinyl-CoA is selected from the group consisting of acid-thiol ligases (EC 6.2.1.-), CoA-transferases (EC 2.8.3.-), acyltransferases (EC 2.3.3.-), carboxy-phosphotransferases (EC 2.7.2.-) in combination with phosphate acyltransferases (EC 2.3.1.8, EC 2.3.1.19, EC 2.3.1.222), functional fragments and functional variants thereof, and combinations thereof.

Carboxy-phosphotransferases (EC 2.7.2.-) can herein convert levulinic acid into levulinyl-phosphate, while phosphate acyltransferases (EC 2.3.1.8, EC 2.3.1.19, EC 2.3.1.222) can herein convert levulinyl-phosphate into levulinyl-CoA.

More preferably, said enzyme converting levulinic acid into levulinyl-CoA is selected from the group consisting of acid-thiol ligases (EC 6.2.1.-), CoA-transferases (EC 2.8.3.-), functional fragments and functional variants thereof, and combinations thereof.

Acid-thiol ligases (EC 6.2.1.-) are enzymes belonging to the acyl-adenylate forming enzyme superfamily. Although members of this superfamily all catalyze mechanistically similar reactions, they share little identity and similarity in amino acid sequence with the exception of a few signature peptide motifs and conserved core peptide sequence motifs (Babbitt et al. 1992, Kleinkauf and Von Dohren 1996, Chang et al., 1997, Marahiel et al., 1997). Among this family, particularly preferred acid-thiol ligases according to the invention belong to the "Uncharacterized subfamily of fatty acid CoA ligases" (FACL_like_2) which all share the conserved domain "cd05917", i.e. the amino-acid sequence SEQ ID NO: 158 (Watkins, 1997; Watkins et al, 2007; Karan et al, 2001). Fatty acyl-CoA ligases typically catalyze the ATP-dependent activation of fatty acids in a two-step reaction. A carboxylate substrate first reacts with ATP to form an acyl-adenylate intermediate, which can then react with CoA to produce an acyl-CoA ester. This is a required step before free fatty acids can participate in most catabolic and anabolic reactions. Fatty acyl-CoA ligases that exhibit the converved domain "cd05917" can be identified by using for example the publicly available NCBI's Conserved Domain Database (Marchler-Bauer et al., 2015).

Particularly preferred CoA-transferases (EC 2.8.3.-) according to the invention are acyl CoA: 3-ketoacid/acetate CoA-transferases (EC 2.8.3.5/EC 2.8.3.8).

Accordingly, the enzyme converting levulinic acid into levulinyl-CoA according to the invention is preferably selected from the group consisting of uncharacterized fatty acid-CoA ligases (FACL) (EC 6.2.1.—with the conserved domain:cd05917), acyl CoA:3-ketoacid/acetate CoA-transferases (EC 2.8.3.5/EC 2.8.3.8), functional fragments and functional variants thereof, and combinations thereof. Said uncharacterized fatty acid-CoA ligases (FACL) (EC 6.2.1.— with the conserved domain: cd05917) are preferably selected from the group consisting of enzymes of amino acid sequence SEQ ID NO: 1 and 25 to 37, and/or said acyl CoA:3-ketoacid/acetate CoA-transferases (EC 2.8.3.5/EC 2.8.3.8) are selected from the group consisting of enzymes of amino acid sequence SEQ ID NO: 3, 5, and 38 to 92.

More preferably, said enzyme converting levulinic acid into levulinyl-CoA is selected from the group consisting of the enzymes of amino acid sequence SEQ ID NO: 1, SEQ ID NO: 3, SEQ ID NO: 5, and combinations thereof.

Most preferably, said enzyme converting levulinic acid into levulinyl-CoA is the combination of the enzymes of amino acid sequence SEQ ID NO: 3 and SEQ ID NO: 5. In other words, both enzymes of amino acid sequence SEQ ID NO: 3 and SEQ ID NO: 5 are overexpressed in the microorganism of the invention so as to maximize the conversion of levulinyl-CoA into propionyl-CoA and acetyl-CoA.

According to a preferred embodiment, said enzyme converting levulinyl-CoA into propionyl-CoA and acetyl-CoA is selected from the group consisting of acetyl-CoA C-acetyltransferases (EC 2.3.1.9/EC 2.3.1.16), 3-oxoadipyl-CoA thiolases (EC 2.3.1.174), acetoacetyl-CoA synthases (EC 2.3.1.194), functional fragments and functional variants thereof, and combinations thereof.

Preferably, said enzyme converting levulinyl-CoA into propionyl-CoA and acetyl-CoA is selected from the group consisting acetyl-CoA C-acetyltransferases (EC 2.3.1.9/EC 2.3.1.16), functional fragments and functional variants thereof, and combinations thereof. Said acetyl-CoA C-acetyltransferases (EC 2.3.1.9/EC 2.3.1.16) are preferably selected from the group consisting of enzymes of amino acid sequence SEQ ID NO: 7, 9 and 93 to 157.

More preferably, said enzyme converting levulinyl-CoA into propionyl-CoA and acetyl-CoA is selected from the group consisting of the enzymes of amino acid sequence SEQ ID NO: 7, SEQ ID NO: 9, and combinations thereof.

Most preferably, said enzyme converting levulinyl-CoA into propionyl-CoA and acetyl-CoA is the enzyme of amino acid sequence SEQ ID NO: 9.

Thus, according to an even more preferred embodiment, said enzyme converting levulinic acid into levulinyl-CoA is selected from the enzymes of amino acid sequence SEQ ID NO: 1, SEQ ID NO: 3, SEQ ID NO: 5, and combinations thereof; and said enzyme converting levulinyl-CoA into propionyl-CoA and acetyl-CoA is selected from the group consisting of the enzymes of amino acid sequence SEQ ID NO: 7, SEQ ID NO: 9, and combinations thereof.

According to the most preferred embodiment, said enzyme converting levulinic acid into levulinyl-CoA is the combination of the enzymes of amino acid sequence SEQ ID NO: 3 and SEQ ID NO: 5; and said enzyme converting levulinyl-CoA into propionyl-CoA and acetyl-CoA is the enzyme of amino acid sequence SEQ ID NO: 9.

As described above, it is within the skill of the person in the art to overexpress in a microorganism the enzymes according to the invention. Preferably, this overexpression can be achieved by overexpressing a nucleotide sequence, such as a gene or a variant thereof, encoding each enzyme. Said nucleotide sequence can be already present in the microorganism of interest, in which case it is said to be an endogenous gene and can be overexpressed according to any of the method described above. By contrast, when a microorganism does not naturally comprise genes coding for such enzymes, said microorganism can be advantageously transformed with one or more exogenous nucleotide sequences, such as genes from other microorganisms or variants thereof, which encode said enzyme(s) according to any of the method described above: said exogenous nucleotide sequences are also said to be overexpressed. A gene encoding a specific protein can be easily retrieved by the skilled practitioner by loading for example the amino-acid sequence of said protein into the UniProt or NCBI database, and by searching for the corresponding encoding nucleotide sequence which can be expressed in a particular microorganism. Moreover, it is possible and well known by the man skilled in the art to deduce artificial nucleotide sequence from amino acid sequence in order to synthesize artificial gene encoding specific protein.

Thus, according to a preferred embodiment, said uncharacterized fatty acid-CoA ligases (FACL) (EC 6.2.1.—with the conserved domain cd05917) as described above are preferably encoded by the nucleotide sequence SEQ ID NO: 2 or by any nucleotide sequence that can be deduced from amino acid sequences SEQ ID NO: 25 to 37; and/or said acyl CoA: 3-ketoacid/acetate CoA-transferases (EC 2.8.3.5/EC 2.8.3.8) as described above are preferably encoded by the nucleotide sequence SEQ ID NO: 4 or SEQ ID NO:6, or by any nucleotide sequence that can be deduced from amino acid sequences SEQ ID NO: 38 to 92.

More preferably, the enzyme converting levulinic acid into levulinyl-CoA according to the invention is encoded by any nucleotide sequence selected from the group consisting of SEQ ID NO: 2, SEQ ID NO: 4, SEQ ID NO: 6, and combinations thereof.

Most preferably, said enzyme converting levulinic acid into levulinyl-CoA is the combination of two enzymes encoded respectively by the nucleotide sequences SEQ ID NO: 4 and SEQ ID NO: 6.

In other words, the genetic modification for the conversion of levulinic acid into levulinyl-CoA is an overexpression of at least one of the above listed nucleotide sequences.

Yet, according to a preferred embodiment, said acetyl-CoA C-acetyltransferases (EC 2.3.1.9/EC 2.3.1.16) as described above are encoded by the nucleotide sequence SEQ ID NO: 8 or SEQ ID NO: 10, or by any nucleotide sequence deduced from amino acid sequence SEQ ID NO: 93 to 157.

More preferably, the enzyme converting levulinyl-CoA into propionyl-CoA and acetyl-CoA according to the invention is encoded by any nucleotide sequence selected from the group consisting of SEQ ID NO: 8, SEQ ID NO: 10, and combinations thereof.

Most preferably, said enzyme converting levulinyl-CoA into propionyl-CoA and acetyl-CoA is encoded by the nucleotide sequence SEQ ID NO: 10.

In other words, the genetic modification for the conversion of levulinyl-CoA into propionyl-CoA and acetyl-CoA is an overexpression of at least one of the above listed nucleotide sequences.

Thus, according an even more preferred embodiment, said enzyme converting levulic acid into levulinyl-CoA is encoded by any nucleotide sequence selected from the group consisting of SEQ ID NO: 2, SEQ ID NO: 4, SEQ ID NO: 6, and combinations thereof; and said enzyme converting levulinyl-CoA into propionyl-CoA and acetyl-CoA is encoded by any nucleotide sequence selected from the group consisting of SEQ ID NO: 8, SEQ ID NO: 10, and combinations thereof.

According the most preferred embodiment, said enzyme converting levulinic acid into levulinyl-CoA is the combination of two enzymes encoded respectively by the nucleotide sequences SEQ ID NO: 4 and SEQ ID NO: 6; and said enzyme converting levulinyl-CoA into propionyl-CoA and acetyl-CoA is encoded by the nucleotide sequence SEQ ID NO: 10.

One skilled person in the art would nevertheless understand that the above list of nucleotide sequences is not limitative: indeed, as explained above, exogenous genes can be synthetic nucleotide sequences that have been codon-optimized for their expression in the microorganism of interest.

In particular, should microorganism of the invention be *Escherichia coli*, the enzymes of amino acid sequences SEQ ID NO: 3 and SEQ ID NO: 5 can preferably be encoded by the codon-optimized nucleotide sequences SEQ ID NO: 11 and SEQ ID NO: 12, respectively; and the enzyme of amino acid sequence SEQ ID NO: 9 can preferably be encoded by the codon-optimized nucleotide sequence SEQ ID NO: 13.

The enzymes and nucleotide sequences according to the invention are described in Table 1 below, according to their sequence identification number and/or version in the UniProt and/or GenBank database.

TABLE 1

Enzymes and nucleotide sequences according to the invention, converting either levulinic acid into levulinyl-CoA (function i); or levulinyl-CoA into propionyl-CoA and acetyl-CoA (function ii).

| Micro-organism | Known function | Function | UniProt Reference | Enzymes sequences SEQ ID NO: | GenBank Reference | Nucleotide sequences SEQ ID NO: |
|---|---|---|---|---|---|---|
| *Ralstonia eutropha* | Acyl-CoA synthetase (AMP forming)/AMP-acid ligase II | i | Q0KA99_CUPNH | 1 | 4248560 | 2 |
| *Ralstonia eutropha* | Succinyl coA: 3-ketoacid transferase subunit B | i | Q0KBZ9_CUPNH | 3 | 4249458 | 4 |
| *Ralstonia eutropha* | Succinyl coA: 3-ketoacid transferase subunit A | i | Q0KKC00_CUPNH | 5 | 4249457 | 6 |
| *Ralstonia eutropha* | Acetyl-coA acetyltransferase. | ii | Q0KBG1_CUPNH | 7 | 4249356 | 8 |
| *Ralstonia eutropha* | Beta-ketothiolase BktB (acetyl-coA acetyltransferase) (acetyl coA-acyltransferase) | ii | BKTB_CUPNH | 9 | 4248815 | 10 |
| none | none (artificial) | i | none | 3 | n/d | 11 |
| none | none (artificial) | i | none | 5 | n/d | 12 |
| none | none (artificial) | ii | none | 9 | n/d | 13 |
| Uncultured marine bacterium 442 | AMP-binding enzyme | i | Q6SH33_9BACT | 25 | n/d | n/d |
| *Bacillus subtilis* | Putative acyl-CoA synthetase YngI | i | YNGI_BACSU | 26 | n/d | n/d |
| *Pseudomonas aeruginosa* PAO1 | AMP-binding protein | i | Q9I0S7_PSEAE | 27 | n/d | n/d |
| *Burkholderia dolosa* AU0158 | Acetyl-coenzyme A synthetase 1 | i | A2W663_9BURK | 28 | n/d | n/d |
| *Bacteroides thetaiotaomicron* VPI-5482 | AMP-binding protein | i | Q8A422_BACTN | 29 | n/d | n/d |
| *Mycobacterium tuberculosis* H37Rv | fatty-acid--CoA ligase FadD35 | i | I6Y0X0_MYCTU | 30 | n/d | n/d |
| *Clostridium botulinum* A str. ATCC 3502 | AMP-binding protein | i | A5I718_CLOBH | 31 | n/d | n/d |
| *Aspergillus oryzae* RIB40 | Unnamed protein product | i | Q2U0G7_ASPOR | 32 | n/d | n/d |
| *Aspergillus oryzae* RIB40 | Unnamed protein product | i | Q2UH98_ASPOR | 33 | n/d | n/d |
| *Mycobacterium smegmatis* str. MC2 155 | AMP-dependent synthetase/ligase | i | A0QZG7_MYCS2 | 34 | n/d | n/d |

TABLE 1-continued

Enzymes and nucleotide sequences according to the invention, converting either levulinic acid into
levulinyl-CoA (function i); or levulinyl-CoA into propionyl-CoA and acetyl-CoA (function ii).

| Micro-organism | Known function | Function | UniProt Reference | Enzymes sequences SEQ ID NO: | GenBank Reference | Nucleotide sequences SEQ ID NO: |
|---|---|---|---|---|---|---|
| *Aspergillus oryzae* RIB40 | Unnamed protein product | i | Q2UDA2_ASPOR | 35 | n/d | n/d |
| uncultured bacterium MedeBAC49C08 | | i | Q4PK67_9BACT | 36 | n/d | n/d |
| *Moorella thermoacetica* ATCC 39073 | AMP-dependent synthetase and ligase | i | Q2RJ14_MOOTA | 37 | n/d | n/d |
| *Bacillus subtilis* | Probable succinyl-CoA: 3-ketoacid coenzyme A transferase subunit A | i | SCOA_BACSU | 38 | n/d | n/d |
| *Bacillus subtilis* | Probable succinyl-CoA: 3-ketoacid coenzyme A transferase subunit B | i | SCOB_BACSU | 39 | n/d | n/d |
| *Helicobacter pylori* | Succinyl-CoA: 3-ketoacid coenzyme A transferase subunit A | i | SCOA_HELPY | 40 | n/d | n/d |
| *Helicobacter pylori* | Succinyl-CoA: 3-ketoacid coenzyme A transferase subunit B | i | SCOB_HELPY | 41 | n/d | n/d |
| *Helicobacter pylori* | Succinyl-CoA: 3-ketoacid coenzyme A transferase subunit A | i | SCOA_HELPJ | 42 | n/d | n/d |
| *Helicobacter pylori* | Succinyl-CoA: 3-ketoacid coenzyme A transferase subunit B | i | SCOB_HELPJ | 43 | n/d | n/d |
| *Mycobacterium bovis* | Probable succinyl-CoA: 3-ketoacid coenzyme A transferase subunit A | i | SCOA_MYCBO | 44 | n/d | n/d |
| *Mycobacterium bovis* | Probable succinyl-CoA: 3-ketoacid coenzyme A transferase subunit B | i | SCOB_MYCBO | 45 | n/d | n/d |
| *Acinetobacter baylyi* | Acetoacetyl-CoA transferase, alpha subunit | i | Q6F9I4_ACIAD | 46 | n/d | n/d |
| *Acinetobacter baylyi* | Acetoacetyl-CoA transferase, beta subunit | i | Q6F9I3_ACIAD | 47 | n/d | n/d |
| *Acinetobacter bereziniae* | Succinyl-CoA: 3-ketoacid-coenzyme A transferase subunit B | i | A0A0A8TUV0_ACIBZ | 48 | n/d | n/d |
| *Acinetobacter bereziniae* | Succinyl-CoA: 3-ketoacid-coenzyme A transferase subunit A | i | A0A0A8TQW8_ACIBZ | 49 | n/d | n/d |
| *Acinetobacter bereziniae* | Acetate CoA-transferase YdiF | i | A0A0A8TSD3_ACIBZ | 50 | n/d | n/d |
| *Bradyrhizobium* sp. YR681 | Acetate CoA-transferase YdiF | i | J3I464_9BRAD | 51 | n/d | n/d |
| *Xanthomonas campestris* pv. *campestris* | Succinyl-CoA: 3-ketoacid coenzyme A transferase subunit A | i | SCOA_XANCB | 52 | n/d | n/d |
| *Xanthomonas campestris* pv. *campestris* | Succinyl-CoA: 3-ketoacid coenzyme A transferase subunit B | i | SCOB_XANCB | 53 | n/d | n/d |
| *Acetobacter aceti* | Succinyl-CoA: acetate CoA-transferase | i | SCACT_ACEAC | 54 | n/d | n/d |

TABLE 1-continued

Enzymes and nucleotide sequences according to the invention, converting either levulinic acid into
levulinyl-CoA (function i); or levulinyl-CoA into propionyl-CoA and acetyl-CoA (function ii).

| Micro-organism | Known function | Function | UniProt Reference | Enzymes sequences SEQ ID NO: | GenBank Reference | Nucleotide sequences SEQ ID NO: |
|---|---|---|---|---|---|---|
| Escherichia coli | Acetate CoA-transferase subunit alpha | i | ATOD_ECOLI | 55 | n/d | n/d |
| Escherichia coli | Acetate CoA-transferase subunit beta | i | ATOA_ECOLI | 56 | n/d | n/d |
| Escherichia coli | Acetate CoA-transferase YdiF | i | YDIF_ECOLI | 57 | n/d | n/d |
| Escherichia coli O157:H7 | Acetate CoA-transferase YdiF | i | YDIF_ECO57 | 58 | n/d | n/d |
| Haemophilus influenzae | Acetate CoA-transferase subunit beta | i | ATOA_HAEIN | 59 | n/d | n/d |
| Haemophilus influenzae | Acetate CoA-transferase subunit alpha | i | ATOD_HAEIN | 60 | n/d | n/d |
| Burkholderia sp. BT03 | 3-oxoacid CoA-transferase, B subunit | i | W6WWU8_9BURK | 61 | n/d | n/d |
| Burkholderia sp. BT03 | 3-oxoacid CoA-transferase, A subunit | i | W6XFN3_9BURK | 62 | n/d | n/d |
| Burkholderia sp. BT03 | Acetate CoA-transferase YdiF | i | W6X0E0_9BURK | 63 | n/d | n/d |
| Citrobacter freundii | Acetate CoA-transferase YdiF | i | A0A0D7M1R1_CITFR | 64 | n/d | n/d |
| Citrobacter rodentium | Acetate CoA-transferase beta subunit | i | D2TK83_CITRI | 65 | n/d | n/d |
| Citrobacter rodentium | Acetate CoA-transferase alpha subunit | i | D2TK84_CITRI | 66 | n/d | n/d |
| Corynebacterium casei UCMA 3821 | Succinyl-CoA: 3-ketoacid-coenzyme A transferase subunit A | i | G7HWY1_9CORY | 67 | n/d | n/d |
| Corynebacterium casei UCMA 3822 | 3-oxoacid CoA-transferase subunit B | i | G7HWY0_9CORY | 68 | n/d | n/d |
| Corynebacterium efficiens | Acetate CoA-transferase YdiF | i | Q8FSQ6_COREF | 69 | n/d | n/d |
| Corynebacterium glutamicum | Acetyl-CoA hydrolase | i | Q8NT12_CORGL | 70 | n/d | n/d |
| Escherichia coli ISC11 | Succinyl-CoA: 3-ketoacid-coenzyme A transferase subunit B | i | W1G4U4_ECOLX | 71 | n/d | n/d |
| Escherichia coli ISC11 | Succinyl-CoA: 3-ketoacid-coenzyme A transferase subunit A | i | W1G4Y6_ECOLX | 72 | n/d | n/d |
| Klebsiella oxytoca 10-5245 | Acetate CoA-transferase YdiF | i | H3MA92_KLEOX | 73 | n/d | n/d |
| Klebsiella pneumoniae | 3-oxoadipate CoA-transferase | i | A0A060VI81_KLEPN | 74 | n/d | n/d |
| Klebsiella pneumoniae | Acetate CoA-transferase YdiF | i | A0A0C7K9R8_KLEPN | 75 | n/d | n/d |
| Klebsiella pneumoniae | Acetate CoA-transferase YdiF | i | R4Y8U6_KLEPN | 76 | n/d | n/d |
| Klebsiella pneumoniae | 3-oxoadipate CoA-transferase | i | A0A085DBP3_KLEPN | 77 | n/d | n/d |
| Klebsiella pneumoniae | Acetyl-CoA: acetoacetyl-CoA transferase, alpha subunit | i | W9B913_KLEPN | 78 | n/d | n/d |
| Klebsiella pneumoniae | Acetyl-CoA: acetoacetyl-CoA transferase, beta subunit | i | W9BPH5_KLEPN | 79 | n/d | n/d |

TABLE 1-continued

Enzymes and nucleotide sequences according to the invention, converting either levulinic acid into levulinyl-CoA (function i); or levulinyl-CoA into propionyl-CoA and acetyl-CoA (function ii).

| Micro-organism | Known function | Function | UniProt Reference | Enzymes sequences SEQ ID NO: | GenBank Reference | Nucleotide sequences SEQ ID NO: |
|---|---|---|---|---|---|---|
| *Phyllobacterium* sp. YR531 | Acetate CoA-transferase YdiF | i | J2VI37_9RHIZ | 80 | n/d | n/d |
| *Pseudomonas alcaligenes* OT 69 | Acetate CoA-transferase YdiF | i | U3H473_PSEAC | 81 | n/d | n/d |
| *Pseudomonas fluorescens* F113 | n/d | i | G8Q6H9_PSEFL | 82 | n/d | n/d |
| *Pseudomonas fluorescens* F113 | n/d | i | G8Q6H8_PSEFL | 83 | n/d | n/d |
| *Pseudomonas putida* | Butyryl-CoA: acetate CoA transferase | i | A5W3L8_PSEP1 | 84 | n/d | n/d |
| *Pseudomonas putida* | 3-oxoacid CoA-transferase, A subunit | i | B0KTE5_PSEPG | 85 | n/d | n/d |
| *Pseudomonas putida* | 3-oxoacid CoA-transferase, B subunit | i | B0KTE4_PSEPG | 86 | n/d | n/d |
| *Ralstonia solanacearum* | Acetate CoA-transferase YdiF | i | D8NYJ4_RALSL | 87 | n/d | n/d |
| *Rhizobium* sp. AP16 | Acetate CoA-transferase YdiF OS | i | J2WFE9_9RHIZ | 88 | n/d | n/d |
| *Rhizobium* sp. CF080 | 3-oxoacid CoA-transferase, A subunit | i | W6W555_9RHIZ | 89 | n/d | n/d |
| *Rhizobium* sp. CF080 | 3-oxoacid CoA-transferase, B subunit | i | W6WQV5_9RHIZ | 90 | n/d | n/d |
| *Salmonella typhimurium* | Acetate CoA-transferase YdiF | i | Q8ZPR5_SALTY | 91 | n/d | n/d |
| *Variovorax* sp. CF313 | Acetate CoA-transferase YdiF | i | J2T0X7_9BURK | 92 | n/d | n/d |
| *Acinetobacter baumannii* | 3-ketoacyl-CoA thiolase | ii | FADA_ACIBT | 93 | n/d | n/d |
| *Acinetobacter baylyi* | Beta-ketoadipyl-CoA thiolase | ii | PCAF_ACIAD | 94 | n/d | n/d |
| *Aeromonas hydrophila* subsp. *hydrophila* | 3-ketoacyl-CoA thiolase | ii | FADA_AERHH | 95 | n/d | n/d |
| *Aeromonas hydrophila* subsp. *hydrophila* | 3-ketoacyl-CoA thiolase | ii | FADI_AERHH | 96 | n/d | n/d |
| *Alcanivorax borkumensis* | 3-ketoacyl-CoA thiolase | ii | FADA_ALCBS | 97 | n/d | n/d |
| *Aliivibrio salmonicida* | 3-ketoacyl-CoA thiolase | ii | FADA_ALISL | 98 | n/d | n/d |
| *Allochromatium vinosum* | Acetyl-CoA acetyltransferase | ii | THIL_ALLVD | 99 | n/d | n/d |
| *Alteromonas macleodii* | 3-ketoacyl-CoA thiolase | ii | FADI_ALTMD | 100 | n/d | n/d |
| *Bacillus subtilis* | 3-ketoacyl-CoA thiolase | ii | FADA_BACSU | 101 | n/d | n/d |
| *Bacillus subtilis* | Acetyl-CoA acetyltransferase | ii | THL_BACSU | 102 | n/d | n/d |
| *Candida tropicalis* | Acetyl-CoA acetyltransferase | ii | THIA_CANTR | 103 | n/d | n/d |
| *Candida tropicalis* | 3-ketoacyl-CoA thiolase | ii | THIKA_CANTR | 104 | n/d | n/d |
| *Chromobacterium violaceum* | Acetyl-CoA acetyltransferase | ii | THIL_CHRVO | 105 | n/d | n/d |
| *Chromohalobacter salexigens* | 3-ketoacyl-CoA thiolase | ii | FADA_CHRSD | 106 | n/d | n/d |
| *Citrobacter koseri* | 3-ketoacyl-CoA thiolase | ii | FADA_CITK8 | 107 | n/d | n/d |
| *Citrobacter koseri* | 3-ketoacyl-CoA thiolase | ii | FADI_CITK8 | 108 | n/d | n/d |
| *Clostridium acetobutylicum* | Acetyl-CoA acetyltransferase | ii | THLA_CLOAB | 109 | n/d | n/d |
| *Cupriavidus necator* | Acetyl-CoA acetyltransferase | ii | THIL_CUPNH | 110 | n/d | n/d |
| *Enterobacter cloacae* | 3-ketoacyl-CoA thiolase | ii | FADA_ENTCL | 111 | n/d | n/d |
| *Erwinia tasmaniensis* | 3-ketoacyl-CoA thiolase | ii | FADA_ERWT9 | 112 | n/d | n/d |

TABLE 1-continued

Enzymes and nucleotide sequences according to the invention, converting either levulinic acid into levulinyl-CoA (function i); or levulinyl-CoA into propionyl-CoA and acetyl-CoA (function ii).

| Micro-organism | Known function | Function | UniProt Reference | Enzymes sequences SEQ ID NO: | GenBank Reference | Nucleotide sequences SEQ ID NO: |
|---|---|---|---|---|---|---|
| Erwinia tasmaniensis | 3-ketoacyl-CoA thiolase | ii | FADI_ERWT9 | 113 | n/d | n/d |
| Escherichia coli | 3-ketoacyl-CoA thiolase | ii | FADA_ECOLI | 114 | n/d | n/d |
| Escherichia coli | 3-ketoacyl-CoA thiolase | ii | FADI_ECOLI | 115 | n/d | n/d |
| Escherichia coli | Acetyl-CoA acetyltransferase | ii | ATOB_ECOLI | 116 | n/d | n/d |
| Escherichia coli | Probable acetyl-CoA acetyltransferase | ii | YQEF_ECOLI | 117 | n/d | n/d |
| Escherichia coli | 3-oxoadipyl-CoA/3-oxo-5,6-dehydrosuberyl-CoA thiolase | ii | PAAJ_ECOLI | 118 | n/d | n/d |
| Haemophilus influenzae | Acetyl-CoA acetyltransferase | ii | ATOB_HAEIN | 119 | n/d | n/d |
| Hahella chejuensis | 3-ketoacyl-CoA thiolase | ii | FADA_HAHCH | 120 | n/d | n/d |
| Klebsiella pneumoniae subsp. pneumoniae | 3-ketoacyl-CoA thiolase | ii | FADA_KLEP7 | 121 | n/d | n/d |
| Klebsiella pneumoniae subsp. pneumoniae | 3-ketoacyl-CoA thiolase | ii | FADI_KLEP7 | 122 | n/d | n/d |
| Marinobacter hydrocarbonoclasticus | 3-ketoacyl-CoA thiolase | ii | FADA_MARHV | 123 | n/d | n/d |
| Mycobacterium tuberculosis | Probable acetyl-CoA acetyltransferase | ii | FADA4_MYCTO | 124 | n/d | n/d |
| Paracoccus denitrificans | Acetyl-CoA acetyltransferase | ii | THIL_PARDE | 125 | n/d | n/d |
| Pectobacterium atrosepticum | 3-ketoacyl-CoA thiolase | ii | FADA_PECAS | 126 | n/d | n/d |
| Pectobacterium atrosepticum | 3-ketoacyl-CoA thiolase | ii | FADI_PECAS | 127 | n/d | n/d |
| Photobacterium profundum | 3-ketoacyl-CoA thiolase | ii | FADA_PHOPR | 128 | n/d | n/d |
| Photobacterium profundum | 3-ketoacyl-CoA thiolase | ii | FADI_PHOPR | 129 | n/d | n/d |
| Pseudoalteromonas atlantica | 3-ketoacyl-CoA thiolase | ii | FADA_PSEA6 | 130 | n/d | n/d |
| Pseudoalteromonas atlantica | 3-ketoacyl-CoA thiolase | ii | FADI_PSEA6 | 131 | n/d | n/d |
| Pseudomonas aeruginosa | Acetyl-CoA acetyltransferase | ii | ATOB_PSEAE | 132 | n/d | n/d |
| Pseudomonas aeruginosa | 3-ketoacyl-CoA thiolase | ii | FADA_PSEAE | 133 | n/d | n/d |
| Pseudomonas putida | 3-ketoacyl-CoA thiolase | ii | FADA_PSEPK | 134 | n/d | n/d |
| Pseudomonas putida | Beta-ketoadipyl-CoA thiolase | ii | PCAF_PSEPU | 135 | n/d | n/d |
| Psychrobacter arcticus | 3-ketoacyl-CoA thiolase | ii | FADA_PSYA2 | 136 | n/d | n/d |
| Rhizobium meliloti | Acetyl-CoA acetyltransferase | ii | THIL_RHIME | 137 | n/d | n/d |
| Saccharomyces cerevisiae | 3-ketoacyl-CoA thiolase | ii | THIK_YEAST | 138 | n/d | n/d |
| Saccharomyces cerevisiae | Acetyl-CoA acetyltransferase | ii | THIL_YEAST | 139 | n/d | n/d |
| Salmonella typhimurium | 3-ketoacyl-CoA thiolase | ii | FADA_SALTY | 140 | n/d | n/d |
| Salmonella typhimurium | 3-ketoacyl-CoA thiolase | ii | FADI_SALTY | 141 | n/d | n/d |
| Schizosaccharomyces pombe | Acetyl-CoA acetyltransferase | ii | THIL_SCHPO | 142 | n/d | n/d |
| Serratia proteamaculans | 3-ketoacyl-CoA thiolase | ii | FADA_SERP5 | 143 | n/d | n/d |
| Serratia proteamaculans | 3-ketoacyl-CoA thiolase | ii | FADI_SERP5 | 144 | n/d | n/d |
| Shewanella denitrificans | 3-ketoacyl-CoA thiolase | ii | FADA_SHEDO | 145 | n/d | n/d |
| Shewanella denitrificans | 3-ketoacyl-CoA thiolase | ii | FADI_SHEDO | 146 | n/d | n/d |

TABLE 1-continued

Enzymes and nucleotide sequences according to the invention, converting either levulinic acid into levulinyl-CoA (function i); or levulinyl-CoA into propionyl-CoA and acetyl-CoA (function ii).

| Micro-organism | Known function | Function | UniProt Reference | Enzymes sequences SEQ ID NO: | GenBank Reference | Nucleotide sequences SEQ ID NO: |
|---|---|---|---|---|---|---|
| Shigella flexneri | 3-ketoacyl-CoA thiolase | ii | FADA_SHIFL | 147 | n/d | n/d |
| Shigella flexneri | 3-ketoacyl-CoA thiolase | ii | FADI_SHIFL | 148 | n/d | n/d |
| Staphylococcus aureus | Probable acetyl-CoA acyltransferase | ii | THLA_STAAM | 149 | n/d | n/d |
| Staphylococcus epidermidis | Probable acetyl-CoA acyltransferase | ii | THLA_STAES | 150 | n/d | n/d |
| Thiocystis violacea | Acetyl-CoA acetyltransferase | ii | THIL_THIVI | 151 | n/d | n/d |
| Vibrio fischeri | 3-ketoacyl-CoA thiolase | ii | FADA_VIBF1 | 152 | n/d | n/d |
| Vibrio fischeri | 3-ketoacyl-CoA thiolase | ii | FADI_VIBF1 | 153 | n/d | n/d |
| Yarrowia lipolytica | 3-ketoacyl-CoA thiolase | ii | THIK_YARLI | 154 | n/d | n/d |
| Yarrowia lipolytica | Acetyl-CoA acetyltransferase | ii | THIL_YARLI | 155 | n/d | n/d |
| Yersinia pestis | 3-ketoacyl-CoA thiolase | ii | FADA_YERPE | 156 | n/d | n/d |
| Yersinia pestis | 3-ketoacyl-CoA thiolase | ii | FADI_YERPE | 157 | n/d | n/d |

(n/d: non disclosed)

As stated above, the invention further encompasses functional fragments and functional mutants of the above listed enzymes and their corresponding nucleotide sequences.

By "functional fragment" of a protein of reference having a biological activity of interest (herein, of an enzyme having a catalytic activity), it is meant parts of the amino acid sequence of this reference protein, said parts comprising at least all the regions essential for exhibiting the biological activity of said protein. These parts of sequences can be of various lengths, provided the biological activity of the amino acid sequence of reference is retained by said parts. In other words, the functional fragments of the enzymes according to the invention are capable herein either to convert levulinic acid into levulinyl-CoA, or to convert levulinyl-CoA into propionyl-CoA and acetyl-CoA, depending upon the enzyme of reference. The capacity of said fragments to exhibit such activity can be assessed for example by contacting in vitro a fragment of the above listed enzymes with levulinic acid (or levulinyl-CoA) as a substrate, and measure its catalytic conversion into levulinyl-CoA (or into propionyl-CoA and acetyl-CoA if the substrate is levulinyl-CoA) by spectrophotometric methods and LC-MS analysis (as described in examples below). It must however be noted that the activity of said fragments may differ in catalytic efficiency compared to the activity of the enzyme of reference.

By "functional variants" or "functional mutants", it is meant herein proteins that structurally differ from the amino acid sequence of a protein of reference but that generally retain all the essential functional characteristics of said protein of reference. A variant or a mutant of a protein may be a naturally-occurring mutant or a non-naturally occurring mutant. Such non-naturally occurring mutants or variants of the reference protein can be made, for example, by mutagenesis techniques on the encoding nucleic acids or genes, for example by random mutagenesis or site-directed mutagenesis or by fusioning at least two fragments of different proteins.

Structural differences may be limited in such a way that the amino acid sequence of reference protein and the amino acid sequence of the mutant may be closely similar overall, and identical in many regions. Structural differences may result from conservative or non-conservative amino acid substitutions, deletions and/or additions between the amino acid sequence of the reference protein and the mutant. The only proviso is that, even if some amino acids are substituted, deleted and/or added, the biological activity of the amino acid sequence of the reference protein is retained by the mutant. That is to say, in the context of the present invention, the functional mutants of the enzymes according to the invention are capable either to convert levulinic acid into levulinyl-CoA, or to convert levulinyl-CoA into propionyl-CoA and acetyl-CoA, depending upon the enzyme of reference. The capacity of said mutants to exhibit such activity can be assessed as described above. It must however be noted that the activity of said mutants may differ in catalytic efficiency compared to the activity of the enzyme of reference.

"Functional variants" of the enzymes according to the present invention include, but are not limited to, proteins having amino acid sequences which are at least 60% identical after alignment to the amino acid sequence encoding said enzymes of reference. Preferably, said mutants have 60% 70%, 75%, 80%, 85%, 90%, 95% sequence identity to said enzymes, and more preferably have 96%, 97%, 98%, 99%, or 99,999% sequence identity to enzymes.

Sequence identity between amino acid sequences can be determined by comparing a position in each of the sequences which may be aligned for the purposes of comparison. When a position in the compared sequences is occupied by the same amino acid, then the sequences are identical at that position. A degree of sequence identity between proteins is a function of the number of identical amino acid residues at positions shared by the sequences of said proteins.

To determine the percentage of identity between two amino acid sequences, the sequences are aligned for optimal comparison. For example, gaps can be introduced in the sequence of a first amino acid sequence for optimal alignment with the second amino acid sequence. The amino acid residues at corresponding amino acid positions are then compared. When a position in the first sequence is occupied by the same amino acid residue as the corresponding position in the second sequence, the molecules are identical at that position.

The percentage of identity between the two sequences is a function of the number of identical positions shared by the sequences. Hence % identity=number of identical positions/total number of overlapping positions×100.

Optimal alignment of sequences may be conducted by the global homology alignment algorithm of Needleman and Wunsch (1972), by computerized implementations of this algorithm (such as CLUSTAL W) or by visual inspection. The best alignment (i.e., resulting in the highest percentage of identity between the compared sequences) generated by the various methods is selected.

In other words, the percentage of sequence identity is calculated by comparing two optimally aligned sequences, determining the number of positions at which the identical amino acid occurs in both sequences to yield the number of matched positions, dividing the number of matched positions by the total number of positions and multiplying the result by 100 to yield the percentage of sequence identity.

The above definitions and preferred embodiments related to the functional fragments and functional variants of proteins apply mutatis mutandis to nucleotide sequences, such as genes, encoding a protein of interest.

According to a preferred embodiment, the microorganism according to the invention is capable of producing, by fermentation culture, alcohols such as 1,2-propanediol, 2,3-butanediol, 1,3-butanediol, 1,4-butanediol, ethanol, propanol, or butanol; amino acids such aslysine or threonine; carboxylic acids such as glycolic acid or succinic acid, or polyhydroxyalkanoates such as polyhydroxyvalerate, or polyhydroxybutyrate-cohydroxyvalerate.

In other words, the microorganism according to the invention is further genetically modified to produce, by fermentation culture, alcohols such as 1,2-propanediol, 2,3-butanediol, 1,3-butanediol, 1,4-butanediol, ethanol, propanol, or butanol; amino acids such as lysine or threonine; carboxylic acids such as glycolic acid or succinic acid, or polyhydroxyalkanoates such as polyhydroxyvalerate, or polyhydroxybutyrate-cohydroxyvalerate.

Indeed, as illustrated in the Examples below, the overexpression of the enzymes and/or nucleotide sequences of Table 1 can, not only enhance the growth of the microorganism in the presence of levulinic acid, but also increase the productivity and yield of the above listed compounds—provided that the microorganism is capable to produce them. This is rendered possible thanks to the conversion of levulinic acid into the metabolic intermediates levulinyl-CoA, propionyl-CoA and acetyl-CoA.

Microorganisms that are genetically modified to produce specific alcohols, amino acids, carboxylic acids, or polyhydroxyalkanoates are widely documented and well-known in the art.

For example, patent applications WO2008/116853, WO2008/116852, WO2011/157728, WO2010/141920, US2015/104822, WO2010/003728, U.S. Pat. No. 9,109, 242, and WO2008/052973, herein incorporated by reference, disclose genetic modifications for the production, from a carbon source, of 1,2-propanediol, glycolic acid, 1,4-butanediol, ethanol, succinic acid, lysine, and butanol, respectively, in microorganisms such as *Escherichia coli, Saccharomyces cerevisiae, Corynebacterium glutamicum* or *Clostridium acetobutylicum.*

As another illustrative example, patent applications EP1078068, EP1015565 U.S. Pat. Nos. 8,980,593, 8,956, 835, herein incorporated by reference, but also, Steinbuchel and Gorenflo, (1997) and Luzier et al. (1992), disclose genetic modifications in several microorganisms such as *Ralstonia eutropha, Escherichia coli, Pseudomonas putida* allowing the microbial production of polyhydroxyalkanoates (PHAs) and more particularly polyhydroxyvalerate (PHV) and polyhydroxybutyrate-cohydroxyvalerate (PHBV) from glucose, hydroxyacids and/or levulinic acid.

As another illustrative example, patent application WO2012/172050, herein incorporated by reference, and Niu and Guo (2014) discloses genetic modifications allowing the microbial production of 1,2-propanediol from propionyl-CoA and lactate.

As another illustrative example, patent application WO2014/099707, herein incorporated by reference, and Srirangan et al. (2013) disclose genetic modifications allowing the microbial production of propanol from propionyl-CoA.

As a last illustrative example, a genetic modification for the production of ethanol from acetyl-CoA is an overexpression of an aldehyde/alcohol dehydrogenase (for example adhE from *Clostridium acetobutylicum* or *Escherichia coli*) in deposited microorganisms such as *Escherichia coli* LY80 or *Clostridium acetobutylicum* ATCC 824.

In another aspect, the present invention relates to a method for the fermentative conversion of levulinic acid into propionyl-CoA and acetyl-CoA, comprising the step of culturing, under fermentation conditions, the genetically modified microorganism according to the invention, in a culture medium containing as a carbon source at least levulinic acid.

The person skilled in the art can easily determine the fermentation conditions necessary for growing the microorganism according to the invention. In particular, it is well known that bacteria and yeasts can be fermented at a temperature comprised between 20° C. and 55° C., preferentially between 25° C. and 40° C. *E. coli, C. glutamicum, C. acetobutylicum* and *S. cerevisiae* can more particularly be cultured at a temperature comprised between about 30° C. and about 37° C.

The method of the invention can be performed either in a batch process, in a fed-batch process or in a continuous process, and under aerobic, micro-aerobic or anaerobic conditions.

A fermentation "under aerobic conditions" means that oxygen is provided to the culture by dissolving gas into the liquid phase of the culture. This can be achieved by (1) sparging oxygen containing gas (e.g. air) into the liquid phase, or (2) shaking the vessel containing the culture medium in order to transfer the oxygen contained in the head space into the liquid phase. The main advantage of the fermentation under aerobic conditions is that the presence of oxygen as an electron acceptor improves the capacity of the strain to produce more energy under the form of ATP for cellular processes, thereby improving the general metabolism of the strain.

Micro-aerobic conditions can be used herein and are defined as culture conditions wherein low percentages of oxygen (e.g. using a mixture of gas containing between 0.1 and 10% of oxygen, completed to 100% with nitrogen) are dissolved into the liquid phase.

By contrast, "anaerobic conditions" are defined as culture conditions wherein no oxygen is provided to the culture medium. Strictly anaerobic conditions can be obtained by sparging an inert gas like nitrogen into the culture medium to remove traces of other gas. Nitrate can be used as an electron acceptor to improve ATP production by the strain and improve its metabolism.

The carbon source used in the above method is preferably at least levulinic acid and optionally at least one carbohydrate substrate.

Still, preferably, said carbohydrate substrate is selected from the group consisting of xylose, glycerol, glucose, arabinose, mannose, galactose, fructose, lactose, maltose, sucrose, and combinations thereof. Even more preferably, said carbohydrate substrate is glucose or xylose.

More preferably, the carbon source used in the above method is a lignocellulosic substrate comprising levulinic acid and optionally at least one carbohydrate substrate.

Even more preferably, the carbohydrate substrate comprised in said lignocellulosic substrate is glucose or xylose.

In a last aspect, the present invention relates to a method for the fermentative production of a product selected from the group consisting of alcohols such as 1,2-propanediol, 1,3-propanediol, 2,3-butanediol, 1,3-butanediol, 1,4-butanediol, ethanol, propanol, or butanol; amino acids such as lysine or threonine; carboxylic acids such as glycolic acid, or succinic acid; or polyhydroxyalkanoates such as polyhydroxyvalerate, or polyhydroxybutyrate-cohydroxyvalerate, said method comprising the steps of:
a) culturing, under fermentation conditions, the genetically modified microorganism according to the invention, in a culture medium comprising as a source of carbon at least levulinic acid, said microorganism being capable to produce at least one of the above products as described above; and
b) recovering said product.

Preferred embodiments for the carbon source described above apply herein mutatis mutandis.

It is within the skill of the person in the art to recover the desired product from the culture medium.

DRAWINGS

EXAMPLES

Molecular Biology Methods

Figure 1:
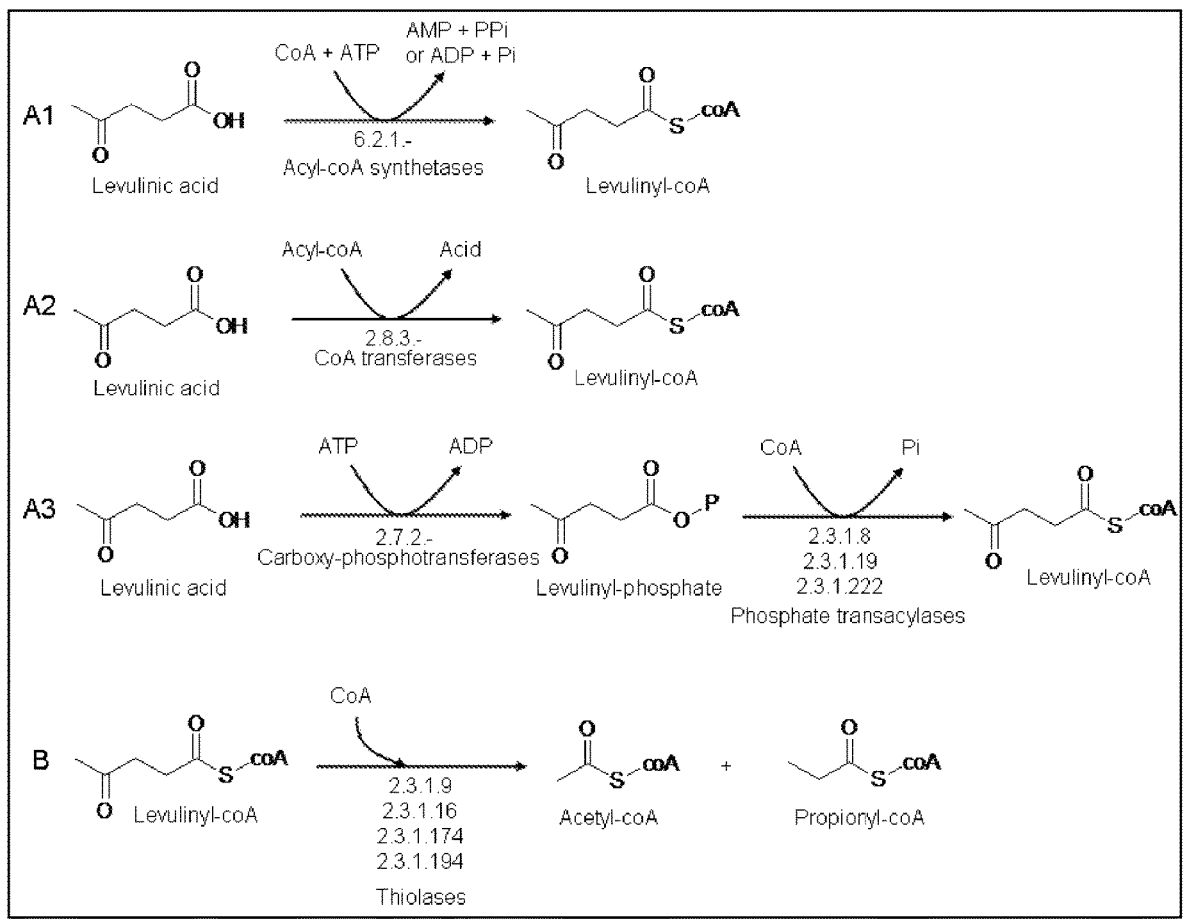
FIG. 1 represents possible enzymes involved in the assimilation of levulinic acid in *Ralstonia euphora*.
Figure 2:
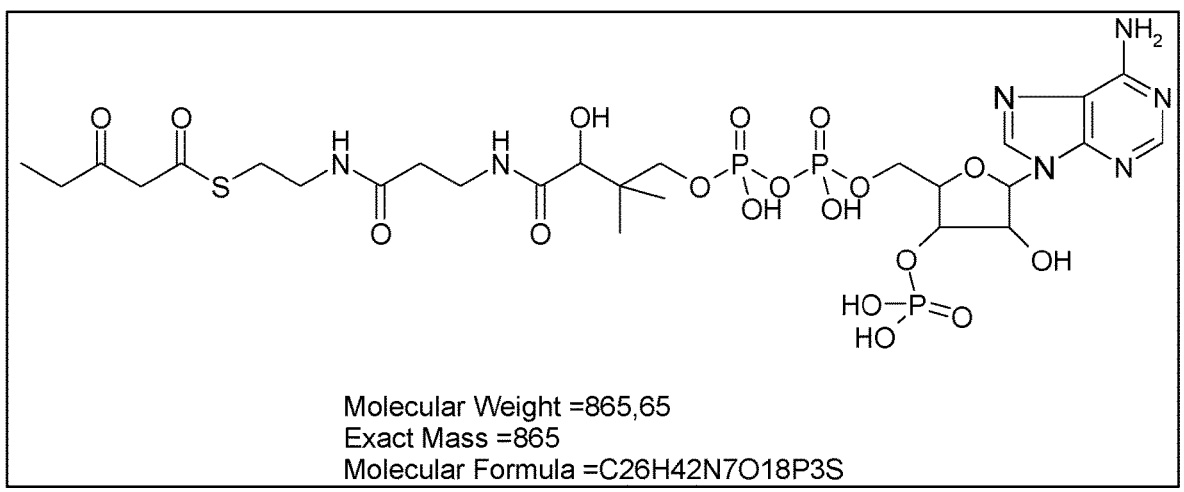
FIG. 2 represents levulinyl-CoA chemical formula.

Methods well known in the art were used to construct *Escherichia coli*, *Saccharomyces cerevisiae*, *Corynebacterium glutamicum* or *Clostridium acetobutylicum* strains containing replicating vectors and/or various chromosomal deletions, and substitutions. For example, chromosomal modification in *E. coli* could be introduced using homologous recombination well described by Datsenko & Wanner (2000). In the same manner, the use of plasmids or vectors to express or overexpress one or several genes in a recombinant microorganisms are well known by the man skilled in the art. Examples of suitable *E. coli* expression vectors include pTrc, pACYC184, pBR322, pUC18, pUC19, pKC30, pRep4, pHS1, pHS2, pPLc236, etc. . . . (Studier et al. 1990, Pouwels et al. 1985). Examples of *E. coli* promoter leading high overexpression of the gene include Ptrc (Brosius et al., 1985), Ptac (de Boer et al., 1983), P/ac (Dickson et al., 1975) etc. . . .

Examples of suitable *S. cerevisiae* vectors are e. g. centromeric and 2p plasmids of the pRS series (Sikorski and Hieter, 1989; Christianson et al., 1992) etc. . . . . Examples of *S. cerevisiae* promoters leading to high overexpression of genes include hxt7, pgk1 (Partow et al., 2010), tef1, tef2 (Nevoigt et al., 2006) etc. . . . . Examples of suitable *S. cerevisiae* terminators are e. g. cyc1, adh1, pgk1 etc. . . . . (Curran et al., 2013). Chromosomal modification could be introduced in *S. cerevisiae* using homologous recombination as described by Güldener et al. (1996).

Examples of suitable *C. glutamicum* vectors are e. g. pClik5aMCS (WO2005059093) plasmids of pEC-X series (Kirchner et al., 2003) other can be found in Eikmanns et al. (1991) etc. . . . . Examples of *C. glutamicum* promoter leading high overexpression of the gene include PgapA, Ptuf, Psod, Ptrc (Eikmanns et al., 1991; Patek et al. 2013) etc. . . . . Chromosomal modifications could be introduced in *C. glutamicum* using homologous recombination as described by Suzuki et al. (2005).

Examples of suitable *C. acetobutylicum* vectors are e. g. pSOS plasmids (Tummala et al. 1999), plasmids of pSYL series (Lee, 1992) others of pMTL series can be found in Chambers et al. (1988) etc. . . . . Examples of *C. acetobutylicum* promoter leading to high overexpression of genes include thl, adc, ptb (Tummala et al., 1999) etc. . . . . Chromosomal modifications could be introduced in *C. acetobutylicum* using homologous recombination as described by Croux & Soucaille in patent application WO2008/040387.

Protocol 1 (chromosomal modifications by homologous recombination, selection of recombinants), Protocol 2 (transduction of phage P1) and Protocol 3 (antibiotic cassette excision, the resistance genes were removed when necessary) were used herein, and have been fully described in patent application EP2532751, incorporated herein by reference. Chromosomal modifications were verified by a PCR analysis with appropriate oligonucleotides that the person skilled in the art is able to design.

Protocol 4: Construction of Recombinant Plasmids

Recombinant DNA technology is described in Molecular Cloning: Sambrook and Russell, 3$^{rd}$ edition (2001) Cold Spring Harbor Laboratory Press, NY, Vol 1, 2, 3. Briefly, the DNA fragments were PCR amplified using oligonucleotides and appropriate genomic DNA as matrix (that the person skilled in the art will be able to define). The DNA fragments and chosen plasmid were digested with compatible restriction enzymes (that the person skilled in the art will be able to define), then ligated and transformed into competent cells. Transformants were analysed and recombinant plasmids of interest were verified by DNA sequencing.

Strain Cultivation Methods

Wild-type *E. coli*, *S. cerevisiae*, *C. glutamicum* and *C. actetobutylicum* strains and their derivatives overexpressing the levulinic acid pathway were cultivated in shake flasks as described in Sambrook and Russel as described above, van Dijken et al. (2000), Keilhauer et al. (1993) and Holt et al. (1984), respectively. Industrial strains producing 1,2-propanediol, glycolic acid, 1,4-butanediol, ethanol, succinic acid, lysine or butanol were cultivated as described in patents WO 2008/116852, WO 2012/055798, WO 2011/

157728, WO 2010/141920, US 2015/104822, WO 2010/003728, U.S. Pat. No. 9,109,242 or WO 2008/052973, respectively. When needed, the appropriate plasmid antibiotics were included in the culture medium.

For each wild-type and industrial strain not expressing the levulinic acid pathway (parent strains), levulinic acid was added to the culture medium at different concentrations ranging from 0.01 g/L (0.1% w/v) to 10 g/L (1% w/v). The half maximal inhibitory concentration (IC50) of levulinic acid was determined as the concentration that led to a 50% decrease of final OD (optical density, reflecting biomass concentration) by comparison to the control culture without levulinic acid.

The strain derivatives overexpressing the levulinic acid pathway were then cultivated with levulinic acid at the IC50 determined for their respective parent strains. Growth was evaluated by measuring the final OD. For industrial strains, production was evaluated by measuring the final concentration of 1,2-propanediol, glycolic acid, 1,4-butanediol, ethanol, succinic acid, lysine or butanol as described in patents WO 2008/116852, WO 2012/055798, WO 2011/157728, WO 2010/141920, US 2015/104822, WO 2010/003728, U.S. Pat. No. 9,109,242 or WO 2008/052973, respectively.

Example 1: Identification of *Ralstonia eutropha* Putative Enzymes and Corresponding Genes Involved in the Assimilation of Levulinic Acid by a Bioinformatics Approach

*Ralstonia eutropha* is known to assimilate levulinic acid. The products of this assimilation have however not been identified to this day. The Inventors hypothesized that assimilation of levulinic acid by *Ralstonia eutropha* proceeds through 2 enzymatic steps as shown in FIG. 1: a first step leading to levulinyl-CoA (A); and a second step leading to acetyl-CoA and propionyl-CoA (B); acetyl-CoA and propionyl-CoA being then integrated into the central carbon metabolism, respectively through the citric acid and the 2-methylcitric acid cycles, or used for the production of polyhydroxyalkanoates (Steinbüchel and Schlegel 1991, Bramer and Steinbuchel 2001, Yu and Si 2004).

Based on this hypothesis, it was considered that the following enzymes might be involved in such conversion:

for step A, in addition to acyl-CoA synthetases (A1: EC 6.2.1.-), coA transferases (A2: EC 2.8.3.-) or a combination (A3) of carboxy-phosphotransferases (A3a: EC 2.7.2.-) and phosphate transacylases (A3b: EC 2.3.1.8/2.3.1.19/2.3.1.222);

for step B, in addition to beta-ketothiolases (EC 2.3.1.16), other thiolases (EC 2.3.1.9/2.3.1.174/2.3.1.194).

Enzymes displaying the above activities were then searched in *Ralstonia eutropha* annotated genome: 37 candidates were found for reaction A1 (as described in FIG. 1 and Table 2), 5 for reaction A2 (as described in FIG. 1 and Table 3), 5 for reaction A3a (as described in FIG. 1 and Table 4), none for reaction A3b, and 24 for reaction B (as described in FIG. 1 and Table 5).

TABLE 2

Putative candidates for reaction A1

| Uniprot entry names | Protein names | Gene names |
| --- | --- | --- |
| ACSA_CUPNH | Acetyl-coenzyme A synthetase (AcCoA synthetase) (Acs) (EC 6.2.1.1) (Acetate--CoA ligase) (Acyl-activating enzyme) | acsA acoE H16_A2525 |
| Q0K466_CUPNH | H16_B0409 protein (EC 6.2.1.—) | H16_B0409 |
| SUCC_CUPNH + Q0KE74_CUPNH | Succinyl-CoA ligase [ADP-forming] (EC 6.2.1.5) | sucC H16_A0547 + sucD H16_A0548 |
| Q0K2Z8_CUPNH | Acetyl-coenzyme A synthetase (AcCoA synthetase) (Acs) (EC 6.2.1.1) (Acetate--CoA ligase) (Acyl-activating enzyme) | acsA H16_B0834 |
| Q0K489_CUPNH | Acetyl-CoA synthetase (NDP-forming) (EC 6.2.1.1) | H16_B0386 |
| Q0K471_CUPNH | Acyl-CoA synthetase (EC 6.2.1.—) | H16_B0404 |
| Q0K8X0_CUPNH | Propionate-CoA ligase (EC 6.2.1.17) | prpE H16_A2462 |
| Q0KB73_CUPNH | Acetyl-coenzyme A synthetase (EC 6.2.1.1) | H16_A1616 |
| Q0KDD5_CUPNH | Acyl-CoA synthetase (AMP-forming)/AMP-acid ligase II (EC 6.2.1.—) | H16_A0839 |
| Q0KA99_CUPNH | Acyl-CoA synthetase (AMP-forming)/AMP-acid ligase II (EC 6.2.1.—) | H16_A1971 |
| Q0K3I3_CUPNH | Acyl-CoA synthetase (AMP-forming)/AMP-acid ligase II (EC 6.2.1.—) | H16_B0644 |
| Q0K4B6_CUPNH | Acyl-CoA synthetase (EC 6.2.1.—) | H16_B0358 |
| Q0KAZ6_CUPNH | Acyl-CoA synthetase (AMP-forming)/AMP-acid ligase II (EC 6.2.1.—) | H16_A1700 |
| Q0K0I0_CUPNH | Acyl-CoA synthetase (AMP-forming)/AMP-acid ligase II (EC 6.2.1.—) | H16_B1709 |
| Q0KCD3_CUPNH | Acyl-CoA synthetase (EC 6.2.1.—) | H16_A1197 |
| Q0K281_CUPNH | Acetyl-CoA synthetase (EC 6.2.1.1) | H16_B1102 |
| Q0K1J9_CUPNH | Acyl-CoA synthetase (AMP-forming)/AMP-acid ligase II (EC 6.2.1.—) | H16_B1335 |
| Q0K7Y6_CUPNH | Acyl-CoA synthetase (AMP-forming)/AMP-acid ligase II (EC 6.2.1.—) | H16_A2807 |
| Q0K3F0_CUPNH | Acyl-CoA synthetase (AMP-forming)/AMP-acid ligase II (EC 6.2.1.—) | H16_B0677 |
| Q0KDA8_CUPNH | Acyl-CoA synthetase (AMP-forming)/AMP-acid ligase II (EC 6.2.1.—) | H16_A0866 |
| Q0K3D1_CUPNH | Acyl-CoA synthetase (AMP-forming) (EC 6.2.1.1) | H16_B0696 |
| Q0K4U9_CUPNH | Acyl-CoA synthetase (AMP-forming)/AMP-acid ligase II (EC 6.2.1.—) | H16_B0174 |

TABLE 2-continued

Putative candidates for reaction A1

| Uniprot entry names | Protein names | Gene names |
|---|---|---|
| Q0K2S2_CUPNH | Acyl-CoA synthetase (AMP-forming)/AMP-acid ligase II (EC 6.2.1.—) | H16_B0910 |
| Q0K1G2_CUPNH | Acyl-CoA synthetase (AMP-forming)/AMP-acid ligase II (EC 6.2.1.—) | H16_B1373 |
| Q0K7G7_CUPNH | Acyl-CoA synthetase (EC 6.2.1.—) | H16_A2978 |
| Q0K7Z8_CUPNH | Acyl-CoA synthetase (AMP-forming)/AMP-acid ligase II (EC 6.2.1.—) | H16_A2794 |
| Q0K9H2_CUPNH | Acyl-CoA synthetase (EC 6.2.1.—) | H16_A2252 |
| Q0KAX9_CUPNH | Acyl-CoA synthetase (AMP-forming)/AMP-acid ligase II (EC 6.2.1.—) | H16_A1718 |
| Q0KCA1_CUPNH | Acyl-CoA synthetase (AMP-forming)/AMP-acid ligase II (EC 6.2.1.—) | H16_A1230 |
| Q0KC36_CUPNH | Acyl-CoA synthetase (AMP-forming)/AMP-acid ligase II (EC 6.2.1.—) | H16_A1295 |
| Q0KDA3_CUPNH | Acyl-CoA synthetase (AMP-forming)/AMP-acid ligase II (EC 6.2.1.—) | H16_A0871 |
| Q0K3N6_CUPNH | Acetyl-CoA synthetase (EC 6.2.1.1) | H16_B0591 |
| Q0KBH0_CUPNH | Acyl-CoA synthetase (AMP-forming)/AMP-acid ligase II (EC 6.2.1.—) | H16_A1519 |
| Q0K235_CUPNH | Acyl-CoA synthetase (EC 6.2.1.—) | H16_B1148 |
| Q0K7T4_CUPNH | Acetoacetyl-CoA synthetase (EC 6.2.1.16) | H16_A2860 |
| Q0K1S0_CUPNH | Acyl-CoA synthetase (AMP-forming)/AMP-acid ligase II (EC 6.2.1.—) | H16_B1264 |
| Q0K1D7_CUPNH | Acyl-CoA synthetase (AMP-forming)/AMP-acid ligase II (EC 6.2.1.—) | H16_B1398 |

TABLE 3

Putative candidates for reaction A2

| Uniprot entry names | Protein names | Gene names |
|---|---|---|
| Q0KC00_CUPNH + Q0KBZ9_CUPNH | Succinyl-CoA:3-ketoacid-coenzyme A transferase (EC 2.8.3.5) | H16_A1331 + H16_A1332 |
| Q0K874_CUPNH | Acetate CoA-transferase YdiF (EC 2.8.3.8) | pct H16_A2718 |
| Q0K4S5_CUPNH + Q0K4S4_CUPNH | 3-Oxoadipate CoA-transferase subunit A (EC 2.8.3.6) | pcaI H16_B0198 + pcaJ H16_B0199 |
| Q0K3Y9_CUPNH | Predicted acyl-CoA transferase (EC 2.8.3.—) | H16_B0488 |
| Q0K3H2_CUPNH + Q0K3H1_CUPNH | Acyl CoA:acetate/3-ketoacid CoA transferase (EC 2.8.3.—) | H16_B0655 + H16_B0656 |

TABLE 4

Putative candidates for reaction A3a

| Uniprot entry names | Protein names | Gene names |
|---|---|---|
| PGKC_CUPNH | Phosphoglycerate kinase, chromosomal (EC 2.7.2.3) | cbbKC cbbK2 H16_B1385 |
| Q0K0Q9_CUPNH | Acetate kinase (EC 2.7.2.1) (Acetokinase) | ackA H16_B1630 |
| Q0KE56_CUPNH | Phosphoglycerate kinase (EC 2.7.2.3) | pgk H16_A0566 |
| Q0KDV3_CUPNH | Acetate kinase (EC 2.7.2.1) (Acetokinase) | ackA2 ackA H16_A0670 |
| PGKP_CUPNH | Phosphoglycerate kinase, plasmid (EC 2.7.2.3) | cbbKP PHG417 |

TABLE 5

Putative candidates for reaction B

| Uniprot entry names | Protein names | Gene names |
|---|---|---|
| BKTB_CUPNH | Beta-ketothiolase (EC 2.3.1.16/EC 2.3.1.9) | bktB H16_A1445 |
| Q0K4S3_CUPNH | Beta-ketoadipyl CoA thiolase (EC 2.3.1.16) | pcaF H16_B0200 |
| Q0KEF9_CUPNH | Acetyl-CoA C-acyltransferase (EC 2.3.1.16) | H16_A0462 |
| Q0KAX7_CUPNH | Acetyl-CoA acetyltransferase (EC 2.3.1.9) | H16_A1720 |
| Q0K0C1_CUPNH | Acetyl-CoA acetyltransferase (EC 2.3.1.9) | H16_A1713 H16_B1771 |

TABLE 5-continued

Putative candidates for reaction B

| Uniprot entry names | Protein names | Gene names |
|---|---|---|
| Q0K3F9_CUPNH | Acetyl-CoA acetyltransferase (EC 2.3.1.9) | H16_B0668 |
| Q0K494_CUPNH | Acetyl-CoA acetyltransferase (EC 2.3.1.9) | H16_B0381 |
| Q0KBG1_CUPNH | Acetyl-CoA acetyltransferase (EC 2.3.1.9) | H16_A1528 |
| Q0KC41_CUPNH | Acetyl-CoA C-acyltransferase (EC 2.3.1.16) | H16_A1290 |
| Q0KDD4_CUPNH | 3-Ketoacyl-CoA-thiolase P-44/SCP2 (EC 2.3.1.16) | paaJ H16_A0840 |
| Q0KDA2_CUPNH | Acetyl-CoA acetyltransferase (EC 2.3.1.9) | H16_A0872 |
| Q0K1G6_CUPNH | Acetyl-CoA acetyltransferase (EC 2.3.1.9) | H16_B1369 |
| Q0K3G5_CUPNH | Acetyl-CoA acetyltransferase (EC 2.3.1.9) | H16_B0662 |
| Q0KF99_CUPNH | Acetyl-CoA acetyltransferase (EC 2.3.1.9) | H16_A0170 |
| Q0KAI3_CUPNH | Acetyl-CoA acetyltransferase (EC 2.3.1.9) | H16_A1887 |
| Q0K368_CUPNH | Acetyl-CoA acetyltransferase (EC 2.3.1.9) | H16_B0759 |
| Q0K9S6_CUPNH | Acetyl-CoA acetyltransferase (EC 2.3.1.9) | H16_A2148 |
| Q0K495_CUPNH | Acetyl-CoA acetyltransferase (EC 2.3.1.9) | H16_B0380 |
| Q0K485_CUPNH | Acyl-CoA transferase (EC 2.3.1.16) | H16_B0390 |
| Q0K497_CUPNH | Acetyl-CoA C-acyltransferase (EC 2.3.1.16) | H16_B0378 |
| Q0KDA7_CUPNH | Acetyl-CoA acetyltransferase (EC 2.3.1.9) | H16_A0867 |
| Q0K469_CUPNH | Acetyl-CoA acetyltransferase (EC 2.3.1.9) | H16_B0406 |
| Q0KDA6_CUPNH | Acetyl-CoA acetyltransferase (EC 2.3.1.9) | H16_A0868 |
| Q0KC34_CUPNH | Acetyl-CoA acetyltransferase (EC 2.3.1.9) | H16_A1297 |

In order to identify the enzymes of Tables 2 to 5 that are involved in the assimilation of levulinic acid, a quantitative proteomics approach was carried out, which allowed the discrimination of the enzymes undergoing a variation in their expression level when *Ralstonia eutropha* is cultured in presence of levulinic acid, from the enzymes that are not affected by the presence of levulinic acid. The enzymes that were overexpressed (i.e. upregulated) were assumed to be involved in the conversion of levulinic acid.

Example 2: Identification of *Ralstonia eutropha* Enzymes and Corresponding Genes Involved in the Assimilation of Levulinic Acid by a Quantitative Proteomics Approach

*Ralstonia eutropha* DSM428 strain was cultivated in shake flasks with LB rich medium with 0 or 5 g/L levulinic acid. Cells were collected by centrifugation and resuspended in potassium phosphate buffer 100 mM pH 7.6. Proteins were extracted by sonication and crude extracts were clarified by centrifugation. The supernatant fractions were then digested with trypsin and analyzed by nanoLC-MS/MS on a Synapt G2 QTOF mass spectrometer. Protein abundancies were calculated as % of total proteins using Waters Identity™ bioinformatics pipeline.

TABLE 6

Quantitative proteomics of *Ralstonia eutropha* DSM428 cultivated with or without levulinic acid (in bold characters: proteins up-regulated in response to levulinic acid, eg for which the quantity is at least multiplied by 2).

| | | | % of total proteins | |
|---|---|---|---|---|
| Uniprot entry names | Protein names | Gene names | Without LA | With LA |
| ACOA_CUPNH | Acetoin:2,6-dichlorophenolindophenol oxidoreductase subunit alpha (Acetoin:DCPIP oxidoreductase-alpha) (Ao:DCPIP OR) (EC 1.1.1.—) | acoA H16_B0144 | 0.23 | <0.06 |
| ACOB_CUPNH | Acetoin:2,6-dichlorophenolindophenol oxidoreductase subunit beta (Acetoin:DCPIP oxidoreductase-beta) (Ao:DCPIP OR) (EC 1.1.1.—) (TPP-dependent acetoin dehydrogenase E1 subunit beta) | acoB H16_B0145 | 0.42 | <0.06 |

TABLE 6-continued

Quantitative proteomics of *Ralstonia eutropha* DSM428 cultivated with or without levulinic acid (in bold characters: proteins up-regulated in response to levulinic acid, eg for which the quantity is at least multiplied by 2).

| Uniprot entry names | Protein names | Gene names | % of total proteins | |
|---|---|---|---|---|
| | | | Without LA | With LA |
| ACOC_CUPNH | Dihydrolipoyllysine-residue acetyltransferase component of acetoin cleaving system (EC 2.3.1.12) (Acetoin dehydrogenase E2 component) (Dihydrolipoamide acetyltransferase component of acetoin cleaving system) (Fast-migrating protein) (FMP) | acoC H16_B0146 | 0.29 | <0.06 |
| ACP_CUPNH | Acyl carrier protein (ACP) | acpP H16_A2566 | 0.33 | 0.42 |
| ACSA_CUPNH | Acetyl-coenzyme A synthetase (AcCoA synthetase) (Acs) (EC 6.2.1.1) (Acetate-CoA ligase) (Acyl-activating enzyme) | acsA acoE H16_A2525 | 0.52 | 0.33 |
| ATPB_CUPNH | ATP synthase subunit beta (EC 3.6.3.14) (ATP synthase F1 sector subunit beta) (F-ATPase subunit beta) | atpD H16_A3637 | 0.42 | 0.46 |
| BDHA_CUPNH | D-beta-hydroxybutyrate dehydrogenase (BDH) (EC 1.1.1.30) (3-hydroxybutyrate dehydrogenase) (3-HBDH) | hbdH1 H16_A1334 | 0.26 | 0.21 |
| BKTB_CUPNH | Beta-ketothiolase BktB (EC 2.3.1.16) (EC 2.3.1.9) (Acetyl-CoA acetyltransferase) (Acetyl-CoA acyltransferase) | bktB H16_A1445 | 0.40 | 2.00 |
| CH10_CUPNH | 10 kDa chaperonin (GroES protein) (Protein Cpn10) | groS groES H16_A0705 | 0.86 | 0.78 |
| CH60_CUPNH | 60 kDa chaperonin (GroEL protein) (Protein Cpn60) | groL groEL H16_A0706 | 4.38 | 4.22 |
| CLPP_CUPNH | ATP-dependent Clp protease proteolytic subunit (EC 3.4.21.92) (Endopeptidase Clp) | clpP H16_A1483 | 0.20 | 0.20 |
| DAPD_CUPNH | 2,3,4,5-tetrahydropyridine-2,6-dicarboxylate N-succinyltransferase (EC 2.3.1.117) (Tetrahydrodipicolinate N-succinyltransferase) (THDP succinyltransferase) (THP succinyltransferase) (Tetrahydropicolinate succinylase) | dapD H16_A2066 | 0.25 | 0.21 |
| DLDH_CUPNH | Dihydrolipoyl dehydrogenase (EC 1.8.1.4) (Dihydrolipoamide dehydrogenase) (E3 component of 2-oxoglutarate dehydrogenase complex) | odhL H16_A2323 | 0.72 | 0.79 |
| DNAK_CUPNH | Chaperone protein DnaK (HSP70) (Heat shock 70 kDa protein) (Heat shock protein 70) | dnaK H16_A3089 | 1.18 | 0.90 |
| EFP_CUPNH | Elongation factor P (EF-P) | efp H16_A2549 | 0.29 | 0.30 |
| EFTS_CUPNH | Elongation factor Ts (EF-Ts) | tsf H16_A2054 | 0.65 | 0.68 |
| EFTU_CUPNH | Elongation factor Tu (EF-Tu) | tuf1 tufA H16_A3491; tuf2 tufB H16_A3505 | 7.24 | 6.51 |
| ENO_CUPNH | Enolase (EC 4.2.1.11) (2-phospho-D-glycerate hydrolyase) (2-phosphoglycerate dehydratase) | eno H16_A1188 | 0.80 | 0.78 |
| GCST_CUPNH | Aminomethyltransferase (EC 2.1.2.10) (Glycine cleavage system T protein) | gcvT H16_A3619 | 0.29 | 0.30 |
| GLYA_CUPNH | Serine hydroxymethyltransferase (SHMT) (Serine methylase) (EC 2.1.2.1) | glyA H16_A2834 | 1.01 | 0.91 |
| ILVC_CUPNH | Ketol-acid reductoisomerase (EC 1.1.1.86) (Acetohydroxy-acid isomeroreductase) (Alpha-keto-beta-hydroxylacyl reductoisomerase) | ilvC H16_A1037 | 1.06 | 0.95 |
| KAD_CUPNH | Adenylate kinase (AK) (EC 2.7.4.3) (ATP-AMP transphosphorylase) (ATP:AMP phosphotransferase) (Adenylate monophosphate kinase) | adk H16_A0603 | 0.16 | 0.15 |
| KDSA_CUPNH | 2-dehydro-3-deoxyphosphooctonate aldolase (EC 2.5.1.55) (3-deoxy-D-manno-octulosonic acid 8-phosphate synthase) (KDO-8-phosphate synthase) (KDO 8-P synthase) (KDOPS) (Phospho-2-dehydro-3-deoxyoctonate aldolase) | kdsA H16_A1186 | 0.14 | 0.11 |
| LPXA_CUPNH | Acyl-[acyl-carrier-protein]--UDP-N-acetylglucosamine O-acyltransferase (UDP-N-acetylglucosamine acyltransferase) (EC 2.3.1.129) | lpxA H16_A2043 | 0.20 | 0.22 |
| MDH_CUPNH | Malate dehydrogenase (EC 1.1.1.37) | mdh H16_A2634 | 1.50 | 1.51 |
| METE_CUPNH | 5-methyltetrahydropteroyltriglutamate--homocysteine methyltransferase (EC 2.1.1.14) (Cobalamin-independent methionine synthase) (Methionine synthase, vitamin-B12 independent isozyme) | metE H16_B1581 | 1.17 | 1.20 |

TABLE 6-continued

Quantitative proteomics of *Ralstonia eutropha* DSM428 cultivated with or without levulinic acid (in bold characters: proteins up-regulated in response to levulinic acid, eg for which the quantity is at least multiplied by 2).

| Uniprot entry names | Protein names | Gene names | % of total proteins Without LA | % of total proteins With LA |
|---|---|---|---|---|
| METK_CUPNH | S-adenosylmethionine synthase (AdoMet synthase) (EC 2.5.1.6) (MAT) (Methionine adenosyltransferase) | metK H16_A0230 | 0.41 | 0.39 |
| NDK_CUPNH | Nucleoside diphosphate kinase (NDK) (NDP kinase) (EC 2.7.4.6) (Nucleoside-2-P kinase) | ndk H16_A2368 | 0.40 | 0.34 |
| ODO1_CUPNH | 2-oxoglutarate dehydrogenase E1 component (EC 1.2.4.2) (Alpha-ketoglutarate dehydrogenase) | odhA H16_A2325 | 0.87 | 1.17 |
| ODO2_CUPNH | Dihydrolipoyllysine-residue succinyltransferase component of 2-oxoglutarate dehydrogenase complex (EC 2.3.1.61) (2-oxoglutarate dehydrogenase complex component E2) (OGDC-E2) (Dihydrolipoamide succinyltransferase component of 2-oxoglutarate dehydrogenase complex) | sucB odhB H16_A2324 | 0.46 | 0.49 |
| ODP1_CUPNH | Pyruvate dehydrogenase E1 component (PDH E1 component) (EC 1.2.4.1) | pdhA H16_A1374 | 0.37 | 0.57 |
| PHBB_CUPNH | Acetoacetyl-CoA reductase (EC 1.1.1.36) | phbB phaB H16_A1439 | 1.14 | 0.85 |
| PNP_CUPNH | Polyribonucleotide nucleotidyltransferase (EC 2.7.7.8) (Polynucleotide phosphorylase) (PNPase) | pnp H16_A1045 | 0.59 | 0.61 |
| PUR7_CUPNH | Phosphoribosylaminoimidazole-succinocarboxamide synthase (EC 6.3.2.6) (SAICAR synthetase) | purC H16_A0569 | 0.19 | 0.17 |
| PUR9_CUPNH | Bifunctional purine biosynthesis protein PurH [Includes: Phosphoribosylaminoimidazolecarboxamide formyltransferase (EC 2.1.2.3) (AICAR transformylase); IMP cyclohydrolase (EC 3.5.4.10) (ATIC) (IMP synthase) (Inosinicase)] | purH H16_A0501 | 0.23 | 0.30 |
| Q0JY61_CUPNH | Argininosuccinate synthase (EC 6.3.4.5) (Citrulline-aspartate ligase) | argG H16_B2531 | 0.37 | 0.34 |
| Q0JZ13_CUPNH | O-Acetylhomoserine sulfhydrylase (EC 2.5.1.49) | metY2 H16_B2229 | 0.24 | 0.48 |
| Q0JZI5_CUPNH | Succinate-semialdehyde dehydrogenase (NADP+) (EC 1.2.1.16) | gabD4 H16_B2057 | 0.30 | 0.48 |
| Q0JZW1_CUPNH | Isocitrate dehydrogenase [NADP] (EC 1.1.1.42) | icd2 H16_B1931 | 0.68 | 0.85 |
| Q0K0L9_CUPNH | Fumarylacetoacetase hydrolase (EC 3.7.1.2) | fahA H16_B1670 | 0.48 | 0.41 |
| Q0K1I7_CUPNH | Putative peptidase, C56 family (EC 3.4.—.—) | H16_B1347 | <0.06 | 0.45 |
| Q0K1T6_CUPNH | Bacterial DNA-binding protein, histone-like | H16_B1248 | 0.16 | 0.19 |
| Q0K1U4_CUPNH | Dehydrogenase with different specificities (EC 1.—.—.—) | H16_B1240 | <0.06 | 0.34 |
| Q0K1U9_CUPNH | DNA-binding protein HU family | hupB3 H16_B1235 | 0.13 | 0.13 |
| Q0K1Z2_CUPNH | Methylmalonate-semialdehyde dehydrogenase (EC 1.2.1.27) | mmsA3 H16_B1191 | 1.27 | 1.02 |
| Q0K1Z3_CUPNH | 3-hydroxyisobutyrate dehydrogenase (HIBADH) (EC 1.1.1.31) | H16_B1190 | 0.72 | 0.47 |
| Q0K1Z4_CUPNH | 3-Hydroxybutyryl-CoA dehydratase (EC 4.2.1.55) | crt H16_B1189 | 0.13 | 0.12 |
| Q0K2A0_CUPNH | 4-Hydroxyphenylpyruvate dioxygenase (EC 1.13.11.27) | hpd H16_B1083 | 0.30 | 0.35 |
| Q0K2A2_CUPNH | Tyrosine aminotransferase (EC 2.6.1.57) | tyrB2 H16_B1081 | 0.33 | 0.22 |
| Q0K3Q9_CUPNH | Aconitate hydratase 2 (EC 4.2.1.3) (EC 4.2.1.99) (2-methylisocitrate dehydratase) | acnB H16_B0568 | <0.06 | 0.35 |
| Q0K4P6_CUPNH | H-NS-like DNA-binding protein | H16_B0227 | 0.15 | 0.10 |
| Q0K5B6_CUPNH | Cold-shock protein, DNA-binding | H16_B0002 | 0.19 | 0.16 |
| Q0K5I0_CUPNH | DNA-binding protein HU family | hupB2 H16_A3684 | 0.48 | 0.69 |
| Q0K5K4_CUPNH | ABC-type transporter, periplasmic component | H16_A3660 | 1.00 | <0.06 |
| Q0K5N4_CUPNH | ABC-type transporter, periplasmic component: HAAT family | H16_A3630 | 0.96 | 0.72 |
| Q0K5P3_CUPNH | Glycine dehydrogenase (decarboxylating) (EC 1.4.4.2) (Glycine cleavage system P-protein) (Glycine decarboxylase) (Glycine dehydrogenase (aminomethyl-transferring)) | gcvP H16_A3621 | 0.50 | 0.60 |
| Q0K6I1_CUPNH | Elongation factor G (EF-G) | fusA H16_A3492 | 2.93 | 2.89 |
| Q0K6A8_CUPNH | Stringent starvation protein A (Glutathione S-transferase) | sspA H16_A3395 | 0.27 | 0.29 |
| Q0K6J9_CUPNH | ABC-type transporter, periplasmic component: PepT family | H16_A3298 | 0.26 | <0.06 |

TABLE 6-continued

Quantitative proteomics of *Ralstonia eutropha* DSM428 cultivated with or without levulinic acid (in bold characters: proteins up-regulated in response to levulinic acid, eg for which the quantity is at least multiplied by 2).

| Uniprot entry names | Protein names | Gene names | % of total proteins Without LA | % of total proteins With LA |
|---|---|---|---|---|
| Q0K6W8_CUPNH | Probable histone H1-like protein (Alanine/lysin-rich protein) | H16_A3178 | 0.69 | 0.64 |
| Q0K6X1_CUPNH | Probable thiol peroxidase (EC 1.11.1.—) | tpx H16_A3175 | 0.36 | 0.20 |
| Q0K6X4_CUPNH | Biotin carboxylase (EC 6.3.4.14) | accC2 H16_A3172 | 0.14 | 0.18 |
| Q0K6Z3_CUPNH | Malic enzyme (NAD-binding) (EC 1.1.1.38) | maeA H16_A3153 | 0.74 | 0.87 |
| Q0K700_CUPNH | Glyceraldehyde-3-phosphate dehydrogenase (EC 1.2.1.—) | gapA H16_A3146 | 0.52 | 0.77 |
| Q0K729_CUPNH | Response regulator | H16_A3117 | 0.23 | 0.17 |
| Q0K737_CUPNH | Catalase (EC 1.11.1.6) | katE1 H16_A3109 | 0.65 | 0.30 |
| Q0K738_CUPNH | Metalloregulation DNA-binding stress protein | H16_A3108 | 0.25 | 0.28 |
| Q0K790_CUPNH | Isocitrate dehydrogenase [NADP] (EC 1.1.1.42) | icd1 H16_A3056 | 0.55 | 0.42 |
| Q0K7C1_CUPNH | Acetylornithine aminotransferase (ACOAT) (EC 2.6.1.11) | argD H16_A3025 | 0.31 | 0.30 |
| Q0K7C4_CUPNH | ABC-type transporter, periplasmic component | H16_A3022 | 0.19 | <0.06 |
| Q0K7C9_CUPNH | Urocanate hydratase (Urocanase) (EC 4.2.1.49) (Imidazolonepropionate hydrolase) | hutU1 hutU H16_A3017 | 0.22 | <0.06 |
| Q0K7D7_CUPNH | L-Aspartate decarboxylase (EC 4.1.1.12) | asdA H16_A3009 | 0.53 | 0.13 |
| Q0K7G8_CUPNH | Predicted periplasmic or secreted protein | H16_A2977 | 0.22 | 0.28 |
| Q0K7X5_CUPNH | Glutaryl-CoA dehydrogenase (EC 1.3.99.7) | gcdH H16_A2818 | 0.22 | 0.12 |
| Q0K840_CUPNH | UTP--glucose-1-phosphate uridylyltransferase (EC 2.7.7.9) (UDP-glucose pyrophosphorylase) | galU H16_A2752 | 0.32 | 0.26 |
| Q0K8F1_CUPNH | Aconitate hydratase (Aconitase) (EC 4.2.1.3) | acnA H16_A2638 | 1.24 | 1.17 |
| Q0K8F2_CUPNH | Hypothetical membrane associated protein | H16_A2637 | <0.06 | 0.13 |
| Q0K8G2_CUPNH | Citrate synthase (EC 2.3.3.16) | cisY H16_A2627 | 1.73 | 1.74 |
| Q0K8G3_CUPNH | ABC-type transporter, periplasmic component: HAAT family | livK1 H16_A2626 | 1.52 | 1.28 |
| Q0K8H1_CUPNH | Aspartate-semialdehyde dehydrogenase (ASA dehydrogenase) (ASADH) (EC 1.2.1.11) (Aspartate-beta-semialdehyde dehydrogenase) | asd H16_A2618 | 0.49 | 0.38 |
| Q0K8M0_CUPNH | Malonyl CoA-acyl carrier protein transacylase (EC 2.3.1.39) | fabD H16_A2568 | 0.33 | 0.29 |
| Q0K8M3_CUPNH | 3-oxoacyl-[acyl-carrier-protein] synthase 2 (EC 2.3.1.179) | fabF H16_A2565 | 0.24 | 0.22 |
| Q0K8P8_CUPNH | Uncharacterized protein, possibly involved in utilization of glycolate and propanediol | H16_A2536 | 0.22 | 0.17 |
| Q0K8X8_CUPNH | Carbamoyl-phosphate synthase small chain (EC 6.3.5.5) (Carbamoyl-phosphate synthetase glutamine chain) | carA H16_A2454 | 0.23 | <0.06 |
| Q0K8Y0_CUPNH | Carbamoyl-phosphate synthase (glutamine-hydrolyzing) (EC 6.3.5.5) | carB2 H16_A2452 | 0.42 | 0.56 |
| Q0K919_CUPNH | Enoyl-[acyl-carrier-protein] reductase [NADH] (EC 1.3.1.9) | fabI1 H16_A2410 | 0.22 | 0.22 |
| Q0K931_CUPNH | Transcription termination factor Rho (EC 3.6.4.—) (ATP-dependent helicase Rho) | rho H16_A2395 | <0.06 | 0.13 |
| Q0K932_CUPNH | Thioredoxin | H16_A2394 | 0.13 | 0.10 |
| Q0K972_CUPNH | Adenylosuccinate synthetase (AMPSase) (AdSS) (EC 6.3.4.4) (IMP--aspartate ligase) | purA H16_A2354 | 0.32 | 0.26 |
| Q0K990_CUPNH | Glutamine synthetase (EC 6.3.1.2) | glnA1 H16_A2335 | 1.11 | 1.15 |
| Q0K9F8_CUPNH | Homoserine dehydrogenase (EC 1.1.1.3) | thrA H16_A2266 | 0.27 | 0.26 |
| Q0K9K7_CUPNH | Malate synthase (EC 2.3.3.9) | aceB H16_A2217 | 0.70 | 0.58 |
| Q0K9L1_CUPNH | Non-heme haloperoxidase | H16_A2213 | 0.65 | 0.27 |
| Q0K9U7_CUPNH | ABC-type transporter, periplasmic component: MUTfamily | H16_A2125 | 0.23 | 0.25 |
| Q0K9X2_CUPNH | ABC-type transporter, periplasmic component: PepT family | dppA1b H16_A2100 | 0.56 | 0.39 |
| Q0KA33_CUPNH | Phosphoenolpyruvate synthase (PEP synthase) (EC 2.7.9.2) (Pyruvate, water dikinase) | ppsA H16_A2038 | 0.32 | 0.50 |

TABLE 6-continued

Quantitative proteomics of *Ralstonia eutropha* DSM428 cultivated with or without levulinic acid (in bold characters: proteins up-regulated in response to levulinic acid, eg for which the quantity is at least multiplied by 2).

| Uniprot entry names | Protein names | Gene names | % of total proteins Without LA | % of total proteins With LA |
|---|---|---|---|---|
| Q0KA41_CUPNH | Inosine-5'-monophosphate dehydrogenase (IMP dehydrogenase) (IMPD) (IMPDH) (EC 1.1.1.205) | guaB H16_A2030 | 0.43 | 0.59 |
| Q0KA97_CUPNH | Acetyl/propionyl-CoA carboxylase, carboxyltransferase subunit (EC 6.4.1.—) | H16_A1973 | 0.56 | 0.41 |
| Q0KA99_CUPNH | Acyl-CoA synthetase (AMP-forming)/AMP-acid ligase II (EC 6.2.1.—) | H16_A1971 | <0.06 | 0.15 |
| Q0KAF1_CUPNH | Putative Lactaldehyde dehydrogenase (EC 1.2.1.22) | H16_A1919 | 0.21 | <0.06 |
| Q0KAG0_CUPNH | Glutaminase-asparaginase (Amidohydrolase) (EC 3.5.1.38) | ansA H16_A1910 | 1.56 | 0.62 |
| Q0KAG3_CUPNH | Aconitate hydratase (Aconitase) (EC 4.2.1.3) | acnM H16_A1907 | <0.06 | 0.64 |
| Q0KAG4_CUPNH | 2-Methylcitrate synthase 1 (EC 2.3.3.5) | prpC1 H16_A1906 | 0.49 | 1.82 |
| Q0KBG1_CUPNH | Acetyl-CoA acetyltransferase (EC 2.3.1.9) | H16_A1528 | <0.06 | 0.30 |
| Q0KBG3_CUPNH | Enoyl-CoA hydratase/Delta(3)-cis-delta(2)-trans-enoyl-CoA isomerase | H16_A1526 | <0.06 | 0.72 |
| Q0KBM6_CUPNH | Peroxiredoxin (EC 1.11.1.—) | H16_A1460 | 1.73 | 1.51 |
| Q0KBM7_CUPNH | Alkyl hydroperoxide reductase AhpD (EC 1.11.1.15) (Alkylhydroperoxidase AhpD) | ahpD H16_A1459 h16_A1459 | 0.06 | 0.08 |
| Q0KBT6_CUPNH | ABC-type transporter, periplasmic component | H16_A1399 | 0.50 | 0.33 |
| Q0KBV4_CUPNH | Phasin (PHA-granule associated protein) | phaP1 H16_A1381 | 0.14 | 0.09 |
| Q0KBX0_CUPNH | Uncharacterized protein | H16_A1365 | 0.07 | <0.06 |
| Q0KBY8_CUPNH | Phenylalanine--tRNA ligase beta subunit (EC 6.1.1.20) (Phenylalanyl-tRNA synthetase beta subunit) | pheT H16_A1344 | 0.24 | 0.39 |
| Q0KBZ9_CUPNH | Succinyl-CoA:3-ketoacid-coenzyme A transferase subunit B (EC 2.8.3.5) | H16_A1332 | 0.26 | 0.76 |
| Q0KC00_CUPNH | Succinyl-CoA:3-ketoacid-coenzyme A transferase subunit A (EC 2.8.3.5) | H16_A1331 | 0.25 | 0.95 |
| Q0KCA5_CUPNH | Aspartokinase (EC 2.7.2.4) | lysC H16_A1225 | 0.30 | 0.31 |
| Q0KCB2_CUPNH | Peptidyl-prolyl cis-trans isomerase (EC 5.2.1.8) | ppiB H16_A1218 | 0.38 | 0.38 |
| Q0KCC6_CUPNH | 4-hydroxy-tetrahydrodipicolinate synthase (HTPA synthase) (EC 4.3.3.7) | dapA dapA1 H16_A1204 | 0.30 | 0.29 |
| Q0KCH9_CUPNH | Tyrosine aminotransferase (EC 2.6.1.57) | tyrB1 H16_A1151 | 0.27 | 0.27 |
| Q0KCJ3_CUPNH | Protein GrpE (HSP-70 cofactor) | grpE H16_A1137 | 0.14 | 0.12 |
| Q0KCN9_CUPNH | FadE2-like Acyl-CoA dehydrogenase (ACAD) | H16_A1091 | <0.06 | 3.16 |
| Q0KCR2_CUPNH | Acyl-CoA dehydrogenase (EC 1.3.99.3) | H16_A1068 | <0.06 | 0.12 |
| Q0KCX7_CUPNH | Malic enzyme (NADP) (EC 1.1.1.40) | maeB H16_A1002 | 1.10 | 0.90 |
| Q0KD01_CUPNH | Uncharacterized protein | H16_A0977 | 0.11 | 0.07 |
| Q0KDF9_CUPNH | Electron transfer flavoprotein alpha subunit | fixB H16_A0815 | 0.74 | 0.96 |
| Q0KDG0_CUPNH | Electron transfer flavoprotein beta-subunit | fixA H16_A0814 | 0.51 | 0.69 |
| Q0KDH6_CUPNH | 30S ribosomal protein S1 | rpsA H16_A0798 | 0.44 | 0.51 |
| Q0KDI4_CUPNH | Uncharacterized protein | H16_A0790 | 0.41 | 0.34 |
| Q0KDI6_CUPNH | Outer membrane protein or related peptidoglycan-associated (Lipo)protein | H16_A0788 | 0.13 | 0.12 |
| Q0KDL4_CUPNH | ABC-type transporter, periplasmic component: FeTfamily | H16_A0759 | 0.55 | 0.32 |
| Q0KDM0_CUPNH | Thioredoxin reductase (EC 1.8.1.9) | H16_A0753 | 0.28 | 0.26 |
| Q0KDM3_CUPNH | Nitrogen regulatory protein PII | H16_A0750 | 0.09 | 0.07 |
| Q0KDM7_CUPNH | Inorganic pyrophosphatase (EC 3.6.1.1) (Pyrophosphate phospho-hydrolase) | ppa H16_A0746 | 0.12 | 0.14 |
| Q0KE13_CUPNH | Superoxide dismutase (EC 1.15.1.1) | sodA H16_A0610 | 1.09 | 0.94 |
| Q0KE21_CUPNH | Short-chain alcohol dehydrogenase/3-hydroxyacyl-CoA dehydrogenase (EC 1.1.1.—) | H16_A0602 | 0.27 | 0.22 |
| Q0KE31_CUPNH | Probable extra-cytoplasmic solute receptor | H16_A0592 | 0.67 | 0.31 |
| Q0KE56_CUPNH | Phosphoglycerate kinase (EC 2.7.2.3) | pgk H16_A0566 | 0.26 | 0.24 |
| Q0KE74_CUPNH | Succinyl-CoA ligase [ADP-forming] subunit alpha (EC 6.2.1.5) | sucD H16_A0548 | 0.64 | 0.60 |

TABLE 6-continued

Quantitative proteomics of *Ralstonia eutropha* DSM428 cultivated with or without levulinic acid (in bold characters: proteins up-regulated in response to levulinic acid, eg for which the quantity is at least multiplied by 2).

| Uniprot entry names | Protein names | Gene names | % of total proteins | |
|---|---|---|---|---|
| | | | Without LA | With LA |
| Q0KEC5_CUPNH | Uncharacterized protein | H16_A0496 | 0.46 | 0.13 |
| Q0KEE9_CUPNH | ABC-type transporter, periplasmic component: PAAT family | H16_A0472 | 2.03 | 1.19 |
| Q0KEF0_CUPNH | Glutamate dehydrogenase (EC 1.4.1.3) | gdhA1 H16_A0471 | 0.83 | 0.69 |
| Q0KEL9_CUPNH | Single-stranded DNA-binding protein | H16_A0402 | 0.15 | 0.15 |
| Q0KEP8_CUPNH | Ribose-phosphate pyrophosphokinase (RPPK) (EC 2.7.6.1) (5-phospho-D-ribosyl alpha-1-diphosphate) (Phosphoribosyl diphosphate synthase) (Phosphoribosyl pyrophosphate synthase) | prsA prs H16_A0372 | 0.98 | 0.29 |
| Q0KF06_CUPNH | Glutamine--fructose-6-phosphate aminotransferase [isomerizing] (EC 2.6.1.16) (D-fructose-6-phosphate amidotransferase) (GFAT) (Glucosamine-6-phosphate synthase) (Hexosephosphate aminotransferase) (L-glutamine--D-fructose-6-phosphate amidotransferase) | glmS H16_A0263 | <0.06 | 0.39 |
| Q0KF17_CUPNH | Glutathione S-transferase (EC 2.5.1.18) | H16_A0252 | 0.14 | 0.13 |
| Q0KF49_CUPNH | N-acetyl-gamma-glutamyl-phosphate reductase (AGPR) (EC 1.2.1.38) (N-acetyl-glutamate semialdehyde dehydrogenase) | argC1 argC H16_A0220 | 0.17 | 0.15 |
| Q0KF71_CUPNH | Probable extra-cytoplasmic solute receptor | H16_A0198 | 0.64 | <0.06 |
| Q0KF75_CUPNH | RNA polymerase-binding transcription factor DksA | dksA1 dksA H16_A0194 | 0.23 | 0.18 |
| Q0KF85_CUPNH | Biotin carboxylase (EC 6.3.4.14) | accC1 H16_A0184 | 0.40 | 0.40 |
| Q0KF90_CUPNH | Enoyl-CoA hydratase/carnithine racemase (EC 4.2.1.17) | H16_A0179 | 0.22 | 0.25 |
| Q0KF99_CUPNH | Acetyl-CoA acetyltransferase (EC 2.3.1.9) | H16_A0170 | 1.06 | 0.96 |
| Q0KFA0_CUPNH | Carbonic anhydrase (EC 4.2.1.1) | can H16_A0169 | <0.06 | 0.16 |
| Q0KFA2_CUPNH | Isovaleryl-CoA dehydrogenase (EC 1.3.99.10) | ivd1 H16_A0167 | 0.43 | 0.39 |
| Q0KFA8_CUPNH | Thiol:disulfide interchange protein | H16_A0161 | 0.30 | 0.22 |
| Q0KFB1_CUPNH | Uncharacterized protein | H16_A0158 | 0.07 | <0.06 |
| Q0KFR7_CUPNH | DNA polymerase III subunit beta (EC 2.7.7.7) | dnaN H16_A0002 | 0.29 | 0.26 |
| RECA_CUPNH | Protein RecA (Recombinase A) | recA H16_A0544 | 0.17 | 0.13 |
| RL1_CUPNH | 50S ribosomal protein L1 | rplA H16_A3500 | 0.32 | 0.39 |
| RL11_CUPNH | 50S ribosomal protein L11 | rplK H16_A3501 | 0.15 | 0.14 |
| RL15_CUPNH | 50S ribosomal protein L15 | rplO H16_A3465 | 0.12 | 0.13 |
| RL16_CUPNH | 50S ribosomal protein L16 | rplP H16_A3477 | 0.08 | 0.10 |
| RL17_CUPNH | 50S ribosomal protein L17 | rplQ H16_A3457 | 0.37 | 0.41 |
| RL18_CUPNH | 50S ribosomal protein L18 | rplR H16_A3468 | 0.08 | 0.33 |
| RL2_CUPNH | 50S ribosomal protein L2 | rplB H16_A3481 | 0.22 | 0.31 |
| RL20_CUPNH | 50S ribosomal protein L20 | rplT H16_A1342 | 0.28 | 0.47 |
| RL21_CUPNH | 50S ribosomal protein L21 | rplU H16_A3252 | 0.13 | 0.19 |
| RL22_CUPNH | 50S ribosomal protein L22 | rplV H16_A3479 | 0.10 | 0.09 |
| RL23_CUPNH | 50S ribosomal protein L23 | rplW H16_A3482 | 0.13 | 0.19 |
| RL24_CUPNH | 50S ribosomal protein L24 | rplX H16_A3473 | 0.14 | 0.14 |
| RL25_CUPNH | 50S ribosomal protein L25 (General stress protein CTC) | rplY ctc H16_A0371 | 0.96 | 1.01 |
| RL29_CUPNH | 50S ribosomal protein L29 | rpmC H16_A3476 | 0.07 | 0.06 |
| RL3_CUPNH | 50S ribosomal protein L3 | rplC H16_A3484 | 0.19 | 0.23 |

TABLE 6-continued

Quantitative proteomics of *Ralstonia eutropha* DSM428 cultivated with or without levulinic acid (in bold characters: proteins up-regulated in response to levulinic acid, eg for which the quantity is at least multiplied by 2).

| Uniprot entry names | Protein names | Gene names | % of total proteins Without LA | % of total proteins With LA |
|---|---|---|---|---|
| RL31B_CUPNH | 50S ribosomal protein L31 type B | rpmE2 H16_A2397 | 0.16 | 0.13 |
| RL4_CUPNH | 50S ribosomal protein L4 | rplD H16_A3483 | 0.13 | 0.22 |
| RL7_CUPNH | 50S ribosomal protein L7/L12 | rplL H16_A3498 | 0.93 | 0.89 |
| RL9_CUPNH | 50S ribosomal protein L9 | rplI H16_A2276 | 0.16 | 0.18 |
| RPIA_CUPNH | Ribose-5-phosphate isomerase A (EC 5.3.1.6) (Phosphoriboisomerase A) (PRI) | rpiA H16_A2345 | 0.11 | 0.13 |
| RPOA_CUPNH | DNA-directed RNA polymerase subunit alpha (RNAP subunit alpha) (EC 2.7.7.6) (RNA polymerase subunit alpha) (Transcriptase subunit alpha) | rpoA H16_A3458 | 1.12 | 1.07 |
| RPOB_CUPNH | DNA-directed RNA polymerase subunit beta (RNAP subunit beta) (EC 2.7.7.6) (RNA polymerase subunit beta) (Transcriptase subunit beta) | rpoB H16_A3497 | 2.55 | 2.85 |
| RPOC_CUPNH | DNA-directed RNA polymerase subunit beta' (RNAP subunit beta') (EC 2.7.7.6) (RNA polymerase subunit beta') (Transcriptase subunit beta') | rpoC H16_A3496 | 1.75 | 1.69 |
| RRF_CUPNH | Ribosome-recycling factor (RRF) (Ribosome-releasing factor) | frr H16_A2052 | 0.27 | 0.20 |
| RS10_CUPNH | 30S ribosomal protein S10 | rpsJ H16_A3490 | 0.11 | <0.06 |
| RS13_CUPNH | 30S ribosomal protein S13 | rpsM H16_A3461 | 0.13 | <0.06 |
| RS15_CUPNH | 30S ribosomal protein S15 | rpsO H16_A1044 | 0.17 | 0.13 |
| RS16_CUPNH | 30S ribosomal protein S16 | rpsP H16_A0894 | 0.16 | 0.11 |
| RS4_CUPNH | 30S ribosomal protein S4 | rpsD H16_A3459 | <0.06 | 0.14 |
| RS7_CUPNH | 30S ribosomal protein S7 | rpsG H16_A3493 | 0.32 | 0.38 |
| RS8_CUPNH | 30S ribosomal protein S8 | rpsH H16_A3470 | 0.18 | 0.20 |
| RS9_CUPNH | 30S ribosomal protein S9 | rpsI H16_A0483 | 0.13 | 0.17 |
| SAHH_CUPNH | Adenosylhomocysteinase (EC 3.3.1.1) (S-adenosyl-L-homocysteine hydrolase) (AdoHcyase) | ahcY H16_A0244 | 0.51 | 0.41 |
| SUCC_CUPNH | Succinyl-CoA ligase [ADP-forming] subunit beta (EC 6.2.1.5) (Succinyl-CoA synthetase subunit beta) (SCS-beta) | sucC H16_A0547 | 1.19 | 1.38 |
| SYDND_CUPNH | Aspartate--tRNA(Asp/Asn) ligase (EC 6.1.1.23) (Aspartyl-tRNA synthetase) (AspRS) (Non-discriminating aspartyl-tRNA synthetase) (ND-AspRS) | aspS H16_A0453 | 0.41 | 0.29 |
| SYT_CUPNH | Threonine--tRNA ligase (EC 6.1.1.3) (Threonyl-tRNA synthetase) (ThrRS) | thrS H16_A1339 | 0.55 | 0.28 |
| THIL_CUPNH | Acetyl-CoA acetyltransferase (EC 2.3.1.9) (Acetoacetyl-CoA thiolase) (Beta-ketothiolase PhbA) | phbA H16_A1438 | 1.77 | 1.46 |
| TIG_CUPNH | Trigger factor (TF) (EC 5.2.1.8) (PPIase) | tig H16_A1482 | 0.51 | 0.56 |
| TPIS_CUPNH | Triosephosphate isomerase (TIM) (EC 5.3.1.1) (Triose-phosphate isomerase) | tpiA H16_A1047 | 0.19 | 0.14 |

As shown in Table 6, several proteins of particular relevance were found to be up-regulated in response to levulinic acid:
- Q0KA99_CUPNH: an acyl-CoA synthetase (AMP-forming)/AMP-acid ligase II (EC 6.2.1.-), one of the putative candidates listed above for reaction A1;
- Q0KBZ9_CUPNH and Q0KC00_CUPNH: 2 subunits of a succinyl-CoA:3-ketoacid-coenzyme A transferase (EC 2.8.3.5), one of the putative candidates listed above for reaction A2;
- BKTB_CUPNH: a beta-ketothiolase (EC 2.3.1.16/EC 2.3.1.9), one of the putative candidates listed above for reaction B;
- Q0KBG1_CUPNH: an acetyl-CoA acetyltransferase (EC 2.3.1.9), one of the putative candidates listed above for reaction B;
- as well as proteins involved in the 2-methylcitric acid cycle: Q0KAG4_CUPNH, a 2-methylcitrate synthase (PrpC), and Q0K3Q9_CUPNH, a 2-methylisocitrate dehydratase (AcnB);
- and proteins involved in fatty acid metabolism: Q0KBG3_CUPNH, an enoyl-CoA hydratase, and Q0KCN9_CUPNH and Q0KCR2_CUPNH, two acyl-CoA dehydrogenases.

To the contrary, the putative candidates listed in Table 2-5 were not overexpressed:

ACSA_CUPNH (putative candidate for reaction A1);
SUCC_CUPNH/Q0KE74_CUPNH (putative candidate for reaction A1); and
Q0KF99_CUPNH (putative candidate for reaction B).

Example 3: In Vitro Validation of the Candidates Identified by Proteomics

To validate the activity of the candidates identified in Example 2 above with regard to reactions A1, A2 and B, their corresponding genes were cloned into the expression plasmid pPAL7 (Biorad®). In the case of Q0KBZ9_CUPNH and Q0KC00_CUPNH, the corresponding genes were cloned in operon into the pPAL7. The resulting plasmids were transformed into E. coli BL21(DE3) strain.

TABLE 7

Proteomics candidates tested

| Protein names | SEQ ID NO: | Gene names | SEQ ID NO: |
| --- | --- | --- | --- |
| Q0KA99_CUPNH | 1 | H16_A1971 | 2 |
| Q0KBZ9_CUPNH | 3 | H16_A1332 | 4 |
| Q0KC00_CUPNH | 5 | H16_A1331 | 6 |
| Q0KBG1_CUPNH | 7 | H16_A1528 | 8 |

The resulting strains were cultivated as described in patent application WO 2010/076324, incorporated herein by reference. Cells were collected by centrifugation and resuspended in potassium phosphate buffer 100 mM pH 7.6. Proteins were extracted by sonication and crude extracts were clarified by centrifugation. Recombinant protein purification was carried out using Biorad® PROfinity EXact cartridges according to the manufacturer's instructions.

Validation of the enzymatic activities of the different candidates was achieved using LC-MS/MS for identifying levulinyl-CoA after incubation of the purified proteins with their respective substrates:
- 50 mM levulinic acid, 0.4 mM ATP and 0.4 mM coenzyme A for Q0KA99_CUPNH (reaction A1);
- 50 mM levulinic acid and 0.3 mM succinyl-coA/acetoacetyl-coA/acetyl-coA for Q0KBZ9_CUPNH/Q0KC00_CUPNH (reaction A2 with either succinyl-coA, acetoacetyl-coA or acetyl-coA as coA donor);
- 0.3 mM acetyl-coA and 0.3 mM propionyl-coA for Q0KBG1_CUPNH (reaction B in the condensation direction, Modis & Wierenga, 1999).

Figure 3:
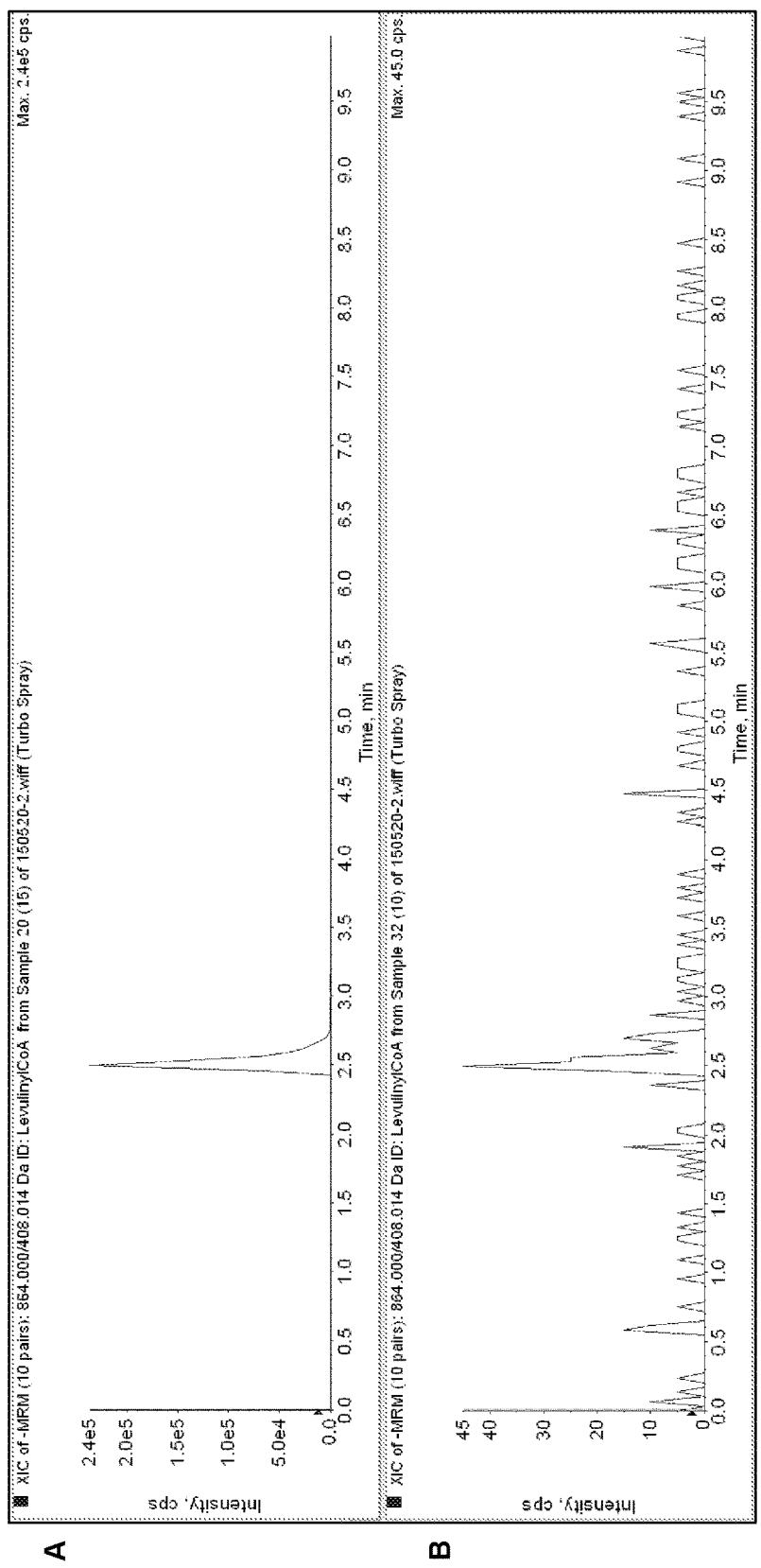
FIG. 3 represents extracted ion chromatograms of transition 864 to 408 from a sample of Q0KBZ9_CUPNH/ Q0KC00_CUPNH reaction mixture (3A), and from a sample of a reaction mixture control (3B). The peaks of the chromatograms show the presence of levulinyl-CoA in the reaction mixture, which demonstrates the conversion of levulinic acid into levulinyl-CoA by the enzyme.

Levulinyl-CoA was detected by reverse phase UPLC coupled to negative ion MS/MS, by searching for the transition from mass 864 (mass of levulinyl-CoA minus 1) to 408 (ion corresponding to the adenine part according to the protocol described by Zirrolli et al. 1994) as shown on FIG. 3.

Levulinyl-CoA was detected in all samples, while no significant signal was detected when either the purified proteins or the substrates were omitted from the reaction mixture.

Example 4: Overexpression of Ralstonia eutropha Genes for the Assimilation of Levulinic Acid in Other Microorganisms Since proteomics showed that Q0KBZ9_CUPNH/Q0KC00_CUPNH and BKTB_CUPNH (SEQ ID NO: 3, 5 and 9) were more abundant than their respective counterparts identified for reactions A and B, those were chosen to be overexpressed in different microbial strains not able to assimilate levulinic acid. Genes H16_A1331 and H16_A1332 were renamed respectively scoA and scoB.

Construction of Strain 1

The scoA (SEQ ID NO: 4) and scoB (SEQ ID NO: 6) operon together with the bktB (SEQ ID NO: 10) gene were cloned in operon into the pBBR1MCS3 plasmid (Kovach et al. 1995). The resulting plasmid named pBBR1MCS3-scoA-Bre-bktBre was then transformed into E. coli MG1655 K12 strain, resulting in strain 1.

Construction of Strain 2

The codon optimized genes scoA (SEQ ID NO: 11), scoB (SEQ ID NO: 12) and bktB (SEQ ID NO: 13) were cloned into the p426-hphMX4 plasmid. The p426-hphMX4 plasmid is a pRS426 plasmid where the URA3 promoter and gene were replaced by the hphMX4 resistance gene (hygromycin resistance) under the tef1 promoter (SEQ ID NO: 14). The scoA, scoB and bktB optimized genes were respectively cloned under the hxt7, tef2 and pgk1 promoters (SEQ ID NO: 15 to 17). Transcriptional terminators cyc1, tef1 and pdc1 (SEQ ID NO: 18 to 20) were respectively added after the scoA, scoB and bktB optimized genes. The resulting plasmid named p426-hph MX4-Phxt7-scoAreO1 sc-TTcyc1-Ptef2-scoBreO1 sc-TTtef1-Ppg k1-bktBreO1 sc-TTpdc1 was then transformed into Saccharomyces cerevisiae CEN.PK2-1C strain, resulting in strain 2.

Construction of Strain 3

The scoA and scoB operon together with the bktB gene were cloned in operon into the pEC-XT99A plasmid. The resulting plasmid named pEC-XT99A-scoABre-bktBre was then transformed into Corynebacterium glutamicum ATCC 13032 strain, resulting in strain 3.

Construction of Strain 4

The scoA and scoB operon together with the bktB gene were cloned in operon into the pSOS95 plasmid digested by the BamHI and SfoI restriction enzymes. The resulting plasmid named pSOS95-scoABre-bktBre was then transformed into Clostridium acetobutylicum ATCC 824 strain, resulting in strain 4.

When cultivated in a medium containing levulinic acid at the IC50 determined for their parent strains, strains 1 to 4 exhibited at least 20% better growth.

Example 5: Overexpression of Ralstonia eutropha Genes for the Assimilation of Levulinic Acid in Industrial Production Strains The plasmids bearing scoA, scoB and bktB genes were then transformed into industrial production strains.

Construction of Strain 5 Producing 1,2-propanediol

The adh gene from Clostridium beijerinckii (Hanai et al. 2007) was cloned into the pME101VB01 plasmid described in patent application WO 2008/116853, incorporated herein by reference, resulting in plasmid named pME101VB01-sadH. To inactivate the fumarate reductase flavoprotein complex encoded by the frdABCD operon and the glucose phophotransferase Enzyme IIBC(Glc) encoded by the ptsG gene, the homologous recombination strategy was used (according to Protocols 1 and 3). Oligonucleotides for DfrdABCD (SEQ ID NO: 21 and 22) and DptsG (SEQ ID NO: 23 and 24), were used to PCR amplify the resistance cassettes. The strains retained were designated MG1655 DfrdABCD::Cm and MG1655 DptsG::Km. Finally, the DfrdABCD::Cm and the DptsG::Km deletions were transferred by P1 phage transduction (according to Protocol 2) into the evolved 1,2-propanediol production strain MG1655 lpd*DtpiA DpflAB DadhE DldhA DgloA DaldA DaldB Dedd DarcA Dndh described in patent application WO 2008/116852, incorporated herein by reference, The resistance genes were removed according to Protocol 3. Plasmids pME101VB01-sadH and pBBR1MCS3-scoABre-bktBre were transformed into the strain, resulting in strain 5.

Construction of Strain 7 Producing Glycolic Acid

The plasmid pBBR1MCS3-scoABre-bktBre was transformed into the glycolic acid production strain described in the Example 2 of patent application WO 2011/157728, incorporated herein by reference, resulting in strain 7.

Construction of Strain 8 Producing 1,4-Butanediol

The plasmid pBBR1MCS3-scoABre-bktBre was transformed into the 1,4-butanediol production strain described in patent application WO 2010/141920, incorporated herein by reference, resulting in strain 8.

Construction of Strain 9 Producing Ethanol

The plasmid p426-hphMX4-Phxt7-scoAreO1sc-TTcyc1-Ptef2-scoBreO1sc-TTtef1-Ppgk1-bktBreO1sc-TTpdc1 was transformed into the ethanol production strain described in patent application US 2015/104822, incorporated herein by reference, resulting in strain 9.

Construction of Strain 10 Producing Succinic Acid

The plasmid p426-hphMX4-Phxt7-scoAreO1sc-TTcyc1-Ptef2-scoBreO1sc-TTtef1-Ppgk1-bktBreO1sc-TTpdc1 was transformed into the succinic acid production strain described in patent application WO 2010/003728, incorporated herein by reference, resulting in strain 10.

Construction of Strain 11 Producing Lysine

The plasmid pEC-XT99A-scoABre-bktBre was transformed into the lysine production strain described in patent application U.S. Pat. No. 9,109,242, incorporated herein by reference, resulting in strain 11.

Construction of Strain 13 Producing Butanol

The plasmid pSOS95-Pthl-scoABre-bktBre was transformed into the butanol producing strain described in patent application WO 2008/052973, incorporated herein by reference resulting in strain 13.

When cultivated in a medium containing levulinic acid at the IC50 determined for their parent strains, strains 5 to 13 exhibited at least 20% better growth and 20% better production.

REFERENCES

Altschul S, Gish W, Miller W, Myers E, Lipman D J (1990). J. Mol. Biol; 215 (3): 403-410.
Babbitt P C, Kenyon G L (1992). Biochemistry, 31: 5594-5604.
M. Bantscheff, M. Schirle, G. Sweetman, J. Rick, and B. Kuster. (2007). Analytical and Bioanalytical Chemistry, vol. 389(4): 1017-1031.
Bramer C O, Steinbuchel A (2001). Microbiology, 147: 2203-2214.
Brosius J, Erfle M, Storella J (1985). The Journal of Biological Chemistry, 260(6): 3539-3541
Burnette W N (1981). Analytical Biochemistry, 112(2): 195-203.
Carrier T & Keasling (1999). J. Biotechnol Prog.; 15 (1): 58-64.
Chambers et al. (1988). Gene; 68(1): 139-49.
Chang K H, Xiang H, Dunaway-Mariano D. (1997). Biochemistry. 36 (50):15650-9.
Christianson et al. (1992). Gene; 110:119-122.
Curran et al. (2013). Metabolic Engineering; 19: 88-97.
Datsenko K. A., Wanner B. L., 2000, Proceedings of the National Academy of Sciences of the USA, 97:6640-6645.
Davis J J & Olsen G J. (2011). Mol. Biol. Evol.; 28(1):211-221.
De Boer H A, Comstock L J, Vasser M (1983). Proc Natl Acad Sci USA, 80(1):21-5.
Deml L, Bojak A, Steck S, Graf M, Wild J, Schirmbeck R, Wolf H, Wagner R. (2011).
Dickson R C, Abelson J, Barnes W M, Reznikoff W S (1975). Science, 187(4171): 27-35
Eikmanns et al. (1991). Gene; 102:93-8.
Engvall E and Perlman P (1981), Immunochemistry, 8: 871-874.
Graf M, Bojak A, Deml L, Bieler K, Wolf H, Wagner R. (2000). J. Virol.; 74(22): 10/22-10826.
Güldener et al. (1996). Nucleic Acids Res.; 24(13):2519-24.
Hasunama T, Sung K M, Sanda T, Yoshimura K, Matsuda F, Kondo A, (2011) Appl Microbiol Biotechnol 90:997-1004.
Holt R A, Stephens G M, Morris J G (1984). Appl Environ Microbiol.; 48 (6), 1166-1170. J. Virol.; 75(22): 10991-11001.
Jaremko M and Yu J (2011). Journal of Biotechnology, 155: 293-298.
Jönsson L J, Alriksson, B, Nilvebrant N O, (2013). Biotechnology for Biofuels, 6:16
Karan D, David J R, Capy P. (2001). Gene. 265(1-2): 95-101.
Keilhauer C, Eggeling L, Sahm H (1993). Journal of bacteriology; 175 (17), 5595-5603.
Kirchner et al. (2003). Journal of biotechnology; 104: 287-299.
Kleinkauf H, Van Dohren H (1996). Eur J. Biochem, 236: 335-351.
Kovach M E, Elzer P H, Hill D S, Robertson G T, Farris M A, Roop R M, Peterson K M (1995) Gene, 166(1):175-176.
Larsson S, Nilvebrant N O, Jonsson L J, (2001); Appl Microbiol Biotechnol; 57:167-174.
Lee S Y, Bennett G N, Papoutsakis E T (1992). Biotechnology Letters, 14(5): 427-432.
Luzier W D (1992) Proc Natl Acad Sci USA.; 89(3):839-42.
Marahiel M A, Stachelhaus T, Mootz H D. (1997) Chem. Rev. 97, 2651-2673.
Marchler-Bauer A, Derbyshire M K, Gonzales N R, Farideh Chitsaz S L, Geer L Y, Geer R C, He J, Gwadz M, Hurwitz D I, Lanczycki C J, Lu F, Marchler G H, Song J S, Thanki N, Wang Z, Yamashita R A, Zhang D, Zheng C, and Bryant S H. (2015). Nucleic Acids Res. 43(Database issue): D222-D226.
Needleman S B and Wunsch C D, 1970, *Journal of Molecular Biology*, 48(3):443-453.
Nevoigt et al. (2006). Applied and environmental microbiology; 72: 5266-5273.
Niu W and Guo J, (2014). ACS Synth Biol., DOI: 10.1021/sb500240p.
Partow et al. (2010). Yeast; 27: 955-964.
Patek et al. 2013. Microbial biotechnology; 6: 103-117.
Pouwels et al. Eds. (1985). Cloning Vectors. Elsevier: New York.
Salis H., (2011), Methods Enzymol., 498:19-42.
Sambrook and Russell, (2001), Molecular Cloning: $3^{rd}$ edition, Cold Spring Harbor Laboratory Press, NY, Vol 1, 2, 3.
Sanchez and Cardona (2008) Bioresource technology, 99: 5270-5295

Segel I H, Enzyme kinetics (1993), John Wiley & Sons, pp. 44-54 and 100-112.

Sikorski and Hieter (1989). Genetics; 122:19-27.

Srirangan K, Akawi L, Liu X, Wesbrook A, Blondeel E J M, Aucoin M G, Moo-Young M, Chou C P (2013). Biotechnology for biofuels, 6:139.

Steinbuchel A and Gorenflo V (1997). Macromol. Symp. 123:61-66.

Steinbuchel A and Schegel H G (1991). Molecular Microbiology, 5(3):535-542.

Studier et al. (1990). Gene Expression Technology: Methods in Enzymology; 185, Academic Press, San Diego, Calif.

Suzuki et al. (2005). Appl Environ Microbiol.; 71(6): 3369-3372.

Tummala et al. (1999). Appl. Environ. Microbiol.; 65(9): 3793-3799.

Van Dijken J P, Bauer J, Brambilla L, Duboc P, Francois J M, Gancedo C, Giuseppin M L et al. (2000). Enzyme Microb Technol.; 26 (9-10), 706-714.

Watkins P A, (1997). Prog. Lipid. Res. 36(1):55-83

Watkins P A, Maiquel D, Jia Z, Pevsner J (2007). J. Lipid. Res. 48(12): 2736-2750.

Yu J and Si Y (2004). Biotechnology Progress, 20: 1015-1024.

Zirrolli, A, Wheelan P, Murphy R C (1994). J Am Soc Mass Spectrom.; 5 (5), 416-424.

---

Boronat et al., J. Bacteriol. 147:181-185 (Year: 1981).*

KEGG Database Entry for EC 2.8.3.5, 2 pages, last viewed on Feb. 24, 2020 (Year: 2020).*

KEGG Database Entry for EC 2.8.3.8, 2 pages, last viewed on Feb. 24, 2020 (Year: 2020).*

Agnew, "Metabolic Engineering of *Escherichia coli* for the Synthesis of Defined Polyhydroxyalkanoates from Unrelated Feedstocks", Ph.D. thesis, Madison, WI, USA, 2013, pp. i-xii, 1-132.

Altschul et al., "Basic local alignment search tool," Journal of Molecular Biology, vol. 215, No. 3, 1990, pp. 403-410.

```
<160> NUMBER OF SEQ ID NOS: 158

<210> SEQ ID NO 1
<211> LENGTH: 574
<212> TYPE: PRT
<213> ORGANISM: Ralstonia eutropha
<220> FEATURE:
<223> OTHER INFORMATION: Uniprot Name: Q0KAG9_CUPNH: Acyl-CoA synthetase
      (AMP forming)/AMP-acid ligase II

<400> SEQUENCE: 1

Met Thr Met Gln Ala Glu Ser Ser Pro Thr Ile Leu Pro Ile Gly Gly
1               5                   10                  15

Leu Ser His Val Arg Gly Asp Thr Thr Ile Pro Leu Ser Glu Gln Thr
            20                  25                  30

Val Pro Glu Leu Leu Ala Gln Thr Val Ala Arg Tyr Pro Glu Arg Lys
        35                  40                  45

Ala Val Ala Phe Arg Glu Gln Gly Val Arg Trp Asn Trp Arg Glu Phe
    50                  55                  60

Ser Asp Ala Val Asp Ala Leu Ala Ala Gly Leu His Thr Leu Gly Leu
65                  70                  75                  80

Ala Arg Gly Asp Arg Val Gly Ile Trp Ser Pro Asn Arg Val Glu Trp
                85                  90                  95

Leu Val Thr Gln Phe Ala Thr Ala Arg Leu Gly Leu Val Leu Val Asn
            100                 105                 110

Ile Asn Pro Ala Tyr Arg Leu Ser Glu Leu Glu Tyr Ala Leu Asn Lys
        115                 120                 125

Val Gly Val Lys Ala Ile Val Ala Ala Glu Ala Phe Lys Thr Ser Arg
    130                 135                 140

Tyr Leu Glu Met Leu Gln Val Leu Ala Pro Glu Leu Ala Thr Cys Ala
145                 150                 155                 160

Pro Gly Glu Leu Gln Ala Ala Arg Leu Pro Ala Leu Arg Cys Val Ile
                165                 170                 175

Arg Met Gly Asp Asp His Thr Pro Gly Met Leu Arg Tyr Ala Asp Val
            180                 185                 190

Ile Ala Arg Gly Thr Gly Val Ala Arg Ser Thr Leu Asp Ala Ile Thr
        195                 200                 205

Ala Gln Leu Asp Arg His Asp Pro Ile Asn Val Gln Phe Thr Ser Gly
    210                 215                 220

Thr Thr Gly Ala Pro Lys Gly Ala Thr Leu His Arg Asn Ile Val
225                 230                 235                 240

Asn Asn Ala Arg Phe Ile Ala Met Ala Met Arg Phe Ser Glu Gln Asp
                245                 250                 255
```

```
Lys Leu Cys Ile Pro Val Pro Phe Tyr His Cys Phe Gly Met Val Leu
            260                 265                 270

Ala Val Leu Ala Cys Val Ser Ser Gly Ala Ala Met Val Phe Pro Gly
            275                 280                 285

Gln Ala Phe Glu Pro Glu Ala Thr Met Gln Ala Val Ser Glu Glu Arg
            290                 295                 300

Cys Thr Ala Leu His Gly Val Pro Thr Met Phe Ile Ala Gln Leu Asp
305                 310                 315                 320

His Pro Asn Phe Ala Ser Tyr Asp Phe Ser Ser Leu Arg Thr Gly Ile
                325                 330                 335

Met Ala Gly Ser Pro Cys Pro Ile Glu Thr Met Lys Arg Val Val Ser
            340                 345                 350

Gln Met His Met Ser Glu Val Thr Ile Ala Tyr Gly Met Thr Glu Thr
            355                 360                 365

Ser Pro Val Ser Phe Gln Ser Ser Thr Thr Asp Pro Leu Asp Lys Arg
            370                 375                 380

Thr Thr Thr Val Gly Arg Ile Gln Pro His Leu Glu Val Arg Ile Val
385                 390                 395                 400

Asp Ala Thr Gly Ala Thr Val Pro Val Gly Glu Thr Gly Glu Leu Cys
                405                 410                 415

Thr Arg Gly Tyr Ser Val Met Leu Gly Tyr Trp Asp Asp Glu Ala Arg
                420                 425                 430

Thr Ala Glu Ala Ile Arg Asp Gly Trp Met His Thr Gly Asp Leu Ala
            435                 440                 445

Thr Ile Asp Ala Glu Gly Tyr Cys Asn Ile Val Gly Arg Val Lys Asp
450                 455                 460

Met Leu Ile Arg Gly Gly Glu Asn Ile Tyr Pro Arg Glu Ile Glu Glu
465                 470                 475                 480

Phe Leu Phe Arg His Pro Lys Val Gln Ala Val Gln Val Phe Gly Val
                485                 490                 495

Pro Asp Gln Lys Tyr Gly Glu Glu Val Cys Ala Trp Ile Val Leu Lys
            500                 505                 510

Pro Gly Ala Ser Ala Thr Glu Asp Glu Ile Arg Asp Phe Cys Arg Asp
            515                 520                 525

Gln Ile Ala His Tyr Lys Ile Pro Arg Tyr Ile Arg Phe Val Asp Glu
            530                 535                 540

Met Pro Met Thr Ile Thr Gly Lys Val Gln Lys Phe Val Met Arg Glu
545                 550                 555                 560

Arg Met Thr Gln Asp Leu Lys Leu Ser Glu Ser Arg Thr Ala
                565                 570

<210> SEQ ID NO 2
<211> LENGTH: 1724
<212> TYPE: DNA
<213> ORGANISM: Ralstonia eutropha
<220> FEATURE:
<221> NAME/KEY: misc_feature
<223> OTHER INFORMATION: Gene Name: H16_A1971.

<400> SEQUENCE: 2
atgacgatgc aggccgagtc ctctcccacc atcctgccga ttggcgggct ttcgcatgtg      60 agagggggaca ccaccattcc gctgtcggaa cagaccgtgc cggagttgct ggcgcaaacg    120
gtggctcgct atcccgagcg gaaagccgtt gcctttcgcg agcaagggt gcgctggaac      180 tggcgcgaat tctccgatgc cgtggacgca ctggcggcag cctgcacac gctgggctg       240
```

```
gccagaggcg accgagtcgg catctggtcc cccaaccggg tcgagtggct ggtcacccag    300
ttcgccacgg cgcggctggg gctggtgctg gtgaacatca atcccgccta ccgcctgtcc    360
gagctggagt acgcgctgaa caaggtgggc gtcaaggcga tcgtcgcggc ggaagccttc    420
aagacctcac ggtacctgga gatgctccag gtactcgccc ccgaactggc cacctgcgcg    480
ccgggcgaac tgcaggcggc gcggctgccg gcactcgcgct gcgtcatccg catgggcgac    540
gaccatacac ccgggatgct ccgctatgcc gacgtgattg cgcgcggcac aggcgtggct    600
cggtcgacgc tggatgccat cacggcacag ctggaccgcc atgacccgat caacgtgcag    660
ttcaccagcg gcactaccgg tgcgcccaag ggcgccacgc tgacccatcg caatatcgtc    720
aacaacgcac gcttcattgc catggcgatg cgtttctccg agcaggacaa gctctgcatc    780
ccggtgccct tctatcactg cttcggcatg gtcctggcgg tgctggcctg cgtgtcctcc    840
ggcgcggcaa tggtgttccc cggccaggcc ttcgagccgg aagccaccat gcaggcagtc    900
agcgaagaac gctgcacggc attgcatggc gtgccgacca tgttcattgc ccagctcgat    960
cacccgaact tcgcgagcta cgacttctct tctctgcgca ccggcatcat ggcggggtca   1020
ccctgcccga tcgaaaccat gaagcgcgtg gtgtcgcaga tgcatatgtc cgaggtgacg   1080
attgcctacg gcatgacgga aactagcccg gtctccttcc agagcagcac caccgatccg   1140
ctggacaagc gcacgaccac ggtgggccgc atccagccgc acctcgaagt caggatcgtg   1200
gatgcgacag gtgccacggt tcccgtagga gaaaccggcg agctgtgtac ccgcggctat   1260
tcggtgatgc tgggctactg ggatgacgag gcgcgtaccg ccgaagccat cgcgacggc    1320
tggatgcaca ccggcgacct cgccaccatc gacgcggaag gctactgcaa catcgtcggc   1380
cgcgtgaagg acatgctgat tcgtggcggc gagaacatct acccgcgcga gatcgaggag   1440
ttcctgttcc gccatccgaa ggtccagggg tccaggtgtt cggcgttccc gaccagaagt   1500
acggcgaaga ggtctgcgcg tggatcgtgc tcaagcccgg cgcgagcgcc acggaggacg   1560
agatccgcga tttctgccgc gaccagatcg cgcactacaa gatcccgcgc tacatccgct   1620
tgtcgacga dgatgcccatg accatcaccg gcaaggtaca gaaattcgtg atgcgcgagc   1680
gcatgacgca ggacctgaaa ctcagcgaat ccaggacggc ctga                     1724
```

<210> SEQ ID NO 3
<211> LENGTH: 212
<212> TYPE: PRT
<213> ORGANISM: Ralstonia eutropha
<220> FEATURE:
<221> NAME/KEY: MISC_FEATURE
<223> OTHER INFORMATION: Uniprot Name: Q0KBZ9_CUPNH:Succinyl coA:3-
      ketoacid transferase subunit B

<400> SEQUENCE: 3

Met Ala Trp Thr Arg Asp Glu Met Ala Ala Arg Ala Ala Thr Glu Leu
1               5                   10                  15

Gln Asp Gly Phe Tyr Val Asn Leu Gly Ile Gly Leu Pro Thr Leu Val
            20                  25                  30

Ala Asn Trp Val Pro Glu Gly Met Glu Val Trp Leu Gln Ser Glu Asn
        35                  40                  45

Gly Leu Leu Gly Ile Gly Pro Phe Pro Thr Glu Asp Glu Val Asp Ala
    50                  55                  60

Asp Met Ile Asn Ala Gly Lys Gln Thr Val Thr Thr Leu Pro Gly Ser
65                  70                  75                  80

Ser Ile Phe Ser Ser Ala Asp Ser Phe Ala Met Ile Arg Gly Gly His

```
                    85                  90                  95
Ile Asn Leu Ala Ile Leu Gly Ala Met Gln Val Ser Glu Lys Gly Asp
            100                 105                 110

Leu Ala Asn Trp Met Ile Pro Gly Lys Met Val Lys Gly Met Gly Gly
        115                 120                 125

Ala Met Asp Leu Val Ala Gly Val Gly Arg Val Val Val Leu Met Glu
    130                 135                 140

His Thr Ala Lys Lys Lys Asp Gly Thr Glu Asp Ile Lys Ile Leu Lys
145                 150                 155                 160

Asp Cys Asn Leu Pro Leu Thr Gly Val Gly Val Val Asn Arg Ile Ile
                165                 170                 175

Thr Asp Leu Gly Val Ile Asp Val Thr Asp Glu Gly Leu Lys Leu Val
            180                 185                 190

Glu Thr Ala Pro Gly Val Ser Arg Glu Glu Ile Gln Ala Lys Thr Gly
        195                 200                 205

Ala Pro Leu Leu
    210
```

<210> SEQ ID NO 4
<211> LENGTH: 639
<212> TYPE: DNA
<213> ORGANISM: Ralstonia eutropha
<220> FEATURE:
<221> NAME/KEY: misc_feature
<223> OTHER INFORMATION: Gene Name: H16_A1332 or scoB.

<400> SEQUENCE: 4

```
atggcatgga cacgtgacga atggccgcg cgcgccgcga ccgagctgca ggacggtttc     60
tacgtcaacc tgggcatcgg cctgccgacg ctggtggcca actgggtgcc cgaaggcatg    120
gaagtgtggc tgcagtccga gaacggactg ctgggcatcg gcccgttccc gaccgaggac    180
gaagtcgacg ccgacatgat caacgccggc aagcaaaccg tgacgacgct gccgggctcg    240
tcgatcttct cgtcggccga ctcgttcgcg atgatccgcg gcggccacat caacctggcg    300
atcctgggtg cgatgcaggt cagcgaaaag ggcgacctgg ccaactggat gatccccggc    360
aagatggtca agggcatggg cggcgcgatg gacctggtcg ccggcgtcgg ccgagtggtg    420
gtgctgatgg aacacaccgc caagaagaag gatggcaccg aggacatcaa gatcctgaag    480
gactgcaacc tgccgctgac cggcgtgggc gtggtcaacc gcatcattac cgacctgggc    540
gtgatcgacg tgaccgacga aggcctgaag ctggtggaaa cggctccggg tgtcagccgc    600
gaggaaatcc aggccaagac tggcgctccg ctgctgtaa                           639
```

<210> SEQ ID NO 5
<211> LENGTH: 233
<212> TYPE: PRT
<213> ORGANISM: Ralstonia eutropha
<220> FEATURE:
<221> NAME/KEY: MISC_FEATURE
<223> OTHER INFORMATION: Uniprot Name: Q0KC00_CUPNH:Succinyl coA:3-
      ketoacid transferase subunit A

<400> SEQUENCE: 5

```
Met Asn Lys Val Tyr Ala Ser Ala Ala Glu Ala Leu Ala Gly Val Val
1               5                   10                  15

Arg Asp Gly Gln Thr Ile Ala Val Gly Gly Phe Gly Leu Cys Gly Ile
            20                  25                  30

Pro Glu Ala Leu Ile Ala Ala Leu Arg Asp Ser Gly Ala Lys Gln Leu
        35                  40                  45
```

```
        Thr Cys Ile Ser Asn Asn Ala Gly Val Asp Gly Phe Gly Leu Gly Leu
         50                  55                  60
        Leu Leu Ala Thr Arg Gln Ile Ser Lys Met Ile Ser Ser Tyr Val Gly
         65                  70                  75                  80
        Glu Asn Lys Glu Phe Glu Arg Gln Tyr Leu Ala Gly Glu Leu Glu Leu
                         85                  90                  95
        Glu Phe Thr Pro Gln Gly Thr Leu Ala Glu Lys Leu Arg Ala Gly Gly
                    100                 105                 110
        Ser Gly Ile Pro Ala Phe Phe Thr Lys Thr Gly Val Gly Thr Ile Val
                115                 120                 125
        Ala Glu Gly Lys Glu Ile Arg Glu Phe Asp Gly Gln Gln Tyr Val Met
        130                 135                 140
        Glu Arg Ser Leu Thr Ala Asp Val Ala Leu Val Lys Ala Tyr Lys Ala
        145                 150                 155                 160
        Asp Lys Ala Gly Asn Leu Val Phe Arg Arg Thr Ala Arg Asn Phe Asn
                        165                 170                 175
        Pro Met Cys Ala Met Ala Gly Lys Val Thr Ile Ala Glu Val Glu His
                    180                 185                 190
        Ile Val Glu Thr Gly Glu Leu Asp Pro Asp Glu Ile His Leu Ala Gly
                195                 200                 205
        Ile Phe Val Lys Arg Leu Val Leu Asn Thr Thr Pro Glu Lys Arg Ile
        210                 215                 220
        Glu Gln Arg Thr Val Arg Ala Ala Ser
        225                 230

<210> SEQ ID NO 6
<211> LENGTH: 702
<212> TYPE: DNA
<213> ORGANISM: Ralstonia eutropha
<220> FEATURE:
<221> NAME/KEY: misc_feature
<223> OTHER INFORMATION: Gene Name: H16_A1331 or scoA.

<400> SEQUENCE: 6
atgaacaagg tctacgccag cgccgcagaa gcgcttgcag cgtcgtccg cgacggccag      60 acgatcgccg tgggcggttt cggcctgtgc ggcatccccg aggcgctgat tgccgcgctg     120
cgcgacagcg cgccaagca gctgacctgt atctccaaca cgccggcgt cgatggcttc      180 ggcctgggcc tgctgctggc cacgcgccag atcagcaaga tgatctcgtc ctacgtgggc    240
gagaacaagg agttcgagcg ccagtacctg gcgggcgaac ttgagctgga attcaccccg    300
caaggcacgc tggccgagaa gctgcgcgcc ggcggctcgg gcatcccggc cttcttcacc    360
aagaccggtg tcggcaccat cgtcgccgaa ggcaaggaaa tccgcgaatt cgacggccag    420
cagtacgtga tggagcgttc gctgaccgcc gacgtggcgc tggtcaaggc atacaaggct    480
gacaaggccg gcaacctggt gttccgccgc accgcgcgca acttcaaccc gatgtgcgcc    540
atggcgggca aggtcaccat cgccgaggtc gagcatatcg tcgagaccgg cgagctggac    600
ccggatgaaa tccacctggc cggcatcttc gtgaagcgcc tggtgctgaa caccaccccc    660
gagaaacgca tcgagcagcg caccgtgcgc gcggccagct aa                       702

<210> SEQ ID NO 7
<211> LENGTH: 392
<212> TYPE: PRT
<213> ORGANISM: Ralstonia eutropha
<220> FEATURE:
<221> NAME/KEY: MISC_FEATURE
```

<223> OTHER INFORMATION: Uniprot name: Q0KBG1_CUPNH: Acetyl-coA acetyltransferase.

<400> SEQUENCE: 7

```
Met Asn Glu Ala Val Ile Val Ser Thr Ala Arg Thr Pro Leu Ala Lys
1               5                   10                  15

Ser Trp Lys Gly Ala Phe Asn Met Thr His Gly Ala Thr Leu Gly Gly
            20                  25                  30

His Ala Val Gln His Ala Ile Ala Arg Ala Lys Ile Glu Ala Ala Glu
        35                  40                  45

Val Glu Asp Val Leu Met Gly Cys Ala Asn Pro Glu Gly Ala Thr Gly
    50                  55                  60

Ala Asn Ile Ala Arg Gln Ile Ala Leu Arg Ala Gly Cys Pro Val Thr
65                  70                  75                  80

Val Pro Gly Ala Thr Val Asn Arg Phe Cys Ser Ser Gly Leu Gln Thr
                85                  90                  95

Ile Ala Met Ala Ala Gln Arg Val Ile Ala Asp Glu Gly Asp Ile Phe
            100                 105                 110

Val Ala Gly Gly Val Glu Ser Ile Ser Cys Val Gln Gln Glu Met Asn
        115                 120                 125

Arg His Met Val Gln Glu Ser Trp Leu Leu Lys Asn Lys Pro Glu Ile
    130                 135                 140

Tyr Trp Asn Met Leu Gln Thr Ala Glu Asn Val Ala Lys Arg Tyr Asn
145                 150                 155                 160

Ile Ser Lys Glu Arg Gln Asp Glu Tyr Gly Val Arg Ser Gln Gln Arg
                165                 170                 175

Ala Ala Ala Gly Gln Glu Ala Gly Lys Phe Lys Asp Glu Ile Val Pro
            180                 185                 190

Met Thr Val Leu Ala Gly Val Ala Asp Lys Ser Thr Gly Gln Leu Val
        195                 200                 205

Thr Lys Glu Val Thr Val Ser Ala Asp Glu Gly Ile Arg Ala Asp Thr
    210                 215                 220

Thr Leu Glu Gly Val Ser Lys Ile Arg Ser Ala Val Pro Gly Gly Val
225                 230                 235                 240

Ile Thr Ala Gly Asn Ala Ser Gln Phe Ser Asp Gly Ala Ser Ala Ala
                245                 250                 255

Val Val Met Asn Ala Arg Val Ala Glu Ala Arg Gly Leu Gln Pro Leu
            260                 265                 270

Gly Val Phe Arg Gly Phe Ala Val Ala Gly Cys Glu Pro Asp Glu Met
        275                 280                 285

Gly Ile Gly Pro Val Phe Ala Val Pro Lys Leu Leu Lys Lys Ala Gly
    290                 295                 300

Leu Lys Val Asp Asp Ile Gly Leu Trp Glu Leu Asn Glu Ala Phe Ala
305                 310                 315                 320

Val Gln Val Leu Tyr Cys Ala Asp Thr Leu Gly Ile Pro Met Asp Arg
                325                 330                 335

Leu Asn Val Asn Gly Gly Ala Ile Ala Val Gly His Pro Tyr Gly Val
            340                 345                 350

Ser Gly Ala Arg Leu Val Gly His Ala Leu Ile Glu Gly Lys Arg Arg
        355                 360                 365

Gly Val Lys Tyr Val Val Thr Met Cys Ile Gly Gly Gln Gly
    370                 375                 380

Ala Ala Gly Leu Phe Glu Val Leu
385                 390
```

<210> SEQ ID NO 8
<211> LENGTH: 1179
<212> TYPE: DNA
<213> ORGANISM: Ralstonia eutropha
<220> FEATURE:
<221> NAME/KEY: misc_feature
<223> OTHER INFORMATION: Gene name : H16_A1528

<400> SEQUENCE: 8

```
atgaacgaag cagtcatcgt atccaccgcg cggaccccgc tggccaagag ctggaagggc      60
gccttcaaca tgacccacgg cgccacgctc ggcggtcatg ccgtccagca cgccattgcc     120
cgcgccaaga tcgaggccgc cgaagtggaa gacgtgctga tgggctgcgc caacccggaa     180
ggtgccaccg cgccaacat cgcacgccag atcgcactgc gcgccggctg cccggtgacc      240
gtgcccggcg ccaccgtcaa ccgcttctgc tcgtccggcc tgcagaccat cgccatggcc     300
gcgcagcgcg tgatcgctga tgagggcgac atcttcgtcg ccggcggcgt ggaaagcatc     360
tcgtgcgtgc agcaggagat gaaccgccat atggtccagg aaagctggct gctgaagaac     420
aagccggaaa tctactggaa catgctgcag accgccgaga cgtggccaa gcgctacaac      480
atctcgaagg agcgccagga cgagtacggc gtgcgcagcc agcaacgcgc cgccgccggg     540
caggaagccg gcaagttcaa ggacgagatc gtgccgatga cggtgctggc gggcgtggcc     600
gacaagtcga ccgccagct ggtgaccaag gaagtcaccg tctccgccga cgagggcatc      660
cgcgccgata ccacgctgga aggcgtctcc aagatccgca gcgcggtgcc gggtggcgtg     720
atcaccgccg gcaatgcctc gcagttctcg gacggcgctt cggcagcggt ggtgatgaat     780
gcgcgcgtcg ccgaggcccg cggcctgcag ccgctgggcg tgttccgcgg ctttgccgtg     840
gctggctgcg agccggacga gatgggtatc ggcccggtct ttgctgtgcc caagctgctg     900
aagaaggccg gcctgaaggt cgacgacatc ggcctgtggg agctgaacga agccttcgcc     960
gtgcaggtgc tgtactgcgc cgacacgctc ggcatcccga tggaccggct gaacgtcaac    1020
ggcggcgcca tcgccgtggg ccacccctac ggtgtgtcgg gcgcgcgcct ggtcggccat    1080
gcgctgatcg aaggcaagcg ccgcggcgtc aagtacgtgg tggtgaccat gtgcatcggc    1140
ggcggccagg gcgcggccgg cctgttcgaa gtgctctga                           1179
```

<210> SEQ ID NO 9
<211> LENGTH: 394
<212> TYPE: PRT
<213> ORGANISM: Ralstonia eutropha
<220> FEATURE:
<221> NAME/KEY: MISC_FEATURE
<223> OTHER INFORMATION: Uniprot name: BKTB_CUPNH : Beta-ketothiolase
      BktB (acetyl-coA acetyltransferase) (acetyl coA-acyltransferase)

<400> SEQUENCE: 9

```
Met Thr Arg Glu Val Val Val Ser Gly Val Arg Thr Ala Ile Gly
1               5                  10                  15

Thr Phe Gly Gly Ser Leu Lys Asp Val Ala Pro Ala Glu Leu Gly Ala
            20                  25                  30

Leu Val Val Arg Glu Ala Leu Ala Arg Ala Gln Val Ser Gly Asp Asp
        35                  40                  45

Val Gly His Val Val Phe Gly Asn Val Ile Gln Thr Glu Pro Arg Asp
    50                  55                  60

Met Tyr Leu Gly Arg Val Ala Val Asn Gly Gly Val Thr Ile Asn
65                  70                  75                  80
```

Ala Pro Ala Leu Thr Val Asn Arg Leu Cys Gly Ser Gly Leu Gln Ala
            85                  90                  95

Ile Val Ser Ala Ala Gln Thr Ile Leu Leu Gly Asp Thr Asp Val Ala
            100                 105                 110

Ile Gly Gly Gly Ala Glu Ser Met Ser Arg Ala Pro Tyr Leu Ala Pro
            115                 120                 125

Ala Ala Arg Trp Gly Ala Arg Met Gly Asp Ala Gly Leu Val Asp Met
            130                 135                 140

Met Leu Gly Ala Leu His Asp Pro Phe His Arg Ile His Met Gly Val
145                 150                 155                 160

Thr Ala Glu Asn Val Ala Lys Glu Tyr Asp Ile Ser Arg Ala Gln Gln
            165                 170                 175

Asp Glu Ala Ala Leu Glu Ser His Arg Arg Ala Ser Ala Ala Ile Lys
            180                 185                 190

Ala Gly Tyr Phe Lys Asp Gln Ile Val Pro Val Val Ser Lys Gly Arg
            195                 200                 205

Lys Gly Asp Val Thr Phe Asp Thr Asp Glu His Val Arg His Asp Ala
            210                 215                 220

Thr Ile Asp Asp Met Thr Lys Leu Arg Pro Val Phe Val Lys Glu Asn
225                 230                 235                 240

Gly Thr Val Thr Ala Gly Asn Ala Ser Gly Leu Asn Asp Ala Ala Ala
            245                 250                 255

Ala Val Val Met Met Glu Arg Ala Glu Ala Arg Arg Gly Leu Lys
            260                 265                 270

Pro Leu Ala Arg Leu Val Ser Tyr Gly His Ala Gly Val Asp Pro Lys
            275                 280                 285

Ala Met Gly Ile Gly Pro Val Pro Ala Thr Lys Ile Ala Leu Glu Arg
            290                 295                 300

Ala Gly Leu Gln Val Ser Asp Leu Asp Val Ile Glu Ala Asn Glu Ala
305                 310                 315                 320

Phe Ala Ala Gln Ala Cys Ala Val Thr Lys Ala Leu Gly Leu Asp Pro
            325                 330                 335

Ala Lys Val Asn Pro Asn Gly Ser Gly Ile Ser Leu Gly His Pro Ile
            340                 345                 350

Gly Ala Thr Gly Ala Leu Ile Thr Val Lys Ala Leu His Glu Leu Asn
            355                 360                 365

Arg Val Gln Gly Arg Tyr Ala Leu Val Thr Met Cys Ile Gly Gly Gly
            370                 375                 380

Gln Gly Ile Ala Ala Ile Phe Glu Arg Ile
385                 390

<210> SEQ ID NO 10
<211> LENGTH: 1185
<212> TYPE: DNA
<213> ORGANISM: Ralstonia eutropha
<220> FEATURE:
<221> NAME/KEY: misc_feature
<223> OTHER INFORMATION: Gene name : H16_A1445 or bktB

<400> SEQUENCE: 10
atgacgcgtg aagtggtagt ggtaagcggt gtccgtaccg cgatcgggac ctttggcggc    60
agcctgaagg atgtggcacc ggcggagctg ggcgcactgg tggtgcgcga ggcgctggcg    120
cgcgcgcagg tgtcgggcga cgatgtcggc cacgtggtat tcggcaacgt gatccagacc    180
gagccgcgcg acatgtatct gggccgcgtc gcggccgtca acggcggggt gacgatcaac    240

| | | |
|---|---|---|
| gcccccgcgc tgaccgtgaa ccgcctgtgc ggctcgggcc tgcaggccat tgtcagcgcc | 300 | |
| gcgcagacca tcctgctggg cgataccgac gtcgccatcg gcggcggcgc ggaaagcatg | 360 | |
| agccgcgcac cgtacctggc gccggcagcg cgctggggcg cacgcatggg cgacgccggc | 420 | |
| ctggtcgaca tgatgctggg tgcgctgcac gatcccttcc atcgcatcca catgggcgtg | 480 | |
| accgccgaga atgtcgccaa ggaatacgac atctcgcgcg cgcagcagga cgaggccgcg | 540 | |
| ctggaatcgc accgccgcgc ttcggcagcg atcaaggccg gctacttcaa ggaccagatc | 600 | |
| gtcccggtgg tgagcaaggg ccgcaagggc gacgtgacct cgacaccga cgagcacgtg | 660 | |
| cgccatgacg ccaccatcga cgacatgacc aagctcaggc cggtcttcgt caaggaaaac | 720 | |
| ggcacggtca cggccggcaa tgcctcgggc ctgaacgacg ccgccgccgc ggtggtgatg | 780 | |
| atggagcgcg ccgaagccga cgcgccgcgg ctgaagccgc tggcccgcct ggtgtcgtac | 840 | |
| ggccatgccg gcgtggaccc gaaggccatg ggcatcggcc cggtgccggc gacgaagatc | 900 | |
| gcgctggagc gcgccggcct gcaggtgtcg gacctggacg tgatcgaagc caacgaagcc | 960 | |
| tttgccgcac aggcgtgcgc cgtgaccaag gcgctcggtc tggaccccggc caaggttaac | 1020 | |
| ccgaacggct cggcatctc gctgggccac ccgatcggcg ccaccggtgc cctgatcacg | 1080 | |
| gtgaaggcgc tgcatgagct gaaccgcgtg cagggccgct acgcgctggt gacgatgtgc | 1140 | |
| atcggcggcg ggcagggcat tgccgccatc ttcgagcgta tctga | 1185 | |

<210> SEQ ID NO 11
<211> LENGTH: 702
<212> TYPE: DNA
<213> ORGANISM: artificial
<220> FEATURE:
<223> OTHER INFORMATION: Codon optimized gene scoA

<400> SEQUENCE: 11

| | | |
|---|---|---|
| atgaacaagg tttatgcttc tgctgctgaa gctttggctg gtgttgttag agatggtcaa | 60 | |
| actattgctg ttggtggttt tggtttgtgt ggtattccag aagctttgat tgctgctttg | 120 | |
| agagattctg gtgctaagca attgacctgc atttctaaca tgccggtgt tgacggtttc | 180 | |
| ggtttgggtt tgttgttggc tactagacaa atctccaaga tgatctcttc ttacgtcggt | 240 | |
| gaaaacaaag aattcgaaag acaatatttg gccggtgaat tggaattaga attcactcca | 300 | |
| caaggtactt tggccgaaaa attgagagct ggtggttctg gtattcctgc tttttttaca | 360 | |
| aaaaccggtg ttggtactat cgtcgctgaa ggtaaagaaa tcagagaatt cgatggtcaa | 420 | |
| caatacgtta tggaaagatc cttgactgct gatgttgctt tggttaaggc ttacaaagct | 480 | |
| gataaggctg gtaacttggt tttcagaaga actgctagaa acttcaaccc aatgtgtgct | 540 | |
| atggctggta agttacaat tgccgaagtt gaacatatcg tcgaaactgg tgaattagat | 600 | |
| ccagacgaaa ttcacttggc tggtatcttt gttaagagat tggttttgaa caccacccca | 660 | |
| gaaaagagaa ttgaacaaag aactgttaga gccgcctctt ga | 702 | |

<210> SEQ ID NO 12
<211> LENGTH: 639
<212> TYPE: DNA
<213> ORGANISM: artificial
<220> FEATURE:
<223> OTHER INFORMATION: Codon optimized gene scoB

<400> SEQUENCE: 12

| | | |
|---|---|---|
| atggcttgga ctagagatga aatggctgct agagctgcta ctgaattgca agatggtttt | 60 | |
| tacgttaact tgggtattgg tttgccaacc ttggttgcta ttgggttcc agaaggtatg | 120 | |

```
gaagtttggt tgcaatctga aaatggtttg ttgggtatag gtccattccc aactgaagat    180
gaagttgatg ctgatatgat taacgctggt aagcaaactg ttactacttt gccaggttcc    240
tctattttct cttctgctga ttctttcgcc atgattagag gtggtcatat taacttggca    300
attttgggtg ctatgcaagt ctctgaaaaa ggtgatttgg ctaactggat gattccaggt    360
aaaatggtta agggtatggg tggtgctatg gatttggttg ctggtgttgg tagagttgtt    420
gttttgatgg aacataccgc caaaaagaag gatggtacta agatattaa gatcttgaag    480 gactgcaact tgccattgac aggtgttggt gttgttaaca gaattatcac cgatttgggt    540
gttatcgatg ttaccgatga aggtttgaag ttggttgaaa ctgctccagg tgtttccaga    600
gaagaaattc aagctaaaac tggtgctcct tgttgtgtaa                         639

<210> SEQ ID NO 13
<211> LENGTH: 1185
<212> TYPE: DNA
<213> ORGANISM: artificial
<220> FEATURE:
<223> OTHER INFORMATION: Codon optimized gene bktB

<400> SEQUENCE: 13
atgaccagag aagttgttgt tgtttctggt gttagaaccg ctattggtac ttttggtggt    60
tctttgaaag atgttgctcc agctgaattg ggtgctttgg ttgttagaga agctttggct    120
agagcacaag tttcaggtga tgatgttggt catgttgttt tcggtaacgt tattcaaacc    180
gaacctagag atatgtactt gggtagagtt gctgctgtta atggtggtgt tactattaac    240
gctccagctt tgactgttaa tagattgtgt ggttctggtt tacaagctat cgtttctgct    300
gctcaaacta tcttgttggg tgatactgat gttgctattg gtggtggtgc tgaatctatg    360
tctagagcac atatttggc tccagcagct agatggggtg ctagaatggg tgatgctggt    420
ttggttgaca tgatgttagg tgctttacat gatccattcc acagaatcca tatgggtgtt    480
actgctgaaa acgttgccaa agaatacgat atttctagag cccaacaaga cgaagctgct    540
ttggaatctc atagaagagc ttcagctgct attaaggctg ttacttaa ggatcaaatc    600 gtcccagttg tttccaaagg tagaaaaggt gatgttacct tcgataccga tgaacatgtt    660
agacatgatg ccaccattga tgatatgacc aagttaagac cagttttcgt caaagaaaac    720
ggtactgtta cagctggtaa tgcttctggt ttgaatgatg ctgctgctgc agttgttatg    780
atggaaagag ctgaagcaga agaagaggt ttgaaaccat ggctagatt ggtttcttat    840 ggtcatgctg tgttgatcc aaaagctatg ggtattggtc cagttccagc tacaaaaatt    900
gctttagaaa gagccggttt acaagtctcc gatttggatg ttattgaagc taatgaagct    960
tttgctgccc aagcttgtgc tgttacaaaa gctttaggtt tggatccagc taaggttaat    1020
ccaaacggtt ctggtatttc tttgggtcat ccaattggtg ctactggtgc tttgattact    1080
gttaaggcat tgcacgaatt gaacagagtt caaggtagaa cgctttggt taccatgtgt    1140 ataggtggtg gtcaaggtat tgctgctatt ttcgaaagaa tttga                  1185

<210> SEQ ID NO 14
<211> LENGTH: 402
<212> TYPE: DNA
<213> ORGANISM: Saccharomyces cerevisiae
<220> FEATURE:
<221> NAME/KEY: misc_feature
<223> OTHER INFORMATION: tef1 promoter

<400> SEQUENCE: 14
```

```
atagcttcaa aatgtttcta ctccttttt actcttccag attttctcgg actccgcgca    60
tcgccgtacc acttcaaaac acccaagcac agcatactaa atttccctc tttcttcctc   120 tagggtgtcg ttaattaccc gtactaaagg tttggaaaag aaaaaagaga ccgcctcgtt   180 tcttttctt cgtcgaaaaa ggcaataaaa attttatca cgtttctttt tcttgaaaat    240 tttttttg attttttct ctttcgatga cctcccattg atatttaagt taataaacgg     300
tcttcaattt ctcaagtttc agtttcattt ttcttgttct attacaactt tttttacttc  360
ttgctcatta gaaagaaagc atagcaatct aatctaagtt tt                     402

<210> SEQ ID NO 15
<211> LENGTH: 394
<212> TYPE: DNA
<213> ORGANISM: Saccharomyces cerevisiae
<220> FEATURE:
<221> NAME/KEY: misc_feature
<223> OTHER INFORMATION: hxt7 promoter

<400> SEQUENCE: 15
gagctcgtag gaacaatttc gggcccctgc gtgttcttct gaggttcatc ttttacattt   60
gcttctgctg gataatttc agaggcaaca aggaaaaatt agatggcaaa aagtcgtctt   120
tcaaggaaaa atccccacca tctttcgaga tcccctgtaa cttattggca actgaaagaa   180
tgaaaaggag gaaaatacaa aatatactag aactgaaaaa aaaaaagtat aaatagagac   240
gatatatgcc aatacttcac aatgttcgaa tctattcttc atttgcagct attgtaaaat   300
aataaaacat caagaacaaa caagctcaac ttgtcttttc taagaacaaa gaataaacac   360
aaaaacaaaa agtttttta atttaatca aaaa                                394

<210> SEQ ID NO 16
<211> LENGTH: 1000
<212> TYPE: DNA
<213> ORGANISM: Saccharomyces cerevisiae
<220> FEATURE:
<221> NAME/KEY: misc_feature
<223> OTHER INFORMATION: tef2 promoter

<400> SEQUENCE: 16
gtaggtgttc cttgagctac cctttaaagc tggggagatg agcttgccct tcctgtcatc   60
gccattatga cgagaaaagt aaaacatgta gaataaggtc cacccaaaca tgtccgagca   120
atgacgttat atatcgtgtt ccctgttcaa agcatggcat atgtgccatt aaaggcgaat   180
ttttgtccct agcaaaggag agacagcgag ccaccattaa gaagtgactt gaaagcaagc   240 gaaatagct acacatatat atcaatatat tgacctataa acccaaaatg tgaaagaaat   300
ttgataggtc aagatcaatg taaacaatta ctttgttatg tagagttttt ttagctacct   360
atattccacc ataacatcaa tcatgcggtt gctggtgtat ttaccaataa tgtttaatgt   420
atatatatat atatatatat ggggccgtat acttacatat agtagatgtc aagcgtaggc   480
gcttcccctg ccggctgtga gggcgccata accaaggtat ctatagaccg ccaatcagca   540
aactacctcc gtacattcat gttgcaccca cacatttata cacccagacc gcgacaaatt   600
acccataagg ttgtttgtga cggcgtcgta caagagaacg tgggaactt ttaggctcac    660 caaaaaagaa agaaaaaata cgagttgctg acagaagcct caagaaaaaa aaaattcttc   720
ttcgactatg ctggaggcag agatgatcga gccggtagtt aactatatat agctaaattg   780
gttccatcac cttctttct ggtgtcgctc cttctagtgc tatttctggc ttttcctatt    840
```

```
ttttttttttc cattttcctt tctctctttc taatatataa attctcttgc attttctatt      900
tttctctcta tctattctac ttgtttattc ccttcaaggt ttttttttaa ggagtacttg      960
tttttagaat atacggtcaa cgaactataa ttaactaaac                           1000

<210> SEQ ID NO 17
<211> LENGTH: 500
<212> TYPE: DNA
<213> ORGANISM: Saccharomyces cerevisiae
<220> FEATURE:
<221> NAME/KEY: misc_feature
<223> OTHER INFORMATION: pgk1 promoter

<400> SEQUENCE: 17
tgtttgcaaa aagaacaaaa ctgaaaaaac ccagacacgc tcgacttcct gtcttcctat       60
tgattgcagc ttccaatttc gtcacacaac aaggtcctag cgacggctca caggttttgt      120
aacaagcaat cgaaggttct ggaatggcgg gaaagggttt agtaccacat gctatgatgc      180
ccactgtgat ctccagagca agttcgttc gatcgtactg ttactctctc tctttcaaac      240
agaattgtcc gaatcgtgtg acaacaacag cctgttctca cacactcttt tcttctaacc      300
aagggggtgg tttagtttag tagaaccctcg tgaaacttac atttacatat atataaactt     360
gcataaattg gtcaatgcaa gaaatacata tttggtcttt tctaattcgt agttttttcaa     420 gttcttagat gctttctttt tctctttttt acagatcatc aaggaagtaa ttatctactt      480
tttacaacaa atataaaaca                                                  500

<210> SEQ ID NO 18
<211> LENGTH: 266
<212> TYPE: DNA
<213> ORGANISM: Saccharomyces cerevisiae
<220> FEATURE:
<221> NAME/KEY: misc_feature
<223> OTHER INFORMATION: Transcriptional terminator cyc1

<400> SEQUENCE: 18
catgtaatta gttatgtcac gcttacattc acgccctccc cccacatccg ctctaaccga       60
aaaggaagga gttagacaac ctgaagtcta ggtccctatt tatttttta tagttatgtt      120 agtattaaga acgttattta tatttcaaat ttttctttttt tttctgtaca gacgcgtgta     180
cgcatgtaac attatactga aaaccttgct tgagaaggtt ttgggacgct cgaaggcttt      240
aatttgcggc cggtacccaa ttcgcc                                           266

<210> SEQ ID NO 19
<211> LENGTH: 259
<212> TYPE: DNA
<213> ORGANISM: Saccharomyces cerevisiae
<220> FEATURE:
<221> NAME/KEY: misc_feature
<223> OTHER INFORMATION: Transcriptional terminator tef1

<400> SEQUENCE: 19
ctgacaataa aaagattctt gttttcaaga acttgtcatt tgtatagttt ttttatattg       60
tagttgttct attttaatca aatgttagcg tgatttatat ttttttttcgc ctcgacatca    120 tctgcccaga tgcgaagtta gtgcgcagaa agtaatatc atgcgtcaat cgtatgtgaa      180
tgctggtcgc tatactgctg tcgattcgat actaacgccg ccatccagtg tcgaaaacga     240
gctctcgaga acccttaat                                                   259

<210> SEQ ID NO 20
```

```
<211> LENGTH: 296
<212> TYPE: DNA
<213> ORGANISM: Saccharomyces cerevisiae
<220> FEATURE:
<221> NAME/KEY: misc_feature
<223> OTHER INFORMATION: Transcriptional terminator pdc1

<400> SEQUENCE: 20
gcgatttaat ctctaattat tagttaaagt tttataagca ttttatgta acgaaaaata      60 aattggttca tattattact gcactgtcac ttaccatgga agaccagac aagaagttgc     120 cgacacgaca gtctgttgaa ttggcttaag tctgggtccg cttctttaca aatttgaaga    180
atttctctta aacgatatgt atattctttt cgttggaaaa gatgtcttcc aaaaaaaaaa    240
accgatgaat tagtggaacc aaggaaaaaa aagaggtat ccttgattaa ggaaca         296

<210> SEQ ID NO 21
<211> LENGTH: 101
<212> TYPE: DNA
<213> ORGANISM: artificial
<220> FEATURE:
<223> OTHER INFORMATION: Oligonucleotide for deletion frdABCD

<400> SEQUENCE: 21
cgtgcaaacc tttcaagccg atcttgccat tgtaggcgcc ggtggcgcgg gattacgtgc     60
tgcaattgct gccgcgcagg ccatatgaat atcctcctta g                       101

<210> SEQ ID NO 22
<211> LENGTH: 100
<212> TYPE: DNA
<213> ORGANISM: artificial
<220> FEATURE:
<223> OTHER INFORMATION: Oligonucleotide for deletion frdABCD

<400> SEQUENCE: 22
cgttagattg taacgacacc aatcagcgtg acaactgtca ggatagcagc cagaccgtag     60
aaaacccatt tgcccgcagg tgtaggctgg agctgcttcg                         100

<210> SEQ ID NO 23
<211> LENGTH: 100
<212> TYPE: DNA
<213> ORGANISM: artificial
<220> FEATURE:
<223> OTHER INFORMATION: Oligonucleotide for deletion ptsG

<400> SEQUENCE: 23
atgtttaaga atgcatttgc taacctgcaa aaggtcggta atcgctgat gctgccggta     60 tccgtactgc ctatcgcagg tgtaggctgg agctgcttcg                         100

<210> SEQ ID NO 24
<211> LENGTH: 100
<212> TYPE: DNA
<213> ORGANISM: artificial
<220> FEATURE:
<223> OTHER INFORMATION: Oligonucleotide for deletion ptsG

<400> SEQUENCE: 24
ttagtggtta cggatgtact catccatctc ggttttcagg ttatcggatt tagtaccgaa     60
aatcgcctga acaccagaac catatgaata tcctccttag                         100

<210> SEQ ID NO 25
<211> LENGTH: 561
<212> TYPE: PRT
```

<213> ORGANISM: Uncultured marine bacterium 442
<220> FEATURE:
<221> NAME/KEY: MISC_FEATURE
<223> OTHER INFORMATION: Uniprot name : Q6SH33_9BACT. AMP-binding enzyme

<400> SEQUENCE: 25

```
Met Lys Asn Leu Met Ile Glu Leu Thr Lys Lys Gly Glu Phe Phe Glu
1               5                   10                  15

Thr Ser Val Lys Gly Phe Asn Lys Ala Gly Glu Pro Ile Met Ala
            20                  25                  30

Tyr Arg Asn Ala Pro Ala Thr Leu Leu Asp Ile Ile Glu Ala Ala Arg
            35                  40                  45

Ala His Lys Asp Gln Glu Phe Leu Val His Gly Lys Arg Arg Ile Ser
        50                  55                  60

Phe Ala Gln Phe Phe Glu Ala Val Asp Ala Phe Ala Val Tyr Leu Gln
65                  70                  75                  80

Phe Ile Gly Leu Lys Pro Gly Phe Arg Leu Ala Ile Ala Met Arg Asn
                85                  90                  95

Asn Pro Glu Trp Leu Ile Ala Phe Ala Ala Gly Val Val Thr Gly Ala
            100                 105                 110

Val Val Val Pro Ile Asn Ser Trp Gly Lys Arg Asp Glu Leu Leu His
            115                 120                 125

Ala Leu Glu Asp Cys Glu Pro Phe Ala Leu Val Cys Asp Ser Pro Arg
130                 135                 140

Ala Ala Leu Leu Lys Asp Ala Leu Glu Thr Val Gln Phe Val Val Val
145                 150                 155                 160

Ala Ala Asp Ser Glu Asn Ser Gly Thr Glu Val Gly Arg Gly Ile Ala
            165                 170                 175

Phe Ser Asn Ala Leu Arg His Ala Gly Gln Pro Thr Val Ser Pro
            180                 185                 190

Thr Pro Glu Gln Leu Ala Leu Ile Leu Tyr Thr Ser Gly Ser Thr Gly
            195                 200                 205

Ala Pro Lys Gly Ala Met His Ser His Glu Gly Ala Ala Gln Ala Val
            210                 215                 220

Phe Asn Met Leu Phe Thr Gly Met Leu Ser Leu Ser Ile Glu Gly Pro
225                 230                 235                 240

Arg Ala Leu Gln Gly Gly Ala Ile Gln Glu Lys Thr Leu Leu Thr Val
            245                 250                 255

Pro Leu Phe His Ala Thr Gly Leu Leu Gly Ser Phe Leu Leu Pro Cys
            260                 265                 270

Val Thr Ala Gln Ser Ile Val Met Leu Asp Lys Trp Asp Pro Gln Val
            275                 280                 285

Ala Leu Arg Leu Ile Glu Glu Arg Ile Thr Leu Leu Ser Ser Val
            290                 295                 300

Pro Ala Leu Val Lys Glu Leu Leu Ser Gln Ser Asn Val Lys Glu Phe
305                 310                 315                 320

Asp Ile Thr Cys Leu Gln Arg Val Ala Ser Gly Gly Ala Ala Met Pro
            325                 330                 335

Ala Asp Leu Pro Asp Leu Ile Gly Lys Tyr Val Arg Asn Pro Ser Ala
            340                 345                 350

Ser Ala Gly Tyr Gly Met Thr Glu Thr Leu Thr Val Gly Ser Gln Gly
            355                 360                 365

Ala Gly Ala Val Phe Asp Ala Lys Pro Glu Ala Ala Gly Val Gln Ser
            370                 375                 380
```

-continued

```
Pro Ile Met Ala Phe Arg Thr Val Ser Asp Ser Gly Asp Val Leu Pro
385                 390                 395                 400

Pro Gly Ser Ile Gly Glu Ile Glu Met Ser Gly Val Ser Cys Thr Leu
            405                 410                 415

Gly Tyr Trp Arg Asn Pro Ser Ala Asp Ala Val Leu Phe Ser Lys Asp
        420                 425                 430

Gly Trp Leu Arg Ser Gly Asp Val Gly Phe Val Asp Asp Glu Gly Tyr
    435                 440                 445

Val Phe Ile Thr Gly Arg Ile Lys Asp Ile Val Ile Arg Gly Gly Glu
    450                 455                 460

Asn Ile Phe Pro Gly Asp Thr Glu Gln Ala Cys Tyr Ser Leu Leu Gly
465                 470                 475                 480

Val Ala Glu Cys Val Val Phe Gly Val Pro Asp Asp Arg Leu Gly Glu
                485                 490                 495

Glu Leu Ala Met Val Val Tyr Cys Gly Pro Asn Gln Thr Leu Thr Ser
            500                 505                 510

Asp Gln Val Arg Ala Gln Leu Gln Gln Ser Ile Ala Gly Tyr Lys Val
        515                 520                 525

Pro Arg Tyr Ile Arg Ile His Asp Arg Pro Leu Leu Lys Gly Ala Thr
    530                 535                 540

Glu Lys Phe Asp Lys Arg Ala Ile Arg Glu Gly Phe Ile Ala Glu Gln
545                 550                 555                 560

Asp

<210> SEQ ID NO 26
<211> LENGTH: 549
<212> TYPE: PRT
<213> ORGANISM: Bacillus subtilis
<220> FEATURE:
<221> NAME/KEY: MISC_FEATURE
<223> OTHER INFORMATION: Uniprot name : YNGI_BACSU. Putative acyl-CoA
      synthetase YngI

<400> SEQUENCE: 26

Met Ala Glu Leu Ile His Ser Thr Ile Gly Arg Leu Leu Glu Gln Thr
1               5                   10                  15

Ala Asp Ala Tyr Pro Asp Arg Asp Ala Val Val Tyr Pro Asp Arg Asn
            20                  25                  30

Ile Arg Tyr Thr Tyr Ala Gln Phe Asp Ser Leu Cys Arg Gln Thr Ala
        35                  40                  45

Lys Gly Leu Met Arg Met Gly Ile Gly Lys Gly Asp His Val Ala Ile
    50                  55                  60

Trp Ala Ser Asn Ile Ser Glu Trp Leu Ala Val Gln Phe Ala Thr Ala
65                  70                  75                  80

Lys Ile Gly Ala Val Leu Val Thr Val Asn Thr Asn Tyr Gln Ala His
                85                  90                  95

Glu Leu Asp Tyr Leu Leu Lys Gln Ser Asp Ala Ala Ala Leu Ile Ile
            100                 105                 110

Met Asp Ser Tyr Arg Gly Thr Ser Tyr Pro Asp Ile Val Asn Ser Leu
        115                 120                 125

Ile Pro Glu Leu Gln Glu Ala Lys Pro Gly Gln Leu Lys Ser Glu Arg
    130                 135                 140

Tyr Pro Phe Leu Lys Thr Leu Ile Tyr Ile Gly Asn Lys Arg Leu Ser
145                 150                 155                 160

Gly Met Tyr His Trp Asp Asp Thr Glu Ile Leu Ala Lys Thr Val Thr
                165                 170                 175
```

```
Asp Ala Glu Leu Glu Glu Arg Met Asn Ser Leu Asp Lys Asp Asn Val
            180                 185                 190

Ile Asn Met Gln Tyr Thr Ser Gly Thr Thr Gly Phe Pro Lys Gly Val
            195                 200                 205

Met Leu Thr His Phe Asn Val Ile Asn Ala Ala Asn Ile Ala Glu
    210                 215                 220

Cys Met Ala Leu Thr Ser Gln Asp Arg Met Cys Ile Pro Val Pro Phe
225                 230                 235                 240

Phe His Cys Phe Gly Cys Val Leu Gly Val Leu Ala Cys Val Ser Val
                245                 250                 255

Gly Ala Ala Met Ile Pro Val Gln Glu Phe Asp Pro Val Thr Val Leu
            260                 265                 270

Lys Thr Val Glu Lys Glu Lys Cys Thr Val Leu His Gly Val Pro Thr
            275                 280                 285

Met Phe Ile Ala Glu Leu His His Pro Asp Phe Asp Ala Tyr Asp Leu
    290                 295                 300

Ser Thr Leu Arg Thr Gly Ile Met Ala Gly Ser Pro Cys Pro Ser Glu
305                 310                 315                 320

Val Met Lys Ala Val Ile Glu Arg Met Gly Met Lys Asp Ile Thr Ile
                325                 330                 335

Ala Tyr Gly Gln Thr Glu Ala Ser Pro Val Ile Thr Gln Thr Arg Ala
            340                 345                 350

Asn Asp Ser Phe Ile Arg Arg Val Glu Thr Thr Gly Arg Ala Leu Pro
            355                 360                 365

His Thr Glu Val Lys Ile Val Glu Pro Gly Thr Cys Gln Glu Val Gln
    370                 375                 380

Arg Gly Met Gln Gly Glu Leu Cys Thr Arg Gly Tyr His Val Met Lys
385                 390                 395                 400

Gly Tyr Tyr Lys Asp Lys Asp Ala Thr Arg Lys Ala Ile Asn His Asp
                405                 410                 415

Gly Trp Leu Phe Thr Gly Asp Leu Ala Val Met Asp Glu Asp Gly Tyr
            420                 425                 430

Cys Arg Ile Thr Gly Arg Leu Lys Asp Met Leu Ile Arg Gly Gly Glu
            435                 440                 445

Asn Ile Tyr Pro Arg Glu Ile Glu Glu Phe Leu Tyr Gln His Pro Ala
    450                 455                 460

Val Leu Asp Val Gln Val Val Gly Val Pro Asp Ala Lys Phe Gly Glu
465                 470                 475                 480

Glu Ala Ala Ala Trp Ile Lys Leu Lys Asp Gly Lys Ser Val Ser Pro
                485                 490                 495

Asp Glu Leu Lys Ala Tyr Cys Lys Gly Lys Ile Ala Arg His Lys Ile
            500                 505                 510

Pro Arg Tyr Val Ile Phe Thr Asp Asp Tyr Pro Met Thr Ala Ser Gly
            515                 520                 525

Lys Ile Gln Lys Tyr Lys Leu Arg Glu Lys Thr Ile Glu Met Phe Asn
    530                 535                 540

Leu Ser Ser Ser Gln
545

<210> SEQ ID NO 27
<211> LENGTH: 564
<212> TYPE: PRT
<213> ORGANISM: Pseudomonas aeruginosa
<220> FEATURE:
```

<221> NAME/KEY: MISC_FEATURE
<223> OTHER INFORMATION: Uniprot name : Q9I0S7_PSEAE. AMP-binding
      protein

<400> SEQUENCE: 27

```
Met Asn Gln Pro Ser Tyr Thr Ser Gly Arg Gln Asp Val Ala Leu Leu
1               5                   10                  15

Ala Thr Thr Val Gly Asp Ala Phe Asp Ala Thr Val Ala Arg His Ala
            20                  25                  30

Glu Arg Glu Ala Leu Val Val Arg His Gln Arg Leu Arg Tyr Ser Trp
        35                  40                  45

Arg Gln Leu Ala Glu Arg Val Asp Ala Tyr Ala Arg Ala Phe Ile Ala
    50                  55                  60

Leu Gly Leu Arg Pro Gly Glu Arg Leu Gly Ile Trp Ala Pro Asn Cys
65                  70                  75                  80

Ala Glu Trp Cys Ile Thr Gln Phe Ala Ser Ala Lys Val Gly Ala Val
                85                  90                  95

Leu Val Asn Ile Asn Pro Ala Tyr Arg Ser Ser Glu Leu Glu Tyr Ala
            100                 105                 110

Leu Lys Gln Ser Gly Cys Ser Trp Leu Ile Cys Ala Asp Ala Phe Lys
        115                 120                 125

Thr Ser Asp Tyr His Ala Met Leu Gly Asp Leu Leu Pro Glu Leu Ala
    130                 135                 140

Arg Ala Arg Pro Gly Glu Leu Ala Ser Glu Arg Leu Pro Glu Leu Arg
145                 150                 155                 160

Gly Val Ile Ser Leu Ala Glu Arg Ala Pro Ala Gly Phe Leu His Trp
                165                 170                 175

Gln Gly Leu Pro Gly Leu Ala Ala Ala Val Gly Ala Glu Glu Leu Arg
            180                 185                 190

Gln Arg Gln Ala Ser Leu Gln Phe Asp Glu Pro Ile Asn Ile Gln Tyr
        195                 200                 205

Thr Ser Gly Thr Thr Gly Phe Pro Lys Gly Ala Thr Leu Ser His Tyr
    210                 215                 220

Asn Ile Leu Asn Asn Gly Tyr Met Val Gly Glu Ser Leu Gly Leu Gly
225                 230                 235                 240

Ala Glu Asp Arg Leu Val Ile Pro Val Pro Leu Tyr His Cys Phe Gly
                245                 250                 255

Met Val Met Gly Asn Leu Gly Cys Val Thr His Gly Ser Thr Met Ile
            260                 265                 270

Tyr Pro Ala Pro Ser Phe Asp Ala Glu Ala Thr Leu Leu Ala Val Ala
        275                 280                 285

Glu Glu Arg Ala Thr Ala Leu Tyr Gly Val Pro Thr Met Phe Ile Ala
    290                 295                 300

Glu Leu Asp His Pro Arg Arg Arg Glu Phe Asp Leu Ser Ser Leu Arg
305                 310                 315                 320

Thr Gly Ile Met Ala Gly Ala Thr Cys Pro Ile Glu Val Met Arg Arg
                325                 330                 335

Val Ile Gly Asp Met His Met Ala Glu Val Gln Ile Ala Tyr Gly Met
            340                 345                 350

Thr Glu Thr Ser Pro Val Ser Leu Gln Thr Gly Pro Asp Asp Gly Leu
        355                 360                 365

Glu Leu Arg Val Thr Thr Val Gly Arg Thr Gln Pro Arg Leu Glu Ser
    370                 375                 380

Lys Ile Val Asp Gln Thr Gly Arg Val Val Pro Arg Gly Glu Ile Gly
```

```
                385                 390                 395                 400
        Glu Leu Cys Thr Arg Gly Tyr Ser Val Met Leu Gly Tyr Trp Asn Asp
                        405                 410                 415

Pro Gln Ala Thr Ala Glu Ala Ile Asp Pro Ala Arg Trp Met His Thr
                        420                 425                 430

Gly Asp Leu Ala Val Met Asp Asp Gly Tyr Val Arg Ile Val Gly
                        435                 440                 445

Arg Ser Lys Asp Met Ile Ile Arg Gly Gly Glu Asn Ile Tyr Pro Arg
        450                 455                 460

Glu Leu Glu Glu Phe Phe Thr His Pro Ala Val Ala Asp Val Gln
        465                 470                 475                 480

Val Ile Gly Ile Pro Asp Glu Arg Tyr Gly Glu Ile Val Ala Trp
                        485                 490                 495

Ile Lys Leu His Pro Gly His His Ala Asp Asp Glu Gln Leu Arg Ala
                        500                 505                 510

Phe Cys Lys Ala Arg Ile Ala His Phe Lys Ile Pro Arg His Phe Lys
                        515                 520                 525

Phe Val Asp Glu Phe Pro Met Thr Val Thr Gly Lys Ile Gln Lys Phe
                        530                 535                 540

Arg Met Arg Glu Ile Ser Ile Glu Glu Ile Arg Leu Leu Ala Leu Arg
        545                 550                 555                 560

Gln Gly Arg Asp

<210> SEQ ID NO 28
<211> LENGTH: 575
<212> TYPE: PRT
<213> ORGANISM: Burkholderia dolosa
<220> FEATURE:
<221> NAME/KEY: MISC_FEATURE
<223> OTHER INFORMATION: Uniprot name: A2W663_9BURK. Acetyl-coenzyme A
      synthetase 1

<400> SEQUENCE: 28

Met Ala Ala Asp Leu Gly Val Arg Ala Leu Ile Ala Pro Glu Asn Gly
1               5                   10                  15

Leu Ser Tyr Val Arg Gly Ala Thr Asp Val Pro Leu Ser Glu Ala Thr
                20                  25                  30

Ile Gly Arg Phe Leu Leu Asp Thr Ala Gly Arg Phe Pro Asp Arg Pro
            35                  40                  45

Ala Val Val Phe Arg Glu Gln Gln Val Arg Trp Thr Trp Arg Glu Phe
        50                  55                  60

Ala Asp Glu Ile Asp Val Leu Ala Gly Leu Ala Ala Leu Gly Ile
65                  70                  75                  80

Val Lys Gly Asp Arg Val Gly Ile Trp Ser Pro Asn Arg Ser Glu Trp
                85                  90                  95

Leu Leu Thr Gln Phe Ala Thr Ala Arg Ile Gly Ala Ile Leu Val Asn
                100                 105                 110

Ile Asn Pro Ala Tyr Arg Leu Ala Glu Leu Glu Tyr Ala Leu Asn Lys
            115                 120                 125

Val Gly Cys Lys Ala Val Ile Ala Ala Glu Arg Phe Lys Ser Ser Ala
        130                 135                 140

Tyr Val Glu Met Leu Gln Thr Ile Ala Pro Glu Leu Ala Thr Ala Thr
145                 150                 155                 160

Pro Gly Asp Leu His Ala Ala Arg Val Pro Ser Leu Arg Thr Ile Val
                165                 170                 175
```

Ser Met Ser Asp Val Ala Pro Pro Gly Met Val Arg Phe Ala Asp Val
            180                 185                 190

Ile Ala Arg Gly Arg Arg Ala Val Asp Ser Ala Leu Leu Asp Ala Ile
        195                 200                 205

Gly Ala Thr Leu Ala Ser Thr Asp Pro Ile Asn Ile Gln Phe Thr Ser
    210                 215                 220

Gly Thr Thr Gly Ser Pro Lys Gly Ala Thr Leu Thr His Arg Asn Val
225                 230                 235                 240

Val Asn Asn Ala Arg Ser Ile Ala Arg Ala Met Arg Phe Thr Glu His
                245                 250                 255

Asp Ser Leu Cys Ile Pro Val Pro Leu Tyr His Cys Phe Gly Met Val
            260                 265                 270

Leu Ala Val Leu Ala Cys Val Ser Thr Gly Ala Ala Met Val Phe Pro
        275                 280                 285

Gly Glu Ala Phe Asp Pro Val Ala Thr Leu Ala Ala Val Ala Glu Glu
    290                 295                 300

Arg Cys Thr Ala Leu His Gly Val Pro Thr Met Phe Ile Ala Glu Leu
305                 310                 315                 320

Asp His Pro Glu Phe Ala Lys Phe Asp Leu Ser Thr Leu Arg Thr Gly
                325                 330                 335

Ile Met Ala Gly Ser Pro Cys Pro Ile Glu Thr Met Lys Arg Val Val
            340                 345                 350

Ser Gln Met His Leu Ser Glu Ile Thr Ile Ala Tyr Gly Met Thr Glu
        355                 360                 365

Thr Ser Pro Val Ser Phe Gln Ser Ser Thr Asp Pro Leu Glu Lys
    370                 375                 380

Arg Thr Thr Thr Val Gly Arg Ile Gln Pro His Leu Glu Val Lys Ile
385                 390                 395                 400

Ile Asp Pro Ser Gly Asp Ile Val Pro Val Gly Ala Thr Gly Glu Leu
                405                 410                 415

Cys Thr Lys Gly Tyr Ser Val Met Leu Gly Tyr Trp Asp Asp Ala
            420                 425                 430

Lys Thr Arg Glu Val Leu Ile Asp Gly Trp Met His Thr Gly Asp Leu
        435                 440                 445

Ala Thr Leu Asp Ala Asp Gly Tyr Cys Asn Ile Val Gly Arg Leu Lys
    450                 455                 460

Asp Met Val Ile Arg Gly Gly Glu Asn Val Tyr Pro Arg Glu Ile Glu
465                 470                 475                 480

Glu Phe Leu Phe Arg His Pro Lys Ile Gln Ser Ala Gln Val Phe Gly
                485                 490                 495

Val Pro Asp Pro Lys Tyr Gly Glu Glu Leu Cys Ala Trp Ile Val Leu
            500                 505                 510

Arg Ala Asn Glu Gln Met Thr Glu Asp Asp Val Arg Ala Phe Cys Gln
        515                 520                 525

Gly Gln Ile Ala His Tyr Lys Ile Pro Arg Tyr Ile Arg Phe Val Asp
    530                 535                 540

Glu Leu Pro Met Thr Val Thr Gly Lys Val Gln Lys Phe Val Met Arg
545                 550                 555                 560

Glu Arg Met Ile Asp Glu Leu Lys Leu Asp Val Gln Lys Thr Ala
                565                 570                 575

<210> SEQ ID NO 29
<211> LENGTH: 549
<212> TYPE: PRT

<213> ORGANISM: Bacteroides thetaiotaomicron
<220> FEATURE:
<221> NAME/KEY: MISC_FEATURE
<223> OTHER INFORMATION: Uniprot name: Q8A422_BACTN. AMP-binding protein

<400> SEQUENCE: 29

```
Met Gln Leu Phe Glu Arg Thr Leu Gly Gln Trp Leu Glu His Trp Ala
1               5                   10                  15

Glu Glu Thr Pro Asp Lys Glu Tyr Ile Val Tyr Ser Asp Arg Asn Leu
            20                  25                  30

Arg Phe Thr Trp Ser Gln Leu Asn Gln Arg Val Asp Asp Met Ala Lys
        35                  40                  45

Gly Leu Ile Ala Val Gly Val Glu Arg Gly Thr His Val Gly Ile Trp
50                  55                  60

Ala Ala Asn Val Pro Asp Trp Leu Thr Leu Leu Tyr Ala Cys Ala Lys
65                  70                  75                  80

Ile Gly Ala Val Tyr Val Thr Val Asn Thr Asn Tyr Lys Gln Ala Glu
                85                  90                  95

Leu Glu Tyr Leu Cys Gln Asn Ser Asp Met His Thr Leu Cys Ile Val
            100                 105                 110

Asn Gly Glu Lys Asp Ser Asp Phe Val Gln Met Thr Tyr Thr Met Leu
        115                 120                 125

Pro Glu Leu Lys Thr Cys Glu Arg Gly His Leu Lys Ser Glu Arg Phe
130                 135                 140

Pro Tyr Met Lys Asn Val Ile Tyr Val Gly Gln Glu Lys His Arg Gly
145                 150                 155                 160

Met Tyr Asn Thr Ala Glu Ile Leu Leu Leu Gly Asn Asn Val Glu Asp
                165                 170                 175

Asp Arg Leu Thr Glu Leu Lys Ser Lys Val Asp Cys His Asp Val Val
            180                 185                 190

Asn Met Gln Tyr Thr Ser Gly Thr Thr Gly Phe Pro Lys Gly Val Met
        195                 200                 205

Leu Thr His Tyr Asn Ile Ala Asn Asn Gly Phe Leu Thr Gly Glu His
210                 215                 220

Met Lys Phe Thr Ala Asp Asp Lys Leu Cys Cys Val Pro Leu Phe
225                 230                 235                 240

His Cys Phe Gly Val Val Leu Ala Thr Met Asn Cys Leu Thr His Gly
                245                 250                 255

Cys Thr Gln Val Met Val Glu Arg Phe Asp Pro Leu Val Leu Ala
            260                 265                 270

Ser Ile His Lys Glu Arg Cys Thr Ala Leu Tyr Gly Val Pro Thr Met
275                 280                 285

Phe Ile Ala Glu Leu His His Pro Met Phe Asp Leu Phe Asp Met Ser
290                 295                 300

Cys Leu Arg Thr Gly Ile Met Ala Gly Ser Leu Cys Pro Val Glu Leu
305                 310                 315                 320

Met Lys Gln Val Glu Glu Lys Met Tyr Met Lys Val Thr Ser Val Tyr
                325                 330                 335

Gly Leu Thr Glu Ala Ala Pro Gly Met Thr Ala Thr Arg Ile Asp Asp
            340                 345                 350

Ser Phe Asp Val Arg Cys Asn Thr Val Gly Arg Asp Phe Glu Phe Thr
        355                 360                 365

Glu Val Arg Val Ile Asp Pro Gly Thr Gly Glu Glu Cys Pro Val Gly
370                 375                 380
```

-continued

```
Val Gln Gly Glu Met Cys Asn Arg Gly Tyr Asn Thr Met Lys Gly Tyr
385                 390                 395                 400

Tyr Lys Asn Pro Glu Ala Thr Ala Glu Val Ile Asp Lys Asp Asn Phe
            405                 410                 415

Leu His Ser Gly Asp Leu Gly Ile Lys Asp Glu Asp Gly Asn Tyr Arg
            420                 425                 430

Ile Thr Gly Arg Ile Lys Asp Met Ile Arg Gly Gly Glu Asn Ile
            435                 440                 445

Tyr Pro Arg Glu Ile Glu Glu Phe Leu Tyr Lys Leu Asp Gly Val Lys
            450                 455                 460

Asp Val Gln Val Ala Gly Ile Pro Ser Lys Lys Tyr Gly Glu Ala Val
465                 470                 475                 480

Gly Ala Phe Ile Ile Leu Gln Glu Gly Val Glu Met His Glu Ser Asp
                485                 490                 495

Val Arg Asp Phe Cys Lys Asn Lys Ile Ser Arg Tyr Lys Ile Pro Lys
                500                 505                 510

Tyr Val Phe Phe Val Lys Glu Phe Pro Met Thr Gly Ser Gly Lys Ile
                515                 520                 525

Gln Lys Phe Arg Leu Lys Asp Leu Gly Leu Gln Leu Cys Lys Glu Gln
530                 535                 540

Gly Ile Glu Ile Ile
545

<210> SEQ ID NO 30
<211> LENGTH: 547
<212> TYPE: PRT
<213> ORGANISM: Mycobacterium tuberculosis
<220> FEATURE:
<221> NAME/KEY: MISC_FEATURE
<223> OTHER INFORMATION: Uniprot name: I6Y0X0_MYCTU. fatty-acid--CoA
      ligase FadD35

<400> SEQUENCE: 30

Met Ala Ala Glu Val Val Asp Pro Asn Arg Leu Ser Tyr Asp Arg
1               5                   10                  15

Gly Pro Ser Ala Pro Ser Leu Leu Glu Ser Thr Ile Gly Ala Asn Leu
            20                  25                  30

Ala Ala Thr Ala Ala Arg Tyr Gly His Arg Glu Ala Leu Val Asp Met
            35                  40                  45

Val Ala Arg Arg Arg Phe Asn Tyr Ser Glu Leu Leu Thr Asp Val His
        50                  55                  60

Arg Leu Ala Thr Gly Leu Val Arg Ala Gly Ile Gly Pro Gly Asp Arg
65                  70                  75                  80

Val Gly Ile Trp Ala Pro Asn Arg Trp Glu Trp Val Leu Val Gln Tyr
                85                  90                  95

Ala Thr Ala Glu Ile Gly Ala Ile Leu Val Thr Ile Asn Pro Ala Tyr
            100                 105                 110

Arg Val Arg Glu Val Glu Tyr Ala Leu Arg Gln Ser Gly Val Ala Met
            115                 120                 125

Val Ile Ala Val Ala Ser Phe Lys Asp Ala Asp Tyr Ala Ala Met Leu
130                 135                 140

Ala Glu Val Gly Pro Arg Cys Pro Asp Leu Asp Val Ile Leu Leu
145                 150                 155                 160

Glu Ser Asp Arg Trp Asp Ala Leu Ala Gly Ala Glu Pro Asp Leu Pro
                165                 170                 175

Ala Leu Gln Gln Thr Ala Ala Arg Leu Asp Gly Ser Asp Pro Val Asn
```

```
            180             185             190
Ile Gln Tyr Thr Ser Gly Thr Thr Ala Tyr Pro Lys Gly Val Thr Leu
        195                 200                 205
Ser His Arg Asn Ile Leu Asn Asn Gly Tyr Leu Val Gly Glu Leu Leu
        210                 215                 220
Gly Tyr Thr Ala Gln Asp Arg Ile Cys Ile Pro Val Pro Phe Tyr His
225                 230                 235                 240
Cys Phe Gly Met Val Met Gly Asn Leu Ala Ala Thr Ser His Gly Ala
                245                 250                 255
Ala Met Val Ile Pro Ala Pro Gly Phe Asp Pro Ala Ala Thr Leu Arg
            260                 265                 270
Ala Val Gln Asp Glu Arg Cys Thr Ser Leu Tyr Gly Val Pro Thr Met
        275                 280                 285
Phe Ile Ala Glu Leu Gly Leu Pro Asp Phe Thr Asp Tyr Glu Leu Gly
        290                 295                 300
Ser Leu Arg Thr Gly Ile Met Ala Gly Ala Ala Cys Pro Val Glu Val
305                 310                 315                 320
Met Arg Lys Val Ile Ser Arg Met His Met Pro Gly Val Ser Ile Cys
                325                 330                 335
Tyr Gly Met Thr Glu Thr Ser Pro Val Ser Thr Gln Thr Arg Ala Asp
                340                 345                 350
Asp Ser Val Asp Arg Arg Val Gly Thr Val Gly Arg Val Gly Pro His
            355                 360                 365
Leu Glu Ile Lys Val Val Asp Pro Ala Thr Gly Glu Thr Val Pro Arg
        370                 375                 380
Gly Val Val Gly Glu Phe Cys Thr Arg Gly Tyr Ser Val Met Ala Gly
385                 390                 395                 400
Tyr Trp Asn Asp Pro Gln Lys Thr Ala Glu Val Ile Asp Ala Asp Gly
                405                 410                 415
Trp Met His Thr Gly Asp Leu Ala Glu Met Asp Pro Ser Gly Tyr Val
                420                 425                 430
Arg Ile Ala Gly Arg Ile Lys Asp Leu Val Val Arg Gly Gly Glu Asn
            435                 440                 445
Ile Ser Pro Arg Glu Ile Glu Glu Leu Leu His Thr His Pro Asp Ile
        450                 455                 460
Val Asp Gly His Val Ile Gly Val Pro Asp Ala Lys Tyr Gly Glu Glu
465                 470                 475                 480
Leu Met Ala Val Val Lys Leu Arg Asn Asp Ala Pro Glu Leu Thr Ile
                485                 490                 495
Glu Arg Leu Arg Glu Tyr Cys Met Gly Arg Ile Ala Arg Phe Lys Ile
                500                 505                 510
Pro Arg Tyr Leu Trp Ile Val Asp Glu Phe Pro Met Thr Val Thr Gly
            515                 520                 525
Lys Val Arg Lys Val Glu Met Arg Gln Gln Ala Leu Glu Tyr Leu Arg
        530                 535                 540
Gly Gln Gln
545

<210> SEQ ID NO 31
<211> LENGTH: 543
<212> TYPE: PRT
<213> ORGANISM: Clostridium botulinum A
<220> FEATURE:
<221> NAME/KEY: MISC_FEATURE
<223> OTHER INFORMATION: Uniprot name: A5I718_CLOBH. AMP-binding protein
```

-continued

<400> SEQUENCE: 31

```
Met Gly Leu Tyr Asn Ile Thr Ile Gly Glu Tyr Leu Lys Arg Thr Cys
1               5                   10                  15

Lys Lys Phe Pro Asn Asp Val Ala Ile Gln Ser Leu Glu Met Pro Glu
            20                  25                  30

Gly Ile Ser Trp Ser Glu Leu Asp Lys Ile Thr Asp Asp Ile Ala Lys
        35                  40                  45

Gly Met Ile Val Leu Gly Lys Lys Gly Asp Asn Leu Val Leu Trp
    50                  55                  60

Gly Ser Asn Lys Lys Glu Trp Val Tyr Ile Phe Leu Ala Ala Ser Lys
65                  70                  75                  80

Ile Gly Val Cys Thr Val Thr Leu Asn Thr Asn Tyr Leu Leu Glu Glu
                85                  90                  95

Val Glu Lys Ile Leu Glu Val Ala Asp Ala Lys Ala Ile Ala Phe Met
                100                 105                 110

Glu Ser Phe Tyr Asn Thr Asn Tyr Val Asp Ile Ile Glu Lys Ala Lys
            115                 120                 125

Glu Arg Tyr Asp Lys Gly Ile Cys Lys Ile Pro Gln Ile Ile Glu Tyr
        130                 135                 140

Phe Ile Tyr Phe Gly Glu Lys Asn Arg Pro Glu Tyr Thr Gly Ile Asp
145                 150                 155                 160

Asn Leu Ile Leu Leu Gly Lys Ser Leu Lys Glu Thr Phe Asn Leu
                165                 170                 175

Ile Cys Asn Asp Val Lys Pro Asp Glu Val Val Asn Ile Gln Phe Thr
                180                 185                 190

Ser Gly Thr Thr Ser Ser Pro Lys Gly Val Met Leu Thr His Tyr Ser
            195                 200                 205

Leu Ile Asn Asn Ser Phe Ile Thr Gly Glu Ala Leu Gly Val Thr Asn
        210                 215                 220

Lys Asp Lys Leu Cys Leu Val Val Pro Phe Phe His Cys Phe Gly Leu
225                 230                 235                 240

Ser Val Gly Ile Leu Leu Ser Val Gly Arg Gly Cys Ser Met Val Leu
                245                 250                 255

Val Glu Ser Tyr Lys Ile Ala Pro Leu Ile Asn Thr Ile Lys Thr Phe
                260                 265                 270

Lys Cys Thr Ile Leu His Gly Val Pro Thr Met Phe Cys Arg Val Leu
            275                 280                 285

Glu Asp Asp Ser Met Asp Ile Asn Asp Phe Lys Thr Ile Arg Thr Gly
        290                 295                 300

Ile Leu Ala Gly Ala Asn Ala Thr Asp Glu Leu Leu Asp Gly Ile Ile
305                 310                 315                 320

Glu Lys Met Asn Ile Arg Asp Ile Gln Ile Ala Tyr Gly Gln Thr Glu
                325                 330                 335

Ala Ser Pro Gly Cys Thr Gln Thr Leu Lys Thr Asp Ser Ile Asp Lys
                340                 345                 350

Lys Tyr Asn Ser Val Gly Lys Pro Leu Pro Phe Val Glu Met Lys Val
            355                 360                 365

Val Asp Met Asp Thr Lys Lys Gln Leu Pro Val Asn Asn Val Gly Glu
        370                 375                 380

Ile Tyr Val Arg Gly Phe Asn Val Met Lys Gly Tyr Tyr Lys Asn Asp
385                 390                 395                 400

Leu Leu Thr Arg Lys Thr Ile Asp Lys Glu Gly Trp Leu His Thr Gly
```

```
                    405                 410                 415
Asp Leu Gly Phe Val Asp Lys Glu Gly Tyr Tyr His Ile Thr Gly Arg
            420                 425                 430

Ile Gln Asp Ile Ile Ile Arg Gly Gly Glu Asn Ile Asn Pro His Glu
            435                 440                 445

Ile Glu Glu Lys Leu Leu Ser His Pro Gly Ile Ser Glu Val Glu Val
            450                 455                 460

Ile Gly Val Pro Asp Lys Arg Tyr Gly Glu Glu Ile Val Ala Cys Ile
465                 470                 475                 480

Ile Leu Lys Pro Glu Ser Cys Leu Thr Lys Gly Asp Ile Lys Lys Tyr
            485                 490                 495

Ile Ser Gln Asn Leu Ala His Tyr Lys Val Pro Lys Tyr Ile Glu Phe
            500                 505                 510

Tyr Asp Glu Phe Pro Leu Thr Asp Thr Gly Lys Ile Lys Arg His Glu
            515                 520                 525

Leu Lys Glu Cys Phe Glu Lys Lys Phe Glu Leu Arg Gln Ser Ile
            530                 535                 540

<210> SEQ ID NO 32
<211> LENGTH: 618
<212> TYPE: PRT
<213> ORGANISM: Aspergillus oryzae
<220> FEATURE:
<221> NAME/KEY: MISC_FEATURE
<223> OTHER INFORMATION: Uniprot name: Q2U0G7_ASPOR. Unnamed protein
      product

<400> SEQUENCE: 32

Met Asn Leu Ala Ser Thr Ala Pro Val Ala Ala Arg Phe Ala Asp Pro
1               5                   10                  15

Glu Leu Cys Ser Trp Thr Thr Arg Gly Thr Leu Val Leu Arg Val Glu
            20                  25                  30

Arg Leu Asp Arg Met Arg Leu Thr Phe Thr Leu Phe Tyr Pro Lys Pro
        35                  40                  45

Pro Leu Leu Glu Ser Thr Ile Gly Asp His Phe Ala Gln Ile Val Ser
    50                  55                  60

Ala Tyr Gly Asp Arg Thr Ala Val Ile Cys Lys His Gln Asn Asp Arg
65                  70                  75                  80

Val Thr Tyr Ala Gly Leu Asp Ala Lys Ser Asn Ala Leu Ala Arg Gly
            85                  90                  95

Leu Glu Ser Val Gly Val Arg Thr Gly Asp Arg Val Gly Val Met Leu
            100                 105                 110

Gly Asn Ser Met Glu Phe Ser Ile Ala Thr Tyr Ala Leu Phe Lys Leu
            115                 120                 125

Gly Ala Ile Leu Val Pro Ile Asn Pro Ser Phe Asn Ala Thr Gln Val
        130                 135                 140

Val Ser Ala Leu Thr His Leu Glu Ala Thr His Met Ile Val Ser Thr
145                 150                 155                 160

Glu Ser Asn Leu Pro Arg Lys Glu Pro Arg Ser Asn Ile Pro Ile Leu
            165                 170                 175

Gln His Leu Val Gln Asp Leu His Lys Ser Lys Leu Glu Ser Ala Leu
            180                 185                 190

Val Pro Ser Leu Lys His Ile Ile Ile Val Asp Asn Ser Ser Gly Arg
            195                 200                 205

Val Asp Ile Ser Glu Tyr Arg Ser Leu Thr Lys Phe Ser Ser Val Thr
        210                 215                 220
```

Ser Ala Ala Lys Ala Asp Glu Ala Ala Leu Pro Tyr Arg Asp Leu Ser
225                 230                 235                 240

Pro His Asp Val Val Asn Ile Gln Phe Thr Ser Gly Thr Thr Ala Met
                245                 250                 255

Pro Lys Ala Ala Cys Leu Thr His Arg Ser Val Leu Asn Asn Gly Ser
            260                 265                 270

Gln Ile Gly Asp Arg Met Arg Leu Thr Pro Glu Asp Ile Val Cys Cys
        275                 280                 285

Pro Pro Pro Leu Phe His Cys Phe Gly Ser Val Leu Gly Tyr Met Ala
    290                 295                 300

Thr Ala Thr His Gly Ser Ala Val Val Phe Pro Thr Glu Ser Phe Asn
305                 310                 315                 320

Ala Arg Ala Ala Leu Thr Ala Val Gln Glu Glu Arg Cys Thr Ala Leu
                325                 330                 335

Tyr Gly Val Pro Thr Met Phe Ile Glu Glu Leu Thr Leu Ile Asp Asp
            340                 345                 350

Gly Glu Val Pro Asn Glu Gly Phe Gly His Leu Arg Thr Gly Ile Ala
        355                 360                 365

Ala Gly Ser Ser Val Pro Ala Ala Leu Met Gln Arg Leu His Lys Val
    370                 375                 380

Leu Asn Leu Thr Glu Leu Thr Ile Cys Tyr Gly Met Thr Glu Thr Ser
385                 390                 395                 400

Pro Val Ser Ala Met Thr Thr Asp Asp Pro Ile Asp Lys Arg Ile
                405                 410                 415

Asn Thr Val Gly Arg Leu Met Pro His Val Glu Ala Lys Ile Val Asn
            420                 425                 430

Pro Ala Asp Arg Ser Gln Ile Leu Pro Val Gly Val Pro Gly Glu Leu
        435                 440                 445

Ala Val Ser Gly Tyr Leu Leu Met Lys Glu Tyr Trp Gly Asp Pro Gln
    450                 455                 460

Arg Thr Ala Glu Ser Met Ile Ala Asp Glu Lys Gly Lys Val Trp Met
465                 470                 475                 480

His Ser Gly Asp Glu Ala Thr Ile Ser Pro Asp Gly Tyr Val Thr Ile
                485                 490                 495

Thr Gly Arg Ile Lys Asp Leu Ile Ile Arg Gly Gly Glu Asn Ile His
            500                 505                 510

Pro Leu Glu Ile Glu Asn Cys Ile Leu Thr His Ala Gly Val Met Asp
        515                 520                 525

Val Ser Val Val Gly Val Pro Asp Glu Lys Tyr Gly Glu Val Val Ala
    530                 535                 540

Ala Phe Ile Ile Pro Lys Glu His Gln Asp Glu Ala Ala Pro Leu Thr
545                 550                 555                 560

Glu Glu Asn Ile Arg Glu Trp Val Arg Gly Arg Leu Ser Asn His Leu
                565                 570                 575

Val Pro Lys Tyr Val Phe Asn Leu Glu His Thr Ile Phe Pro Lys
            580                 585                 590

Thr Ala Ser Gly Lys Ile Gln Lys Phe Lys Leu Lys Glu Asp Ala Ile
        595                 600                 605

Arg Thr Leu Lys Glu Arg Asn Ser Leu Ser
    610                 615

<210> SEQ ID NO 33
<211> LENGTH: 606

```
<212> TYPE: PRT
<213> ORGANISM: Aspergillus oryzae
<220> FEATURE:
<221> NAME/KEY: MISC_FEATURE
<223> OTHER INFORMATION: Uniprot name: Q2UH98_ASPOR. Unnamed protein
      product

<400> SEQUENCE: 33

Met Ala Ala Thr Arg Arg Leu Gln Gln Thr Leu Ser His Ile Gln Pro
1               5                   10                  15

Pro Lys Ala Val Glu Gln Leu Ser Ile Val Tyr Gly Pro Thr Gln Pro
            20                  25                  30

Pro Leu Leu Asp Ile Thr Leu Gly Glu Leu Leu Ala Leu Gln Ser Leu
        35                  40                  45

Gln Tyr Gly Glu His Glu Cys Leu Val Phe Pro Trp Thr Gly Thr Arg
50                  55                  60

Trp Thr Tyr Ser Ala Leu Asn Asp Glu Ala Asp Arg Leu Ala Gln Gly
65                  70                  75                  80

Leu Leu Ala Ile Gly Ile His Lys Gly Asp Arg Ile Gly Ile Met Ala
                85                  90                  95

Gly Asn Cys Glu Gln Tyr Ile Ser Val Phe Ala Ala Ala Arg Val
            100                 105                 110

Gly Ala Ile Leu Val Val Leu Asn Asn Thr Tyr Thr Pro Ser Glu Leu
            115                 120                 125

Tyr Tyr Ala Leu Glu His Thr Gly Ser Cys Ala Phe Ile His Tyr Glu
            130                 135                 140

Leu Ala Ser Met Leu Thr Val Phe Ser Cys Tyr Leu Asp Cys Arg Leu
145                 150                 155                 160

Leu Phe Met Thr Pro Arg Ile Gly Arg His Asn Leu Glu Glu Val Leu
                165                 170                 175

Ser Lys Met Gly Pro His Pro Lys Arg Lys Gly Ser Ser Ala Ala Leu
            180                 185                 190

Glu Glu Ile Val Ile Leu Arg Gly Glu His Ser Asn Phe Pro Thr Tyr
            195                 200                 205

Ser Ser Val Ile Glu Arg Gly Leu Ser Val Ser Ser Asn Ala Leu Leu
210                 215                 220

Asp Arg Gln Ala Gln Leu Arg Pro Asp Val Cys Asn Leu Gln Phe
225                 230                 235                 240

Thr Ser Gly Ser Thr Gly Asn Pro Lys Ala Ala Met Leu Thr His His
                245                 250                 255

Asn Leu Val Asn Asn Ser Arg Phe Ile Gly Asp Arg Met Asp Leu Thr
            260                 265                 270

Ser Phe Asp Ile Leu Cys Cys Pro Pro Leu Phe His Cys Phe Gly
            275                 280                 285

Leu Val Leu Gly Met Leu Ala Val Val Thr His Gly Ala Lys Ile Val
            290                 295                 300

Phe Pro Ser Glu Thr Phe Asp Pro Lys Ser Val Leu His Ala Ile Ser
305                 310                 315                 320

Asp Glu Lys Cys Thr Ala Leu His Gly Val Pro Thr Met Phe Glu Ala
                325                 330                 335

Ile Leu Ser Leu Pro Lys Pro Asn Phe Asp Thr His Asn Leu Arg
            340                 345                 350

Thr Gly Ile Ile Ala Gly Ala Pro Val Pro Arg Pro Leu Met Lys Arg
            355                 360                 365

Leu Phe Glu Glu Leu Asn Met Thr Gln Tyr Thr Ser Ser Tyr Gly Leu
```

```
                    370                 375                 380
Thr Glu Ala Ser Pro Thr Cys Phe Asn Ala Val Thr Thr Asp Thr Ile
385                 390                 395                 400

Glu Thr Arg Leu Arg Thr Val Gly Lys Val Met Pro His Ala Lys Ala
                405                 410                 415

Lys Ile Ile Asp Ala Glu Gly Arg Ile Val Pro Val Gly Gln Arg Gly
                420                 425                 430

Glu Leu Cys Ile Ala Gly Tyr Gln Leu Thr Lys Gly Tyr Trp Asn Asn
                435                 440                 445

Pro Asp Lys Thr Ala Glu Thr Leu Thr Thr Asp Ala Asp Gly Thr Thr
                450                 455                 460

Trp Leu Lys Thr Gly Asp Glu Ala Ile Phe Asp Pro Gln Gly Arg Cys
465                 470                 475                 480

Thr Ile Thr Gly Arg Phe Lys Asp Ile Ile Arg Gly Gly Glu Asn
                485                 490                 495

Ile Tyr Pro Leu Glu Ile Glu Arg Leu Ala Ser His Pro Ala Ile
                500                 505                 510

Glu Val Ala Ser Val Ile Gly Ile Pro Asp His Lys Tyr Gly Glu Val
                515                 520                 525

Val Gly Ala Phe Ile Ala Leu Ala Pro Gly Tyr Glu Asn Lys Arg Pro
                530                 535                 540

Ser Asp Glu Glu Leu Arg Val Trp Thr Arg Glu Lys Leu Gly Arg His
545                 550                 555                 560

Lys Ala Pro Gln Tyr Val Phe Val Phe Gly Glu Glu Gly Val Asp Arg
                565                 570                 575

Thr Ile Pro Ile Thr Gly Ser Gly Lys Val Arg Lys Val Asp Leu Arg
                580                 585                 590

Lys Thr Ala Ala Gln Val Leu Glu Arg Thr Lys Ala Asn
                595                 600                 605

<210> SEQ ID NO 34
<211> LENGTH: 577
<212> TYPE: PRT
<213> ORGANISM: Mycobacterium smegmatis
<220> FEATURE:
<221> NAME/KEY: MISC_FEATURE
<223> OTHER INFORMATION: Uniprot name: A0QZG7_MYCS2. AMP-dependent
      synthetase/ligase

<400> SEQUENCE: 34

Met Gln Trp Asn Arg Ala Ile Thr Met Thr Glu Ala Val Pro Arg Asn
1               5                   10                  15

Leu Ser Asp Leu Leu Arg Arg Ser Ala Ser Ala His Pro Asp Ser Val
                20                  25                  30

Phe Ala Phe Pro Asp Gln Arg Tyr Thr Tyr Ala Glu Met Asp Val Arg
            35                  40                  45

Val Gly Asp Phe Val Arg Met Leu Arg Arg Ala Gly Val Gln Ala Gly
        50                  55                  60

Asp His Val Gly Leu Trp Met Pro Ala Ser Leu Asp Met Ile Ala Ala
65              70                  75                  80

Ile Val Ala Cys Ala Arg Ala Gly Ala Val Thr Val Ala Ile Asn Asp
                85                  90                  95

Arg Phe Arg Ile Asp Glu Leu Ser Tyr Val Ile Ala His Ser Asp Leu
            100                 105                 110

Ala Ala Val Ile Thr Ile Ala Pro Thr Gln His Ser Asp Arg Pro Ala
        115                 120                 125
```

Glu Leu Leu Ser Ala Ile Pro Gly Leu Ala Glu Ala Pro Gly Pro Asp
    130                 135                 140

Leu Ala Leu Thr Ala Thr Pro Arg Leu Arg Arg Ile Ile Val Leu Ala
145                 150                 155                 160

Asp Asp Gly Tyr Ser Pro Pro Ala Arg Ala Phe Thr His Gln Ser Ala
                165                 170                 175

Val Gly Leu Pro Thr Thr His Pro Arg Glu Arg Thr Ser Arg His Gly
            180                 185                 190

Val Glu Glu Glu Pro Ala Pro Gly Gly Glu Val Ala Tyr Leu Met
        195                 200                 205

Tyr Thr Ser Gly Thr Ser Ala Ser Pro Lys Ala Cys Met Ile Ala His
    210                 215                 220

Val Ala Val Val Ala Gln Gly Thr Ser Leu Ala Phe Asp Arg Tyr Leu
225                 230                 235                 240

Leu Asp Glu Thr Ser Val Phe Trp Cys Pro Leu Pro Leu Phe His Thr
                245                 250                 255

Ala Gly Leu Ala Thr Leu Thr Ala Cys Ile Thr Ala Gly Ala Ser Phe
                260                 265                 270

Val His Ala Gly Val Phe Asp Pro Ala Gln Ser Leu Arg Ala Met Val
            275                 280                 285

Glu Glu Arg Val Thr His Ala Ile Pro Cys Phe Glu Thr Ile Trp Met
    290                 295                 300

Arg Ile Leu Asp His Pro Asp Phe Ala Val Ala Asp Leu Ser Ser Leu
305                 310                 315                 320

Arg Val Leu Met Asn Thr Gly Gly Glu Asp Leu Leu Arg Lys Leu Gln
                325                 330                 335

Ala Arg Val Pro His Ala Ile Gln Leu Ala Asn Tyr Gly Ile Thr Glu
            340                 345                 350

Gly Ser Gly His Val Ala Met Thr Thr Val Ala Asp Pro Leu Asp Val
    355                 360                 365

Arg Val Cys Thr Gly Gly Lys Pro Leu Pro Gly Met Glu Ala Arg Ile
370                 375                 380

Val Asp Leu Asp Thr Arg Glu Pro Val Ala Pro Asn Val Leu Gly Glu
385                 390                 395                 400

Ile Gln Phe Arg Gly Glu Ser Arg Phe Leu Gly Tyr Tyr Arg Asp Glu
                405                 410                 415

Glu Ala Asn Ala Ala Cys Ile Asp Ala Glu Gly Trp Phe Thr Ser Gly
            420                 425                 430

Asp Leu Gly Val Leu Asp Glu Ala Gly Arg Leu Thr Phe Lys Gly Arg
    435                 440                 445

Ile Lys Asp Met Leu Lys Val Gly Gly Glu Asn Val Ser Ala Leu Glu
    450                 455                 460

Val Glu Ser Tyr Leu Leu Arg His Pro Ala Val Ala Val Val Ala Val
465                 470                 475                 480

Val Gly Ala Pro Asp Ala Tyr Tyr Gly Glu Val Pro Val Ala Tyr Ile
                485                 490                 495

Gln Leu Thr Arg Glu His Lys Leu Thr Glu Ala Asp Val Ile Asp Phe
                500                 505                 510

Cys Leu Asp Arg Ile Ala Thr Tyr Lys Val Pro Arg Tyr Val Arg Phe
            515                 520                 525

Val Asp Glu Trp Pro Met Ser Gly Thr Lys Ile Arg Lys Val Glu Leu
530                 535                 540

-continued

```
Arg Glu Arg Ile Arg Thr Glu Leu Thr Ala Gly Gly Ile Thr Gln Ala
545                 550                 555                 560

Pro Arg Leu Gln Ser Arg Arg Ala Arg Ser Val Val Gln His Ser Ser
                565                 570                 575

Glu

<210> SEQ ID NO 35
<211> LENGTH: 581
<212> TYPE: PRT
<213> ORGANISM: Aspergillus oryzae
<220> FEATURE:
<221> NAME/KEY: MISC_FEATURE
<223> OTHER INFORMATION: Uniprot name: Q2UDA2_ASPOR. Unnamed protein
      product

<400> SEQUENCE: 35

Met Ser Asp Asn Ile Ser Ser Leu Ser Phe Leu His Gly Pro Ser Glu
1               5                   10                  15

Pro Ala Leu Lys Ser Tyr Ser Ile Gly Gln Leu Leu Asn Gln Gln Ala
                20                  25                  30

Ala His Phe Pro Thr Lys Glu Ala Val Ile Phe Pro Thr Glu Gly Thr
            35                  40                  45

Arg Tyr Thr Tyr Gln Glu Leu Asn Leu Arg Val Gln Thr Val Ser Arg
50                  55                  60

Ala Leu Ile Ala His Gly Val Lys Ala Gly Asp Arg Ile Gly Val Phe
65                  70                  75                  80

Cys Gly Asn Cys Val Gly Tyr Val Glu Val Phe Leu Ala Ala Thr Arg
                85                  90                  95

Ile Gly Ala Ile Thr Val Leu Asn Asn Ala Tyr Ser Thr Thr Glu
            100                 105                 110

Cys Leu Asn Val Leu Arg Thr Thr Gly Cys Ser Leu Leu Phe Thr Ala
            115                 120                 125

Thr His Ile Gly Gln Arg Asp Leu Thr Ser Cys Leu Arg Val Leu Lys
130                 135                 140

Ala Ser Leu Asp Gly Asp Glu Leu Pro Ala Leu Lys Gln Ile Ile Leu
145                 150                 155                 160

Leu Lys Thr Asp Gly Asp Ile Ser Lys Gln Phe Gln Ser Phe Ala Ser
                165                 170                 175

Phe Leu Gly Gln Ser Ser Thr Ile Pro Asp Ser Arg Leu Cys Glu Ile
            180                 185                 190

Glu Gln Lys Val Gln Pro Asp Gln Thr Cys Thr Phe Gln Phe Thr Ser
            195                 200                 205

Gly Thr Gly Ala Pro Lys Ile Ala Met Leu Thr His Arg Asn Val Ile
210                 215                 220

Ser Asn Ala His Ser Ile Gly His Arg Leu Leu Leu Ser Glu Asn Asp
225                 230                 235                 240

Val Ile Cys Cys Pro Tyr Pro Leu Phe His Ile Ser Gly Leu Val Ile
                245                 250                 255

Gly Leu Leu Ser Ser Leu Thr Tyr Gly Ala Ala Ile Val Tyr Pro Ser
            260                 265                 270

Pro Thr Phe Asp Pro Ser Ala Val Leu His Glu Val Val Arg Glu Lys
            275                 280                 285

Cys Thr Gly Leu His Gly Val Pro Thr Ile Phe Ile Ala Leu Leu Glu
290                 295                 300

Arg His Arg Gln Leu Lys Thr Ser Pro Ile His Val Arg Thr Gly Leu
305                 310                 315                 320
```

```
Ile Gly Gly Ala Pro Ile Pro Ser Ala Leu Leu Lys Glu Met His Lys
            325                 330                 335

Ala Phe Gly Phe Glu Asp Leu Thr Val Ala Tyr Gly Met Thr Glu Thr
            340                 345                 350

Ser Pro Ile Ser Phe Met Ser Arg Ser Ala Glu Gln Pro Ser Asp Val
            355                 360                 365

Val Val Val His Arg Asp Ile Leu Pro His Thr Phe Ala Lys Ile Ile
            370                 375                 380

Asp Ser Thr Gly Asn Ile Val Pro Arg Gly Ile Arg Gly Glu Leu Cys
385                 390                 395                 400

Ile Ala Gly Ser Gly Val Gln Lys Gly Tyr Tyr Gln Asn Pro Glu Lys
            405                 410                 415

Thr Arg Glu Ala Leu Lys Thr Asp His Ser Gly Val Met Trp Met His
            420                 425                 430

Thr Gly Asp Glu Ala Val Met Asp Thr Gln Gly His Cys Val Ile Thr
            435                 440                 445

Gly Arg Ile Lys Asp Ile Ile Ile Arg Gly Ala Glu Asn Ile Tyr Pro
            450                 455                 460

Ala Glu Ile Glu Glu Leu Asn Lys His His Ala Ile Ser Gln Ser
465                 470                 475                 480

Cys Val Val Gly Val Lys His Glu Thr Leu Gly Glu Glu Val Ala Ala
            485                 490                 495

Phe Leu Gln Gly Thr Pro Gly Gln Pro Arg Pro Ser Gly Ala Glu Ile
            500                 505                 510

Ile Glu Trp Leu Gln Leu Ser Leu Gly Ala Gln Lys Ala Pro Ala Trp
            515                 520                 525

Val Phe Trp Leu Gly Asp Gly Asp Val Pro Val Phe Pro Ile Thr
            530                 535                 540

Asp Ser Gly Lys Ile Lys Arg Asn Glu Met Ala Asp Leu Gly Asn Arg
545                 550                 555                 560

Leu Val Gly Lys Ile Arg Gly Ser Val Pro Ser Met Ser Cys Met Thr
            565                 570                 575

Ile Thr Val Leu Pro
            580

<210> SEQ ID NO 36
<211> LENGTH: 570
<212> TYPE: PRT
<213> ORGANISM: uncultured bacterium MedeBAC49C08
<220> FEATURE:
<221> NAME/KEY: MISC_FEATURE
<223> OTHER INFORMATION: Uniprot name: Q4PK67_9BACT.

<400> SEQUENCE: 36

Met Ala Gly Gln Leu Asp Leu Ile Asp Pro Gln Lys Arg Leu Glu Thr
1               5                   10                  15

Phe Glu Lys Ile Ser Ser Glu Gly Leu Leu Gly Val Ser Lys Glu Thr
            20                  25                  30

Val Arg Gly Asn Glu Tyr Tyr Val Phe Ser Glu Ser Pro Asp Asn Leu
            35                  40                  45

Leu Gly Tyr Tyr Gln Leu Gly Leu Thr His Gly Glu Trp Thr His Val
            50                  55                  60

Val Phe Glu Asp Gln Gln Ile Pro Tyr Ser Glu Thr Leu Ser Arg Ser
65                  70                  75                  80

Tyr Gln Leu Ala Asn Ser Leu Gln Asn Ile Tyr Gly Ile Glu Lys Gly
```

```
                    85                  90                  95
Asp Lys Val Ala Phe Ser Met Arg Asn Tyr Pro Glu Trp Met Phe Ala
                100                 105                 110

Tyr Met Ala Val Thr Ser Ile Gly Ala Val Ala Val Pro Leu Asn Ser
            115                 120                 125

Trp Trp Gln Gly Asp Glu Leu Glu Tyr Gly Leu Asn Asn Ser Glu Ser
        130                 135                 140

Lys Leu Phe Ile Ala Asp Gln Asp Arg Leu Glu Arg Leu Gly Asp Lys
145                 150                 155                 160

Cys Pro Glu Ile Lys Arg Ile Ser Val Arg Ser Glu Asn Pro Asp His
                165                 170                 175

Ser Asp Ile Asp Phe Tyr Lys Val Ile Glu Asn Gln Asn Lys Thr Leu
            180                 185                 190

Asp Asn Glu Val Ala Val Ser Pro Asp Ala Ser Ile Met Tyr Thr
        195                 200                 205

Ser Gly Ser Thr Gly His Pro Lys Gly Val Val Ser Ser His Arg Ser
    210                 215                 220

Val Met Phe Ala Pro Phe Tyr Trp Ile Ala Leu Gln Thr Leu Leu Lys
225                 230                 235                 240

Glu Ser Ser Asp Glu Asp Asn Leu Gly Ile Met Gly Glu Gly Asp Gln
                245                 250                 255

Ala Ala Val Leu Val Ser Val Pro Leu Phe His Val Thr Gly Ser His
            260                 265                 270

Ala Ile Phe Leu Leu Ser Ile Pro Val Gly Arg Lys Thr Val Leu Met
        275                 280                 285

His Lys Trp Asp Pro Glu Val Ala Leu Asp Leu Ile Glu Arg Glu Lys
    290                 295                 300

Ile Ser Asp Phe Thr Gly Val Pro Thr Met Ser Tyr Glu Leu Val Glu
305                 310                 315                 320

Ala Gln Lys Lys Asn Pro Arg Asp Ile Ser Ser Leu Arg Gly Leu Asn
                325                 330                 335

Gly Gly Gly Ala Ala Arg Pro Pro Glu Gln Val Lys Glu Met Arg Glu
            340                 345                 350

Asn Phe Lys Asp Thr Ser Pro Gly Ile Gly Tyr Gly Leu Thr Glu Thr
        355                 360                 365

Asn Ala Leu Ala Ala Asn Asn Ala Gly Asp Leu Tyr Ser Glu Lys Pro
    370                 375                 380

Ser Ser Thr Gly Phe Pro Leu Pro Lys Leu Ile Asp Leu Lys Ile Val
385                 390                 395                 400

Asp Asp Asp Gly Asn Asp Leu Gly Thr Asn Glu Ile Gly Glu Val Cys
                405                 410                 415

Ile Arg Gly Ala Cys Asn Phe Lys Asn Tyr Trp Lys Asn Gln Asp Ala
            420                 425                 430

Thr Asp Glu Val Leu Asp Glu Gly Trp Phe Arg Ser Gly Asp Leu
        435                 440                 445

Gly Leu Leu Asp Ser Asp Gly Phe Leu Tyr Ile Lys Asp Arg Lys Lys
    450                 455                 460

Asp Ile Val Ile Arg Gly Gly Glu Asn Ile Ala Cys Leu Glu Val Glu
465                 470                 475                 480

Ala Ala Ile Thr Glu His Pro Ser Val Leu Glu Ala Ser Val Phe Gly
                485                 490                 495

Ile Pro Asp Glu Arg Leu Gly Glu Lys Leu Ala Thr Val Val Ser Cys
            500                 505                 510
```

-continued

```
Arg Glu Asp Gln Met Ile Asp Glu Val Glu Leu Ser Gly Phe Leu Ala
            515                 520                 525

Ser Lys Leu Ala Lys Phe Lys Ile Pro Glu Phe Met Lys Phe Gln Thr
    530                 535                 540

Glu Lys Leu Pro Arg Ile Ala Ser Gly Lys Ile Ala Lys Lys Gln Leu
545                 550                 555                 560

Arg Glu Glu Ala Val Ser Thr Ile Gly Lys
                565                 570

<210> SEQ ID NO 37
<211> LENGTH: 546
<212> TYPE: PRT
<213> ORGANISM: Moorella thermoacetica
<220> FEATURE:
<221> NAME/KEY: MISC_FEATURE
<223> OTHER INFORMATION: Uniprot name: Q2RJ14_MOOTA. AMP-dependent
      synthetase and ligase

<400> SEQUENCE: 37

Met Ala Val Ser Gly Tyr Gly Lys Trp Phe Glu Leu Ala Glu Lys Asp
1               5                   10                  15

Leu Lys Thr Arg Lys Phe Asn Gly Val Glu Tyr Arg Tyr Tyr Asp His
            20                  25                  30

Gly Thr Thr Asn Leu Trp Glu Asp Phe Ser Arg Ser Val Ser Arg Gln
        35                  40                  45

Pro Asp Lys Thr Ala Leu Arg Ala Gly Asn Ser Ser Leu Ser Tyr Arg
    50                  55                  60

Glu Met Gln Glu Ala Ser Arg Arg Leu Ala Ser Gly Leu Trp Asn Lys
65                  70                  75                  80

Tyr Gln Val Lys Lys Gly Asp Val Val Ala Leu Leu Val Asn Ser
                85                  90                  95

Ile Asp Phe Cys Leu Ser Phe Tyr Ala Ala Met Tyr Leu Gly Ala Ile
                100                 105                 110

Ala Leu Pro Leu Ser Thr Lys Leu Lys Ala Thr Glu Leu Asn Phe Met
            115                 120                 125

Leu Lys Asp Ser Gly Ala Arg Ile Leu Ile Thr Asn Pro Glu Trp Leu
    130                 135                 140

Pro Asn Val Leu Pro Phe Ile Lys Glu Thr Ser Ile Glu Gln Ile Ile
145                 150                 155                 160

Val Thr Glu Pro Ile Thr Asp Lys Ile Asn Ile Asn Phe Gly Asn Ala
                165                 170                 175

Ser Ile Ile Thr Leu Lys Asn Val Phe Arg Glu Thr Glu Ile Pro Pro
            180                 185                 190

Ala Pro Val Asp Glu Gln Asp Gly Ala Val Ile Met Tyr Thr Ser Gly
        195                 200                 205

Thr Thr Gly Lys Pro Lys Gly Ala Tyr Leu Thr His Phe Asn Leu Leu
    210                 215                 220

Gln Ser Val Ile Ser Tyr Glu Arg Thr Leu Gln Leu Thr Ala Ala Asp
225                 230                 235                 240

Ser Thr Leu Ile Ala Val Pro Ile Phe His Ile Thr Gly Leu Ala Ala
                245                 250                 255

Leu Phe Leu Leu Phe Met His Ile Gly Gly Thr Val Tyr Leu Leu Pro
            260                 265                 270

Phe Phe Asn Thr Gln Glu Val Leu Asn Ile Leu Thr Cys Tyr Ser Ile
        275                 280                 285
```

```
Thr Phe Phe His Ala Ala Pro Thr Val Tyr Ile Met Leu Leu Glu Gln
            290                 295                 300

Gly Tyr Arg His Tyr Gln Leu Pro Asp Leu Arg Lys Ala Ala Cys Gly
305                 310                 315                 320

Gly Gly Ala Ile Pro Ile Glu Thr Ile Lys Lys Ile Lys Thr Trp Ile
                325                 330                 335

Pro Gln Leu Glu Phe His Thr Val Tyr Gly Leu Thr Glu Thr Ser Ser
            340                 345                 350

Pro Ala Thr Leu Phe Pro Gly Asp Val Ala Thr Ser Pro Arg Ile Gly
            355                 360                 365

Thr Ser Gly Ile Pro Ile Pro Val Val Asp Cys Lys Val Ile Asp Ala
370                 375                 380

Glu Gly Arg Asp Ile Thr Gly Lys Gly Val Gly Glu Leu Cys Ile Arg
385                 390                 395                 400

Gly Pro Val Val Thr Gln Gln Tyr Trp Asn Asn Asp Glu Ala Thr Thr
                405                 410                 415

Arg Ala Phe Gln Gly Gly Trp Phe Arg Thr Gly Asp Val Ala Arg Ile
            420                 425                 430

Asp Gly Asp Gly Tyr Val Tyr Ile Met Asp Arg Leu Lys Asp Met Ile
            435                 440                 445

Asn Arg Gly Gly Glu Lys Ile Tyr Ser Leu Glu Val Glu Asn Val Ile
450                 455                 460

Tyr Ser His Pro Gly Val Lys Glu Val Ala Val Ile Gly Ser Val Asp
465                 470                 475                 480

Pro Ile Tyr Gly Glu Val Ala Arg Ala Val Val Pro Asn Asn His
                485                 490                 495

Gly Ser Ser Ile Thr Gly Arg Glu Ile Gln Asp Trp Val Arg Ala Arg
            500                 505                 510

Leu Ala Lys Tyr Lys Val Pro Gln Tyr Val Asn Phe Val Asn Glu Leu
            515                 520                 525

Pro Lys Asn Ala Asn Gly Lys Ile Asp Lys Lys Leu Leu Arg Gln Gln
            530                 535                 540

Phe Gln
545

<210> SEQ ID NO 38
<211> LENGTH: 238
<212> TYPE: PRT
<213> ORGANISM: Bacillus subtilis
<220> FEATURE:
<221> NAME/KEY: MISC_FEATURE
<223> OTHER INFORMATION: Uniprot name: SCOA_BACSU. Probable succinyl-
      CoA:3-ketoacid coenzyme A transferase subunit A

<400> SEQUENCE: 38

Met Gly Lys Val Leu Ser Ser Ser Lys Glu Ala Ala Lys Leu Ile His
1               5                   10                  15

Asp Gly Asp Thr Leu Ile Ala Gly Gly Phe Gly Leu Cys Gly Ile Pro
                20                  25                  30

Glu Gln Leu Ile Leu Ser Ile Arg Asp Gln Gly Val Lys Asp Leu Thr
            35                  40                  45

Val Val Ser Asn Asn Cys Gly Val Asp Asp Trp Gly Leu Gly Leu Leu
        50                  55                  60

Leu Ala Asn Lys Gln Ile Lys Lys Met Ile Ala Ser Tyr Val Gly Glu
65                  70                  75                  80

Asn Lys Ile Phe Glu Arg Gln Phe Leu Ser Gly Glu Leu Glu Val Glu
```

```
                 85                  90                  95

Leu Val Pro Gln Gly Thr Leu Ala Glu Arg Ile Arg Ala Gly Gly Ala
            100                 105                 110

Gly Ile Pro Gly Phe Tyr Thr Ala Thr Gly Val Gly Thr Ser Ile Ala
            115                 120                 125

Glu Gly Lys Glu His Lys Thr Phe Gly Gly Arg Thr Tyr Val Leu Glu
        130                 135                 140

Arg Gly Ile Thr Gly Asp Val Ala Ile Val Lys Ala Trp Lys Ala Asp
145                 150                 155                 160

Thr Met Gly Asn Leu Ile Phe Arg Lys Thr Ala Arg Asn Phe Asn Pro
                165                 170                 175

Ile Ala Ala Met Ala Gly Lys Ile Thr Ile Ala Glu Ala Glu Glu Ile
            180                 185                 190

Val Glu Ala Gly Glu Leu Asp Pro Asp His Ile His Thr Pro Gly Ile
        195                 200                 205

Tyr Val Gln His Val Val Leu Gly Ala Ser Gln Glu Lys Arg Ile Glu
    210                 215                 220

Lys Arg Thr Val Gln Gln Ala Ser Gly Lys Gly Glu Ala Lys
225                 230                 235

<210> SEQ ID NO 39
<211> LENGTH: 216
<212> TYPE: PRT
<213> ORGANISM: Bacillus subtilis
<220> FEATURE:
<221> NAME/KEY: MISC_FEATURE
<223> OTHER INFORMATION: Uniprot name: SCOB_BACSU. Probable succinyl-
      CoA:3-ketoacid coenzyme A transferase subunit B

<400> SEQUENCE: 39

Met Lys Glu Ala Arg Lys Arg Met Val Lys Arg Ala Val Gln Glu Ile
1               5                   10                  15

Lys Asp Gly Met Asn Val Asn Leu Gly Ile Gly Met Pro Thr Leu Val
            20                  25                  30

Ala Asn Glu Ile Pro Asp Gly Val His Val Met Leu Gln Ser Glu Asn
        35                  40                  45

Gly Leu Leu Gly Ile Gly Pro Tyr Pro Leu Glu Gly Thr Glu Asp Ala
    50                  55                  60

Asp Leu Ile Asn Ala Gly Lys Glu Thr Ile Thr Glu Val Thr Gly Ala
65                  70                  75                  80

Ser Tyr Phe Asp Ser Ala Glu Ser Phe Ala Met Ile Arg Gly Gly His
                85                  90                  95

Ile Asp Leu Ala Ile Leu Gly Gly Met Glu Val Ser Glu Gln Gly Asp
            100                 105                 110

Leu Ala Asn Trp Met Ile Pro Gly Lys Met Val Lys Gly Met Gly Gly
        115                 120                 125

Ala Met Asp Leu Val Asn Gly Ala Lys Arg Ile Val Val Ile Met Glu
    130                 135                 140

His Val Asn Lys His Gly Glu Ser Lys Val Lys Lys Thr Cys Ser Leu
145                 150                 155                 160

Pro Leu Thr Gly Gln Lys Val His Arg Leu Ile Thr Asp Leu Ala
                165                 170                 175

Val Phe Asp Phe Val Asn Gly Arg Met Thr Leu Thr Glu Leu Gln Asp
            180                 185                 190

Gly Val Thr Ile Glu Glu Val Tyr Glu Lys Thr Glu Ala Asp Phe Ala
        195                 200                 205
```

```
Val Ser Gln Ser Val Leu Asn Ser
    210             215

<210> SEQ ID NO 40
<211> LENGTH: 232
<212> TYPE: PRT
<213> ORGANISM: Helicobacter pylori (Campylobacter pylori)
<220> FEATURE:
<221> NAME/KEY: MISC_FEATURE
<223> OTHER INFORMATION: Uniprot name: SCOA_HELPY. Succinyl-CoA:3-
      ketoacid coenzyme A transferase subunit A

<400> SEQUENCE: 40

Met Asn Lys Val Ile Thr Asp Leu Asp Lys Ala Leu Ser Ala Leu Lys
1               5                   10                  15

Asp Gly Asp Thr Ile Leu Val Gly Gly Phe Gly Leu Cys Gly Ile Pro
            20                  25                  30

Glu Tyr Ala Ile Asp Tyr Ile Tyr Lys Lys Gly Ile Lys Asp Leu Ile
        35                  40                  45

Val Val Ser Asn Asn Cys Gly Val Asp Asp Phe Gly Leu Gly Ile Leu
    50                  55                  60

Leu Glu Lys Lys Gln Ile Lys Lys Ile Ile Ala Ser Tyr Val Gly Glu
65                  70                  75                  80

Asn Lys Ile Phe Glu Ser Gln Met Leu Asn Gly Glu Ile Glu Val Val
                85                  90                  95

Leu Thr Pro Gln Gly Thr Leu Ala Glu Asn Leu His Ala Gly Gly Ala
            100                 105                 110

Gly Ile Pro Ala Tyr Tyr Thr Pro Thr Gly Val Gly Thr Leu Ile Ala
        115                 120                 125

Gln Gly Lys Glu Ser Arg Glu Phe Asn Gly Lys Glu Tyr Ile Leu Glu
    130                 135                 140

Arg Ala Ile Thr Gly Asp Tyr Gly Leu Ile Lys Ala Tyr Lys Ser Asp
145                 150                 155                 160

Thr Leu Gly Asn Leu Val Phe Arg Lys Thr Ala Arg Asn Phe Asn Pro
                165                 170                 175

Leu Cys Ala Met Ala Ala Lys Ile Cys Val Ala Glu Val Glu Glu Ile
            180                 185                 190

Val Pro Ala Gly Glu Leu Asp Pro Asp Glu Ile His Leu Pro Gly Ile
        195                 200                 205

Tyr Val Gln His Ile Tyr Lys Gly Glu Lys Phe Glu Lys Arg Ile Glu
    210                 215                 220

Lys Ile Thr Thr Arg Ser Thr Lys
225                 230

<210> SEQ ID NO 41
<211> LENGTH: 207
<212> TYPE: PRT
<213> ORGANISM: Helicobacter pylori (Campylobacter pylori)
<220> FEATURE:
<221> NAME/KEY: MISC_FEATURE
<223> OTHER INFORMATION: Uniprot name: SCOB_HELPY. Succinyl-CoA:3-
      ketoacid coenzyme A transferase subunit B

<400> SEQUENCE: 41

Met Arg Glu Ala Ile Ile Lys Arg Ala Ala Lys Glu Leu Lys Glu Gly
1               5                   10                  15

Met Tyr Val Asn Leu Gly Ile Gly Leu Pro Thr Leu Val Ala Asn Glu
            20                  25                  30
```

Val Ser Gly Met Asn Ile Val Phe Gln Ser Glu Asn Gly Leu Leu Gly
        35                  40                  45

Ile Gly Ala Tyr Pro Leu Glu Gly Ser Val Asp Ala Asp Leu Ile Asn
 50                  55                  60

Ala Gly Lys Glu Thr Ile Thr Val Val Pro Gly Ala Ser Phe Phe Asn
 65                  70                  75                  80

Ser Ala Asp Ser Phe Ala Met Ile Arg Gly His Ile Asp Leu Ala
                85                  90                  95

Ile Leu Gly Gly Met Glu Val Ser Gln Asn Gly Asp Leu Ala Asn Trp
                100                 105                 110

Met Ile Pro Lys Lys Leu Ile Lys Gly Met Gly Ala Met Asp Leu
                115                 120                 125

Val His Gly Ala Lys Lys Val Ile Val Ile Met Glu His Cys Asn Lys
    130                 135                 140

Tyr Gly Glu Ser Lys Val Lys Lys Glu Cys Ser Leu Pro Leu Thr Gly
145                 150                 155                 160

Lys Gly Val Val His Gln Leu Ile Thr Asp Leu Ala Val Phe Glu Phe
                165                 170                 175

Ser Asn Asn Ala Met Lys Leu Val Glu Leu Gln Glu Gly Val Ser Leu
                180                 185                 190

Asp Gln Val Lys Glu Lys Thr Glu Ala Glu Phe Glu Val Arg Leu
                195                 200                 205

<210> SEQ ID NO 42
<211> LENGTH: 232
<212> TYPE: PRT
<213> ORGANISM: Helicobacter pylori (Campylobacter pylori)
<220> FEATURE:
<221> NAME/KEY: MISC_FEATURE
<223> OTHER INFORMATION: Uniprot name: SCOA_HELPJ. Succinyl-CoA:3-
      ketoacid coenzyme A transferase subunit A

<400> SEQUENCE: 42

Met Asn Lys Val Ile Thr Asp Leu Asp Lys Ala Leu Ser Gly Leu Lys
 1               5                   10                  15

Asp Gly Asp Thr Ile Leu Val Gly Gly Phe Gly Leu Cys Gly Ile Pro
                20                  25                  30

Glu Tyr Ala Ile Asp Tyr Ile Tyr Lys Lys Gly Ile Lys Asp Leu Ile
        35                  40                  45

Val Val Ser Asn Asn Cys Gly Val Asp Asp Phe Gly Leu Gly Ile Leu
 50                  55                  60

Leu Glu Lys Lys Gln Ile Lys Lys Ile Ala Ser Tyr Val Gly Glu
 65                  70                  75                  80

Asn Lys Ile Phe Glu Ser Gln Met Leu Asn Gly Glu Ile Glu Val Val
                85                  90                  95

Leu Thr Pro Gln Gly Thr Leu Ala Glu Asn Leu Arg Ala Gly Gly Ala
                100                 105                 110

Gly Ile Pro Ala Tyr Tyr Thr Pro Thr Gly Val Gly Thr Leu Ile Ala
                115                 120                 125

Gln Gly Lys Glu Ser Arg Glu Phe Asn Gly Lys Glu Tyr Ile Leu Glu
    130                 135                 140

Arg Ala Ile Thr Gly Asp Tyr Gly Leu Ile Lys Ala Tyr Lys Ser Asp
145                 150                 155                 160

Thr Leu Gly Asn Leu Val Phe Arg Lys Thr Ala Arg Asn Phe Asn Pro
                165                 170                 175

Leu Cys Ala Met Ala Ala Lys Ile Cys Val Ala Glu Val Glu Glu Ile

```
                   180                 185                 190
Val Pro Ala Gly Glu Leu Asp Pro Asp Glu Ile His Leu Pro Gly Ile
            195                 200                 205

Tyr Val Gln His Ile Tyr Lys Gly Glu Lys Phe Glu Lys Arg Ile Glu
            210                 215                 220

Lys Thr Thr Thr Arg Ser Ala Lys
225                 230

<210> SEQ ID NO 43
<211> LENGTH: 207
<212> TYPE: PRT
<213> ORGANISM: Helicobacter pylori (Campylobacter pylori)
<220> FEATURE:
<221> NAME/KEY: MISC_FEATURE
<223> OTHER INFORMATION: Uniprot name: SCOB_HELPJ. Succinyl-CoA:3-
      ketoacid coenzyme A transferase subunit B

<400> SEQUENCE: 43

Met Arg Glu Ala Ile Ile Lys Arg Ala Ala Lys Glu Leu Lys Glu Gly
1               5                   10                  15

Met Tyr Val Asn Leu Gly Ile Gly Leu Pro Thr Leu Val Ala Asn Glu
            20                  25                  30

Val Ser Gly Met Asn Ile Val Phe Gln Ser Glu Asn Gly Leu Leu Gly
        35                  40                  45

Ile Gly Ala Tyr Pro Leu Glu Gly Gly Val Asp Ala Asp Leu Ile Asn
    50                  55                  60

Ala Gly Lys Glu Thr Ile Thr Val Val Pro Gly Ala Ser Phe Phe Asn
65                  70                  75                  80

Ser Ala Asp Ser Phe Ala Met Ile Arg Gly Gly His Ile Asp Leu Ala
                85                  90                  95

Ile Leu Gly Gly Met Glu Val Ser Gln Asn Gly Asp Leu Ala Asn Trp
            100                 105                 110

Met Ile Pro Lys Lys Leu Ile Lys Gly Met Gly Gly Ala Met Asp Leu
        115                 120                 125

Val His Gly Ala Lys Lys Val Ile Val Ile Met Glu His Cys Asn Lys
    130                 135                 140

Tyr Gly Glu Ser Lys Val Lys Lys Glu Cys Ser Leu Pro Leu Thr Gly
145                 150                 155                 160

Lys Gly Val Val His Gln Leu Ile Thr Asp Leu Ala Val Phe Glu Phe
                165                 170                 175

Ser Asn Asn Ala Met Glu Leu Val Glu Leu Gln Glu Gly Val Ser Leu
            180                 185                 190

Asp Gln Val Lys Glu Lys Thr Glu Ala Glu Phe Glu Val His Leu
        195                 200                 205

<210> SEQ ID NO 44
<211> LENGTH: 248
<212> TYPE: PRT
<213> ORGANISM: Mycobacterium bovis
<220> FEATURE:
<221> NAME/KEY: MISC_FEATURE
<223> OTHER INFORMATION: Uniprot name: SCOA_MYCBO. Probable succinyl-
      CoA:3-ketoacid coenzyme A transferase subunit A

<400> SEQUENCE: 44

Met Asp Lys Val Val Ala Thr Ala Ala Glu Ala Val Ala Asp Ile Ala
1               5                   10                  15

Asn Gly Ser Ser Leu Ala Val Gly Gly Phe Gly Leu Cys Gly Ile Pro
            20                  25                  30
```

Glu Ala Leu Ile Ala Ala Leu Val Asp Ser Gly Val Thr Asp Leu Glu
35 40 45

Thr Val Ser Asn Asn Cys Gly Ile Asp Gly Val Gly Leu Gly Leu Leu
50 55 60

Leu Gln His Lys Arg Ile Arg Arg Thr Val Ser Ser Tyr Val Gly Glu
65 70 75 80

Asn Lys Glu Phe Ala Arg Gln Phe Leu Ala Gly Glu Leu Glu Val Glu
85 90 95

Leu Thr Pro Gln Gly Thr Leu Ala Glu Arg Leu Arg Ala Gly Gly Met
100 105 110

Gly Ile Pro Ala Phe Tyr Thr Pro Ala Gly Val Gly Thr Gln Val Ala
115 120 125

Asp Gly Gly Leu Pro Trp Arg Tyr Asp Ala Ser Gly Gly Val Ala Val
130 135 140

Val Ser Pro Ala Lys Glu Thr Arg Glu Phe Asp Gly Val Thr Tyr Val
145 150 155 160

Leu Glu Arg Gly Ile Arg Thr Asp Phe Ala Leu Val His Ala Trp Gln
165 170 175

Gly Asp Arg His Gly Asn Leu Met Tyr Arg His Ala Ala Ala Asn Phe
180 185 190

Asn Pro Glu Cys Ala Ser Ala Gly Arg Ile Thr Ile Ala Glu Val Glu
195 200 205

His Leu Val Glu Pro Gly Glu Ile Asp Pro Ala Thr Val His Thr Pro
210 215 220

Gly Val Phe Val His Arg Val Val His Val Pro Asn Pro Ala Lys Lys
225 230 235 240

Ile Glu Arg Glu Thr Val Arg Gln
245

<210> SEQ ID NO 45
<211> LENGTH: 218
<212> TYPE: PRT
<213> ORGANISM: Mycobacterium bovis
<220> FEATURE:
<221> NAME/KEY: MISC_FEATURE
<223> OTHER INFORMATION: Uniprot name: SCOB_MYCBO. Probable succinyl-
CoA:3-ketoacid coenzyme A transferase subunit B

<400> SEQUENCE: 45

Met Ser Ala Pro Gly Trp Ser Arg Asp Glu Met Ala Ala Arg Val Ala
1 5 10 15

Ala Glu Phe Glu Asp Gly Gln Tyr Val Asn Leu Gly Ile Gly Met Pro
20 25 30

Thr Leu Ile Pro Asn His Ile Pro Asp Gly Val His Val Val Leu His
35 40 45

Ser Glu Asn Gly Ile Leu Gly Val Gly Pro Tyr Pro Arg Arg Glu Asp
50 55 60

Val Asp Ala Asp Leu Ile Asn Ala Gly Lys Glu Thr Val Thr Thr Leu
65 70 75 80

Pro Gly Ala Ala Phe Phe Ser Ser Ser Thr Ser Phe Gly Ile Ile Arg
85 90 95

Gly Gly His Leu Asp Val Ala Val Leu Gly Ala Met Gln Val Ser Val
100 105 110

Thr Gly Asp Leu Ala Asn Trp Met Ile Pro Gly Lys Met Val Lys Gly
115 120 125

```
Met Gly Gly Ala Met Asp Leu Val His Gly Ala Arg Lys Val Ile Val
    130                 135                 140

Met Met Glu His Thr Ala Lys Asp Gly Ser Pro Lys Ile Leu Glu Arg
145                 150                 155                 160

Cys Thr Leu Pro Leu Thr Gly Val Gly Cys Val Asp Arg Ile Val Thr
                165                 170                 175

Glu Leu Ala Val Ile Asp Val Cys Ala Asp Gly Leu His Leu Val Gln
                180                 185                 190

Thr Ala Pro Gly Val Ser Val Asp Glu Val Val Ala Lys Thr Gln Pro
            195                 200                 205

Pro Leu Val Leu Arg Asp Leu Ala Thr Gln
    210                 215

<210> SEQ ID NO 46
<211> LENGTH: 234
<212> TYPE: PRT
<213> ORGANISM: Acinetobacter baylyi
<220> FEATURE:
<221> NAME/KEY: MISC_FEATURE
<223> OTHER INFORMATION: Uniprot name: Q6F9I4_ACIAD. Acetoacetyl-CoA
      transferase, alpha subunit

<400> SEQUENCE: 46

Met Asp Lys Val Tyr Lys Ser Ala Ala Leu Ala Leu Gln Asp Ile Val
1               5                   10                  15

Lys Asp His Gln Thr Leu Ala Val Gly Gly Phe Gly Leu Cys Gly Ile
                20                  25                  30

Pro Glu Ala Leu Ile Gly Ala Leu Lys Asp Thr Gln Val Lys His Leu
            35                  40                  45

Thr Cys Ile Ser Asn Asn Ala Gly Val Asp Asp Phe Gly Leu Gly Leu
        50                  55                  60

Leu Leu Gln Thr Lys Gln Ile Lys Lys Met Ile Ser Ser Tyr Val Gly
65                  70                  75                  80

Glu Asn Lys Glu Phe Glu Arg Gln Tyr Leu Asn Gly Glu Leu Glu Val
                85                  90                  95

Glu Leu Thr Pro Gln Gly Thr Leu Ala Glu Lys Leu Arg Ala Gly Gly
            100                 105                 110

Ala Gly Ile Pro Ala Phe Tyr Thr Gln Thr Gly Val Gly Thr Leu Ile
        115                 120                 125

Ala Glu Gly Lys Glu Gln Arg Glu Phe Asp Gly Lys Thr Tyr Ile Leu
    130                 135                 140

Glu Pro Ser Leu Thr Ala Asp Ile Ala Leu Val Lys Ala Tyr Lys Ala
145                 150                 155                 160

Asp Arg Ala Gly Asn Leu Val Phe Arg Lys Thr Ala Arg Asn Phe Asn
                165                 170                 175

Pro Glu Cys Ala Met Ala Gly Lys Ile Thr Val Ala Glu Val Glu Gln
            180                 185                 190

Ile Val Glu Thr Gly Glu Leu Asp Pro Asp Glu Ile His Leu Ala Gly
        195                 200                 205

Ile Phe Val His Arg Val Val Leu Asn Ser Ala Pro Glu Lys Arg Ile
    210                 215                 220

Glu Gln Lys Thr Leu Lys Ala Gln Gly Ala
225                 230

<210> SEQ ID NO 47
<211> LENGTH: 214
<212> TYPE: PRT
```

-continued

<213> ORGANISM: Acinetobacter baylyi
<220> FEATURE:
<221> NAME/KEY: MISC_FEATURE
<223> OTHER INFORMATION: Uniprot name: Q6F9I3_ACIAD. Acetoacetyl-CoA
      transferase, beta subunit

<400> SEQUENCE: 47

Met Ala Trp Thr Arg Glu Gln Met Ala Gln Arg Ala Ala Gln Glu Leu
1               5                   10                  15

Gln Asp Gly Phe Tyr Val Asn Leu Gly Ile Gly Leu Pro Thr Leu Val
            20                  25                  30

Ala Asn Tyr Ile Pro Ala Asp Val Glu Val Trp Leu Gln Ser Glu Asn
        35                  40                  45

Gly Leu Leu Gly Ile Gly Glu Phe Pro Thr Glu Asp Thr Val Asp Ala
    50                  55                  60

Asp Leu Ile Asn Ala Gly Lys Gln Thr Val Thr Ala Arg Ala Gly Ala
65                  70                  75                  80

Ala Phe Phe Ser Ser Ser Glu Ser Phe Gly Met Ile Arg Gly Gly His
                85                  90                  95

Val Asn Ile Ala Ile Leu Gly Ala Met Glu Val Ser Glu Lys Gly Asp
            100                 105                 110

Leu Ala Asn Trp Met Ile Pro Gly Lys Lys Val Lys Gly Met Gly Gly
        115                 120                 125

Ala Met Asp Leu Val Val Gly Val Gln Arg Val Val Leu Met Glu
    130                 135                 140

His Cys Ala Lys Asp Gly Ser Ala Lys Ile Val Ser Glu Cys Ser Leu
145                 150                 155                 160

Pro Leu Thr Gly Gln Gly Val Val His Arg Ile Ile Thr Asp Leu Gly
                165                 170                 175

Val Met Asp Ile Val Pro Glu Gly Ile Gln Leu Val Glu Leu Ala Asp
            180                 185                 190

Gly Val Thr Leu Gln Gln Ile Gln Ala Ala Ser Gly Val Glu Leu Leu
        195                 200                 205

Gln His Ala Ala Leu Ala
    210

<210> SEQ ID NO 48
<211> LENGTH: 213
<212> TYPE: PRT
<213> ORGANISM: Acinetobacter bereziniae (Acinetobacter genomosp. 10)
<220> FEATURE:
<221> NAME/KEY: MISC_FEATURE
<223> OTHER INFORMATION: Uniprot name: A0A0A8TUV0_ACIBZ . Succinyl-
      CoA:3-ketoacid-coenzyme A transferase subunit B

<400> SEQUENCE: 48

Met Ala Trp Thr Lys Gln Gln Met Ala Gln Arg Ala Ala Lys Glu Leu
1               5                   10                  15

Gln Asp Gly Phe Tyr Val Asn Leu Gly Ile Gly Leu Pro Thr Leu Val
            20                  25                  30

Ala Asn Tyr Ile Pro Glu Gly Met Asp Val Trp Leu Gln Ser Glu Asn
        35                  40                  45

Gly Leu Leu Gly Ile Asp Glu Phe Pro Thr Glu Asp Asn Val Asp Ala
    50                  55                  60

Asp Leu Ile Asn Ala Gly Lys Gln Thr Val Thr Val Lys Lys Gly Gly
65                  70                  75                  80

Ala Phe Phe Ser Ser Ser Glu Ser Phe Ala Met Ile Arg Gly Gly Arg
                85                  90                  95

Val Asp Leu Ala Ile Leu Gly Ala Met Glu Val Ser Glu His Gly Asp
            100                 105                 110

Leu Ala Asn Trp Met Ile Pro Gly Lys Lys Val Lys Gly Met Gly Gly
            115                 120                 125

Ala Met Asp Leu Val Ala Gly Val Arg Lys Val Ile Leu Met Glu
130                 135                 140

His Thr Thr Lys Glu Gly Gln Ala Lys Ile Leu Pro Gln Cys Thr Leu
145                 150                 155                 160

Pro Leu Thr Gly Arg Arg Val Val His Arg Ile Ile Ser Asp Leu Gly
            165                 170                 175

Val Leu Asp Val Thr Gln Asn Gly Leu Glu Leu Val Glu Leu Ala Asp
            180                 185                 190

Asn Val Ser Phe Asp Asp Ile Gln Ala Ala Thr Ala Val Arg Ile Lys
            195                 200                 205

Asn Ile Gln Ala Ala
            210

<210> SEQ ID NO 49
<211> LENGTH: 234
<212> TYPE: PRT
<213> ORGANISM: Acinetobacter bereziniae (Acinetobacter genomosp. 10)
<220> FEATURE:
<221> NAME/KEY: MISC_FEATURE
<223> OTHER INFORMATION: Uniprot name: A0A0A8TQW8_ACIBZ.  Succinyl-
      CoA:3-ketoacid-coenzyme A transferase subunit A

<400> SEQUENCE: 49

Met Val Asn Lys Val Ser Thr Ser Ala Glu Ala Ala Leu Gln Gly Ile
1               5                   10                  15

Val Gln Asp Gly Gln Thr Ile Ala Val Gly Gly Phe Gly Leu Cys Gly
            20                  25                  30

Ile Pro Glu Ala Leu Ile Lys Ala Leu Lys Gln Ser Gly Val Lys Gln
            35                  40                  45

Leu Thr Cys Ile Ser Asn Asn Ala Gly Val Asp Asp Tyr Gly Leu Gly
50                  55                  60

Leu Leu Leu Gln Ser Lys Gln Ile Lys Lys Met Ile Ser Ser Tyr Val
65                  70                  75                  80

Gly Glu Asn Lys Val Phe Glu Arg Gln Phe Leu Asn Gly Glu Leu Glu
            85                  90                  95

Val Glu Leu Thr Pro Gln Gly Thr Leu Ala Glu Lys Leu Arg Ala Gly
            100                 105                 110

Gly Ala Gly Ile Pro Ala Phe Tyr Thr Ala Thr Gly Val Gly Thr Ser
            115                 120                 125

Ile Ala Glu Gly Lys Glu Leu Arg Glu Phe Asn Gly Gln Ser Phe Leu
130                 135                 140

Leu Glu Thr Ser Leu Cys Ala Asp Ile Ala Leu Ile Lys Ala Tyr Lys
145                 150                 155                 160

Ala Asp Lys Ala Gly Asn Leu Val Phe Arg Lys Thr Ala Arg Asn Phe
            165                 170                 175

Asn Pro Glu Cys Ala Met Ala Gly Arg Tyr Thr Ile Val Glu Val Glu
            180                 185                 190

His Ile Val Glu Leu Gly Glu Ile Asp Pro Asp Ile His Leu Ala
            195                 200                 205

Gly Ile Tyr Val Asn Ala Ile Val Leu Asn Ala Gln Pro Glu Lys Arg
210                 215                 220

Ile Glu Gln Arg Thr Leu Lys Val Ala Val
225                 230

<210> SEQ ID NO 50
<211> LENGTH: 528
<212> TYPE: PRT
<213> ORGANISM: Acinetobacter bereziniae (Acinetobacter genomosp. 10)
<220> FEATURE:
<221> NAME/KEY: MISC_FEATURE
<223> OTHER INFORMATION: Uniprot name: A0A0A8TSD3_ACIBZ. Acetate CoA-
      transferase YdiF

<400> SEQUENCE: 50

Met Asn Lys Leu Ile Ser Ala Glu Gln Ala Ala Lys Leu Ile Ile Asp
1               5                   10                  15

Gly Asp Ile Val Thr Val Ser Ser Ser Gly Leu Ala Cys Pro Asp
                20                  25                  30

His Ile Leu Ser Ala Ile Gly Lys Arg Tyr Gln His Ile Ala Gln Pro
            35                  40                  45

Lys Asp Leu Thr Leu Leu His Pro Ile Ala Ala Gly Asp Leu Tyr Gly
        50                  55                  60

Ile Lys Gly Ile Glu His Leu Ala Gln Thr Gly Leu Ile Lys Lys Val
65                  70                  75                  80

Ile Ala Gly Ser Phe Pro Ser Gly Pro Ser Ser Leu Pro Met Pro Glu
                85                  90                  95

Ile Trp Lys Met Ile Val Asn Asn Glu Ile Ala Ala Tyr Asn Val Pro
            100                 105                 110

Ser Gly Ile Met Phe Asp Leu His Arg Asp Val Ala Ala Lys Arg Pro
        115                 120                 125

Gly Val Leu Thr Lys Val Gly Phe Asn Thr Phe Val Asp Pro Asp Leu
    130                 135                 140

Gln Gly Cys Ala Met Asn Ala Lys Ala Glu Ala Gln Pro Ile Val Glu
145                 150                 155                 160

Lys Val Asn Phe Ala Gly Glu Asp Trp Leu Phe Phe Pro Asn Ile Ile
                165                 170                 175

Pro Asn Val Ala Ile Ile Arg Ala Thr Thr Ala Asp Glu Lys Gly Asn
            180                 185                 190

Leu Ser Phe Glu His Glu Gly Gly Leu Leu Gly Ala Leu Asp Gln Ala
        195                 200                 205

Leu Ala Val Arg Asn Asn Gly Gly Ile Val Ile Val Gln Val Lys Arg
    210                 215                 220

Met Val Arg Ala Gly Ser Ile Lys Pro His His Val His Ile Pro Cys
225                 230                 235                 240

Asn Leu Val Asp Tyr Ile Val Val Ala Pro Asp Gln Met Gln Thr Thr
                245                 250                 255

Gln Ile Ser Tyr Asp Pro Ala Ile Ser Gly Glu Ile Gln Gln Pro Asp
            260                 265                 270

Ser Val Phe Asp Met Thr Pro Trp Gly Ala Glu Lys Val Ile Ala Arg
        275                 280                 285

Arg Ala Ala Met Gln Val Glu Lys Gly Met Ser Val Asn Leu Gly Phe
    290                 295                 300

Gly Ile Ser Ala Asn Val Pro Arg Ile Leu Leu Glu Glu Gly Tyr His
305                 310                 315                 320

Asp Glu Val Thr Trp Leu Ile Glu Gln Gly Ala Val Gly Gly Met Pro
                325                 330                 335

Leu Leu Asp Phe Ala Phe Gly Cys Ala Val Asn Ala Asp Ala Ile Met

```
                    340                 345                 350
Pro Ser Ser Ala Gln Phe Thr Tyr Phe Gln Gly Gly Gly Phe Asn Leu
            355                 360                 365

Ser Leu Leu Ser Phe Leu Gln Ile Asp Arg Glu Gly Asn Val Asn Val
    370                 375                 380

Ser Lys Leu Pro Ser Lys Pro Tyr Leu Thr Ala Gly Cys Gly Gly Phe
385                 390                 395                 400

Val Asp Ile Thr Thr His Ala Lys Asn Ile Val Phe Ser Gly Phe Phe
                405                 410                 415

Thr Ala Gly Ala Lys Leu Thr Val Gly Asp Gly Ala Leu Lys Ile His
            420                 425                 430

Gln Glu Gly Lys Ser Arg Lys Leu Val Asn Lys Val Asp His Val Thr
        435                 440                 445

Phe Ser Gly His Met Ala Leu Gln Arg Gly Gln Asn Ile Leu Tyr Ile
    450                 455                 460

Thr Glu Arg Cys Val Met Lys Leu Thr Thr Glu Gly Leu Leu Ile Thr
465                 470                 475                 480

Glu Ile Ala Pro Gly Ile Asp Leu Glu Lys Asp Val Leu Ser Gln Ala
                485                 490                 495

Glu Phe Pro Leu Leu Val Ser Asp Asp Leu Lys Ile Met Arg Pro Ser
            500                 505                 510

Leu Phe Thr Asp Ala Val Met Gly Leu Glu Leu Lys Glu Tyr Ala Ala
        515                 520                 525

<210> SEQ ID NO 51
<211> LENGTH: 527
<212> TYPE: PRT
<213> ORGANISM: Bradyrhizobium sp.
<220> FEATURE:
<221> NAME/KEY: MISC_FEATURE
<223> OTHER INFORMATION: Uniprot name: J3I464_9BRAD Acetate CoA-
      transferase YdiF

<400> SEQUENCE: 51

Met Leu Ser Ile Ile Thr Ala Glu Gln Ala Ala Gly Leu Ile Arg Asp
1               5                   10                  15

Thr Asp Thr Leu Ile Val Gly Gly Asn Gly Gly Thr Gly Ala Ala Glu
            20                  25                  30

Ala Ile Leu Asp Ala Leu Glu Gln Arg Phe Val Ser Gly Gln Gly Pro
        35                  40                  45

His Asn Leu Thr Leu Ile Asn Ile Thr Gly Val Gly Ala Val Thr Glu
    50                  55                  60

Lys Gly Leu Cys His Leu Ala His Glu Gly Met Ile Ala Arg Val Ile
65                  70                  75                  80

Gly Gly Asn Phe Gly Leu Gln Val Pro Phe Met Arg Leu Val Arg Asp
                85                  90                  95

Glu Leu Ile Asp Ala Tyr Asn Phe Pro Gln Gly Val Met Ser Gln Leu
            100                 105                 110

Cys Arg Ala Met Ala Ala Lys His Pro Gly Val Leu Thr His Val Gly
        115                 120                 125

Leu Asn Thr Tyr Met Asp Pro Arg Gln Asp Gly Arg Met Asn Lys
    130                 135                 140

Arg Thr Thr Ala Pro Leu Val Asp Leu Leu Glu Leu His Gly Gln Ser
145                 150                 155                 160

Tyr Leu Leu Tyr Arg Val Pro Thr Pro Pro Asp Val Ala Ile Ile Arg
                165                 170                 175
```

```
Gly Thr Ser Ala Asp Glu Asp Gly Tyr Ile Ser Met Glu His Glu Gly
                180                 185                 190

Thr Thr Arg Glu Asp Leu Ser Ile Ala Gln Ala Val His Asn Ala Gly
            195                 200                 205

Gly Thr Val Ile Cys Gln Val Lys Arg Ile Val Lys Arg Gly Ser Ile
        210                 215                 220

His Pro Gln Met Val Lys Ile Pro Gly Phe Leu Ile Asp His Ile Val
225                 230                 235                 240

Leu Glu Pro Asp Gln Met Gln Thr Tyr Gly Thr Val Tyr Asp Pro Ala
                245                 250                 255

Arg Cys Gly Glu Thr Arg Val Pro Glu Ala Met Ile Thr Pro Asp Pro
            260                 265                 270

Leu Thr Glu Arg Arg Val Ile Ala Arg Ala Ala Phe Glu Leu Arg
        275                 280                 285

Pro Arg Asp Val Val Asn Leu Gly Val Gly Ile Ser Ala Met Ile Pro
290                 295                 300

Asn Val Ala Ala Glu Glu Gly Ile Ser Asp Leu Ile Thr Leu Thr Val
305                 310                 315                 320

Glu Ser Gly Val Val Gly Gly Val Pro Gly His Ala Arg Glu Phe Gly
                325                 330                 335

Thr Ala Ile Asn Pro Arg Val Ile Leu Asp Gln Ala Tyr Gln Phe Asp
            340                 345                 350

Phe Tyr Asp Gly Gly Gly Leu Ser Cys Ala Phe Leu Ser Phe Ala Glu
        355                 360                 365

Val Asp Glu Thr Gly Asn Val Asn Val Thr Arg Phe Gly Glu Arg Arg
370                 375                 380

Asp Gly Ser Gly Gly Phe Ile Asp Ile Thr Gln Asn Ala Lys Arg Leu
385                 390                 395                 400

Ile Phe Ser Gly Thr Met Thr Gly Gly Lys Phe Asp Ile Gly Val Glu
                405                 410                 415

Asn Gly Arg Leu Ala Ile Arg Arg Asp Gly Ala Phe Arg Lys Phe Val
            420                 425                 430

Pro Glu Val Gly Gln Ile Ser Phe Ser Ala Ser Leu Ala Ala Gln Arg
        435                 440                 445

Gly Gln His Val Ser Tyr Val Thr Glu Arg Ala Val Phe Glu Leu Glu
450                 455                 460

Asn Gly His Val Thr Leu Thr Glu Ile Ala Pro Gly Val Arg Leu Glu
465                 470                 475                 480

Glu Asp Ile Leu Ala Asn Met Gly Phe Lys Pro Arg Ile Ser Pro Gln
                485                 490                 495

Leu Lys Asp Met Asp Ala Arg Ile Phe Arg Ser Gly Pro Met Gly Ile
            500                 505                 510

Ala Gln Ser Phe Lys Ala Leu Pro Ala Arg Pro Arg Lys Val Ala
        515                 520                 525

<210> SEQ ID NO 52
<211> LENGTH: 242
<212> TYPE: PRT
<213> ORGANISM: Xanthomonas campestris pv. campestris
<220> FEATURE:
<221> NAME/KEY: MISC_FEATURE
<223> OTHER INFORMATION: Uniprot name: SCOA_XANCB. Succinyl-CoA:3-
      ketoacid coenzyme A transferase subunit A

<400> SEQUENCE: 52
```

```
Met Asn Gln Val Ala Arg Gly Ala Gly Ala Lys Arg Tyr Ala Asp Ala
1               5                   10                  15

Lys Ala Ala Leu Ala Gly Val Val Ala Asp Gly Gln Thr Leu Ala Val
            20                  25                  30

Gly Gly Phe Gly Leu Cys Gly Ile Pro Glu Ala Leu Ile Thr Ala Leu
            35                  40                  45

Arg Asp Ser Ala Val Ser Gly Leu Thr Val Ile Ser Asn Asn Ala Gly
50                  55                  60

Val Asp Gly Phe Gly Leu Gly Gln Leu Leu Ala Thr Arg Gln Ile Arg
65                  70                  75                  80

Lys Met Ile Ser Ser Tyr Val Gly Glu Asn Lys Glu Phe Glu Arg Gln
            85                  90                  95

Tyr Leu Ala Gly Glu Leu Glu Leu Glu Phe Asn Pro Gln Gly Thr Leu
            100                 105                 110

Ala Glu Arg Leu Arg Ala Gly Gly Ala Gly Ile Pro Ala Phe Tyr Thr
            115                 120                 125

Ala Thr Gly Tyr Gly Thr Ile Val Ala Asp Gly Lys Glu Thr Arg Glu
            130                 135                 140

Phe Asp Gly Lys His Tyr Val Leu Glu Thr Ala Leu Gln Ala Asp Val
145                 150                 155                 160

Ala Leu Ile Lys Ala Trp Arg Ala Asp Thr Ala Gly Asn Leu Val Phe
                165                 170                 175

Arg Lys Thr Ala Arg Asn Phe Asn Pro Ala Cys Ala Met Ala Gly Arg
                180                 185                 190

Ile Cys Ile Ala Glu Val Glu Glu Ile Val Glu Leu Gly Ala Ile Asp
            195                 200                 205

Pro Asp Gln Val His Leu Pro Gly Ile Tyr Val Asp Arg Leu Val Leu
            210                 215                 220

Asn Ala Thr Pro Glu Lys Arg Ile Glu Gln Arg Thr Val Arg Gln Gly
225                 230                 235                 240

Asp Lys

<210> SEQ ID NO 53
<211> LENGTH: 213
<212> TYPE: PRT
<213> ORGANISM: Xanthomonas campestris pv. campestris
<220> FEATURE:
<221> NAME/KEY: MISC_FEATURE
<223> OTHER INFORMATION: Uniprot name: SCOB_XANCB. Succinyl-CoA:3-
      ketoacid coenzyme A transferase subunit B

<400> SEQUENCE: 53

Met Ala Trp Thr Arg Asp Gln Met Ala Ala Arg Ala Ala Arg Glu Leu
1               5                   10                  15

Thr Asp Gly Ala Tyr Val Asn Leu Gly Ile Gly Leu Pro Thr Leu Val
            20                  25                  30

Ala Asn His Ile Pro Asp Gly Val Asp Val Trp Leu Gln Ser Glu Asn
            35                  40                  45

Gly Leu Leu Gly Ile Gly Pro Phe Pro Gly Glu Asp Glu Val Asp Ala
            50                  55                  60

Asp Leu Ile Asn Ala Gly Lys Gln Thr Val Thr Ala Arg Ala Gly Ala
65                  70                  75                  80

Ser Tyr Phe Gly Ser His Asp Ser Phe Ala Met Ile Arg Gly Gly His
                85                  90                  95

Ile Asp Leu Ala Ile Leu Gly Ala Met Gln Val Thr Asp Arg Gly Asp
            100                 105                 110
```

```
Leu Ala Asn Trp Met Val Pro Gly Lys Met Val Lys Gly Met Gly Gly
            115                 120                 125

Ala Met Asp Leu Val Ala Gly Val Lys Arg Val Val Val Leu Met Glu
130                 135                 140

His Val Ala Lys Asp Gly Thr His Lys Ile Leu Pro Gln Cys Asp Leu
145                 150                 155                 160

Pro Leu Thr Gly Val Gly Val Val Asp Arg Ile Ile Thr Asp Leu Ala
                165                 170                 175

Val Phe Asp Val Thr Asp Gly Gly Leu Val Leu Val Glu Ala Ala Glu
                180                 185                 190

Gly Val Gly Leu Glu Glu Leu Arg Ala Lys Thr Gly Val Ala Phe Val
            195                 200                 205

Val Gln Thr Arg Gly
        210
```

<210> SEQ ID NO 54
<211> LENGTH: 505
<212> TYPE: PRT
<213> ORGANISM: Acetobacter aceti
<220> FEATURE:
<221> NAME/KEY: MISC_FEATURE
<223> OTHER INFORMATION: Uniprot name: SCACT_ACEAC. Succinyl-CoA:acetate
      CoA-transferase

<400> SEQUENCE: 54

```
Met Thr Glu Arg Ile Arg Asn Val Ala Leu Arg Ser Lys Val Cys Pro
1               5                   10                  15

Ala Glu Thr Ala Ser Glu Leu Ile Lys His Gly Asp Val Val Gly Thr
                20                  25                  30

Ser Gly Phe Thr Gly Ala Gly Tyr Pro Lys Glu Val Pro Lys Ala Leu
            35                  40                  45

Ala Gln Arg Met Glu Ala Ala His Asp Arg Gly Glu Lys Tyr Gln Ile
        50                  55                  60

Ser Leu Ile Thr Gly Ala Ser Thr Gly Pro Gln Leu Asp Gly Glu Leu
65                  70                  75                  80

Ala Lys Ala Asn Gly Val Tyr Phe Arg Ser Pro Phe Asn Thr Asp Ala
                85                  90                  95

Thr Met Arg Asn Arg Ile Asn Ala Gly Glu Thr Glu Tyr Phe Asp Asn
                100                 105                 110

His Leu Gly Gln Val Ala Gly Arg Ala Val Gln Gly Asn Tyr Gly Lys
            115                 120                 125

Phe Asn Ile Ala Leu Val Glu Ala Thr Ala Ile Thr Glu Asp Gly Gly
        130                 135                 140

Ile Val Pro Thr Ser Ser Val Gly Asn Ser Gln Thr Phe Leu Asn Leu
145                 150                 155                 160

Ala Glu Lys Val Ile Ile Glu Val Asn Glu Trp Gln Asn Pro Met Leu
                165                 170                 175

Glu Gly Ile His Asp Ile Trp Asp Gly Asn Val Ser Gly Val Pro Thr
                180                 185                 190

Arg Asp Ile Val Pro Ile Val Arg Ala Asp Gln Arg Val Gly Gly Pro
            195                 200                 205

Val Leu Arg Val Asn Pro Asp Lys Ile Ala Ala Ile Val Arg Thr Asn
        210                 215                 220

Asp Arg Asp Arg Asn Ala Pro Phe Ala Ala Pro Asp Glu Thr Ala Lys
225                 230                 235                 240
```

-continued

Ala Ile Ala Gly Tyr Leu Leu Asp Phe Phe Gly His Glu Val Lys Gln
                245                 250                 255

Asn Arg Leu Pro Pro Ser Leu Leu Pro Leu Gln Ser Gly Val Gly Asn
            260                 265                 270

Val Ala Asn Ala Val Leu Glu Gly Leu Lys Glu Gly Pro Phe Glu Asn
        275                 280                 285

Leu Val Gly Tyr Ser Glu Val Ile Gln Asp Gly Met Leu Ala Met Leu
    290                 295                 300

Asp Ser Gly Arg Met Arg Ile Ala Ser Ala Ser Phe Ser Leu Ser
305                 310                 315                 320

Pro Glu Ala Ala Glu Glu Ile Asn Asn Arg Met Asp Phe Phe Arg Ser
                325                 330                 335

Lys Ile Ile Leu Arg Gln Gln Asp Val Ser Asn Ser Pro Gly Ile Ile
            340                 345                 350

Arg Arg Leu Gly Cys Ile Ala Met Asn Gly Met Ile Glu Ala Asp Ile
        355                 360                 365

Tyr Gly Asn Val Asn Ser Thr Arg Val Met Gly Ser Lys Met Met Asn
    370                 375                 380

Gly Ile Gly Gly Ser Gly Asp Phe Ala Arg Ser Ser Tyr Leu Ser Ile
385                 390                 395                 400

Phe Leu Ser Pro Ser Thr Ala Lys Gly Gly Lys Ile Ser Ala Ile Val
                405                 410                 415

Pro Met Ala Ala His Val Asp His Ile Met Gln Asp Ala Gln Ile Phe
            420                 425                 430

Val Thr Glu Gln Gly Leu Ala Asp Leu Arg Gly Leu Ser Pro Val Gln
        435                 440                 445

Arg Ala Arg Glu Ile Ile Ser Lys Cys Ala His Pro Asp Tyr Arg Pro
    450                 455                 460

Met Leu Gln Asp Tyr Phe Asp Arg Ala Leu Lys Asn Ser Phe Gly Lys
465                 470                 475                 480

His Thr Pro His Leu Leu Thr Glu Ala Leu Ser Trp His Gln Arg Phe
                485                 490                 495

Ile Asp Thr Gly Thr Met Leu Pro Ser
            500                 505

<210> SEQ ID NO 55
<211> LENGTH: 220
<212> TYPE: PRT
<213> ORGANISM: Escherichia coli
<220> FEATURE:
<221> NAME/KEY: MISC_FEATURE
<223> OTHER INFORMATION: Uniprot name: ATOD_ECOLI. Acetate CoA-
      transferase subunit alpha

<400> SEQUENCE: 55

Met Lys Thr Lys Leu Met Thr Leu Gln Asp Ala Thr Gly Phe Phe Arg
1               5                   10                  15

Asp Gly Met Thr Ile Met Val Gly Gly Phe Met Gly Ile Gly Thr Pro
            20                  25                  30

Ser Arg Leu Val Glu Ala Leu Leu Glu Ser Gly Val Arg Asp Leu Thr
        35                  40                  45

Leu Ile Ala Asn Asp Thr Ala Phe Val Asp Thr Gly Ile Gly Pro Leu
    50                  55                  60

Ile Val Asn Gly Arg Val Arg Lys Val Ile Ala Ser His Ile Gly Thr
65                  70                  75                  80

Asn Pro Glu Thr Gly Arg Arg Met Ile Ser Gly Glu Met Asp Val Val

```
                     85                  90                  95

Leu Val Pro Gln Gly Thr Leu Ile Glu Gln Ile Arg Cys Gly Gly Ala
                100                 105                 110

Gly Leu Gly Gly Phe Leu Thr Pro Thr Gly Val Gly Thr Val Val Glu
                115                 120                 125

Glu Gly Lys Gln Thr Leu Thr Leu Asp Gly Lys Thr Trp Leu Leu Glu
            130                 135                 140

Arg Pro Leu Arg Ala Asp Leu Ala Leu Ile Arg Ala His Arg Cys Asp
145                 150                 155                 160

Thr Leu Gly Asn Leu Thr Tyr Gln Leu Ser Ala Arg Asn Phe Asn Pro
                165                 170                 175

Leu Ile Ala Leu Ala Ala Asp Ile Thr Leu Val Glu Pro Asp Glu Leu
                180                 185                 190

Val Glu Thr Gly Glu Leu Gln Pro Asp His Ile Val Thr Pro Gly Ala
                195                 200                 205

Val Ile Asp His Ile Ile Val Ser Gln Glu Ser Lys
                210                 215                 220

<210> SEQ ID NO 56
<211> LENGTH: 216
<212> TYPE: PRT
<213> ORGANISM: Escherichia coli
<220> FEATURE:
<221> NAME/KEY: MISC_FEATURE
<223> OTHER INFORMATION: Uniprot name: ATOA_ECOLI. Acetate CoA-
      transferase subunit beta

<400> SEQUENCE: 56

Met Asp Ala Lys Gln Arg Ile Ala Arg Arg Val Ala Gln Glu Leu Arg
1               5                   10                  15

Asp Gly Asp Ile Val Asn Leu Gly Ile Gly Leu Pro Thr Met Val Ala
                20                  25                  30

Asn Tyr Leu Pro Glu Gly Ile His Ile Thr Leu Gln Ser Glu Asn Gly
            35                  40                  45

Phe Leu Gly Leu Gly Pro Val Thr Thr Ala His Pro Asp Leu Val Asn
50                  55                  60

Ala Gly Gly Gln Pro Cys Gly Val Leu Pro Gly Ala Ala Met Phe Asp
65                  70                  75                  80

Ser Ala Met Ser Phe Ala Leu Ile Arg Gly Gly His Ile Asp Ala Cys
                85                  90                  95

Val Leu Gly Gly Leu Gln Val Asp Glu Glu Ala Asn Leu Ala Asn Trp
                100                 105                 110

Val Val Pro Gly Lys Met Val Pro Gly Met Gly Gly Ala Met Asp Leu
            115                 120                 125

Val Thr Gly Ser Arg Lys Val Ile Ile Ala Met Glu His Cys Ala Lys
            130                 135                 140

Asp Gly Ser Ala Lys Ile Leu Arg Arg Cys Thr Met Pro Leu Thr Ala
145                 150                 155                 160

Gln His Ala Val His Met Leu Val Thr Glu Leu Ala Val Phe Arg Phe
                165                 170                 175

Ile Asp Gly Lys Met Trp Leu Thr Glu Ile Ala Asp Gly Cys Asp Leu
                180                 185                 190

Ala Thr Val Arg Ala Lys Thr Glu Ala Arg Phe Glu Val Ala Ala Asp
            195                 200                 205

Leu Asn Thr Gln Arg Gly Asp Leu
            210                 215
```

<210> SEQ ID NO 57
<211> LENGTH: 531
<212> TYPE: PRT
<213> ORGANISM: Escherichia coli
<220> FEATURE:
<221> NAME/KEY: MISC_FEATURE
<223> OTHER INFORMATION: Uniprot name: YDIF_ECOLI. Acetate CoA-
      transferase YdiF

<400> SEQUENCE: 57

Met Lys Pro Val Lys Pro Arg Ile Asn Gly Arg Val Pro Val Leu
1               5                   10                  15

Ser Ala Gln Glu Ala Val Asn Tyr Ile Pro Asp Glu Ala Thr Leu Cys
            20                  25                  30

Val Leu Gly Ala Gly Gly Ile Leu Glu Ala Thr Thr Leu Ile Thr
        35                  40                  45

Ala Leu Ala Asp Lys Tyr Lys Gln Thr Gln Thr Pro Arg Asn Leu Ser
    50                  55                  60

Ile Ile Ser Pro Thr Gly Leu Gly Asp Arg Ala Asp Arg Gly Ile Ser
65                  70                  75                  80

Pro Leu Ala Gln Glu Gly Leu Val Lys Trp Ala Leu Cys Gly His Trp
                85                  90                  95

Gly Gln Ser Pro Arg Ile Ser Glu Leu Ala Glu Gln Asn Lys Ile Ile
            100                 105                 110

Ala Tyr Asn Tyr Pro Gln Gly Val Leu Thr Gln Thr Leu Arg Ala Ala
        115                 120                 125

Ala Ala His Gln Pro Gly Ile Ile Ser Asp Ile Gly Ile Gly Thr Phe
    130                 135                 140

Val Asp Pro Arg Gln Gln Gly Gly Lys Leu Asn Glu Val Thr Lys Glu
145                 150                 155                 160

Asp Leu Ile Lys Leu Val Glu Phe Asp Asn Lys Glu Tyr Leu Tyr Tyr
                165                 170                 175

Lys Ala Ile Ala Pro Asp Ile Ala Phe Ile Arg Ala Thr Thr Cys Asp
            180                 185                 190

Ser Glu Gly Tyr Ala Thr Phe Glu Asp Glu Val Met Tyr Leu Asp Ala
        195                 200                 205

Leu Val Ile Ala Gln Ala Val His Asn Asn Gly Gly Ile Val Met Met
    210                 215                 220

Gln Val Gln Lys Met Val Lys Ala Thr Leu His Pro Lys Ser Val
225                 230                 235                 240

Arg Ile Pro Gly Tyr Leu Val Asp Ile Val Val Asp Pro Asp Gln
                245                 250                 255

Thr Gln Leu Tyr Gly Gly Ala Pro Val Asn Arg Phe Ile Ser Gly Asp
            260                 265                 270

Phe Thr Leu Asp Asp Ser Thr Lys Leu Ser Leu Pro Leu Asn Gln Arg
        275                 280                 285

Lys Leu Val Ala Arg Arg Ala Leu Phe Glu Met Arg Lys Gly Ala Val
    290                 295                 300

Gly Asn Val Gly Val Gly Ile Ala Asp Gly Ile Gly Leu Val Ala Arg
305                 310                 315                 320

Glu Glu Gly Cys Ala Asp Asp Phe Ile Leu Thr Val Glu Thr Gly Pro
                325                 330                 335

Ile Gly Gly Ile Thr Ser Gln Gly Ile Ala Phe Gly Ala Asn Val Asn
            340                 345                 350

Thr Arg Ala Ile Leu Asp Met Thr Ser Gln Phe Asp Phe Tyr His Gly
                355                 360                 365

Gly Gly Leu Asp Val Cys Tyr Leu Ser Phe Ala Glu Val Asp Gln His
        370                 375                 380

Gly Asn Val Gly Val His Lys Phe Asn Gly Lys Ile Met Gly Thr Gly
385                 390                 395                 400

Gly Phe Ile Asp Ile Ser Ala Thr Ser Lys Lys Ile Ile Phe Cys Gly
                405                 410                 415

Thr Leu Thr Ala Gly Ser Leu Lys Thr Glu Ile Thr Asp Gly Lys Leu
                420                 425                 430

Asn Ile Val Gln Glu Gly Arg Val Lys Lys Phe Ile Arg Glu Leu Pro
                435                 440                 445

Glu Ile Thr Phe Ser Gly Lys Ile Ala Leu Glu Arg Gly Leu Asp Val
                450                 455                 460

Arg Tyr Ile Thr Glu Arg Ala Val Phe Thr Leu Lys Glu Asp Gly Leu
465                 470                 475                 480

His Leu Ile Glu Ile Ala Pro Gly Val Asp Leu Gln Lys Asp Ile Leu
                485                 490                 495

Asp Lys Met Asp Phe Thr Pro Val Ile Ser Pro Glu Leu Lys Leu Met
                500                 505                 510

Asp Glu Arg Leu Phe Ile Asp Ala Ala Met Gly Phe Val Leu Pro Glu
                515                 520                 525

Ala Ala His
    530

<210> SEQ ID NO 58
<211> LENGTH: 531
<212> TYPE: PRT
<213> ORGANISM: Escherichia coli
<220> FEATURE:
<221> NAME/KEY: MISC_FEATURE
<223> OTHER INFORMATION: Uniprot name: YDIF_ECO57. Acetate CoA-
      transferase YdiF

<400> SEQUENCE: 58

Met Lys Pro Val Lys Pro Pro Arg Ile Asn Gly Arg Val Pro Val Leu
1               5                   10                  15

Ser Ala Gln Glu Ala Val Asn Tyr Ile Pro Asp Glu Ala Thr Leu Cys
                20                  25                  30

Val Leu Gly Ala Gly Gly Gly Ile Leu Glu Ala Thr Thr Leu Ile Thr
            35                  40                  45

Ala Leu Ala Asp Lys Tyr Lys Gln Thr Gln Thr Pro Arg Asn Leu Ser
        50                  55                  60

Ile Ile Ser Pro Thr Gly Leu Gly Asp Arg Ala Asp Arg Gly Ile Ser
65                  70                  75                  80

Pro Leu Ala Gln Glu Gly Leu Val Lys Trp Ala Leu Cys Gly His Trp
                85                  90                  95

Gly Gln Ser Pro Arg Ile Ser Asp Leu Ala Glu Gln Asn Lys Ile Ile
                100                 105                 110

Ala Tyr Asn Tyr Pro Gln Gly Val Leu Thr Gln Thr Leu Arg Ala Ala
            115                 120                 125

Ala Ala His Gln Pro Gly Ile Ile Ser Asp Ile Gly Ile Gly Thr Phe
        130                 135                 140

Val Asp Pro Arg Gln Gln Gly Gly Lys Leu Asn Glu Val Thr Lys Glu
145                 150                 155                 160

Asp Leu Ile Lys Leu Val Glu Phe Asp Asn Lys Glu Tyr Leu Tyr Tyr

```
                        165                 170                 175
Lys Ala Ile Ala Pro Asp Ile Ala Phe Ile Arg Ala Thr Thr Cys Asp
                180                 185                 190

Ser Glu Gly Tyr Ala Thr Phe Glu Asp Glu Val Met Tyr Leu Asp Ala
            195                 200                 205

Leu Val Ile Ala Gln Ala Val His Asn Asn Gly Ile Val Met Met
        210                 215                 220

Gln Val Gln Lys Met Val Lys Lys Ala Thr Leu His Pro Lys Ser Val
225                 230                 235                 240

Arg Ile Pro Gly Tyr Leu Val Asp Ile Val Val Asp Pro Asp Gln
                245                 250                 255

Ser Gln Leu Tyr Gly Gly Ala Pro Val Asn Arg Phe Ile Ser Gly Asp
                260                 265                 270

Phe Thr Leu Asp Asp Ser Thr Lys Leu Ser Leu Pro Leu Asn Gln Arg
                275                 280                 285

Lys Leu Val Ala Arg Arg Ala Leu Phe Glu Met Arg Lys Gly Ala Val
            290                 295                 300

Gly Asn Val Gly Val Gly Ile Ala Asp Gly Ile Gly Leu Val Ala Arg
305                 310                 315                 320

Glu Glu Gly Cys Ala Asp Asp Phe Ile Leu Thr Val Glu Thr Gly Pro
                325                 330                 335

Ile Gly Gly Ile Thr Ser Gln Gly Ile Ala Phe Gly Ala Asn Val Asn
            340                 345                 350

Thr Arg Ala Ile Leu Asp Met Thr Ser Gln Phe Asp Phe Tyr His Gly
            355                 360                 365

Gly Gly Leu Asp Val Cys Tyr Leu Ser Phe Ala Glu Val Asp Gln His
        370                 375                 380

Gly Asn Val Gly Val His Lys Phe Asn Gly Lys Ile Met Gly Thr Gly
385                 390                 395                 400

Gly Phe Ile Asp Ile Ser Ala Thr Ser Lys Lys Ile Ile Phe Cys Gly
                405                 410                 415

Thr Leu Thr Ala Gly Ser Leu Lys Thr Glu Ile Ala Asp Gly Lys Leu
                420                 425                 430

Asn Ile Val Gln Glu Gly Arg Val Lys Phe Ile Arg Glu Leu Pro
            435                 440                 445

Glu Ile Thr Phe Ser Gly Lys Ile Ala Leu Glu Arg Gly Leu Asp Val
        450                 455                 460

Arg Tyr Ile Thr Glu Arg Ala Val Phe Thr Leu Lys Glu Asp Gly Leu
465                 470                 475                 480

His Leu Ile Glu Ile Ala Pro Gly Val Asp Leu Gln Lys Asp Ile Leu
                485                 490                 495

Asp Lys Met Asp Phe Thr Pro Val Ile Ser Pro Glu Leu Lys Leu Met
                500                 505                 510

Asp Glu Arg Leu Phe Ile Asp Ala Ala Met Gly Phe Val Leu Pro Glu
            515                 520                 525

Ala Ala His
    530
```

<210> SEQ ID NO 59
<211> LENGTH: 223
<212> TYPE: PRT
<213> ORGANISM: Haemophilus influenzae
<220> FEATURE:
<221> NAME/KEY: MISC_FEATURE
<223> OTHER INFORMATION: Uniprot name: ATOA_HAEIN. Acetate CoA-transferase subunit beta

<400> SEQUENCE: 59

Met Asn Ala Lys Glu Leu Ile Ala Arg Arg Ile Ala Met Glu Leu His
1               5                   10                  15

Asp Gly Asp Ile Val Asn Leu Gly Ile Gly Leu Pro Thr Gln Val Val
            20                  25                  30

Asn Tyr Leu Pro Asp Asn Val Asn Ile Thr Leu Gln Ser Glu Asn Gly
        35                  40                  45

Phe Leu Gly Leu Thr Ala Phe Asp Pro Glu Asn Ala Asn Ser Asn Leu
    50                  55                  60

Val Asn Ala Gly Gly Gln Pro Cys Gly Ile Lys Lys Gly Gly Ser Thr
65                  70                  75                  80

Phe Asp Ser Ala Phe Ser Phe Ala Leu Ile Arg Gly Gly His Val Asp
                85                  90                  95

Ala Cys Val Leu Gly Gly Leu Glu Val Asp Gln Glu Ala Asn Leu Ala
            100                 105                 110

Asn Trp Met Val Pro Gly Lys Met Val Pro Gly Met Gly Gly Ala Met
        115                 120                 125

Asp Leu Val Thr Gly Ala Lys Lys Val Ile Ile Gly Met Glu His Cys
    130                 135                 140

Ala Lys Ser Gly Ser Ser Lys Ile Leu Lys Lys Cys Thr Leu Pro Leu
145                 150                 155                 160

Thr Ala Ser Lys Lys Val Ala Met Val Val Thr Glu Leu Ala Val Phe
                165                 170                 175

Asn Phe Ile Glu Gly Arg Leu Val Leu Lys Glu His Ala Pro His Val
            180                 185                 190

Asp Leu Glu Thr Ile Lys Ala Lys Thr Glu Ala Asp Phe Ile Val Ala
        195                 200                 205

Asp Asp Phe Lys Glu Met Gln Ile Ser Gln Lys Gly Leu Glu Leu
    210                 215                 220

<210> SEQ ID NO 60
<211> LENGTH: 217
<212> TYPE: PRT
<213> ORGANISM: Haemophilus influenzae
<220> FEATURE:
<221> NAME/KEY: MISC_FEATURE
<223> OTHER INFORMATION: Uniprot name: ATOD_HAEIN. Acetate CoA-
      transferase subunit alpha

<400> SEQUENCE: 60

Met Thr Gln Lys His Leu Lys Leu Asn Asn Leu Asn Gln His Leu His
1               5                   10                  15

Asp Gly Met Ser Ile Met Phe Gly Gly Phe Met Gly Ile Gly Thr Pro
            20                  25                  30

Ala Lys Leu Val Gln Gln Ile Leu Asp Ser Gly Val Lys Asp Leu Thr
        35                  40                  45

Leu Ile Gly Asn Asp Thr Ala Phe Ile Asp Thr Gly Val Gly Pro Leu
    50                  55                  60

Ile Val Asn Asn Arg Val Lys Arg Leu Ile Thr Ser His Ile Gly Thr
65                  70                  75                  80

Asn Pro Glu Thr Gly Lys Lys Met Ile Ala Gly Glu Ile Asp Val Glu
                85                  90                  95

Leu Val Pro Gln Gly Thr Leu Ala Glu Arg Ile Arg Ala Gly Gly Ala
            100                 105                 110

```
Gly Leu Gly Gly Ile Leu Thr Pro Thr Gly Val Gly Thr Val Val Glu
            115                 120                 125
Glu Gly Lys Gln Lys Ile Gln Ile Asp Gly Arg Glu Tyr Leu Leu Glu
        130                 135                 140
Leu Pro Leu Lys Ala Asp Ile Ala Ile Ile His Ala Gln Lys Gly Asp
145                 150                 155                 160
Met Asn Gly Asn Leu Ala Tyr Glu Leu Ser Ala Arg Asn Phe Asn Pro
                165                 170                 175
Leu Val Ala Leu Ala Ala Lys Thr Val Ile Ala Gln Val Asp Asn Leu
            180                 185                 190
Leu Glu Val Gly Gln Leu Pro Pro Asp Glu Val Ile Thr Pro Ala Ala
        195                 200                 205
Leu Ile Asp Tyr Ile Val Cys Ser Glu
    210                 215
```

<210> SEQ ID NO 61
<211> LENGTH: 213
<212> TYPE: PRT
<213> ORGANISM: Burkholderia sp.
<220> FEATURE:
<221> NAME/KEY: MISC_FEATURE
<223> OTHER INFORMATION: Uniprot name: W6WWU8_9BURK. 3-oxoacid CoA-
      transferase, B subunit

<400> SEQUENCE: 61

```
Met Ala Trp Asn Arg Asp Gln Met Ala Ala Arg Ala Ala Gln Glu Leu
1               5                   10                  15
Gln Asp Gly Phe Tyr Val Asn Leu Gly Ile Gly Leu Pro Thr Leu Val
            20                  25                  30
Ala Asn His Val Pro Ala Gly Met Glu Val Trp Leu Gln Ser Glu Asn
        35                  40                  45
Gly Leu Leu Gly Ile Gly Pro Ser Pro Tyr Glu Asp Glu Val Asp Ala
    50                  55                  60
Asp Leu Ile Asn Ala Gly Lys Gln Thr Val Thr Thr Leu Pro Gly Ser
65                  70                  75                  80
Ser Ile Phe Ser Ser Ala Asp Ser Phe Ala Met Ile Arg Gly Gly His
                85                  90                  95
Ile Asn Leu Ala Ile Leu Gly Ala Met Gln Ile Ser Lys Lys Gly Asp
            100                 105                 110
Leu Ala Asn Trp Met Ile Pro Gly Lys Met Ile Lys Gly Met Gly Gly
        115                 120                 125
Ala Met Asp Leu Val Ala Gly Val Lys Lys Val Val Leu Met Glu
    130                 135                 140
His Val Ala Lys Gly Asp Gln His Lys Ile Leu Glu Glu Cys Thr Leu
145                 150                 155                 160
Pro Leu Thr Gly Val Gly Val Asp Arg Ile Ile Thr Asp Leu Gly
                165                 170                 175
Val Ile Asp Val Val Asp Gly Gly Leu Lys Leu Val Glu Leu Ala Asp
            180                 185                 190
Gly Val Thr Val Asp Glu Ile Lys Ala Lys Thr Gly Ala Pro Leu Asp
        195                 200                 205
Thr Ser Ala Val Gly
    210
```

<210> SEQ ID NO 62
<211> LENGTH: 234
<212> TYPE: PRT

<213> ORGANISM: Burkholderia sp.
<220> FEATURE:
<221> NAME/KEY: MISC_FEATURE
<223> OTHER INFORMATION: Uniprot name: W6XFN3_9BURK. 3-oxoacid CoA-
      transferase, A subunit

<400> SEQUENCE: 62

Met Asn Lys Val Tyr Ala Ser Ala Ala Ser Ala Leu Glu Gly Ile Val
1               5                   10                  15

Lys Asp Gly Gln Thr Phe Ala Val Gly Gly Phe Gly Leu Cys Gly Ile
            20                  25                  30

Pro Glu Ala Leu Ile Ala Ala Leu Arg Asp Ser Gly Val Lys Gly Ile
        35                  40                  45

Thr Cys Ile Ser Asn Asn Ala Gly Val Asp Gly Phe Gly Leu Gly Leu
    50                  55                  60

Leu Leu Glu Thr Arg Gln Ile Lys Lys Met Ile Ser Ser Tyr Val Gly
65                  70                  75                  80

Glu Asn Lys Glu Phe Glu Arg Gln Tyr Leu Ala Gly Glu Leu Glu Leu
                85                  90                  95

Glu Phe Thr Pro Gln Gly Thr Leu Ala Glu Lys Leu Arg Ala Gly Gly
            100                 105                 110

Ser Gly Ile Pro Ala Phe Phe Thr Asn Thr Gly Tyr Gly Thr Ile Ile
        115                 120                 125

Ala Asp Gly Lys Glu Thr Arg Gln Phe Gly Glu Asn His Tyr Val Leu
    130                 135                 140

Glu His Ser Leu Thr Ala Asp Val Ala Leu Val Lys Ala Trp Lys Ala
145                 150                 155                 160

Asp Lys Ser Gly Asn Leu Ile Tyr Arg Arg Thr Ala Arg Asn Phe Asn
                165                 170                 175

Pro Met Cys Ala Met Ala Gly Lys Ile Thr Val Val Glu Val Glu Glu
            180                 185                 190

Ile Val Glu Thr Gly Glu Leu Asp Pro Asp Ala Ile His Thr Pro Gly
        195                 200                 205

Ile Phe Val Gln Arg Ile Val Leu Asn Ala Asn Pro Glu Lys Arg Ile
    210                 215                 220

Glu Gln Arg Ile Val Arg Ala Lys Gly Glu
225                 230

<210> SEQ ID NO 63
<211> LENGTH: 530
<212> TYPE: PRT
<213> ORGANISM: Burkholderia sp.
<220> FEATURE:
<221> NAME/KEY: MISC_FEATURE
<223> OTHER INFORMATION: Uniprot name: W6X0E0_9BURK. Acetate CoA-
      transferase YdiF

<400> SEQUENCE: 63

Met Arg Ser Ser Lys Val Val Ser Leu Ala His Ala Ala Ser Leu Ile
1               5                   10                  15

Asn Asp Asp Asp Val Val Thr Val Ser Ser Ser Ser Gly Leu Gly Cys
            20                  25                  30

Pro Asp Ala Met Leu Ala Ala Ile Gly Ala Arg Phe Glu Ser Glu Asp
        35                  40                  45

His Pro Arg Asn Leu Thr Met Leu His Pro Ile Ala Ala Gly Asp Met
    50                  55                  60

Tyr Gly Ile Lys Gly Ile Asp His Ile Ala Lys Lys Gly Leu Ile His
65                  70                  75                  80

-continued

```
Thr Val Ile Ala Gly Ser Phe Pro Ser Gly Pro Ser Ser Leu Pro Met
                85                  90                  95
Pro Asp Ile Trp His Leu Ile Thr Asp Asn Asp Ile Arg Ala Tyr Asn
            100                 105                 110
Leu Pro Ser Gly Val Leu Phe Asp Met His Arg Glu Val Ala Ala Lys
        115                 120                 125
Arg Pro Gly Val Leu Thr Lys Val Gly Leu Asp Thr Tyr Val Asp Pro
    130                 135                 140
Asp Arg Gln Gly Gly Ala Met Asn Ala Gln Ala Ala Glu His Pro Ile
145                 150                 155                 160
Val Glu Lys Val Thr Phe Ala Gly Asp Glu Trp Leu His Tyr Lys Asn
                165                 170                 175
Phe Val Pro Arg Val Ala Ile Val Arg Ala Thr Thr Ala Asp Glu Arg
            180                 185                 190
Gly Asn Leu Ser Phe Glu His Glu Gly Ala Leu Leu Gly Gly Arg Asp
        195                 200                 205
Gln Ala Leu Ala Val Arg Asn Asn Gly Gly Ile Val Ile Ala Gln Val
    210                 215                 220
Lys Arg Val Val Lys Ala Gly Ser Leu His Thr Gln Val His Ile
225                 230                 235                 240
Pro Cys Asn Leu Val Asp Tyr Val Val Asp Ala Glu Gln Lys Gln
                245                 250                 255
Thr Thr Gln Ile Glu Tyr Asp Pro Glu Ile Ser Gly Glu Ile Lys Leu
            260                 265                 270
Pro Glu Ser Ala Phe Ala Phe Ala Asp Trp His Ala Asp Lys Val Ile
        275                 280                 285
Ala Arg Arg Ala Ala Leu Glu Leu Ala Gln Asn Asp Ala Val Asn Leu
    290                 295                 300
Gly Phe Gly Ile Ser Ala Asn Val Pro Arg Val Leu Glu Glu Gly
305                 310                 315                 320
Tyr Arg Asp Asp Val Thr Trp Val Ile Glu Gln Gly Ala Val Gly Gly
                325                 330                 335
Val Pro Leu Leu Gly Phe Ala Phe Gly Cys Ser Gly Asn Ala Asp Ala
            340                 345                 350
Ile Met Pro Ser Pro Ser Gln Phe Val Tyr Phe Gln Gly Gly Gly Phe
        355                 360                 365
Asp Val Ser Leu Leu Ser Phe Leu Gln Val Asp Arg Phe Gly Asn Val
    370                 375                 380
Asn Val Ser Lys Leu Pro Ser Lys Pro Tyr Leu Thr Ala Gly Cys Gly
385                 390                 395                 400
Gly Phe Ile Asp Ile Thr Thr His Ala Lys Arg Val Val Phe Ser Gly
                405                 410                 415
Tyr Phe Thr Ala Gly Ala Lys Ile Glu Val Gly Asp Gly Arg Leu Lys
            420                 425                 430
Ile Val Lys Glu Gly Lys Lys Phe Ile Ala Asp Val Asp His Val
        435                 440                 445
Thr Phe Ser Gly Arg Met Gly Arg Gln Arg Asn Gln Gln Ala Leu Tyr
    450                 455                 460
Val Thr Glu Arg Cys Val Ile Gln Leu Ser Asp Lys Gly Leu Glu Val
465                 470                 475                 480
Ile Glu Ile Ala Pro Gly Val Asp Leu Gln Lys Asp Val Leu Asp Gln
                485                 490                 495
```

```
Cys Asp Ile Glu Leu Ala Val Ser Pro Ala Leu Lys Thr Met Asp Ala
                500                 505                 510

Ser Ile Phe Thr Asp Ala Pro Phe Gly Leu Lys Leu Lys Glu Ala Arg
        515                 520                 525

His Gly
    530

<210> SEQ ID NO 64
<211> LENGTH: 531
<212> TYPE: PRT
<213> ORGANISM: Citrobacter freundii
<220> FEATURE:
<221> NAME/KEY: MISC_FEATURE
<223> OTHER INFORMATION: Uniprot name: A0A0D7M1R1_CITFR. Acetate CoA-
      transferase YdiF

<400> SEQUENCE: 64

Met Lys Phe Ser Arg Pro Asn Arg Ile Asp Gly Arg Val Pro Val Leu
1               5                   10                  15

Ser Ala Ala Asp Ala Val Asn Tyr Ile Pro Asp Glu Ala Thr Leu Cys
            20                  25                  30

Val Leu Gly Ala Gly Gly Gly Ile Leu Glu Ala Thr Thr Leu Ile Asn
        35                  40                  45

Ala Leu Ala Glu Lys Tyr Lys Asn Ser Gln Ser Pro Arg Asn Leu Ala
    50                  55                  60

Leu Ile Ser Pro Thr Gly Leu Gly Asp Arg Ala Asp Arg Gly Ile Ser
65                  70                  75                  80

Pro Leu Ala Gln Glu Gly Leu Val Lys Trp Ala Leu Cys Gly His Trp
                85                  90                  95

Gly Gln Ser Pro Arg Ile Ser Asp Leu Ala Glu Gln Asn Lys Ile Ala
            100                 105                 110

Ala Tyr Asn Tyr Pro Gln Gly Val Leu Thr Gln Thr Leu Arg Ala Ser
        115                 120                 125

Ala Ala His Gln Pro Gly Ile Leu Ser Asp Ile Gly Ile Gly Thr Phe
    130                 135                 140

Val Asp Pro Arg Gln Gln Gly Gly Lys Leu Asn Glu Val Thr Thr Glu
145                 150                 155                 160

Asp Leu Ile Lys Leu Val Glu Ile Asp Asn Lys Glu Tyr Leu Tyr Tyr
                165                 170                 175

Lys Ala Ile Ala Pro Asn Ile Ala Phe Ile Arg Ala Thr Thr Cys Asp
            180                 185                 190

Ser Glu Gly Tyr Ala Thr Phe Glu Asp Glu Val Met Tyr Leu Asp Ala
        195                 200                 205

Leu Val Ile Ala Gln Ala Val His Asn Asn Gly Gly Ile Val Met Met
    210                 215                 220

Gln Val Gln Lys Met Val Lys Ala Thr Leu His Pro Lys Ser Val
225                 230                 235                 240

Arg Ile Pro Gly Tyr Leu Val Asp Ile Val Ile Asp Pro Asp Gln
                245                 250                 255

Thr Gln Leu Tyr Gly Gly Ala Pro Val Asn Arg Phe Ile Ser Gly Asp
            260                 265                 270

Phe Val Leu Asp Asp Ser Gln Thr Ala Leu Pro Leu Asn Gln Arg
        275                 280                 285

Lys Leu Val Ala Arg Arg Ala Leu Phe Glu Met Arg Lys Gly Ala Val
    290                 295                 300

Gly Asn Val Gly Val Gly Ile Ala Asp Gly Ile Gly Leu Val Ala Arg
```

```
                305                 310                 315                 320
Glu Glu Gly Cys Ala Asp Asp Phe Ile Leu Thr Val Glu Thr Gly Pro
                    325                 330                 335

Ile Gly Gly Ile Thr Ser Gln Gly Ile Ala Phe Gly Ala Asn Val Asn
                    340                 345                 350

Thr Arg Ala Ile Leu Asp Met Thr Ser Gln Phe Asp Phe Tyr His Gly
                    355                 360                 365

Gly Gly Leu Asp Val Cys Tyr Leu Ser Phe Ala Glu Val Asp Arg His
                    370                 375                 380

Gly Asn Val Gly Val His Lys Phe Asn Gly Lys Ile Met Gly Thr Gly
385                 390                 395                 400

Gly Phe Ile Asp Ile Ser Ala Thr Ser Lys Lys Ile Ile Phe Cys Gly
                    405                 410                 415

Thr Leu Thr Ala Gly Ser Leu Lys Thr Glu Val Ala Asp Gly Lys Leu
                    420                 425                 430

Asn Ile Val Gln Glu Gly Arg Val Lys Lys Phe Val Asn Glu Leu Pro
                    435                 440                 445

Glu Val Thr Phe Ser Gly Lys Ile Ala Leu Glu Arg Gly Leu Asp Val
                    450                 455                 460

Arg Tyr Ile Thr Glu Arg Ala Val Phe Thr Leu Lys Ala Asp Gly Leu
465                 470                 475                 480

His Leu Ile Glu Ile Ala Pro Gly Val Ser Leu Gln Glu Asp Ile Leu
                    485                 490                 495

Asp Lys Met Asp Phe Thr Pro Ile Ile Ser Pro Asp Leu Lys Leu Met
                    500                 505                 510

Asp Glu Arg Leu Phe Ile Asp Ala Ser Met Gly Phe Val Leu Pro Asp
                    515                 520                 525

Ala Ala Asn
    530

<210> SEQ ID NO 65
<211> LENGTH: 218
<212> TYPE: PRT
<213> ORGANISM: Citrobacter rodentium (Citrobacter freundii)
<220> FEATURE:
<221> NAME/KEY: MISC_FEATURE
<223> OTHER INFORMATION: Uniprot name: D2TK83_CITRI.  Acetate CoA-
      transferase beta subunit

<400> SEQUENCE: 65

Met Lys Lys Leu Thr Arg Asp Glu Met Ala Arg Arg Val Ala Gln Asp
1               5                   10                  15

Ile Pro Glu Gly Ala Tyr Val Asn Leu Gly Ile Gly Leu Pro Thr Arg
                20                  25                  30

Ile Ala Asn Tyr Leu Pro Ala Glu Lys Glu Ile Phe Leu His Ser Glu
                35                  40                  45

Asn Gly Leu Leu Gly Met Gly Leu Lys Pro Ala Glu Gly Ala Glu Asp
                50                  55                  60

Pro Glu Leu Ile Asn Ala Gly Lys Glu Tyr Val Thr Leu Leu Lys Gly
65                  70                  75                  80

Gly Cys Tyr Phe His His Gly Asp Ser Phe Ala Met Met Arg Gly Gly
                85                  90                  95

His Leu Asp Ile Cys Val Leu Gly Ala Tyr Gln Val Ser Ala Thr Gly
                100                 105                 110

Asp Leu Ala Asn Trp Ser Thr Gly Ala Pro Asp Ala Ile Pro Ala Val
                115                 120                 125
```

```
Gly Gly Ala Met Asp Leu Ala Ile Gly Ala Arg Gln Val Phe Val Met
            130                 135                 140

Met Asp Tyr Leu Thr Arg Asp Gly Glu Cys Lys Leu Val Gly Gln Cys
145                 150                 155                 160

Ser Tyr Pro Leu Thr Gly Ile Gly Cys Val Ser Arg Ile Tyr Thr Asp
                165                 170                 175

Leu Ala Val Ile Asp Ile Thr Glu Lys Gly Pro Val Val Arg Glu Ile
            180                 185                 190

Phe Asn Gly Ile Ser Phe Glu Glu Leu Gln Arg Leu Thr Pro Val Thr
            195                 200                 205

Leu Arg Phe Glu Gln Leu Ala Gln Ser Ala
            210                 215

<210> SEQ ID NO 66
<211> LENGTH: 240
<212> TYPE: PRT
<213> ORGANISM: Citrobacter rodentium (Citrobacter freundii)
<220> FEATURE:
<221> NAME/KEY: MISC_FEATURE
<223> OTHER INFORMATION: Uniprot name: D2TK84_CITRI. Acetate CoA-
      transferase alpha subunit

<400> SEQUENCE: 66

Met Cys Glu Ile Arg Thr Thr Arg Ser Glu Gln Met Ile Asp Lys Ser
1               5                   10                  15

Val Pro Ser Leu Glu Glu Ala Ile Ala Gly Ile Pro Asp Gly Ala Thr
            20                  25                  30

Ile Met Ile Gly Gly Phe Gly Thr Ala Gly Gln Pro Thr Trp Leu Ile
            35                  40                  45

Glu Ala Leu Ile Ala Gln Asp Ala Arg Asp Leu Thr Ile Ile Asn Asn
50                  55                  60

Asn Ala Gly Asn Gly Glu Val Gly Leu Ala Ala Leu Leu Lys Ala Lys
65                  70                  75                  80

Arg Val Arg Lys Met Ile Cys Ser Phe Pro Arg Gln Val Asp Ser Gln
            85                  90                  95

Ile Phe Asp Asp Leu Tyr Arg Arg Gly Glu Val Glu Leu Glu Leu Val
            100                 105                 110

Pro Gln Gly Asn Leu Ala Ala Arg Ile Gln Ala Ala Gly Ala Gly Leu
            115                 120                 125

Gly Ala Ile Tyr Thr Pro Thr Gly Phe Gly Thr Pro Leu Ala Glu Gly
            130                 135                 140

Lys Glu Thr Arg Cys Ile Asp Gly Lys His Tyr Val Leu Glu Tyr Pro
145                 150                 155                 160

Ile Lys Ala Asp Phe Ala Leu Ile Lys Ala His Leu Ala Asp Arg Trp
                165                 170                 175

Gly Asn Leu Val Tyr Arg Lys Ala Ala Arg Asn Phe Gly Pro Ile Met
            180                 185                 190

Ala Thr Ala Ala Ala Thr Thr Val Glu Val Asn Arg Leu Val Pro
            195                 200                 205

Leu Gly Glu Leu Asp Pro Glu His Ile Val Thr Pro Gly Ile Phe Val
            210                 215                 220

Gln Arg Val Phe Ser Leu Glu Asn Val Ala Asp Ala Ala Leu Ser Ala
225                 230                 235                 240

<210> SEQ ID NO 67
<211> LENGTH: 247
```

```
<212> TYPE: PRT
<213> ORGANISM: Corynebacterium casei
<220> FEATURE:
<221> NAME/KEY: MISC_FEATURE
<223> OTHER INFORMATION: Uniprot name: G7HWY1_9CORY. Succinyl-CoA:3-
      ketoacid-coenzyme A transferase subunit A

<400> SEQUENCE: 67

Met Val Asp Lys Arg Thr Asn Ser Ala Thr Glu Ala Val Gln Asp Ile
1               5                   10                  15

Ser Ser Gly Ser Ser Ile Ala Val Gly Gly Phe Gly Leu Val Gly Ile
            20                  25                  30

Pro Thr Val Leu Ile Glu Ala Leu Arg Ala Ser Gly Pro Asn Asp Leu
        35                  40                  45

Thr Ile Val Ser Asn Asn Leu Gly Ala Asp Gly Phe Gly Leu Ser Leu
    50                  55                  60

Leu Leu Glu Asp Gly Leu Ile Ser His Ser Ile Gly Ser Tyr Ile Gly
65                  70                  75                  80

Phe Asn Lys Glu Tyr Ala Arg Gln Tyr Leu Ala Gly Glu Leu Thr Val
                85                  90                  95

Glu Phe Thr Pro Gln Gly Thr Leu Ala Glu Arg Met Arg Ala Gly Gly
            100                 105                 110

Ala Gly Ile Pro Ala Phe Tyr Thr Ile Ala Gly Val Gly Thr Gln Val
        115                 120                 125

Ala Glu Gly Gly Leu Pro Met Arg Tyr Asn Ser Asp Gly Ser Val Ala
    130                 135                 140

Glu Tyr Ser Gln Pro Lys Glu Thr Arg Glu Phe Asp Gly Glu Thr Tyr
145                 150                 155                 160

Val Leu Glu Thr Gly Ile Arg Thr Asp Phe Ala Leu Val His Ala His
                165                 170                 175

Lys Gly Asp Arg Tyr Gly Asn Leu Ser Phe Arg Lys Thr Ala Gln Asn
            180                 185                 190

Phe Asn Pro Asp Ala Ala Met Ser Gly Lys Val Thr Ile Ala Gln Val
        195                 200                 205

Glu His Phe Val Asp Val Leu Asp Pro Glu Glu Val Asp Leu Ser Gly
    210                 215                 220

Ile Phe Val Asp Arg Val Val Val Gly Glu Gln Glu Thr Gly Ile
225                 230                 235                 240

Glu Tyr Arg Thr Val Gln Ser
            245

<210> SEQ ID NO 68
<211> LENGTH: 208
<212> TYPE: PRT
<213> ORGANISM: Corynebacterium casei
<220> FEATURE:
<221> NAME/KEY: MISC_FEATURE
<223> OTHER INFORMATION: Uniprot name: G7HWY0_9CORY . 3-oxoacid CoA-
      transferase subunit B

<400> SEQUENCE: 68

Met Ala Ala Arg Val Ala Ala Glu Leu Glu Asp Gly Gln Tyr Val Asn
1               5                   10                  15

Leu Gly Ile Gly Ile Pro Thr Lys Val Pro Gly Phe Val Pro Ala Asp
            20                  25                  30

Lys Glu Val Ile Leu His Ser Glu Asn Gly Ile Leu Gly Val Gly Ala
            35                  40                  45

Tyr Pro Thr Glu Glu Gln Met Asp Pro Glu Leu Ile Asn Ala Gly Lys
```

-continued

```
                50                  55                  60
Glu Thr Ile Thr Ala Ala Pro Gly Ala Ser Tyr Phe Ser Ser Thr
 65                  70                  75                  80

Ser Phe Ala Met Ile Arg Ser Arg Ser Val Asp Val Ala Val Leu Gly
                 85                  90                  95

Ala Met Glu Ile Ser Gln Tyr Gly Asp Leu Ala Asn Trp Met Ile Pro
                100                 105                 110

Gly Lys Met Val Arg Gly Met Gly Ala Met Asp Leu Val His Gly
                115                 120                 125

Ala Glu Thr Ile Ile Val Met Thr Asp His Val Thr Lys Lys Gly Thr
130                 135                 140

Pro Lys Ile Leu Ser Glu Cys Ala Leu Pro Leu Thr Gly Ala Lys Cys
145                 150                 155                 160

Val Gly Lys Ile Val Ser Thr His Ala Val Phe Asp Val Asp Ala Glu
                165                 170                 175

Glu Gly Leu Thr Leu Val Glu Leu Ala Pro Glu Val Thr Leu Glu Glu
                180                 185                 190

Leu Lys Glu Ile Thr Gly Ala Pro Phe Lys Val Ala Glu Gly Val Ala
                195                 200                 205
```

<210> SEQ ID NO 69
<211> LENGTH: 488
<212> TYPE: PRT
<213> ORGANISM: Corynebacterium efficiens
<220> FEATURE:
<221> NAME/KEY: MISC_FEATURE
<223> OTHER INFORMATION: Uniprot name: Q8FSQ6_COREF. Acetate CoA-
      transferase YdiF

<400> SEQUENCE: 69

```
Met Val Asn Lys Ile Val Glu Ser Val Asp Glu Ala Ile Ala Gly Ile
 1               5                  10                  15

Glu Asp Gly Met Val Leu Ala Val Gly Gly Phe Gly Pro Ala Gly Val
                20                  25                  30

Pro Phe Thr Leu Ile Asp Gly Val Tyr His Ser Gly Thr His Asn Leu
                35                  40                  45

Ser Val Tyr Ser Asn Asn Pro Gly Gly Thr Gly Asp Asp Gly Ser Ile
 50                  55                  60

Ser Gly Leu Ala Lys Leu Ile Gln Gly Arg Arg Ile Arg Arg Phe Ala
 65                  70                  75                  80

Gly Ser His Ile Gly Tyr Asn Lys Asn Phe Glu Ala Gln Tyr Leu Ser
                 85                  90                  95

Gly Glu Ile Glu Leu Glu Leu Ile Pro Gln Gly Ser Leu Ser Glu Arg
                100                 105                 110

Met Arg Ala Gly Gly Ala Gly Ile Pro Ala Phe Tyr Thr Pro Thr Gly
                115                 120                 125

Ala Asn Ser Leu Val Ala Gln Gly Gly Ile Pro Ile Lys Tyr Asp Glu
130                 135                 140

Asn Gly Asn Val Thr Val Val Ser Ser Pro Lys Glu Thr Arg Thr Phe
145                 150                 155                 160

Thr Arg Asn Gly Asp Thr Arg Asp Tyr Val Leu Glu Glu Ala Ile Thr
                165                 170                 175

Ala Asp Phe Ser Leu Ile His Ala Tyr Lys Ala Asp Pro Glu Gly Asn
                180                 185                 190

Leu Val Phe Arg Ala Ser Gly Gln Asn Phe Asn Pro Asp Ala Ala Met
                195                 200                 205
```

```
Cys Gly Thr Val Thr Val Val Glu Ala Glu Tyr Ile Val Pro Thr Gly
        210                 215                 220
Ser Leu Lys Asn Asp Glu Ile His Leu Pro Gly Ile Tyr Val Asp Arg
225                 230                 235                 240
Val Leu Pro Leu Thr Pro Glu Gln Arg Ser Phe Lys Pro Phe Gly Ala
                245                 250                 255
Leu Pro Pro Ala Ser Gly Glu Gln Val Val Gln Pro Thr His Pro His
                260                 265                 270
Asn Gln Met Gly Trp Asn Arg Asp Glu Met Ala Val Arg Ala Ala Gln
            275                 280                 285
Glu Leu Asn Asp Gly Glu Tyr Val Asn Leu Gly Ile Gly Leu Pro Thr
290                 295                 300
Arg Val Ala Asp Phe Val Pro Ala Gly Thr Arg Val Thr Leu Gln Ser
305                 310                 315                 320
Glu Asn Gly Ile Met Lys Met Gly Pro Ala Pro Asn Tyr Tyr Glu Leu
                325                 330                 335
Asp Pro Asp Ile Ile Asn Ala Gly Lys Asp Ser Val Thr Ile Leu Pro
                340                 345                 350
Gly Gly Ser Thr Phe Gly Ser Ser Ala Ser Phe Ala Met Ile Arg Gly
                355                 360                 365
Gly His Ile Asp Lys Ala Ile Leu Gly Ser Leu Gln Val Ser Glu Asn
            370                 375                 380
Gly Asp Leu Ala Asn Trp Ala Ile Pro Gly Lys Lys Ile Arg Gly Met
385                 390                 395                 400
Gly Gly Ala Met Asp Leu Val Glu Gly Ala Lys Thr Val Ile Val Leu
                405                 410                 415
Met Glu His Leu Asp Pro Glu Gly Ala Pro Arg Val Leu Pro Glu Cys
            420                 425                 430
Thr Tyr Pro Leu Thr Gly Arg Gly Val Val Asp Arg Ile Ile Thr Asn
                435                 440                 445
Leu Gly Val Phe Asp Val Asp Asp Glu Gly Leu Val Leu Ile Glu Thr
            450                 455                 460
Ala Pro Gly Val Thr Leu Glu Met Ile Glu Glu Arg Thr Pro Val His
465                 470                 475                 480
Phe Arg Met Ala Leu Gln Thr Val
                485

<210> SEQ ID NO 70
<211> LENGTH: 172
<212> TYPE: PRT
<213> ORGANISM: Corynebacterium glutamicum
<220> FEATURE:
<221> NAME/KEY: MISC_FEATURE
<223> OTHER INFORMATION: Uniprot name: Q8NT12_CORGL. Acetyl-CoA
      hydrolase

<400> SEQUENCE: 70

Met Gly Ile Leu Lys Ala Thr Ser Arg Ala Leu Thr Ser Arg Ala Gln
1               5                   10                  15
Phe His Thr Thr Arg His His Trp Lys Asn Leu Thr Ser Pro Ala Asp
                20                  25                  30
Ile Tyr Gly Asn Ile Asn Ser Thr His Val Ala Gly Thr Arg Val Met
            35                  40                  45
Asn Gly Ile Gly Gly Ser Gly Asp Phe Thr Arg Asn Ala Phe Ala Ser
        50                  55                  60
```

```
Thr Phe Ile Ser Pro Ser Ala Ala Lys Val Asp Ala Ile Ser Ala Ile
 65                  70                  75                  80

Val Pro Phe Ala Ser His Ile Asp His Thr Glu His Asp Ala Met Val
                 85                  90                  95

Val Ile Thr Glu Tyr Gly Tyr Ala Asp Leu Arg Gly Leu Ser Pro Lys
            100                 105                 110

Gln Arg Val Pro Lys Met Ile Ala Ile Ala His Pro Asp Tyr Arg Pro
        115                 120                 125

Leu Leu Glu Ala Tyr Phe Asp Arg Ala Leu Asn Ser Ala Asp Ser Tyr
    130                 135                 140

Gln His Thr Leu His Asp Leu Arg Thr Ala Phe Asp Phe His Asn Arg
145                 150                 155                 160

Leu Asn Ser Gln Gly Thr Met Lys Ile Glu Lys Ala
                165                 170
```

<210> SEQ ID NO 71
<211> LENGTH: 218
<212> TYPE: PRT
<213> ORGANISM: Escherichia coli
<220> FEATURE:
<221> NAME/KEY: MISC_FEATURE
<223> OTHER INFORMATION: Uniprot name: W1G4U4_ECOLX. Succinyl-CoA:3-
      ketoacid-coenzyme A transferase subunit B

<400> SEQUENCE: 71

```
Met Leu Thr Arg Glu Gln Met Ala Met Arg Val Ala Arg Glu Leu Arg
  1               5                  10                  15

Asp Gly Tyr Tyr Val Asn Leu Gly Ile Gly Ile Pro Thr Leu Val Ala
                 20                  25                  30

Asn Tyr Ile Pro Asp Gly Met Asp Val Met Leu Gln Ser Glu Asn Gly
             35                  40                  45

Leu Leu Gly Met Gly Pro Phe Pro Thr Glu Asp Glu Ile Asp Ala Asp
     50                  55                  60

Met Ile Asn Ala Gly Lys Gln Thr Val Thr Ala Arg Lys Gly Ala Ala
 65                  70                  75                  80

Ile Phe Asp Ser Ala Gln Ser Phe Ala Met Ile Arg Gly Gly His Val
                 85                  90                  95

Asp Leu Thr Val Leu Gly Ala Phe Glu Val Asp Val Asn Gly Asn Ile
            100                 105                 110

Ala Ser Trp Met Ile Pro Gly Lys Met Val Lys Gly Met Gly Gly Ala
        115                 120                 125

Met Asp Leu Val Ala Gly Ala Asp Asn Ile Ile Val Val Met Thr His
    130                 135                 140

Ala Ser Lys Ser Gly Glu Ser Lys Leu Leu Pro Ala Cys Thr Leu Pro
145                 150                 155                 160

Leu Thr Gly Val Ala Cys Ile Lys Arg Val Leu Thr Asp Leu Ala Leu
                165                 170                 175

Leu Glu Ile Ala Asp Gly Ala Phe Ile Leu Arg Glu Arg Ala Pro Gly
            180                 185                 190

Ile Ser Val Asp Glu Ile Val Ala Arg Thr Ala Gly Lys Leu Ile Val
        195                 200                 205

Pro Glu Thr Val Pro Glu Met Gln Phe Asn
    210                 215
```

<210> SEQ ID NO 72
<211> LENGTH: 146
<212> TYPE: PRT

<213> ORGANISM: Escherichia coli
<220> FEATURE:
<221> NAME/KEY: MISC_FEATURE
<223> OTHER INFORMATION: Uniprot name: W1G4Y6_ECOLX. Succinyl-CoA:3-
      ketoacid-coenzyme A transferase subunit A

<400> SEQUENCE: 72

Met Ala Gly Leu Asp Lys Arg Val Ala Thr Tyr Gln Glu Ala Leu Glu
1               5                   10                  15

Gly Leu Thr Asp Asn Met Thr Leu Leu Ala Gly Gly Phe Gly Leu Cys
            20                  25                  30

Gly Ile Pro Glu Asn Leu Ile Thr Glu Val Arg Arg Arg Glu Val Gln
        35                  40                  45

Gly Leu Thr Val Val Ser Asn Asn Cys Gly Val Asp Gly Phe Gly Leu
    50                  55                  60

Gly Val Leu Leu Glu Thr Arg Gln Val Arg Lys Val Val Ala Ser Tyr
65                  70                  75                  80

Val Gly Glu Asn Ala Leu Phe Glu Lys Gln Val Leu Ser Gly Glu Leu
                85                  90                  95

Glu Ala Ile Leu Thr Pro Gln Gly Thr Leu Ala Glu Gln Leu Arg Ala
            100                 105                 110

Gly Gly Ala Gly Ile Pro Ala Phe Phe Tyr Arg Asp Arg Ile Trp Asn
        115                 120                 125

Pro Arg Gly Gly Arg Glu Arg Gly Ser Arg Val Cys Arg Thr Pro Leu
    130                 135                 140

His Pro
145

<210> SEQ ID NO 73
<211> LENGTH: 533
<212> TYPE: PRT
<213> ORGANISM: Klebsiella oxytoca
<220> FEATURE:
<221> NAME/KEY: MISC_FEATURE
<223> OTHER INFORMATION: Uniprot name: H3MA92_KLEOX. Acetate CoA-
      transferase YdiF

<400> SEQUENCE: 73

Met Ser Ser Lys Phe Ile Asp Ala His Gln Ala Ala Gln Trp Val Ala
1               5                   10                  15

Ser Gly Asp Thr Val Cys Thr Val Gly Met Thr Leu Ile Gly Ala Ala
            20                  25                  30

Glu Ser Ile Leu Ser Ala Ile Glu Ala Arg Phe Leu Thr Ala Gly Glu
        35                  40                  45

Pro Arg Asp Leu Thr Leu Leu His Ala Ala Gly Gln Ser Asp Arg Gln
    50                  55                  60

Arg Gly Ile Gln His Phe Ala His Pro Gly Met Val Thr Arg Leu Ile
65                  70                  75                  80

Gly Ser His Trp Gly Leu Ala Pro Arg Trp Met Ala Met Ile Asn Asn
                85                  90                  95

Asn Glu Val Glu Ala Trp Cys Leu Pro Gln Gly Gln Ile Val His Leu
            100                 105                 110

Tyr Ser Ala Met Ala Ala Gly Leu Thr Gly Arg Leu Ser Pro Val Gly
        115                 120                 125

Leu Gly Thr Phe Val Asp Pro Arg Met Glu Gly Gly Arg Met Asn Ala
    130                 135                 140

Arg Thr Arg Glu Arg Pro Asp Leu Ile Glu His Val Thr Phe Arg Gly
145                 150                 155                 160

Asp Glu Tyr Leu Phe Tyr Pro Ala Ile Pro Leu Asp Val Val Ile Val
            165                 170                 175

Arg Gly Thr His Ala Asp Glu Asp Ser Asn Leu Thr Thr Asp Glu Glu
        180                 185                 190

Val Met Lys Leu Glu Val Leu His Ala Val Leu Ala Ala Arg Arg Tyr
    195                 200                 205

Gly Ala Lys Val Leu Ala Gln Val Lys Tyr Arg Val Ala Lys Gly Ser
    210                 215                 220

Leu His Pro Lys Ser Ile Thr Val Pro Gly Asn Leu Ile Asp Ala Ile
225                 230                 235                 240

Val Val Cys Glu Glu Pro Gln Ala Asp His Arg Gln Thr Ser Ser Trp
                245                 250                 255

Asp Phe Asp Pro Ala Leu Cys Gly Asp Ile Gln Leu Pro Ala Ala Gln
            260                 265                 270

Asn Ala Pro Leu Pro Leu Asp Leu Arg Lys Leu Ile Gly Arg Ile Ala
        275                 280                 285

Cys Arg Tyr Leu Thr Pro Gly Cys Val Ile Asn Leu Gly Thr Gly Ile
    290                 295                 300

Pro Asn Asp Val Ile Gly Ala Ile Ile His Glu Glu Arg Leu Gly Glu
305                 310                 315                 320

Gln Val Thr Ile Thr Val Glu Ser Gly Ile Tyr Gly Gly Gln Gln Ala
                325                 330                 335

Gly Gly Val Asp Phe Gly Ile Gly Arg Asn Leu Ser Ala Met Ile Ser
            340                 345                 350

His Gln Asp Gln Met Leu Tyr Tyr Asn Gly Ala Gly Val Asp Ile Thr
        355                 360                 365

Phe Met Gly Ala Gly Glu Met Asp Pro His Gly His Val Asn Ala Thr
    370                 375                 380

Arg Leu Gly Ala Ser Cys Pro Gly Ala Gly Gly Phe Ile Asp Ile Thr
385                 390                 395                 400

Gln Asn Ala Arg His Val Val Phe Cys Ser Ser Phe Thr Ala Lys Gly
                405                 410                 415

Leu Glu Ile Ala Cys Glu Gln Gly Ala Leu His Ile Arg Arg Glu Gly
            420                 425                 430

Glu Val Arg Lys Phe Val Ala Gly Val Asn Gln Ile Ser Tyr Asn Gly
        435                 440                 445

Glu Leu Ala Arg Ala Lys Gly Gln Thr Met His Tyr Val Thr Glu Arg
    450                 455                 460

Ala Val Phe Glu Leu Arg Pro Glu Gly Pro Val Leu Thr Glu Ile Ala
465                 470                 475                 480

Pro Gly Ile Asp Leu Glu Arg Asp Ile Leu Ala His Met Asp Phe Arg
                485                 490                 495

Pro Ala Ile Ala Ala Asp Leu Gln Val Met Asp Ser Arg Leu Phe Thr
            500                 505                 510

Pro Gln Pro Cys Gly Leu Ala Glu His Leu Ser Arg Asn Ser Ser Ser
        515                 520                 525

Asp Ser Gln Gly Asn
    530

<210> SEQ ID NO 74
<211> LENGTH: 218
<212> TYPE: PRT
<213> ORGANISM: Klebsiella pneumoniae
<220> FEATURE:

-continued

<221> NAME/KEY: MISC_FEATURE
<223> OTHER INFORMATION: Uniprot name: A0A060VI81_KLEPN. 3-oxoadipate
      CoA-transferase

<400> SEQUENCE: 74

Met Gln Lys Leu Thr Arg Asp Glu Met Ala Gln Arg Val Ala Arg Asp
1               5                   10                  15

Ile Pro Glu Gly Ala Tyr Val Asn Leu Gly Ile Gly Leu Pro Thr Arg
            20                  25                  30

Ile Ala Asn Tyr Leu Pro Ala Asp Lys Glu Val Phe Leu His Ser Glu
        35                  40                  45

Asn Gly Leu Leu Gly Met Gly Pro Lys Pro Gln Pro Gly Glu Glu Asp
50                  55                  60

Pro Glu Leu Ile Asn Ala Gly Lys Glu Tyr Val Thr Leu Leu Gln Gly
65                  70                  75                  80

Gly Cys Tyr Phe His His Gly Asp Ser Phe Ala Met Met Arg Gly Gly
                85                  90                  95

His Leu Asp Ile Cys Val Leu Gly Ala Tyr Gln Val Ser Ala Ser Gly
            100                 105                 110

Asp Leu Ala Asn Trp Ser Thr Gly Ala Pro Asp Ala Ile Pro Ala Val
        115                 120                 125

Gly Gly Ala Met Asp Leu Ala Ile Gly Ala Arg Gln Val Phe Val Met
130                 135                 140

Met Asp His Leu Thr Arg Asp Gly Glu Cys Lys Leu Val Ala Gln Cys
145                 150                 155                 160

Ser Tyr Pro Leu Thr Gly Val Gly Cys Val Ser Arg Ile Tyr Thr Asp
                165                 170                 175

Leu Ala Val Ile Asp Ile Thr Asp Arg Gly Pro Val Val Arg Glu Ile
            180                 185                 190

Phe Asn Gly Leu Ser Phe Glu Glu Leu Gln Arg Ile Thr Pro Val Ala
        195                 200                 205

Leu Thr Phe Gln Gln Leu Ala Glu Ser Ala
    210                 215

<210> SEQ ID NO 75
<211> LENGTH: 530
<212> TYPE: PRT
<213> ORGANISM: Klebsiella pneumoniae
<220> FEATURE:
<221> NAME/KEY: MISC_FEATURE
<223> OTHER INFORMATION: Uniprot name: A0A0C7K9R8_KLEPN. Acetate CoA-
      transferase YdiF

<400> SEQUENCE: 75

Met Ser Ser Lys Phe Ile Asp Ala His Glu Ala Ala Arg Trp Val Ala
1               5                   10                  15

Ser Gly Asp Thr Val Cys Thr Val Gly Met Thr Leu Ile Gly Ala Ala
            20                  25                  30

Glu Ser Ile Leu Ser Ala Ile Glu Ala Arg Phe Leu Thr Ala Gly Glu
        35                  40                  45

Pro Arg Asp Leu Thr Leu Leu His Ala Ala Gly Gln Ser Asp Arg Gln
50                  55                  60

Arg Gly Ile Gln His Phe Ala His Pro Gly Met Val Thr Arg Leu Ile
65                  70                  75                  80

Gly Ser His Trp Gly Leu Ala Pro Arg Trp Met Ala Met Ile Asn Asn
                85                  90                  95

Asn Glu Val Glu Ala Trp Cys Leu Pro Gln Gly Gln Ile Val His Leu

-continued

```
                100                 105                 110
Tyr Ser Ala Met Ala Ala Gly Leu Pro Gly Arg Leu Ser Pro Val Gly
            115                 120                 125
Leu Gly Thr Phe Val Asp Pro Arg Ile Glu Gly Gly Arg Met Asn Ala
            130                 135                 140
Arg Thr Arg Glu Arg Pro Asn Leu Ile Glu His Val Thr Phe Arg Gly
145                 150                 155                 160
Asp Glu Tyr Leu Phe Tyr Pro Ala Leu Pro Leu Asp Val Val Ile Val
                165                 170                 175
Arg Gly Thr His Ala Asp Glu Asp Gly Asn Leu Thr Thr Asp Glu Glu
            180                 185                 190
Val Met Lys Leu Glu Val Leu His Ala Val Leu Ala Ala Arg Arg Tyr
            195                 200                 205
Gly Ala Lys Val Leu Ala Gln Val Lys Tyr Arg Val Ala Lys Gly Ser
            210                 215                 220
Leu His Pro Lys Ser Ile Thr Val Pro Gly Asn Leu Ile Asp Ala Ile
225                 230                 235                 240
Val Val Cys Glu Glu Pro Gln Thr Asp His Arg Gln Thr Ser Ser Trp
                245                 250                 255
Ala Phe Asp Pro Ala Leu Cys Gly Asp Ile Gln Leu Pro Ala Ala Gln
            260                 265                 270
Asn Ala Pro Leu Pro Leu Asp Leu Arg Lys Leu Ile Gly Arg Ile Ala
            275                 280                 285
Cys Arg Tyr Leu Thr Pro Gly Cys Val Ile Asn Leu Gly Thr Gly Ile
            290                 295                 300
Pro Asn Asp Val Ile Gly Ala Ile Ile His Glu Glu Gln Leu Gly Glu
305                 310                 315                 320
Gln Val Thr Ile Thr Val Glu Ser Gly Ile Tyr Gly Gly Gln Gln Ala
                325                 330                 335
Gly Gly Val Asp Phe Gly Ile Gly Arg Asn Leu Ser Ala Met Ile Ser
            340                 345                 350
His Gln Asp Gln Met Leu Tyr Tyr Asn Gly Ala Gly Val Asp Ile Thr
            355                 360                 365
Phe Met Gly Ala Gly Glu Met Asp Pro His Gly His Val Asn Ala Thr
            370                 375                 380
Arg Leu Gly Ala Ser Cys Pro Gly Ala Gly Gly Phe Ile Asp Ile Thr
385                 390                 395                 400
Gln Asn Ala Arg His Val Val Phe Cys Ser Ser Phe Thr Ala Lys Gly
                405                 410                 415
Leu Glu Ile Ala Cys Glu His Gly Ala Leu His Ile Arg Arg Glu Gly
            420                 425                 430
Glu Val Arg Lys Phe Val Ala Gly Val Asn Gln Ile Ser Tyr Asn Gly
            435                 440                 445
Glu Leu Ala Arg Ala Lys Gly Gln Thr Met His Tyr Val Thr Glu Arg
            450                 455                 460
Ala Val Phe Glu Leu Arg Pro Glu Gly Pro Val Leu Thr Glu Ile Ala
465                 470                 475                 480
Pro Gly Ile Asp Leu Glu Arg Asp Ile Leu Ala His Met Asp Phe His
                485                 490                 495
Pro Ala Ile Ala Ala Asp Leu Gln Val Met Asp Ser Arg Leu Phe Ala
            500                 505                 510
Pro Pro Pro Cys Gly Leu Ala Glu His Leu Ser Arg Asn Ser Ser Ser
            515                 520                 525
```

Asp Ser
    530

<210> SEQ ID NO 76
<211> LENGTH: 530
<212> TYPE: PRT
<213> ORGANISM: Klebsiella pneumoniae
<220> FEATURE:
<221> NAME/KEY: MISC_FEATURE
<223> OTHER INFORMATION: Uniprot name: R4Y8U6_KLEPN. Acetate CoA-
      transferase YdiF

<400> SEQUENCE: 76

Met Ser Ser Lys Phe Ile Asp Ala His Glu Ala Ala Arg Trp Val Ala
1               5                   10                  15

Ser Gly Asp Thr Val Cys Thr Val Gly Met Thr Leu Ile Gly Ala Ala
            20                  25                  30

Glu Ser Ile Leu Ser Ala Ile Glu Ala Arg Phe Leu Thr Ala Gly Glu
        35                  40                  45

Pro Arg Asp Leu Thr Leu Leu His Ala Ala Gly Gln Ser Asp Arg Gln
    50                  55                  60

Arg Gly Ile Gln His Phe Ala His Pro Gly Met Val Thr Arg Leu Ile
65                  70                  75                  80

Gly Ser His Trp Gly Leu Ala Pro Arg Trp Met Ala Met Ile Asn Asn
                85                  90                  95

Asn Glu Val Glu Ala Trp Cys Leu Pro Gln Gly Gln Ile Val His Leu
            100                 105                 110

Tyr Ser Ala Met Ala Ala Gly Leu Pro Gly Arg Leu Ser Pro Val Gly
        115                 120                 125

Leu Gly Thr Phe Val Asp Pro Arg Ile Glu Gly Gly Arg Met Asn Ala
    130                 135                 140

Arg Thr Arg Glu Arg Pro Asn Leu Ile Glu His Val Thr Phe Arg Gly
145                 150                 155                 160

Asp Glu Tyr Leu Phe Tyr Pro Ala Leu Pro Leu Asp Val Val Ile Val
                165                 170                 175

Arg Gly Thr His Ala Asp Glu Asp Gly Asn Leu Thr Thr Asp Glu Glu
            180                 185                 190

Val Met Lys Leu Glu Val Leu His Ala Val Leu Ala Ala Arg Arg Tyr
        195                 200                 205

Gly Ala Lys Val Leu Ala Gln Val Lys Tyr Arg Val Ala Lys Gly Ser
    210                 215                 220

Leu His Pro Lys Ser Ile Thr Val Pro Gly Asn Leu Ile Asp Ala Ile
225                 230                 235                 240

Val Val Cys Glu Glu Pro Gln Thr Asp His Arg Gln Thr Ser Ser Trp
                245                 250                 255

Ala Phe Asp Pro Ala Leu Cys Gly Asp Ile Gln Leu Pro Ala Ala Gln
            260                 265                 270

Asn Ala Pro Leu Pro Leu Asp Leu Arg Lys Leu Ile Gly Arg Ile Ala
        275                 280                 285

Cys Arg Tyr Leu Thr Pro Gly Cys Val Ile Asn Leu Gly Thr Gly Ile
    290                 295                 300

Pro Asn Asp Val Ile Gly Ala Ile Ile His Glu Glu Gln Leu Gly Glu
305                 310                 315                 320

Gln Val Thr Ile Thr Val Glu Ser Gly Ile Tyr Gly Gly Gln Gln Ala
                325                 330                 335

-continued

```
Gly Gly Val Asp Phe Gly Ile Gly Arg Asn Leu Ser Ala Met Ile Ser
                340                 345                 350

His Gln Asp Gln Met Leu Tyr Tyr Asn Gly Ala Gly Val Asp Ile Thr
            355                 360                 365

Phe Met Gly Ala Gly Glu Met Asp Pro His Gly His Val Asn Ala Thr
370                 375                 380

Arg Leu Gly Ala Ser Cys Pro Gly Ala Gly Phe Ile Asp Ile Thr
385                 390                 395                 400

Gln Asn Ala Arg His Val Val Phe Cys Ser Ser Phe Thr Ala Lys Gly
                405                 410                 415

Leu Glu Ile Ala Cys Glu His Gly Ala Leu His Ile Arg Arg Glu Gly
            420                 425                 430

Glu Val Arg Lys Phe Val Ala Gly Val Asn Gln Ile Ser Tyr Asn Gly
435                 440                 445

Glu Leu Ala Arg Ala Lys Gly Gln Thr Met His Tyr Val Thr Glu Arg
        450                 455                 460

Ala Val Phe Glu Leu Arg Pro Glu Gly Pro Val Leu Thr Glu Ile Ala
465                 470                 475                 480

Pro Gly Ile Asp Leu Glu Arg Asp Ile Leu Ala His Met Asp Phe His
                485                 490                 495

Pro Ala Ile Ala Ala Asp Leu Gln Val Met Asp Ser Arg Leu Phe Thr
            500                 505                 510

Pro Pro Pro Cys Gly Leu Ala Glu His Leu Ser Arg Asn Ser Ser Ser
        515                 520                 525

Asp Ser
    530

<210> SEQ ID NO 77
<211> LENGTH: 228
<212> TYPE: PRT
<213> ORGANISM: Klebsiella pneumoniae
<220> FEATURE:
<221> NAME/KEY: MISC_FEATURE
<223> OTHER INFORMATION: Uniprot name: A0A085DBP3_KLEPN. 3-oxoadipate
      CoA-transferase

<400> SEQUENCE: 77

Met Ile Asp Lys Ser Val Ser Thr Leu Ser Glu Ala Ile Ala Gly Ile
1               5                   10                  15

His Asp Gly Ala Thr Ile Met Ile Gly Gly Phe Gly Pro Ala Gly Gln
            20                  25                  30

Pro Thr Phe Leu Ile Asp Ala Leu Ile Asp Gln Gly Ala Arg Asp Leu
        35                  40                  45

Thr Ile Ile Asn Asn Asn Ala Gly Asn Gly Glu Val Gly Leu Ala Ala
    50                  55                  60

Leu Leu Lys Ala Gly Arg Val Arg Lys Met Ile Cys Ser Phe Pro Arg
65                  70                  75                  80

Gln Val Asp Ser Gln Ile Phe Asp Leu Tyr Arg Arg Gly Lys Val
                85                  90                  95

Glu Leu Glu Leu Val Pro Gln Gly Asn Leu Ala Ala Arg Ile Gln Ala
            100                 105                 110

Ala Gly Ala Gly Leu Gly Ala Val Phe Thr Pro Thr Gly Tyr Gly Thr
        115                 120                 125

Pro Leu Ala Glu Gly Lys Glu Thr Arg Glu Ile Asp Gly Arg His Tyr
    130                 135                 140

Val Leu Glu Tyr Pro Ile Lys Ala Asp Phe Ala Leu Ile Lys Ala His
```

```
                145                 150                 155                 160
Gln Gly Asp Arg Trp Gly Asn Leu Val Tyr Arg Lys Ala Ala Arg Asn
                    165                 170                 175

Phe Gly Pro Ile Met Ala Thr Ala Ala Lys Thr Thr Ile Val Glu Val
                    180                 185                 190

Ser Gln Leu Val Ala Leu Gly Leu Asp Pro Glu Asn Ile Ile Thr
                195                 200                 205

Pro Gly Ile Phe Val Gln Arg Val Phe Ser Leu Glu Asn Leu Thr Ala
                210                 215                 220

Ala Gln Arg Ala
225

<210> SEQ ID NO 78
<211> LENGTH: 235
<212> TYPE: PRT
<213> ORGANISM: Klebsiella pneumoniae
<220> FEATURE:
<221> NAME/KEY: MISC_FEATURE
<223> OTHER INFORMATION: Uniprot name: W9B913_KLEPN.  Acetyl-
      CoA:acetoacetyl-CoA transferase, alpha subunit

<400> SEQUENCE: 78

Met Ala Gly Leu Asp Lys Arg Val Ala Ser Tyr Glu Ala Ala Leu Glu
1               5                   10                  15

Gly Leu Thr Asp Gly Met Thr Leu Leu Ala Gly Gly Phe Gly Leu Cys
                20                  25                  30

Gly Ile Pro Glu Asn Leu Ile Ala Glu Val Gln Arg Arg Gln Val Gln
            35                  40                  45

Gly Leu Thr Val Val Ser Asn Asn Cys Gly Val Asp Gly Phe Gly Leu
        50                  55                  60

Gly Met Leu Leu Glu Ser Arg Gln Val Ser Lys Val Val Ala Ser Tyr
65                  70                  75                  80

Val Gly Glu Asn Ala Leu Phe Glu Gln Leu Val Leu Ser Gly Glu Leu
                85                  90                  95

Ala Val Glu Leu Thr Pro Gln Gly Thr Leu Ala Glu Lys Ile Arg Ala
                100                 105                 110

Gly Gly Ala Gly Ile Pro Gly Phe Tyr Thr Ala Thr Gly Tyr Gly Thr
            115                 120                 125

Pro Val Ala Glu Gly Lys Glu Val Arg Gln Phe Asp Gly Arg His Tyr
        130                 135                 140

Ile Leu Glu Glu Ala Ile Arg Gly Asp Phe Ala Leu Val Lys Gly Trp
145                 150                 155                 160

Lys Ala Asp Trp Tyr Gly Asn Val Val Tyr Arg His Thr Ala Gln Asn
                165                 170                 175

Phe Asn Pro Leu Met Ala Thr Ala Gly Arg Ile Thr Val Val Glu Val
                180                 185                 190

Glu Glu Ile Val Pro Pro Gly Glu Leu Pro Ser Ala Ile His Thr
            195                 200                 205

Pro Gly Ile Tyr Val Asp Arg Leu Ile Val Gly Gln Phe Glu Lys Arg
        210                 215                 220

Ile Glu Gln Arg Thr Leu Arg Ala Gly Gly His
225                 230                 235

<210> SEQ ID NO 79
<211> LENGTH: 218
<212> TYPE: PRT
<213> ORGANISM: Klebsiella pneumoniae
```

```
<220> FEATURE:
<221> NAME/KEY: MISC_FEATURE
<223> OTHER INFORMATION: Uniprot name: W9BPH5_KLEPN. Acetyl-
      CoA:acetoacetyl-CoA transferase, beta subunit

<400> SEQUENCE: 79

Met Leu Thr Arg Glu Gln Met Ala Met Arg Val Ala Gln Glu Leu Arg
1               5                   10                  15

Asp Gly Asp Tyr Val Asn Leu Gly Ile Gly Ile Pro Thr Leu Val Ala
            20                  25                  30

Asn Tyr Ile Pro Ala Gly Ile Glu Val Met Leu Gln Ser Glu Asn Gly
        35                  40                  45

Leu Leu Gly Met Gly Glu Phe Pro Asp Glu Thr Ile Asp Ala Asp
    50                  55                  60

Met Ile Asn Ala Gly Lys Gln Thr Val Thr Ala Gln Thr Gly Ala Ala
65                  70                  75                  80

Ile Phe Asp Ser Ala Gln Ser Phe Ala Met Ile Arg Gly Gly His Val
                85                  90                  95

Asp Leu Thr Val Leu Gly Ala Phe Glu Val Asp Val Ala Gly Asn Ile
            100                 105                 110

Ala Ser Trp Met Ile Pro Gly Lys Met Val Lys Gly Met Gly Gly Ala
        115                 120                 125

Met Asp Leu Val Ala Gly Ala Gln Asn Ile Ile Val Val Met Thr His
130                 135                 140

Ala Ser Lys Asn Gly Glu Ser Lys Leu Leu Pro Gln Cys Thr Leu Pro
145                 150                 155                 160

Leu Thr Gly Val Gly Cys Ile Arg Arg Val Leu Thr Asp Leu Ala Leu
                165                 170                 175

Leu Glu Ile Val Asp Gly Ala Phe Val Leu Arg Glu Val Ala Pro Gly
            180                 185                 190

Val Ser Pro Asp Glu Val Ile Arg Lys Thr Ala Gly Arg Leu Ile Val
        195                 200                 205

Ala Asp Asp Val Arg Glu Met Arg Phe Ser
    210                 215

<210> SEQ ID NO 80
<211> LENGTH: 533
<212> TYPE: PRT
<213> ORGANISM: Phyllobacterium sp.
<220> FEATURE:
<221> NAME/KEY: MISC_FEATURE
<223> OTHER INFORMATION: Uniprot name: J2VI37_9RHIZ. Acetate CoA-
      transferase YdiF

<400> SEQUENCE: 80

Met Asn Lys His Ile Thr Pro Glu Gln Ala Ala Glu Leu Ile Pro Asp
1               5                   10                  15

Glu Ala Val Val Thr Val Ser Ser Ser Gly Leu Gly Cys Pro Asp
            20                  25                  30

Leu Met Leu Lys Ala Ile Gly Ala Arg Phe Asp Ala Thr Gly His Pro
        35                  40                  45

Arg Asp Leu Thr Thr Leu His Pro Ile Ala Ala Gly Asp Met Ser Gly
    50                  55                  60

Ile Lys Gly Val Asp Tyr Ile Ala Lys Lys Gly Leu Leu Lys Lys Ile
65                  70                  75                  80

Ile Gly Gly Ser Tyr Pro Ser Gly Pro Ser Thr Ala Glu Pro Pro Leu
                85                  90                  95
```

```
Ile Trp Gln Met Ile Gly Asn Asp Glu Val Ala Ala Tyr Asn Val Pro
                100                 105                 110

Ser Gly Ile Leu Phe Asp Met His Arg Glu Ala Ala Lys Arg Pro
            115                 120                 125

Gly Val Leu Thr Lys Val Gly Leu Asp Thr Phe Val Asp Pro Asp Arg
130                 135                 140

Gln Gly Cys Ala Met Asn Ala Pro Ala Ala Gln Glu Pro Leu Val Arg
145                 150                 155                 160

Lys Ile Asp Phe Asp Gly Glu Glu Trp Leu Phe Phe Lys Pro Val Ile
                165                 170                 175

Pro Gln Val Ala Ile Ile Arg Ala Thr Thr Ala Asp Glu Arg Gly Asn
            180                 185                 190

Leu Thr Tyr Glu His Glu Gly Ala Tyr Leu Gly Gly Phe Asp Gln Ala
        195                 200                 205

Leu Ala Val Arg Asn Asn Gly Ile Val Ile Ala Gln Val Lys Arg
            210                 215                 220

Ile Thr Lys Ser Gly Ser Leu Lys Pro His Asp Val Arg Val Pro Gly
225                 230                 235                 240

Ile Leu Val Asp Tyr Ile Val Val Asp Pro Asp Gln Lys Gln Thr Thr
                245                 250                 255

Gln Thr Leu Tyr Asp Pro Ala Ile Ser Gly Glu Ile Phe His Pro Leu
            260                 265                 270

Glu Asp Phe Ala Leu Ala Asp Phe Asn Ile Gln Lys Val Ile Ala Arg
        275                 280                 285

Arg Val Ala Ser Glu Leu Glu Ala Gly Ser Ala Val Asn Leu Gly Phe
        290                 295                 300

Gly Ile Ser Ala Asn Val Pro Arg Ile Leu Leu Glu Glu Gly Leu His
305                 310                 315                 320

Gly Ala Val Thr Trp Val Ile Glu Gln Gly Pro Val Gly Ile Pro
                325                 330                 335

Leu Leu Asp Phe Ala Phe Gly Cys Ala Ser Asn Ala Glu Ala Phe Val
            340                 345                 350

Pro Ser Pro His Gln Phe Thr Tyr Phe Gln Gly Ala Gly Phe Asp Ala
            355                 360                 365

Ser Leu Leu Ser Phe Leu Glu Ile Asp Lys Ser Gly Ser Val Asn Val
370                 375                 380

Ser Lys Leu Ser Phe Arg Pro His Val Thr Ala Gly Ala Gly Gly Phe
385                 390                 395                 400

Val Asp Ile Thr Ala Arg Ala Arg Lys Ile Val Phe Ser Gly Met Phe
                405                 410                 415

Asn Ala Gly Ala Lys Val His Ile Glu Asn Gly Lys Leu Val Ile Glu
            420                 425                 430

Lys Glu Gly Lys Leu Lys Leu Val Asn Glu Val Glu His Val Thr
        435                 440                 445

Phe Ser Gly Arg Arg Ala Val Glu Gln Gly Gln Asp Ile Thr Tyr Val
        450                 455                 460

Thr Glu Arg Cys Val Met Val Leu Arg Pro Glu Gly Leu Val Leu Thr
465                 470                 475                 480

Glu Ile Ala Pro Gly Ile Asp Leu Gln Ala His Ile Leu Asp Gln Ser
                485                 490                 495

Glu Phe Pro Leu Val Val Ala Arg Asp Leu Lys Leu Met Asp Ala His
            500                 505                 510

Leu Phe Ser Pro Glu Pro Phe Gly Leu Lys Leu Pro Gln Lys Met Gln
```

-continued

```
          515                 520                 525
Arg Lys Leu His Gly
        530

<210> SEQ ID NO 81
<211> LENGTH: 519
<212> TYPE: PRT
<213> ORGANISM: Pseudomonas alcaligenes
<220> FEATURE:
<221> NAME/KEY: MISC_FEATURE
<223> OTHER INFORMATION: Uniprot name: U3H473_PSEAC. Acetate CoA-
      transferase YdiF

<400> SEQUENCE: 81

Met Ser Lys Val Met Ser Ala Ala Glu Ala Val Ala Arg Ile Pro Asp
1               5                   10                  15

Asn Ala His Leu Ala Thr Gly Gly Phe Val Gly Ile Gly Phe Ala Glu
            20                  25                  30

Ala Ile Ala Ile Ala Leu Glu Gln Arg Phe Gln Ala Glu Gln Ala Pro
        35                  40                  45

Arg Asp Leu Thr Leu Val Tyr Ala Ala Gly Gln Gly Asp Gly Lys Gly
    50                  55                  60

Arg Gly Leu Asn His Leu Ala His Glu Gly Leu Val Arg Arg Val Ile
65                  70                  75                  80

Gly Gly His Trp Gly Leu Val Pro Gly Leu Gln Lys Leu Ala Val Glu
                85                  90                  95

Asn Arg Ile Glu Ala Tyr Asn Leu Pro Gln Gly Val Ile Ser Gln Leu
            100                 105                 110

Phe Arg Asp Ile Ala Ala Gly Lys Pro Gly Gln Leu Ser Arg Val Gly
        115                 120                 125

Leu Gly Thr Phe Val Asp Pro Glu His Gly Gly Gly Lys Leu Asn Ala
    130                 135                 140

Arg Thr Thr Glu Glu Leu Val Arg Arg Met Pro Leu Asp Gly Glu Asp
145                 150                 155                 160

Tyr Leu Phe Tyr Lys Thr Phe Pro Ile His Val Gly Val Val Arg Ala
                165                 170                 175

Thr Ser Ala Asp Glu Asp Gly Asn Leu Thr Met Glu Arg Glu Ala Leu
            180                 185                 190

Thr Ile Glu Ser Leu Ala Ile Ala Met Ala Ala Arg Asn Ser Gly Gly
        195                 200                 205

Leu Val Ile Ala Gln Val Glu Arg Val Ala Arg Gly Ser Leu Asn
    210                 215                 220

Pro Arg Gln Val Lys Ile Pro Gly Ile Leu Val Asp Cys Val Val Val
225                 230                 235                 240

Ala Ala Pro Glu His His Gln Gln Thr Phe Ala Thr Ala Tyr Asn Pro
                245                 250                 255

Ala Phe Ala Ala Glu Val Arg Val Pro Glu Gly Ser Leu Pro Pro Met
            260                 265                 270

Pro Leu Asp Leu Arg Lys Leu Ile Ala Arg Arg Ala Ala Leu Glu Leu
        275                 280                 285

Lys Pro Gly Ala Val Val Asn Leu Gly Ile Gly Met Pro Glu Gly Val
    290                 295                 300

Ala Ala Val Ala Ala Glu Glu Gly Val Ile Asp Leu Leu Thr Leu Thr
305                 310                 315                 320

Ala Glu Pro Gly Val Ile Gly Gly Val Pro Ala Ser Gly Leu Asp Phe
                325                 330                 335
```

Gly Ala Ala Cys Asn His Ser Ala Leu Ile Asp Gln Pro Tyr Gln Phe
                340                 345                 350

Asp Phe Tyr Asp Gly Gly Leu Asp Leu Ala Phe Leu Gly Leu Ala
            355                 360                 365

Gln Ala Asp Ala Ala Gly Asn Leu Asn Val Ser Lys Phe Gly Thr Arg
370                 375                 380

Leu Ala Gly Ala Gly Phe Ile Asn Ile Ser Gln Asn Ala Lys Ala
385                 390                 395                 400

Val Val Phe Val Gly Thr Phe Ser Ala Gly Pro Gln Asp Ile Arg Ile
                405                 410                 415

Glu Asn Gly Ala Leu Arg Ile Val Gln Asp Gly Ala Leu Arg Lys Phe
            420                 425                 430

Val Arg Glu Val Glu His Arg Thr Phe Ala Gly Arg Leu Ala Ala Glu
        435                 440                 445

Ala Gly Lys Pro Val Leu Tyr Val Thr Glu Arg Cys Val Phe Arg Leu
450                 455                 460

Thr Thr Glu Gly Leu Glu Leu Ile Glu Val Ala Pro Gly Val Asp Ile
465                 470                 475                 480

Glu Arg Asp Ile Leu Ala Arg Met Asp Phe Arg Pro Leu Val Arg Ala
                485                 490                 495

Pro Lys Leu Met Asp Val Arg Leu Phe Gly Glu Thr Arg Met Gly Leu
            500                 505                 510

Arg Gly Met Ile Asp Glu Ala
        515

<210> SEQ ID NO 82
<211> LENGTH: 232
<212> TYPE: PRT
<213> ORGANISM: Pseudomonas fluorescens
<220> FEATURE:
<221> NAME/KEY: MISC_FEATURE
<223> OTHER INFORMATION: Uniprot name: G8Q6H9_PSEFL. DhcA

<400> SEQUENCE: 82

Met Ala Gly Phe Asp Lys Arg Val Ser Ser Tyr Glu Glu Ala Leu Glu
1               5                   10                  15

Gly Leu Lys Asp Gly Met Thr Val Ile Ala Gly Gly Phe Gly Leu Cys
            20                  25                  30

Gly Ile Pro Glu Asn Leu Ile Ala Glu Ile Lys Arg Lys Gly Ile Arg
        35                  40                  45

Asp Leu Thr Val Val Ser Asn Asn Cys Gly Val Asp Gly Phe Gly Leu
50                  55                  60

Gly Val Leu Leu Glu Asp Arg Gln Ile Arg Lys Val Val Ala Ser Tyr
65                  70                  75                  80

Val Gly Glu Asn Ala Leu Phe Glu Lys Gln Leu Leu Ser Gly Glu Ile
                85                  90                  95

Glu Val Val Leu Thr Pro Gln Gly Thr Leu Ala Glu Lys Met Arg Ala
            100                 105                 110

Gly Gly Ala Gly Ile Pro Ala Phe Phe Thr Ala Thr Gly Val Gly Thr
        115                 120                 125

Pro Val Ala Glu Gly Lys Glu Val Arg Glu Phe His Gly Arg Gln Tyr
130                 135                 140

Leu Met Glu Glu Ser Ile Thr Gly Asp Phe Ala Ile Val Lys Gly Trp
145                 150                 155                 160

Lys Ala Asp His Phe Gly Asn Val Ile Tyr Arg His Thr Ala Gln Asn

```
                165                 170                 175
Phe Asn Pro Leu Ala Thr Ala Gly Lys Ile Thr Val Val Glu Val
            180                 185                 190

Glu Glu Ile Val Glu Pro Gly Glu Leu Asp Pro Thr Gln Ile His Thr
            195                 200                 205

Pro Gly Ile Tyr Val Asp Arg Val Ile Cys Gly Thr Phe Glu Lys Arg
            210                 215                 220

Ile Glu Gln Arg Thr Val Arg Lys
225                 230

<210> SEQ ID NO 83
<211> LENGTH: 221
<212> TYPE: PRT
<213> ORGANISM: Pseudomonas fluorescens
<220> FEATURE:
<221> NAME/KEY: MISC_FEATURE
<223> OTHER INFORMATION: Uniprot name: G8Q6H8_PSEFL. DhcB

<400> SEQUENCE: 83

Met Ala Leu Ser Arg Glu Gln Met Ala Gln Arg Val Ala Arg Glu Met
1               5                   10                  15

Gln Asp Gly Tyr Tyr Val Asn Leu Gly Ile Gly Ile Pro Thr Leu Val
            20                  25                  30

Ala Asn Tyr Ile Pro Glu Gly Met Glu Val Met Leu Gln Ser Glu Asn
            35                  40                  45

Gly Leu Leu Gly Met Gly Ala Phe Pro Thr Glu Ala Glu Val Asp Ala
        50                  55                  60

Asp Met Ile Asn Ala Gly Lys Gln Thr Val Thr Ala Arg Ile Gly Ala
65                  70                  75                  80

Ser Ile Phe Ser Ser Ala Glu Ser Phe Ala Met Ile Arg Gly Gly His
                85                  90                  95

Ile Asp Leu Thr Val Leu Gly Ala Phe Glu Val Asp Val Glu Gly Asn
            100                 105                 110

Ile Ala Ser Trp Met Ile Pro Gly Lys Leu Val Lys Gly Met Gly Gly
        115                 120                 125

Ala Met Asp Leu Val Ala Gly Ala Glu Asn Ile Ile Val Thr Met Thr
    130                 135                 140

His Ala Ser Lys Asp Gly Glu Ser Lys Leu Leu Pro Arg Cys Ser Leu
145                 150                 155                 160

Pro Leu Thr Gly Ala Gly Cys Ile Lys Arg Val Leu Thr Asp Leu Ala
                165                 170                 175

Tyr Leu Glu Ile Gln Asp Gly Ala Phe Ile Leu Lys Glu Arg Ala Pro
            180                 185                 190

Gly Val Ser Val Glu Glu Ile Val Ala Lys Thr Ala Gly Lys Leu Ile
        195                 200                 205

Val Pro Asp His Val Pro Glu Met Gln Phe Ala Ala Gln
    210                 215                 220

<210> SEQ ID NO 84
<211> LENGTH: 218
<212> TYPE: PRT
<213> ORGANISM: Pseudomonas putida
<220> FEATURE:
<221> NAME/KEY: MISC_FEATURE
<223> OTHER INFORMATION: Uniprot name: A5W3L8_PSEP1. Butyryl-
      CoA:acetate CoA transferase

<400> SEQUENCE: 84
```

Met Ala Leu Thr Arg Glu Gln Met Ala Gln Arg Val Ala Arg Glu Leu
1               5                   10                  15

Lys Asp Gly Tyr Tyr Val Asn Leu Gly Ile Gly Ile Pro Thr Leu Val
            20                  25                  30

Ala Asn Tyr Val Pro Ala Asp Met Asp Val Met Leu Gln Ser Glu Asn
        35                  40                  45

Gly Leu Leu Gly Met Gly Glu Phe Pro Thr Glu Ser Thr Leu Asp Ala
    50                  55                  60

Asp Met Ile Asn Ala Gly Lys Gln Thr Val Thr Ala Arg Arg Gly Ala
65                  70                  75                  80

Ser Ile Phe Asp Ser Ala Gln Ser Phe Ala Met Ile Arg Gly Gly His
            85                  90                  95

Val Asp Leu Thr Val Leu Gly Ala Phe Glu Val Asp Val Gln Gly Asn
            100                 105                 110

Ile Ala Ser Trp Met Ile Pro Gly Lys Leu Val Lys Gly Met Gly Gly
            115                 120                 125

Ala Met Asp Leu Val Ala Gly Ala Asp Asn Ile Ile Val Thr Met Thr
        130                 135                 140

His Ala Ser Lys Asp Gly Glu Ser Lys Leu Leu Pro Gln Cys Ser Leu
145                 150                 155                 160

Pro Leu Thr Gly Ala Gly Cys Ile Arg Lys Val Leu Thr Asp Leu Ala
            165                 170                 175

Tyr Leu Glu Ile Glu Asp Gly Ala Phe Ile Leu Arg Glu Thr Ala Pro
            180                 185                 190

Gly Val Ser Val Glu Glu Ile Ile Glu Lys Thr Ala Gly Lys Leu Ile
            195                 200                 205

Val Pro Asp Asp Val Lys Glu Met Thr Phe
        210                 215

<210> SEQ ID NO 85
<211> LENGTH: 232
<212> TYPE: PRT
<213> ORGANISM: Pseudomonas putida
<220> FEATURE:
<221> NAME/KEY: MISC_FEATURE
<223> OTHER INFORMATION: Uniprot name: B0KTE5_PSEPG. 3-oxoacid CoA-
      transferase, A subunit

<400> SEQUENCE: 85

Met Ala Gly Leu Asp Lys Arg Val Ala Thr Tyr Glu Gln Ala Leu Glu
1               5                   10                  15

Gly Leu Thr Asp Asn Met Thr Val Leu Ala Gly Gly Phe Gly Leu Cys
            20                  25                  30

Gly Ile Pro Glu Asn Leu Ile Ser Glu Ile Lys Arg Arg Gly Val Lys
        35                  40                  45

Gly Leu Thr Val Val Ser Asn Asn Cys Gly Val Asp Gly Phe Gly Leu
    50                  55                  60

Gly Val Leu Leu Glu Asp Arg Gln Ile Arg Lys Met Ile Ala Ser Tyr
65                  70                  75                  80

Val Gly Glu Asn Ala Glu Phe Glu Arg Gln Leu Leu Ser Gly Glu Leu
            85                  90                  95

Glu Val Glu Leu Thr Pro Gln Gly Thr Leu Ala Glu Lys Met Arg Ala
            100                 105                 110

Gly Gly Ala Gly Ile Pro Ala Phe Tyr Thr Ala Thr Gly Tyr Gly Thr
        115                 120                 125

Pro Val Ala Asp Gly Lys Glu Val Arg Glu Phe Lys Gly Arg Lys Tyr

```
                130             135             140
Ile Leu Glu Glu Ser Ile Thr Gly Asp Phe Ala Ile Val Lys Gly Trp
145                 150                 155                 160

Lys Ala Asp His Tyr Gly Asn Val Val Tyr Arg Asn Thr Ala Gln Asn
                165                 170                 175

Phe Asn Pro Leu Ala Ala Thr Ala Gly Lys Ile Thr Val Val Glu Val
            180                 185                 190

Glu Glu Ile Val Glu Pro Gly Val Leu Leu Pro Ser Glu Ile His Thr
        195                 200                 205

Pro Gly Ile Tyr Val Asp Arg Val Ile Val Gly Thr Phe Glu Lys Arg
    210                 215                 220

Ile Glu Lys Arg Thr Val Lys Ala
225                 230
```

<210> SEQ ID NO 86
<211> LENGTH: 218
<212> TYPE: PRT
<213> ORGANISM: Pseudomonas putida
<220> FEATURE:
<221> NAME/KEY: MISC_FEATURE
<223> OTHER INFORMATION: Uniprot name: B0KTE4_PSEPG. 3-oxoacid CoA-
      transferase, B subunit

<400> SEQUENCE: 86

```
Met Ala Leu Thr Arg Glu Gln Met Ala Gln Arg Val Ala Arg Glu Leu
1               5                   10                  15

Lys Asp Gly Tyr Tyr Val Asn Leu Gly Ile Gly Ile Pro Thr Leu Val
            20                  25                  30

Ala Asn Tyr Val Pro Ala Asp Met Asp Val Met Leu Gln Ser Glu Asn
        35                  40                  45

Gly Leu Leu Gly Met Gly Glu Phe Pro Thr Glu Ser Thr Ile Asp Ala
    50                  55                  60

Asp Met Ile Asn Ala Gly Lys Gln Thr Val Thr Ala Arg Arg Gly Ala
65                  70                  75                  80

Ser Ile Phe Asp Ser Ala Gln Ser Phe Ala Met Ile Arg Gly Gly His
                85                  90                  95

Val Asp Leu Thr Val Leu Gly Ala Phe Glu Val Asp Val Gln Gly Asn
            100                 105                 110

Ile Ala Ser Trp Met Ile Pro Gly Lys Leu Val Lys Gly Met Gly Gly
        115                 120                 125

Ala Met Asp Leu Val Ala Gly Ala Asp Asn Ile Ile Val Thr Met Thr
    130                 135                 140

His Ala Ser Lys Asp Gly Glu Ser Lys Leu Leu Pro Gln Cys Ser Leu
145                 150                 155                 160

Pro Leu Thr Gly Ala Gly Cys Ile Arg Lys Val Leu Thr Asp Leu Ala
                165                 170                 175

Tyr Leu Glu Ile Glu Asp Gly Ala Phe Ile Leu Arg Glu Thr Ala Pro
            180                 185                 190

Gly Val Ser Val Glu Glu Ile Ile Glu Lys Thr Ala Gly Lys Leu Ile
        195                 200                 205

Val Pro Asp Asp Val Lys Glu Met Thr Phe
    210                 215
```

<210> SEQ ID NO 87
<211> LENGTH: 554
<212> TYPE: PRT
<213> ORGANISM: Ralstonia solanacearum (Pseudomonas solanacearum)

-continued

```
<220> FEATURE:
<221> NAME/KEY: MISC_FEATURE
<223> OTHER INFORMATION: Uniprot name: D8NYJ4_RALSL. Acetate CoA-
      transferase YdiF

<400> SEQUENCE: 87
```

| Met | Gln | Val | Ile | Thr | Ala | Glu | Glu | Ala | Ala | Arg | Leu | Val | Gln | Pro | Gly |
|---|---|---|---|---|---|---|---|---|---|---|---|---|---|---|---|
| 1 | | | | 5 | | | | | 10 | | | | | 15 | |

| Trp | Thr | Val | Ala | Cys | Ala | Gly | Phe | Val | Gly | Ala | Gly | His | Ala | Glu | Ala |
|---|---|---|---|---|---|---|---|---|---|---|---|---|---|---|---|
| | | | 20 | | | | | 25 | | | | | 30 | | |

| Val | Thr | His | Ala | Leu | Glu | Arg | Arg | Phe | Leu | Ala | Thr | Gly | Glu | Pro | Arg |
|---|---|---|---|---|---|---|---|---|---|---|---|---|---|---|---|
| | | 35 | | | | | 40 | | | | | 45 | | | |

| Asp | Leu | Thr | Leu | Val | Tyr | Ser | Ala | Gly | Gln | Gly | Asp | Arg | Ala | Thr | Arg |
|---|---|---|---|---|---|---|---|---|---|---|---|---|---|---|---|
| 50 | | | | | 55 | | | | | 60 | | | | | |

| Gly | Val | Asn | His | Phe | Gly | Asn | Pro | Gly | Met | Thr | Arg | Cys | Val | Val | Gly |
|---|---|---|---|---|---|---|---|---|---|---|---|---|---|---|---|
| 65 | | | | 70 | | | | | 75 | | | | | 80 | |

| Gly | His | Trp | Arg | Ser | Ala | Thr | Arg | Leu | Ala | Ala | Leu | Ala | Leu | Ala | Glu |
|---|---|---|---|---|---|---|---|---|---|---|---|---|---|---|---|
| | | | 85 | | | | | 90 | | | | | 95 | | |

| Gln | Cys | Glu | Ala | Phe | Asn | Leu | Pro | Gln | Gly | Val | Leu | Thr | His | Leu | Tyr |
|---|---|---|---|---|---|---|---|---|---|---|---|---|---|---|---|
| | | | 100 | | | | | 105 | | | | | 110 | | |

| Arg | Ala | Ile | Ala | Gly | Gly | Lys | Pro | Gly | Val | Leu | Thr | Arg | Ile | Gly | Leu |
|---|---|---|---|---|---|---|---|---|---|---|---|---|---|---|---|
| | | 115 | | | | | 120 | | | | | 125 | | | |

| His | Thr | Phe | Val | Asp | Pro | Arg | Thr | Ser | Leu | Asp | Ala | Arg | Tyr | His | Gly |
|---|---|---|---|---|---|---|---|---|---|---|---|---|---|---|---|
| 130 | | | | | 135 | | | | | 140 | | | | | |

| Ala | Ala | Ile | Asn | Ala | Arg | Ala | Arg | Ala | Ala | Arg | Glu | Ala | Gly | Thr | Ala |
|---|---|---|---|---|---|---|---|---|---|---|---|---|---|---|---|
| 145 | | | | | 150 | | | | | 155 | | | | | 160 |

| Ser | Trp | Val | Glu | Tyr | Glu | Arg | Phe | Arg | Gly | Asp | Tyr | Leu | Phe | Tyr |
|---|---|---|---|---|---|---|---|---|---|---|---|---|---|---|
| | | | | 165 | | | | | 170 | | | | | 175 |

| Pro | Arg | Phe | Pro | Leu | His | Gly | Val | Phe | Leu | Arg | Gly | Thr | Ala | Ala | Asp |
|---|---|---|---|---|---|---|---|---|---|---|---|---|---|---|---|
| | | | 180 | | | | | 185 | | | | | 190 | | |

| Pro | Arg | Gly | Asn | Ile | Ser | Thr | His | Glu | Glu | Ala | Phe | His | His | Glu | Leu |
|---|---|---|---|---|---|---|---|---|---|---|---|---|---|---|---|
| | | 195 | | | | | 200 | | | | | 205 | | | |

| Leu | Ala | Met | Ala | Gln | Ala | Ala | Arg | Asn | Ala | Gly | Gly | Ile | Val | Ile | Ala |
|---|---|---|---|---|---|---|---|---|---|---|---|---|---|---|---|
| | 210 | | | | | 215 | | | | | 220 | | | | |

| Gln | Val | Arg | Arg | Leu | Val | Asp | Arg | His | Asp | Asn | Leu | Gln | Ala | Ile | His |
|---|---|---|---|---|---|---|---|---|---|---|---|---|---|---|---|
| 225 | | | | | 230 | | | | | 235 | | | | | 240 |

| Val | Pro | Gly | Ile | Leu | Val | Asp | Tyr | Val | Val | Ala | Glu | Asp | Pro | Ala |
|---|---|---|---|---|---|---|---|---|---|---|---|---|---|---|
| | | | | 245 | | | | | 250 | | | | | 255 |

| Glu | His | Gln | Met | Thr | Phe | Gly | Glu | Ala | Phe | Asn | Pro | Thr | Tyr | Leu | Arg |
|---|---|---|---|---|---|---|---|---|---|---|---|---|---|---|---|
| | | | 260 | | | | | 265 | | | | | 270 | | |

| Pro | Trp | Gln | Gly | Glu | Ala | Ile | Gln | Leu | Arg | Glu | Asp | Ala | Leu | Glu | Ala |
|---|---|---|---|---|---|---|---|---|---|---|---|---|---|---|---|
| | | 275 | | | | | 280 | | | | | 285 | | | |

| Gly | Ala | Ala | Ile | Glu | Thr | Ser | Leu | His | Gly | Ala | Leu | Asp | Ala | Arg | Thr |
|---|---|---|---|---|---|---|---|---|---|---|---|---|---|---|---|
| | 290 | | | | | 295 | | | | | 300 | | | | |

| Leu | Val | Gln | Arg | Arg | Ala | Val | Leu | Glu | Leu | Met | Ala | Gln | Arg | Pro | Arg |
|---|---|---|---|---|---|---|---|---|---|---|---|---|---|---|---|
| 305 | | | | | 310 | | | | | 315 | | | | | 320 |

| Val | Val | Asn | Leu | Gly | Val | Gly | Met | Pro | Ala | Ala | Val | Gly | Ala | Leu | Ala |
|---|---|---|---|---|---|---|---|---|---|---|---|---|---|---|---|
| | | | | 325 | | | | | 330 | | | | | 335 | |

| Glu | Gln | Glu | Gly | Ala | Arg | Gly | Phe | Thr | Leu | Thr | Val | Glu | Ala | Gly | Pro |
|---|---|---|---|---|---|---|---|---|---|---|---|---|---|---|---|
| | | | 340 | | | | | 345 | | | | | 350 | | |

| Ile | Gly | Gly | Thr | Pro | Ala | Asp | Gly | Leu | Ser | Phe | Gly | Ala | Ser | Ala | Tyr |
|---|---|---|---|---|---|---|---|---|---|---|---|---|---|---|---|
| | | 355 | | | | | 360 | | | | | 365 | | | |

| Pro | Glu | Ala | Val | Val | Asp | Gln | Pro | Ala | Gln | Phe | Asp | Phe | Tyr | Glu | Gly |
|---|---|---|---|---|---|---|---|---|---|---|---|---|---|---|---|
| | 370 | | | | | 375 | | | | | 380 | | | | |

```
Gly Gly Ile Asp Leu Ala Ile Leu Gly Leu Ala Glu Leu Asp Gly Gln
385                 390                 395                 400

Gly Asn Val Asn Val Ser Leu Phe Gly Glu Gly Asp Asp Thr Ile Val
                405                 410                 415

Ala Gly Val Gly Gly Phe Ile Asn Ile Thr Gln Ser Ala Arg Ala Leu
            420                 425                 430

Val Phe Met Gly Thr Leu Thr Ala Gly Gly Leu Gln Val Glu Ala Gly
        435                 440                 445

Asp Gly Arg Leu Arg Ile Val Arg Glu Gly Arg Leu Lys Lys Ile Val
    450                 455                 460

Pro Ala Val Ser His Leu Thr Phe Asn Gly Ala Tyr Ala Ala Arg Ser
465                 470                 475                 480

Gly Ile Pro Val Arg Tyr Val Thr Glu Arg Ala Val Phe Glu Met Arg
                485                 490                 495

Asp Asp Gly His Gly Gly Arg Arg Leu Thr Leu Thr Glu Ile Ala Pro
            500                 505                 510

Gly Ile Asp Leu Gln Arg Asp Val Leu Asp Gln Cys Ala Ala Glu Val
        515                 520                 525

Ala Val Ala Ala Asp Leu Arg Glu Met Asp His Arg Ile Phe Arg Arg
    530                 535                 540

Gly Pro Met Cys Ala Gly Pro Ala Ala Ala
545                 550

<210> SEQ ID NO 88
<211> LENGTH: 518
<212> TYPE: PRT
<213> ORGANISM: Rhizobium sp.
<220> FEATURE:
<221> NAME/KEY: MISC_FEATURE
<223> OTHER INFORMATION: Uniprot name: J2WFE9_9RHIZ. Acetate CoA-
      transferase YdiF OS

<400> SEQUENCE: 88

Met Gln Ile Ile Thr Ser Asn Glu Ala Ala Leu Leu Lys Asp Gly
1               5                   10                  15

Met Thr Val Ala Ala Ser Ala Phe Gly Gly Cys Cys His Pro Glu Ala
            20                  25                  30

Ile Ser Ala Ala Val Glu Glu Arg Tyr Leu Ala Glu Gly Thr Pro Arg
        35                  40                  45

Asp Leu Thr Leu Leu Phe Ala Ala Ser Ala Gly Asp Arg Lys Thr Arg
    50                  55                  60

Gly Met Gly His Phe Gly Tyr Glu Gly Leu Val Lys Arg Val Ile Ala
65                  70                  75                  80

Gly Gly Trp Arg Gly Thr Pro Arg Leu Gly Glu Leu Ala Leu Ala Glu
                85                  90                  95

Lys Ile Asp Ala Tyr Cys Trp Pro Gln Gly Val Ile Ala Gln Leu Tyr
            100                 105                 110

Arg Ala Ile Ala Ser Gly Gln Pro Gly Val Ile Thr His Ile Gly Leu
        115                 120                 125

Gly Ser Phe Met Asp Pro Leu His Gly Gly Arg Leu Asn Glu Ser
    130                 135                 140

Thr Thr Thr Glu Leu Val Glu Arg Val Thr Leu Arg Gly Arg Asp Trp
145                 150                 155                 160

Leu Leu Tyr Pro Ser Met Pro Leu Asp Cys Val Leu Leu Arg Gly Thr
                165                 170                 175

Thr Ala Asp Glu Asp Gly Asn Ile Thr Met Glu Asp Glu Ala Phe Pro
```

180                 185                 190
Val Asp Val Leu Ala Met Ala Gln Ala Gly Arg Asn Ser Gly Gly Ile
            195                 200                 205
Val Ile Val Gln Val Lys Arg Ile Ala Glu Arg Gly Ser Leu Arg Ala
        210                 215                 220
Ala Asp Val Arg Ile Pro Gly Met Leu Val Asp Tyr Val Val Val Cys
225                 230                 235                 240
Asp Asp Pro Ala Gln His Gly Val Ser Phe Gly Glu Thr Asp Asn Ile
                245                 250                 255
Ala Tyr Thr Gly Arg Phe Arg Ala Ala Thr Gly Gln Leu Pro Pro Leu
            260                 265                 270
Ser Leu Ser Val Asp Lys Val Ile Gln Arg Arg Ala Phe Gln Glu Leu
        275                 280                 285
Leu Ser His Ser Arg Ala Thr Ile Asn Leu Gly Ile Gly Ile Ala Ala
            290                 295                 300
Gly Ile Gly Arg Ile Ala Ser Glu Glu Ala Tyr Asp Asp Tyr Thr Val
305                 310                 315                 320
Thr Ile Glu Ser Gly Val Ile Gly Ile Pro Ala Glu Glu Leu Ser
                325                 330                 335
Phe Gly Ala Ala Val Asn Pro Ser Ala Ile Ile Ala Gln Ala Ser Gln
            340                 345                 350
Phe Asp Phe Tyr Asp Gly Gly Leu Asp Val Ala Phe Leu Gly Met
        355                 360                 365
Ala Glu Val Asp Val Arg Gly Ala Val Asn Val Ser Arg Phe Gly Lys
    370                 375                 380
Ser Ile Val Gly Val Gly Phe Thr Asn Ile Ser Gln Thr Ala Gly
385                 390                 395                 400
Thr Val Val Tyr Met Gly Ser Phe Ser His Gly Gly Ala Asp Ile Arg
                405                 410                 415
Val Glu Asp Gly Lys Leu Ser Ile Met Ala Asp Gly Arg Ser Cys Lys
            420                 425                 430
Ile Val Glu Lys Val Ala Gln Val Ser Ser Asp Pro Gly Ala Ala Pro
        435                 440                 445
Gln Gly Gln Lys Gln Ile Val Ile Thr Glu Arg Ala Val Phe His Val
    450                 455                 460
Ile Asp Ser Arg Leu Thr Leu Thr Glu Ile Ala Pro Gly Ile Asp Ala
465                 470                 475                 480
Lys Ala His Val Ile Asp Arg Leu Pro Ser Gly Val Ala Ile Ala Asp
                485                 490                 495
Lys Leu Gly Gln Met Asp Thr Arg Leu Phe Arg Pro Ser Ala Met Lys
            500                 505                 510
Asp Ser Gly His Glu Asp
        515

<210> SEQ ID NO 89
<211> LENGTH: 237
<212> TYPE: PRT
<213> ORGANISM: Rhizobium sp.
<220> FEATURE:
<221> NAME/KEY: MISC_FEATURE
<223> OTHER INFORMATION: Uniprot name: W6W555_9RHIZ. 3-oxoacid CoA-
      transferase, A subunit

<400> SEQUENCE: 89

Met Gln Lys Ile Val Ser Ser Ala Thr Glu Ala Leu Ala Asp Val Leu
1               5                   10                  15

-continued

Lys Asp Gly Met Val Ile Met Ser Gly Gly Phe Gly Leu Cys Gly Ile
            20                  25                  30

Pro Glu Thr Leu Ile Glu Ala Val Lys Leu Ser Gly Val Lys Asp Leu
        35                  40                  45

Thr Val Ile Ser Asn Asn Ala Gly Val Asp Gly Ile Gly Leu Gly Leu
50                  55                  60

Leu Leu Glu Thr Arg Gln Ile Arg Lys Met Ile Ser Ser Tyr Val Gly
65                  70                  75                  80

Glu Asn Lys Leu Phe Ala Gln Gln Phe Leu Ser Gly Glu Leu Glu Leu
                85                  90                  95

Glu Phe Asn Pro Gln Gly Thr Leu Ala Glu Arg Ile Arg Ala Gly Gly
            100                 105                 110

Ala Gly Ile Pro Ala Phe Phe Thr Lys Thr Gly Val Gly Thr Ile Ile
        115                 120                 125

Ser Glu Gly Lys Glu Ile Arg Glu Phe Gly Gly Glu Gln Tyr Val Met
130                 135                 140

Glu Met Ala Leu Leu Ala Asp Val Ser Leu Ile His Ala Trp Lys Gly
145                 150                 155                 160

Asp Thr Glu Gly Asn Leu Val Tyr Arg Lys Thr Ala Arg Asn Phe Asn
                165                 170                 175

Pro Met Met Ala Thr Ala Gly Lys Phe Thr Val Ala Glu Val Glu His
            180                 185                 190

Leu Val Asp Val Gly Gln Ile Asp Ala Asp His Ile His Thr Pro Gly
        195                 200                 205

Ile Phe Val Ser Lys Leu Leu His Val Pro Asp Ala Lys Lys His Ile
210                 215                 220

Glu Gln Arg Thr Val Arg Ser Ala Gln Thr Glu Ala Val
225                 230                 235

<210> SEQ ID NO 90
<211> LENGTH: 213
<212> TYPE: PRT
<213> ORGANISM: Rhizobium sp.
<220> FEATURE:
<221> NAME/KEY: MISC_FEATURE
<223> OTHER INFORMATION: Uniprot name: W6WQV5_9RHIZ.  3-oxoacid CoA-
      transferase, B subunit

<400> SEQUENCE: 90

Met Ala Trp Thr Arg Asp Gln Met Ala Ala Arg Ala Ala Arg Glu Leu
1               5                   10                  15

Gln Asp Gly Phe Tyr Val Asn Leu Gly Ile Gly Ile Pro Thr Leu Val
            20                  25                  30

Ala Asn His Ile Pro Asp Gly Ile Asp Val Val Leu Gln Ser Glu Asn
        35                  40                  45

Gly Met Leu Gly Ile Gly Pro Phe Pro Leu Glu Asn Glu Val Asp Ala
50                  55                  60

Asp Leu Ile Asn Ala Gly Lys Gln Thr Val Ser Glu Leu Pro Met Thr
65                  70                  75                  80

Ser Phe Phe Ser Ser Ala Asp Ser Phe Ala Met Ile Arg Gly Gly His
                85                  90                  95

Ile Asp Leu Ser Ile Leu Gly Ala Met Gln Val Ala Ser Asn Gly Asp
            100                 105                 110

Leu Ala Asn Trp Met Ile Pro Gly Lys Met Ala Lys Gly Met Gly Gly
        115                 120                 125

```
Ala Met Asp Leu Val Ala Gly Val Lys Arg Val Val Leu Met Glu
    130                 135                 140

His Glu Ala Lys Gly Glu Ser Lys Leu Leu Pro Glu Cys Asp Leu Pro
145                 150                 155                 160

Leu Thr Gly Lys Arg Val Val Asp Leu Val Ile Thr Asp Leu Gly Val
                165                 170                 175

Phe Thr Ile Ala Arg Thr Gly Ala Pro Glu Met Val Leu Ile Glu Leu
            180                 185                 190

Ala Glu Gly Val Thr Leu Glu Glu Ile Lys Ala Lys Thr Lys Ala Glu
        195                 200                 205

Phe Lys Val Gly Leu
    210

<210> SEQ ID NO 91
<211> LENGTH: 517
<212> TYPE: PRT
<213> ORGANISM: Salmonella typhimurium
<220> FEATURE:
<221> NAME/KEY: MISC_FEATURE
<223> OTHER INFORMATION: Uniprot name: Q8ZPR5_SALTY. Acetate CoA-
      transferase YdiF

<400> SEQUENCE: 91

Met Leu Ser Ala Gln Glu Ala Val Asn Tyr Ile Pro Asp Glu Ala Thr
1               5                   10                  15

Leu Cys Ile Leu Gly Ala Gly Gly Ile Leu Glu Ala Thr Thr Leu
            20                  25                  30

Ile Thr Ala Leu Ala Asp Lys Tyr Gln Thr Thr Gln Ser Pro Arg Asp
            35                  40                  45

Leu Ser Ile Ile Ser Pro Thr Gly Leu Gly Asp Arg Ala Asp Arg Gly
50                  55                  60

Ile Ser Pro Leu Ala Gln Glu Gly Leu Val Lys Trp Ala Leu Cys Gly
65                  70                  75                  80

His Trp Gly Gln Ser Pro Arg Ile Ser Glu Leu Ala Glu Gln Asn Lys
                85                  90                  95

Ile Ala Ala Tyr Asn Tyr Pro Gln Gly Val Leu Thr Gln Thr Leu Arg
            100                 105                 110

Ala Ser Ala Ala His Gln Pro Gly Ile Leu Ser Asp Ile Gly Ile Gly
        115                 120                 125

Thr Phe Val Asp Pro Arg Gln Gln Gly Gly Lys Leu Asn Asp Val Thr
130                 135                 140

Lys Glu Asp Leu Ile Lys Leu Val Glu Ile Asp Asn Lys Glu Tyr Leu
145                 150                 155                 160

Tyr Tyr Lys Ala Ile Ala Pro Asn Val Ala Phe Ile Arg Ala Thr Thr
                165                 170                 175

Cys Asp Ser Glu Gly Tyr Ala Ser Phe Glu Asp Glu Val Met Tyr Leu
            180                 185                 190

Asp Ala Leu Val Ile Ala Gln Ala Val His Asn Asn Gly Gly Ile Val
        195                 200                 205

Met Met Gln Val Gln Lys Met Val Lys Lys Ala Thr Leu His Pro Lys
    210                 215                 220

Ser Val Arg Ile Pro Gly Tyr Leu Val Asp Ile Val Val Asp Ala
225                 230                 235                 240

Asp Gln Thr Gln Leu Tyr Gly Gly Ala Pro Val Asn Arg Phe Ile Ser
                245                 250                 255

Gly Asp Phe Thr Leu Asp Asp Ser Thr Gln Leu Thr Leu Pro Leu Asn
```

```
            260                 265                 270
Gln Arg Lys Leu Val Ala Arg Arg Ala Leu Phe Glu Met Arg Lys Gly
            275                 280                 285
Ala Val Gly Asn Val Gly Val Gly Ile Ala Asp Gly Ile Gly Leu Val
            290                 295                 300
Ala Arg Glu Glu Gly Cys Ala Asp Asp Phe Val Leu Thr Val Glu Thr
305                 310                 315                 320
Gly Pro Val Gly Gly Ile Thr Ser Gln Gly Val Ala Phe Gly Ala Asn
            325                 330                 335
Val Asn Thr Arg Ala Ile Leu Asp Met Thr Ser Gln Phe Asp Phe Tyr
            340                 345                 350
His Gly Gly Gly Leu Asp Val Cys Tyr Leu Ser Phe Ala Glu Val Asp
            355                 360                 365
Gln His Gly Asn Val Gly Val His Lys Phe Asn Gly Lys Ile Met Gly
            370                 375                 380
Thr Gly Gly Phe Ile Asp Ile Ser Ala Thr Ser Gln Lys Ile Ile Phe
385                 390                 395                 400
Cys Gly Thr Leu Thr Ala Gly Ser Leu Lys Thr Glu Ile Thr Asp Gly
            405                 410                 415
Lys Leu Asn Ile Leu Gln Glu Gly Arg Val Lys Phe Val Ser Glu
            420                 425                 430
Leu Pro Glu Ile Thr Phe Ser Gly Lys Ile Ala Leu Glu Arg Gly Leu
            435                 440                 445
Asp Val Arg Tyr Ile Thr Glu Arg Ala Val Phe Thr Leu Lys Gln Asp
            450                 455                 460
Gly Leu His Leu Ile Glu Ile Ala Pro Gly Val Asp Leu Gln Arg Asp
465                 470                 475                 480
Ile Leu Asp Lys Met Asp Phe Ser Pro Val Ile Ser Pro Asp Leu Lys
            485                 490                 495
Leu Met Asp Thr Arg Leu Phe Asp Ser Thr Met Gly Phe Thr Leu
            500                 505                 510
Pro Asp Ala Thr His
            515

<210> SEQ ID NO 92
<211> LENGTH: 523
<212> TYPE: PRT
<213> ORGANISM: Variovorax sp.
<220> FEATURE:
<221> NAME/KEY: MISC_FEATURE
<223> OTHER INFORMATION: Uniprot name: J2T0X7_9BURK.  Acetate CoA-
      transferase YdiF

<400> SEQUENCE: 92

Met Lys Ile Ile Thr Ala Ala Gln Ala Gly Ala Leu Ile Pro Asp Asp
1               5                   10                  15
Ala Thr Ile Phe Leu Gly Gly Leu Ala Val Thr Ser Leu Pro Glu Glu
            20                  25                  30
Val Leu Lys Gly Val Glu Gln Thr Phe Leu Asp Thr Gly His Pro Arg
            35                  40                  45
Asn Val Thr Thr Trp Ala Cys Gly Ala Ile Gly Asn Ser Lys Asp Ala
            50                  55                  60
Gly Met Val His Phe Ala His Pro Gly Met Ile Lys Arg Thr Val Ala
65                  70                  75                  80
Gly His Phe Gly Gln Thr Gly Ala Glu Met Met Lys Met Val Phe Glu
            85                  90                  95
```

```
Gly Glu Val Glu Ala Tyr Asn Phe Pro Gln Gly Ser Leu Ser His Leu
                100                 105                 110

Thr Arg His Ile Ala Ser Arg Ser Pro Gly Leu Leu Thr Lys Val Gly
            115                 120                 125

Leu Gly Thr Phe Val Asp Pro Arg Ile Glu Gly Lys Leu Asn Gly
        130                 135                 140

Lys Ser Thr Glu Asp Leu Val Arg Leu Val Glu Phe Asn Gly Glu Glu
145                 150                 155                 160

Trp Leu Phe Tyr Pro Ser Pro Lys Ile Asp Val Ala Ile Ile Arg Gly
                165                 170                 175

Thr Leu Ala Asp Glu Asn Gly Asn Ile Thr Leu Asp Lys Glu Gly Met
            180                 185                 190

Leu Leu Glu Gln Ile Asn Ile Ala His Ala Ala Lys Ala Cys Gly Gly
        195                 200                 205

Ile Val Ile Ala Gln Val Glu Arg Ile Val Gln Ala Gly Ser Leu His
210                 215                 220

Pro Lys Ser Val Lys Val Pro Gly Val Ser Val Asp Tyr Val Val Val
225                 230                 235                 240

Ser Gln Pro Glu Asn His Met Gln Thr Ile Thr Thr Gln Phe Ser Pro
                245                 250                 255

Ala Leu Cys Gly Asp Val Arg Val Pro Val Asn Ser Leu Glu Pro Met
            260                 265                 270

Pro Leu Asp Glu Arg Lys Val Ile Ala Arg Arg Ser Ala Leu Glu Leu
        275                 280                 285

Ala Pro Gly Ala Ile Thr Asn Leu Gly Ile Gly Ile Pro Ala Gly Val
                290                 295                 300

Pro Ser Val Ala Ala Glu Glu Gly Val Ala Asp Gln Leu Thr Leu Ser
305                 310                 315                 320

Val Glu Ser Gly Ile Thr Gly Gly Ile Pro Ala Gln Gly Gly Asp Phe
                325                 330                 335

Gly Val Ala Tyr Asn Ala Asp Ala Ile Ile Glu Gln Ser Leu Gln Phe
            340                 345                 350

Asp Phe Tyr Asp Gly Gly Gly Leu Asp Ala Ser Phe Leu Gly Leu Ala
        355                 360                 365

Gln Val Asp Asn His Gly Asn Val Asn Val Ser Lys Phe Asn Gly Arg
                370                 375                 380

Pro Val Gly Cys Gly Gly Phe Val Asn Ile Thr Cys Ser Thr Lys Asn
385                 390                 395                 400

Leu Val Phe Cys Gly Thr Phe Thr Ala Gly Leu Gln Val Lys Val
                405                 410                 415

Ala Asp Gly Gln Leu Thr Ile Val Lys Glu Gly Lys Ser Arg Lys Phe
            420                 425                 430

Ile Glu Lys Val Glu Gln Ile Thr Phe Asn Gly Leu Asp Ala Ala Arg
        435                 440                 445

Arg Gln Gln Asn Val Leu Phe Val Thr Glu Arg Ala Val Phe His Leu
                450                 455                 460

Thr Thr Glu Gly Leu Glu Leu Ile Glu Ile Ala Pro Gly Ile Asp Leu
465                 470                 475                 480

Glu Arg Asp Val Leu Ala His Met Gly Phe Arg Pro Leu Met Arg Asp
                485                 490                 495

Val Lys Thr Met Asp Pro Gly Leu Phe Arg Ala Gln Trp Gly Gly Leu
            500                 505                 510
```

```
Ala Lys Ala Met Ala Glu Arg Ser Arg Val Glu
        515                 520
```

```
<210> SEQ ID NO 93
<211> LENGTH: 390
<212> TYPE: PRT
<213> ORGANISM: Acinetobacter baumannii
<220> FEATURE:
<221> NAME/KEY: MISC_FEATURE
<223> OTHER INFORMATION: Uniprot name: FADA_ACIBT.  3-ketoacyl-CoA
      thiolase

<400> SEQUENCE: 93
```

```
Met Ala Thr Leu Asn Pro Arg Asp Val Ile Val Asp Gly Val Arg
1               5                   10                  15

Ser Ala Met Gly Lys Ser Lys Asn Gly Met Phe Arg Asn Val Arg Ala
                20                  25                  30

Asp Ser Leu Ser Ala Glu Leu Val Arg Ala Leu Ile Ala Arg Asn Gln
            35                  40                  45

Phe Asp Val Asn Glu Val Glu Asp Leu Ile Trp Gly Cys Val Asn Gln
    50                  55                  60

Thr Leu Glu Gln Gly Met Asn Ile Gly Arg Asn Ile Gly Leu Leu Ala
65                  70                  75                  80

Gly Leu Pro Lys Thr Val Ala Gly Gln Thr Val Asn Arg Leu Cys Gly
                85                  90                  95

Ser Ser Met Gln Ala Ile His Thr Ala Ala Gln Ile Ala Thr Asn
                100                 105                 110

Gln Gly Asp Ile Phe Ile Ile Gly Gly Val Glu His Met Gly His Val
            115                 120                 125

Gly Met Met His Gly Ile Asp Leu Asn Pro Glu Ala Ser Lys His Tyr
    130                 135                 140

Ala Lys Ala Ser Asn Met Met Gly Leu Thr Ala Glu Met Leu Gly Arg
145                 150                 155                 160

Met Asn Gly Ile Thr Arg Glu Glu Gln Asp Thr Phe Gly Val Glu Ser
                165                 170                 175

His Arg Arg Ala Trp Ala Ala Thr Gln Glu Gly Arg Phe Lys Asn Glu
            180                 185                 190

Ile Ile Gly Val Glu Gly His Asp Ala Asn Gly Phe Lys Ile Leu Cys
    195                 200                 205

Asp Ile Asp Glu Val Ile Arg Pro Asp Ala Asn Leu Glu Ala Phe Lys
    210                 215                 220

Ala Leu Lys Pro Val Phe Asp Pro Lys Gly Gly Ser Val Thr Ala Ala
225                 230                 235                 240

Thr Ser Ser Ala Leu Ser Asp Gly Ala Ser Ala Met Leu Leu Met Ser
                245                 250                 255

Ala Glu Arg Ala Gln Ala Leu Gly Leu Lys Pro Arg Ala Val Ile Arg
            260                 265                 270

Ser Met Ala Val Ala Gly Cys Asp Ala Ala Ile Met Gly Tyr Gly Pro
    275                 280                 285

Val Pro Ala Thr Gln Lys Ala Leu Lys Arg Ala Gly Leu Ser Ile Ala
    290                 295                 300

Asp Ile Gln Thr Val Glu Leu Asn Glu Ala Phe Ala Ala Gln Gly Leu
305                 310                 315                 320

Ser Val Leu Lys Gly Leu Gly Leu Tyr Asp Lys Gln Asp Ile Val Asn
                325                 330                 335

Leu Asn Gly Gly Ala Ile Ala Leu Gly His Pro Leu Gly Cys Ser Gly
```

```
                340             345             350
Ala Arg Ile Thr Thr Thr Leu Leu Asn Val Met Glu Gln Gln Asp Thr
            355                 360                 365

Gln Ile Gly Leu Ala Thr Met Cys Ile Gly Leu Gly Gln Gly Ile Ala
            370                 375                 380

Thr Val Ile Glu Arg Val
385                 390

<210> SEQ ID NO 94
<211> LENGTH: 401
<212> TYPE: PRT
<213> ORGANISM: Acinetobacter baylyi
<220> FEATURE:
<221> NAME/KEY: MISC_FEATURE
<223> OTHER INFORMATION: Uniprot name: PCAF_ACIAD.  Beta-ketoadipyl-CoA
      thiolase

<400> SEQUENCE: 94

Met Lys His Ala Tyr Ile Val Asp Ala Ile Arg Thr Pro Phe Gly Arg
1               5                   10                  15

Tyr Ala Gly Gly Leu Ala Ala Val Arg Ala Asp Asp Leu Gly Ala Ile
            20                  25                  30

Pro Ile Ala Ala Leu Ile Glu Arg Asn Pro Ser Val Asn Trp Ala Gln
        35                  40                  45

Val Asp Asp Val Ile Tyr Gly Cys Ala Asn Gln Ala Gly Glu Asp Asn
    50                  55                  60

Arg Asn Val Gly Arg Met Ser Ala Leu Leu Ala Gly Leu Pro Val Glu
65                  70                  75                  80

Val Pro Ala Thr Thr Val Asn Arg Leu Cys Gly Ser Ser Leu Asp Ala
                85                  90                  95

Ile Ala Met Ala Ala Arg Ala Ile Lys Ala Gly Glu Ala His Leu Ile
            100                 105                 110

Ile Ala Gly Gly Val Glu Ser Met Ser Arg Ala Pro Tyr Val Met Gly
        115                 120                 125

Lys Ser Glu Gly Ala Phe Gly Arg Thr Gln Lys Ile Glu Asp Thr Thr
    130                 135                 140

Met Gly Trp Arg Phe Ile Asn Pro Lys Leu Lys Ala Met Tyr Gly Val
145                 150                 155                 160

Asp Thr Met Pro Gln Thr Ala Glu Asn Val Ala Glu Gln Phe Gly Ile
                165                 170                 175

Gln Arg Glu Asp Gln Asp Gln Phe Ala Tyr Thr Ser Gln Gln Arg Thr
            180                 185                 190

Ala Ala Ala Gln Ala Lys Gly Tyr Phe Ala Lys Glu Ile Val Pro Val
        195                 200                 205

Thr Ile Pro Gln Arg Lys Gly Glu Pro Val Val Ile Asp Thr Asp Glu
    210                 215                 220

His Pro Arg Ala Ser Thr Thr Leu Glu Gly Leu Ala Lys Leu Lys Gly
225                 230                 235                 240

Val Val Lys Pro Glu Gly Ser Val Thr Ala Gly Asn Ala Ser Gly Ile
                245                 250                 255

Asn Asp Gly Ala Ala Ala Val Leu Ile Ala Ser Asp Glu Ala Val Ala
            260                 265                 270

Gln Tyr Gln Leu Lys Ala Arg Ala Lys Ile Ile Ala Ser Thr Thr Val
        275                 280                 285

Gly Ile Glu Pro Arg Ile Met Gly Phe Ala Pro Ala Pro Ala Ile Lys
    290                 295                 300
```

```
Lys Leu Leu Lys Gln Ala Asn Leu Thr Leu Asp Gln Met Asp Val Ile
305                 310                 315                 320

Glu Leu Asn Glu Ala Phe Ala Ala Gln Ala Leu Ala Cys Thr Arg Asp
                325                 330                 335

Leu Gly Leu Ala Asp Asp Ala Arg Val Asn Pro Asn Gly Gly Ala
            340                 345                 350

Ile Ala Leu Gly His Pro Leu Gly Ala Ser Gly Ala Arg Leu Val Thr
                355                 360                 365

Thr Ala Leu Asn Gln Leu Glu Gln Ser Gly Gly Lys Tyr Ala Leu Cys
        370                 375                 380

Ser Met Cys Ile Gly Val Gly Gln Gly Ile Ala Leu Ile Ile Glu Arg
385                 390                 395                 400

Val

<210> SEQ ID NO 95
<211> LENGTH: 387
<212> TYPE: PRT
<213> ORGANISM: Aeromonas hydrophila subsp. hydrophila
<220> FEATURE:
<221> NAME/KEY: MISC_FEATURE
<223> OTHER INFORMATION: Uniprot name: FADA_AERHH.  3-ketoacyl-CoA
      thiolase

<400> SEQUENCE: 95

Met Lys Asp Val Val Ile Val Asp Cys Ile Arg Thr Pro Met Gly Arg
1               5                   10                  15

Ser Lys Gly Gly Ala Phe Arg Asn Val Arg Ala Glu Asp Leu Ser Ala
            20                  25                  30

His Leu Met Lys Ser Ile Leu Leu Arg Asn Pro Asn Leu Asp Pro Asn
        35                  40                  45

Glu Ile Glu Asp Ile Tyr Trp Gly Cys Val Gln Gln Thr Leu Glu Gln
    50                  55                  60

Gly Phe Asn Ile Ala Arg Asn Ala Ala Leu Leu Ala Gly Ile Pro Lys
65                  70                  75                  80

Gln Val Gly Ala Val Thr Val Asn Arg Leu Cys Gly Ser Ser Met Gln
                85                  90                  95

Ala Leu His Asp Ala Ser Arg Ala Ile Gln Val Gly Asp Gly Asp Ile
            100                 105                 110

Phe Ile Ile Gly Gly Val Glu His Met Gly His Val Pro Met Ser His
        115                 120                 125

Gly Val Asp Phe His Pro Gly Met Ala Lys Ser Val Ala Lys Ala Ser
    130                 135                 140

Gly Met Met Gly Leu Thr Ala Glu Met Leu Gly Lys Leu His Gly Ile
145                 150                 155                 160

Ser Arg Gln Gln Gln Asp Glu Phe Ala Ala Arg Ser His Arg Arg Ala
                165                 170                 175

His Ala Ala Thr Val Glu Gly Arg Phe Ala Lys Glu Ile Val Gly Leu
            180                 185                 190

Glu Gly His Asp Ala Ser Gly Ala Arg Phe Phe Tyr Asp Tyr Asp Glu
        195                 200                 205

Val Ile Arg Pro Glu Thr Thr Val Glu Thr Leu Ser Gln Leu Arg Pro
    210                 215                 220

Val Phe Asp Pro Val Asn Gly Thr Val Thr Ala Gly Thr Ser Ser Ala
225                 230                 235                 240

Leu Ser Asp Gly Ala Ala Ala Met Leu Val Met Ser Ala Asp Arg Ala
```

```
                    245                 250                 255
Lys Ala Leu Gly Leu Thr Pro Arg Ala Lys Ile Arg Ala Met Ala Val
            260                 265                 270

Ala Gly Cys Asp Ala Ala Ile Met Gly Tyr Gly Pro Val Pro Ala Thr
            275                 280                 285

Gln Lys Ala Leu Lys Arg Ala Gly Leu Thr Ile Gly Asp Ile Asp Leu
            290                 295                 300

Phe Glu Leu Asn Glu Ala Phe Ala Ala Gln Ser Leu Pro Cys Val Lys
305                 310                 315                 320

Asp Leu Gly Leu Gln Asp Val Val Asp Glu Lys Val Asn Leu Asn Gly
            325                 330                 335

Gly Ala Ile Ala Leu Gly His Pro Leu Gly Cys Ser Gly Ala Arg Ile
            340                 345                 350

Ser Thr Thr Leu Leu Asn Leu Met Glu Glu Lys Asp Ala Thr Leu Gly
            355                 360                 365

Val Ala Thr Met Cys Ile Gly Leu Gly Gln Gly Ile Ala Thr Val Phe
            370                 375                 380

Glu Arg Val
385

<210> SEQ ID NO 96
<211> LENGTH: 436
<212> TYPE: PRT
<213> ORGANISM: Aeromonas hydrophila subsp. hydrophila
<220> FEATURE:
<221> NAME/KEY: MISC_FEATURE
<223> OTHER INFORMATION: Uniprot name: FADI_AERHH.  3-ketoacyl-CoA
      thiolase

<400> SEQUENCE: 96

Met Lys Glu Pro Leu Lys Leu Thr Thr Arg Gln Gly Glu Arg Ile Ala
1               5                   10                  15

Val Val Ala Gly Leu Arg Thr Pro Phe Ala Lys Gln Ala Thr Ala Phe
            20                  25                  30

His Gly Val Pro Ala Val Asp Leu Gly Lys Leu Val Val Ser Glu Met
            35                  40                  45

Leu Ala Arg Thr Asp Leu Asp Pro Lys Leu Ile Asp Gln Leu Val Phe
        50                  55                  60

Gly Gln Val Val Gln Met Pro Glu Ala Pro Asn Ile Ala Arg Glu Ile
65              70                  75                  80

Val Leu Gly Thr Gly Met Ser Val Ser Thr Asp Ala Tyr Ser Val Ser
            85                  90                  95

Arg Ala Cys Ala Thr Ser Phe Gln Ala Val Ala Asn Val Thr Glu Ser
            100                 105                 110

Ile Met Ala Gly Thr Val Asp Ile Ala Ile Ala Gly Gly Ala Asp Ser
            115                 120                 125

Ser Ser Val Leu Pro Ile Gly Val Ser Lys Lys Leu Ala Arg Ala Leu
            130                 135                 140

Val Asp Leu Asn Lys Ala Arg Asn Leu Gln Gln Arg Phe Asn Ile Leu
145                 150                 155                 160

Arg Gln Leu Arg Val Lys Asp Leu Leu Pro Val Pro Pro Ala Val Ala
            165                 170                 175

Glu Tyr Ser Thr Gly Leu Ser Met Gly Gln Thr Ala Glu Gln Met Ala
            180                 185                 190

Lys Ser His Gln Ile Ser Arg Glu Ala Gln Asp Ala Leu Ala His Arg
            195                 200                 205
```

Ser His Thr Leu Ala Ala Gln Ala Trp Ala Asp Gly Lys Leu Ser Gly
    210                 215                 220

Glu Val Phe Thr Ala His Val Pro Pro Tyr Lys Ala Pro Leu Glu Arg
225                 230                 235                 240

Asp Asn Asn Ile Arg Glu Ser Ser Asp Leu Ala Ser Tyr Ala Lys Leu
                245                 250                 255

Lys Pro Val Phe Asp Arg Val His Gly Ser Val Thr Ala Ala Asn Ala
                260                 265                 270

Thr Pro Leu Thr Asp Gly Ala Ala Val Leu Leu Met Arg Glu Gly
                275                 280                 285

Arg Ala Arg Glu Leu Gly Leu Glu Pro Leu Gly Tyr Ile Arg Ser Phe
    290                 295                 300

Ala Phe Ser Ala Ile Asp Val Trp Gln Asp Met Leu Met Gly Pro Ser
305                 310                 315                 320

Tyr Ala Thr Pro Leu Ala Leu Asp Arg Ala Gly Ile Thr Leu Ser Asp
                325                 330                 335

Leu Thr Leu Ile Asp Met His Glu Ala Phe Ala Ala Gln Thr Leu Ala
                340                 345                 350

Asn Leu Lys Met Phe Ala Ser Lys Glu Phe Ala Gln Ser Lys Leu Gly
                355                 360                 365

Arg Asp Gln Ala Ile Gly Glu Val Asp Met Asp Lys Phe Asn Val Leu
    370                 375                 380

Gly Gly Ser Leu Ala Phe Gly His Pro Phe Ala Ala Thr Gly Ala Arg
385                 390                 395                 400

Met Ile Thr Gln Thr Leu His Glu Leu Arg Arg Gly Gly Leu
                405                 410                 415

Gly Leu Asn Thr Ala Cys Ala Ala Gly Gly Leu Gly Val Ala Met Val
                420                 425                 430

Leu Glu Val Glu
        435

<210> SEQ ID NO 97
<211> LENGTH: 391
<212> TYPE: PRT
<213> ORGANISM: Alcanivorax borkumensis
<220> FEATURE:
<221> NAME/KEY: MISC_FEATURE
<223> OTHER INFORMATION: Uniprot name: FADA_ALCBS. 3-ketoacyl-CoA
      thiolase

<400> SEQUENCE: 97

Met Ser Leu Asn Pro Lys Asp Val Val Ile Val Asp Ala Val Arg Thr
1               5                   10                  15

Pro Met Gly Lys Ser Arg Asn Gly Gln Phe Arg His Val Arg Ala Glu
                20                  25                  30

Lys Leu Ser Ala Gln Leu Ile Gln Ala Leu Met Ala Arg Asn Pro Asn
            35                  40                  45

Trp Asp Ile Gln Leu Thr Glu Asp Val Ile Trp Gly Cys Val Asn Gln
    50                  55                  60

Thr Lys Glu Gln Gly Met Asn Ile Ala Arg Asn Ile Ser Met Leu Ala
65                  70                  75                  80

Gly Leu Pro Arg Thr Ser Ala Ala Gln Thr Val Asn Arg Leu Cys Gly
                85                  90                  95

Ser Ser Met Gln Ala Leu His Ser Ala Ser Gln Ser Ile Met Thr Gly
                100                 105                 110

```
Asn Gly Asp Val Phe Val Ile Gly Val Glu His Met Gly His Val
            115                 120                 125

Ala Met Asp His Gly Ile Asp Leu Asn Pro Glu Met Ser Lys Val Thr
130                 135                 140

Ala Lys Ala Ser Asn Met Met Gly Leu Thr Ala Glu Met Leu Gly Lys
145                 150                 155                 160

Met His Gly Ile Thr Arg Glu Gln Gln Asp Ala Phe Gly Val Arg Ser
                165                 170                 175

His Lys Leu Ala Trp Glu Ala Thr Gln Gln Gly Arg Trp Asp Asn Glu
            180                 185                 190

Ile Val Pro Ile Glu Gly His Asp Gln Asn Gly His Lys Val Leu Cys
        195                 200                 205

Glu Ile Asp Glu Val Ile Arg Pro Gly Ala Ser Ile Glu Asp Met Gln
    210                 215                 220

Lys Leu Arg Pro Val Phe Asp Pro Ala Asn Gly Thr Val Thr Ala Gly
225                 230                 235                 240

Thr Ser Ser Ala Leu Ser Asp Gly Ala Ser Ala Met Leu Val Met Ser
                245                 250                 255

Ala Glu Arg Ala Gln Ala Leu Gly Leu Lys Pro Arg Ala Lys Ile Arg
            260                 265                 270

Ser Met Ala Val Ala Gly Cys Asp Ala Ala Ile Met Gly Tyr Gly Pro
        275                 280                 285

Val Pro Ala Thr Gln Lys Ala Leu Ala Arg Ala Gly Leu Thr Ile Asp
    290                 295                 300

Asp Ile Asp Tyr Val Glu Leu Asn Glu Ala Phe Ala Ala Gln Ser Leu
305                 310                 315                 320

Pro Val Ala Lys Asp Leu Lys Leu Leu Asp Lys Met Glu Glu Lys Val
                325                 330                 335

Asn Leu Asn Gly Gly Ala Ile Ala Leu Gly His Pro Leu Gly Cys Ser
            340                 345                 350

Gly Ala Arg Ile Thr Gly Thr Leu Leu Asn Val Met Glu Trp Lys Asp
        355                 360                 365

Gly Gln Ile Gly Leu Ala Thr Met Cys Ile Gly Leu Gly Gln Gly Ile
    370                 375                 380

Ala Thr Ile Ile Glu Arg Val
385                 390

<210> SEQ ID NO 98
<211> LENGTH: 387
<212> TYPE: PRT
<213> ORGANISM: Aliivibrio salmonicida (Vibrio salmonicida)
<220> FEATURE:
<221> NAME/KEY: MISC_FEATURE
<223> OTHER INFORMATION: Uniprot name: FADA_ALISL. 3-ketoacyl-CoA
      thiolase

<400> SEQUENCE: 98

Met Lys Asn Val Val Ile Val Asp Cys Ile Arg Thr Pro Met Gly Arg
1               5                   10                  15

Ser Lys Asn Gly Val Phe Arg His Thr Arg Ala Glu Asp Leu Ser Ala
            20                  25                  30

His Leu Met Lys Gly Leu Leu Glu Arg Asn Pro Asn Val Asp Pro Asn
        35                  40                  45

Gln Ile Glu Asp Ile Tyr Trp Gly Cys Val Gln Gln Thr Leu Glu Gln
    50                  55                  60

Gly Phe Asn Ile Ala Arg Asn Ala Ser Leu Leu Ala Gly Leu Pro Lys
```

```
                65                  70                  75                  80
        Ser Ile Ala Ala Thr Thr Val Asn Arg Leu Cys Gly Ser Ser Met Gln
                        85                  90                  95

Ala Leu His Asp Ala Ser Arg Ala Ile Met Val Gly Asp Ala Asp Ile
                        100                 105                 110

Cys Ile Ile Gly Gly Val Glu His Met Gly His Val Pro Met Asn His
                        115                 120                 125

Gly Val Asp Phe His Ser Gly Leu Ser Lys Asn Val Ala Lys Ala Ser
                        130                 135                 140

Gly Met Met Gly Leu Thr Ala Glu Met Leu Gly Lys Met His Gly Ile
        145                 150                 155                 160

Ser Arg Glu Gln Gln Asp Ala Phe Ala Phe Ala Ser His Gln Lys Ala
                        165                 170                 175

His Arg Ala Thr Ile Glu Gly His Phe Asp Ser Glu Ile Leu Pro Met
                        180                 185                 190

Glu Gly His Asp Glu Asn Gly Ala Leu Thr Leu Val Lys His Asp Glu
                        195                 200                 205

Val Ile Arg Pro Glu Thr Thr Leu Glu Gly Leu Ala Ala Leu Arg Pro
                        210                 215                 220

Ala Phe Asp Pro Ala Asn Gly Thr Val Thr Ala Gly Ser Ser Ser Ala
        225                 230                 235                 240

Leu Ser Asp Gly Ala Ser Ala Met Leu Ile Met Ser Glu Glu Lys Ala
                        245                 250                 255

Asn Glu Leu Gly Leu Thr Ile Arg Ala Lys Ile Arg Ser Met Ala Val
                        260                 265                 270

Ser Gly Cys Asp Pro Ala Ile Met Gly Tyr Gly Pro Val Pro Ala Thr
                        275                 280                 285

Lys Lys Ala Leu Lys Arg Ala Gly Leu Ser Ile Asp Asp Ile Asp Leu
                        290                 295                 300

Phe Glu Leu Asn Glu Ala Phe Ala Ala Gln Ser Leu Pro Cys Ile Lys
        305                 310                 315                 320

Asp Leu Gly Leu Phe Asp Val Met Glu Glu Lys Ile Asn Leu Asn Gly
                        325                 330                 335

Gly Ala Ile Ala Leu Gly His Pro Leu Gly Cys Ser Gly Ser Arg Ile
                        340                 345                 350

Ala Thr Thr Leu Ile Asn Asn Met Glu Arg Thr Gly Ala Lys Leu Gly
                        355                 360                 365

Val Ala Thr Met Cys Ile Gly Leu Gly Gln Gly Ile Ala Thr Val Phe
                        370                 375                 380

Glu Arg Pro
        385

<210> SEQ ID NO 99
<211> LENGTH: 394
<212> TYPE: PRT
<213> ORGANISM: Allochromatium vinosum (Chromatium vinosum)
<220> FEATURE:
<221> NAME/KEY: MISC_FEATURE
<223> OTHER INFORMATION: Uniprot name: THIL_ALLVD.  Acetyl-CoA
      acetyltransferase

<400> SEQUENCE: 99

Met Asn Glu Asn Ile Val Ile Val Asp Ala Gly Arg Ser Ala Ile Gly
1               5                   10                  15

Thr Phe Ser Gly Ser Leu Ser Ser Leu Ser Ala Thr Glu Ile Gly Thr
                20                  25                  30
```

```
Ala Val Leu Lys Gly Leu Leu Ala Arg Thr Gly Leu Ala Pro Glu Gln
         35                  40                  45

Ile Asp Glu Val Ile Leu Gly Gln Val Leu Thr Ala Gly Val Gly Gln
 50                  55                  60

Asn Pro Ala Arg Gln Thr Thr Leu Lys Ala Gly Leu Pro His Ser Val
 65                  70                  75                  80

Pro Ala Met Thr Ile Asn Lys Val Cys Gly Ser Gly Leu Lys Ala Val
                 85                  90                  95

His Leu Ala Met Gln Ala Ile Ala Cys Gly Asp Ala Asp Ile Val Ile
                100                 105                 110

Ala Gly Gly Gln Glu Ser Met Ser Gln Ser Ser His Val Leu Pro Arg
            115                 120                 125

Ser Arg Asp Gly Gln Arg Met Gly Asp Trp Ser Met Lys Asp Thr Met
130                 135                 140

Ile Val Asp Gly Leu Trp Asp Ala Phe Asn Asn Tyr His Met Gly Thr
145                 150                 155                 160

Thr Ala Glu Asn Ile Ala Gln Lys Tyr Gly Phe Thr Arg Glu Gln Gln
                165                 170                 175

Asp Ala Phe Ala Ala Ser Gln Gln Lys Thr Glu Ala Ala Gln Lys
            180                 185                 190

Ala Gly Arg Phe Gln Asp Glu Ile Ile Pro Ile Glu Ile Pro Gln Arg
            195                 200                 205

Lys Gly Asp Pro Lys Val Phe Asp Ala Asp Glu Phe Pro Arg His Gly
210                 215                 220

Thr Thr Ala Glu Ser Leu Gly Lys Leu Arg Pro Ala Phe Ser Arg Asp
225                 230                 235                 240

Gly Ser Val Thr Ala Gly Asn Ala Ser Gly Ile Asn Asp Gly Ala Ala
                245                 250                 255

Met Val Val Met Lys Glu Ser Lys Ala Lys Glu Leu Gly Leu Lys
            260                 265                 270

Pro Met Ala Arg Leu Val Ala Phe Ala Ser Ala Gly Val Asp Pro Ala
            275                 280                 285

Ile Met Gly Thr Gly Pro Ile Pro Ala Ser Thr Lys Cys Leu Glu Lys
            290                 295                 300

Ala Gly Trp Thr Pro Ala Asp Leu Asp Leu Ile Glu Ala Asn Glu Ala
305                 310                 315                 320

Phe Ala Ala Gln Ala Met Ser Val Asn Gln Asp Met Gly Trp Asp Leu
                325                 330                 335

Ser Lys Val Asn Val Asn Gly Gly Ala Ile Ala Ile Gly His Pro Ile
            340                 345                 350

Gly Ala Ser Gly Ala Arg Val Leu Val Thr Leu Leu Tyr Glu Met Gln
            355                 360                 365

Lys Arg Asp Ala Lys Lys Gly Leu Ala Thr Leu Cys Ile Gly Gly Gly
            370                 375                 380

Gln Gly Val Ala Leu Ala Val Glu Arg Met
385                 390

<210> SEQ ID NO 100
<211> LENGTH: 436
<212> TYPE: PRT
<213> ORGANISM: Alteromonas macleodii
<220> FEATURE:
<221> NAME/KEY: MISC_FEATURE
<223> OTHER INFORMATION: Uniprot name: FADI_ALTMD.  3-ketoacyl-CoA
      thiolase
```

<400> SEQUENCE: 100

Met Ala Thr Lys Gln Ser Val Thr Thr Arg Glu Gly Asp Arg Ile Ala
1               5                   10                  15

Ile Val Ala Gly Leu Arg Thr Pro Phe Ala Lys Met Ala Thr Tyr Phe
            20                  25                  30

His Gly Val Pro Ala Val Asp Leu Gly Lys Met Val Val Asn Glu Leu
        35                  40                  45

Leu Val Arg His Gly Val Gln Lys Glu Trp Val Asp Gln Val Val Tyr
    50                  55                  60

Gly Gln Val Val Gln Met Pro Glu Ala Pro Asn Ile Ala Arg Glu Ile
65                  70                  75                  80

Val Leu Gly Thr Gly Met Asn Val His Thr Asp Ala Tyr Ser Val Ser
                85                  90                  95

Arg Ala Cys Ala Thr Ser Phe Gln Ser Thr Val Asn Ile Ala Glu Ser
            100                 105                 110

Met Met Ala Gly Thr Val Gln Val Gly Ile Ala Gly Gly Ala Asp Ser
        115                 120                 125

Thr Ser Val Ser Pro Ile Gly Val Ser Lys Asn Leu Ala Arg Ala Leu
130                 135                 140

Val Asp Leu Gln Lys Thr Lys Thr Leu Gly Gln Lys Leu Asn Ile Phe
145                 150                 155                 160

Lys Arg Leu Ser Leu Arg Asp Leu Ala Pro Val Pro Ala Val Ala
            165                 170                 175

Glu Tyr Ser Thr Gly Leu Ser Met Gly Gln Thr Ala Glu Gln Met Ala
            180                 185                 190

Lys Thr His Gln Ile Ser Arg Glu Glu Gln Asp Lys Leu Ala His Arg
        195                 200                 205

Ser His Ser Leu Ala Ala Glu Ser Trp Glu Ala Gly Lys Leu Ser Ser
    210                 215                 220

Glu Val Met Thr Ala Tyr Ala Glu Pro Tyr Lys Ala Ala Leu Glu Arg
225                 230                 235                 240

Asp Asn Asn Val Arg Phe Asp Ser Lys Leu Glu Gly Tyr Ala Lys Leu
            245                 250                 255

Arg Pro Val Phe Asp Lys Lys Tyr Gly Ser Val Thr Ala Ala Asn Ala
            260                 265                 270

Thr Pro Leu Thr Asp Gly Ala Ser Ala Val Leu Met Met Thr Glu Ser
        275                 280                 285

Arg Ala Lys Glu Leu Gly Tyr Thr Pro Leu Gly Tyr Ile Lys Ser Tyr
    290                 295                 300

Ala Phe Ala Ala Ile Asp Val Trp Glu Asp Met Leu Met Gly Pro Ser
305                 310                 315                 320

Tyr Ala Thr Pro Ile Ala Leu Asp Arg Ala Gly Met Thr Leu Asn Asp
            325                 330                 335

Leu Thr Leu Ile Glu Met His Glu Ala Phe Ala Ala Gln Thr Leu Ala
        340                 345                 350

Asn Val Lys Met Phe Ala Ser Asp Lys Phe Ala Lys Glu Lys Leu Gly
    355                 360                 365

Arg Asp Lys Ala Thr Gly Glu Ile Asp Met Asp Lys Phe Asn Val Met
    370                 375                 380

Gly Ser Ser Ile Ala Tyr Gly His Pro Phe Ala Ala Thr Gly Thr Arg
385                 390                 395                 400

Met Ile Thr Gln Met Leu Asn Glu Leu Asn Arg Arg Gly Gly Gly Ser

```
                        405                 410                 415

Gly Leu Thr Ala Cys Ala Ala Gly Gly Leu Gly Ala Ala Met Ile
                420                 425                 430

Val Glu Thr Glu
            435

<210> SEQ ID NO 101
<211> LENGTH: 391
<212> TYPE: PRT
<213> ORGANISM: Bacillus subtilis
<220> FEATURE:
<221> NAME/KEY: MISC_FEATURE
<223> OTHER INFORMATION: Uniprot name: FADA_BACSU.  3-ketoacyl-CoA
      thiolase

<400> SEQUENCE: 101

Met Lys Glu Ala Val Ile Val Ser Gly Ala Arg Thr Pro Val Gly Lys
1               5                   10                  15

Ala Lys Lys Gly Ser Leu Ala Thr Val Arg Pro Asp Asp Leu Gly Ala
            20                  25                  30

Ile Cys Val Lys Glu Thr Leu Lys Arg Ala Gly Gly Tyr Glu Gly Asn
        35                  40                  45

Ile Asp Asp Leu Ile Ile Gly Cys Ala Thr Pro Glu Ala Glu Gln Gly
    50                  55                  60

Leu Asn Met Ala Arg Asn Ile Gly Ala Leu Ala Gly Leu Pro Tyr Thr
65                  70                  75                  80

Val Pro Ala Ile Thr Val Asn Arg Tyr Cys Ser Ser Gly Leu Gln Ser
                85                  90                  95

Ile Ala Tyr Ala Ala Glu Lys Ile Met Leu Gly Ala Tyr Asp Thr Ala
            100                 105                 110

Ile Ala Gly Gly Ala Glu Ser Met Ser Gln Val Pro Met Met Gly His
        115                 120                 125

Val Thr Arg Pro Asn Leu Ala Leu Ala Glu Lys Ala Pro Glu Tyr Tyr
    130                 135                 140

Met Ser Met Gly His Thr Ala Glu Gln Val Ala Lys Lys Tyr Gly Val
145                 150                 155                 160

Ser Arg Glu Asp Gln Asp Ala Phe Ala Val Arg Ser His Gln Asn Ala
                165                 170                 175

Ala Lys Ala Leu Ala Glu Gly Lys Phe Lys Asp Glu Ile Val Pro Val
            180                 185                 190

Glu Val Thr Val Thr Glu Ile Gly Gly Asp His Lys Pro Met Glu Lys
        195                 200                 205

Gln Phe Val Phe Ser Gln Asp Glu Gly Val Arg Pro Gln Thr Thr Ala
    210                 215                 220

Asp Ile Leu Ser Thr Leu Arg Pro Ala Phe Ser Val Asp Gly Thr Val
225                 230                 235                 240

Thr Ala Gly Asn Ser Ser Gln Thr Ser Asp Gly Ala Ala Ala Val Met
                245                 250                 255

Leu Met Asp Arg Glu Lys Ala Asp Ala Leu Gly Leu Ala Pro Leu Val
            260                 265                 270

Lys Phe Arg Ser Phe Ala Val Gly Gly Val Pro Glu Val Met Gly
        275                 280                 285

Ile Gly Pro Val Glu Ala Ile Pro Arg Ala Leu Lys Leu Ala Gly Leu
    290                 295                 300

Gln Leu Gln Asp Ile Gly Leu Phe Glu Leu Asn Glu Ala Phe Ala Ser
305                 310                 315                 320
```

Gln Ala Ile Gln Val Ile Arg Glu Leu Gly Ile Asp Glu Glu Lys Val
                    325                 330                 335

Asn Val Asn Gly Gly Ala Ile Ala Leu Gly His Pro Leu Gly Cys Thr
                340                 345                 350

Gly Thr Lys Leu Thr Leu Ser Leu Ile His Glu Met Lys Arg Arg Asn
            355                 360                 365

Glu Gln Phe Gly Val Val Thr Met Cys Ile Gly Gly Met Gly Ala
        370                 375                 380

Ala Gly Val Phe Glu Leu Cys
385                 390

<210> SEQ ID NO 102
<211> LENGTH: 393
<212> TYPE: PRT
<213> ORGANISM: Bacillus subtilis
<220> FEATURE:
<221> NAME/KEY: MISC_FEATURE
<223> OTHER INFORMATION: Uniprot name: THL_BACSU. Acetyl-CoA
      acetyltransferase

<400> SEQUENCE: 102

Met Arg Lys Thr Val Ile Val Ser Ala Ala Arg Thr Pro Phe Gly Lys
1               5                   10                  15

Phe Gly Gly Val Leu Lys Glu Val Lys Ala Ala Glu Leu Gly Gly Ile
            20                  25                  30

Val Met Lys Glu Ala Leu Gln Gln Ala Gly Val Ser Gly Asp Asp Val
        35                  40                  45

Glu Gly Asn Val Met Gly Met Val Val Gln Ala Gly Ser Gly Gln Ile
50                  55                  60

Pro Ser Arg Gln Ala Ala Arg Leu Ala Gly Met Pro Trp Ser Val Pro
65                  70                  75                  80

Ser Glu Thr Leu Asn Lys Val Cys Ala Ser Gly Leu Arg Ala Val Thr
                85                  90                  95

Leu Cys Asp Gln Met Ile Arg Ala Gln Asp Ala Asp Ile Leu Val Ala
            100                 105                 110

Gly Gly Met Glu Ser Met Ser Asn Ile Pro Tyr Ala Val Pro Ala Gly
        115                 120                 125

Arg Trp Gly Ala Arg Met Gly Asp Gly Glu Leu Arg Asp Leu Met Val
130                 135                 140

Tyr Asp Gly Leu Thr Cys Ala Phe Asp Glu Val His Met Ala Val His
145                 150                 155                 160

Gly Asn Thr Ala Ala Lys Glu Tyr Ala Ile Ser Arg Arg Glu Gln Asp
                165                 170                 175

Glu Trp Ala Leu Arg Ser His Ala Arg Ala Ala Lys Ala Ala Asp Glu
            180                 185                 190

Gly Lys Phe Gln Asp Glu Ile Val Pro Val Asn Trp Ile Gly Arg Lys
        195                 200                 205

Gly Lys Pro Asn Val Val Asp Lys Glu Ala Ile Arg Arg Asp Thr
210                 215                 220

Ser Leu Asp Gln Leu Ala Lys Leu Ala Pro Ile Tyr Ala Ser Asp Gly
225                 230                 235                 240

Ser Ile Thr Ala Gly Asn Ala Pro Gly Val Asn Asp Gly Ala Gly Ala
                245                 250                 255

Phe Val Leu Met Ser Glu Glu Lys Ala Ala Glu Leu Gly Lys Arg Pro
            260                 265                 270

```
Leu Ala Thr Ile Leu Gly Phe Ser Thr Thr Gly Met Pro Ala His Glu
            275                 280                 285

Leu Ala Ala Ala Pro Gly Phe Ala Ile Asn Lys Leu Leu Lys Lys Asn
            290                 295                 300

Gly Leu Thr Val Gln Asp Ile Asp Leu Phe Glu Val Asn Glu Ala Phe
305                 310                 315                 320

Ala Ser Val Val Leu Thr Cys Glu Lys Ile Val Gly Phe Asp Leu Glu
            325                 330                 335

Lys Val Asn Val Asn Gly Ala Ile Ala Leu Gly His Pro Ile Gly
            340                 345                 350

Ala Ser Gly Ala Arg Ile Leu Met Thr Leu Val Tyr Glu Leu Lys Arg
            355                 360                 365

Arg Gly Gly Gly Leu Gly Val Ala Ala Ile Cys Ser Gly Ala Ala Gln
            370                 375                 380

Gly Asp Ala Val Leu Val Gln Val His
385                 390

<210> SEQ ID NO 103
<211> LENGTH: 403
<212> TYPE: PRT
<213> ORGANISM: Candida tropicalis
<220> FEATURE:
<221> NAME/KEY: MISC_FEATURE
<223> OTHER INFORMATION: Uniprot name: THIA_CANTR.  Acetyl-CoA
      acetyltransferase

<400> SEQUENCE: 103

Met Ala Leu Pro Pro Val Tyr Ile Val Ser Thr Ala Arg Thr Pro Ile
1               5                   10                  15

Gly Ser Phe Gln Gly Ser Leu Ser Ser Leu Thr Tyr Ser Asp Leu Gly
            20                  25                  30

Ala His Ala Val Lys Ala Ala Leu Ala Lys Val Pro Gln Ile Lys Pro
            35                  40                  45

Gln Asp Val Asp Glu Ile Val Phe Gly Gly Val Leu Gln Ala Asn Val
        50                  55                  60

Gly Gln Ala Pro Ala Arg Gln Val Ala Leu Lys Ala Gly Leu Pro Asp
65                  70                  75                  80

Ser Ile Val Ala Ser Thr Ile Asn Lys Val Cys Ala Ser Gly Met Lys
                85                  90                  95

Ala Val Ile Ile Gly Ala Gln Asn Ile Ile Cys Gly Thr Ser Asp Ile
            100                 105                 110

Val Val Val Gly Gly Ala Glu Ser Met Ser Asn Thr Pro Tyr Tyr Leu
            115                 120                 125

Pro Ser Ala Arg Ser Gly Ala Arg Tyr Gly Asp Ala Ile Met Val Asp
        130                 135                 140

Gly Val Gln Lys Asp Gly Leu Leu Asp Val Tyr Glu Glu Lys Leu Met
145                 150                 155                 160

Gly Val Ala Ala Glu Lys Cys Ala Lys Asp His Gly Phe Ser Arg Glu
                165                 170                 175

Asp Gln Asp Asn Phe Ala Ile Asn Ser Tyr Lys Lys Ala Gly Lys Ala
            180                 185                 190

Leu Ser Glu Gly Lys Phe Lys Ser Glu Ile Ala Pro Val Thr Ile Lys
            195                 200                 205

Gly Phe Arg Gly Lys Pro Asp Thr Val Ile Glu Asn Asp Glu Glu Ile
        210                 215                 220

Gly Lys Phe Asn Glu Glu Arg Leu Lys Ser Ala Arg Thr Val Phe Gln
```

```
            225                 230                 235                 240
Lys Glu Asn Gly Thr Val Thr Ala Pro Asn Ala Ser Lys Leu Asn Asp
                    245                 250                 255

Gly Gly Ala Ala Leu Val Leu Val Ser Glu Ala Lys Leu Lys Gln Leu
                    260                 265                 270

Gly Leu Lys Pro Leu Ala Lys Ile Ser Gly Trp Gly Glu Ala Ala Arg
                    275                 280                 285

Thr Pro Phe Asp Phe Thr Ile Ala Pro Ala Leu Ala Val Pro Lys Ala
                    290                 295                 300

Val Lys His Ala Gly Leu Thr Val Asp Arg Val Asp Phe Phe Glu Leu
305                 310                 315                 320

Asn Glu Ala Phe Ser Val Val Gly Leu Ala Asn Ala Glu Leu Val Asn
                    325                 330                 335

Ile Pro Leu Glu Lys Leu Asn Val Tyr Gly Gly Ala Val Ala Met Gly
                    340                 345                 350

His Pro Leu Gly Cys Ser Gly Ala Arg Ile Ile Val Thr Leu Leu Ser
                    355                 360                 365

Val Leu Thr Gln Glu Gly Gly Arg Phe Gly Val Ala Gly Val Cys Asn
                    370                 375                 380

Gly Gly Gly Gly Ala Ser Ala Val Val Ile Glu Lys Ile Asp Ala Asp
385                 390                 395                 400

Ala Lys Leu

<210> SEQ ID NO 104
<211> LENGTH: 408
<212> TYPE: PRT
<213> ORGANISM: Candida tropicalis
<220> FEATURE:
<221> NAME/KEY: MISC_FEATURE
<223> OTHER INFORMATION: Uniprot name: THIKA_CANTR.  3-ketoacyl-CoA
      thiolase

<400> SEQUENCE: 104

Met Asp Arg Leu Asn Gln Leu Ser Gly Gln Leu Lys Pro Asn Ala Lys
1               5                   10                  15

Gln Ser Ile Leu Gln Lys Asn Pro Asp Asp Val Val Ile Val Ala Ala
                    20                  25                  30

Tyr Arg Thr Ala Ile Gly Lys Gly Phe Lys Gly Ser Phe Arg Ser Val
                    35                  40                  45

Arg Ser Glu Phe Ile Leu Thr Glu Phe Leu Lys Glu Phe Ile Lys Lys
            50                  55                  60

Thr Asn Ile Asp Pro Ser Leu Ile Glu Asp Val Ala Ile Gly Asn Val
65                  70                  75                  80

Leu Asn Gln Ala Ala Gly Ala Thr Glu His Arg Gly Ala Cys Leu Ala
                    85                  90                  95

Ala Gly Ile Pro Tyr Thr Ala Ala Phe Ile Ala Val Asn Arg Phe Cys
                    100                 105                 110

Ser Ser Gly Leu Met Ala Ile Ser Asp Ile Ala Asn Lys Ile Lys Thr
                    115                 120                 125

Gly Glu Ile Glu Cys Gly Leu Ala Gly Gly Ala Glu Ser Met Ser Thr
            130                 135                 140

Asn Tyr Arg Asp Pro Arg Val Ala Pro Arg Ile Asp Pro His Leu Ala
145                 150                 155                 160

Asp Asp Ala Gln Met Glu Lys Cys Leu Ile Pro Met Gly Ile Thr Asn
                    165                 170                 175
```

Glu Asn Val Ala Asn Gln Phe Asn Ile Ser Arg Glu Arg Gln Asp Glu
                180                 185                 190

Phe Ala Ala Lys Ser Tyr Asn Lys Ala Lys Ala Val Ala Ala Gly
            195                 200                 205

Ala Phe Lys Ser Glu Ile Leu Pro Ile Arg Ser Ile Ile Arg Asn Ser
        210                 215                 220

Asp Gly Thr Glu Lys Glu Ile Ile Val Asp Thr Asp Glu Gly Pro Arg
225                 230                 235                 240

Glu Gly Val Thr Ala Glu Ser Leu Gly Lys Leu Arg Pro Ala Phe Asp
                245                 250                 255

Gly Thr Thr Thr Ala Gly Asn Ala Ser Gln Val Ser Asp Gly Ala Ala
                260                 265                 270

Ala Val Leu Leu Met Lys Arg Ser Leu Ala Glu Ala Lys Gly Tyr Pro
            275                 280                 285

Ile Ile Gly Lys Tyr Val Leu Cys Ser Thr Ala Gly Val Pro Pro Glu
        290                 295                 300

Ile Met Gly Val Gly Pro Ala Tyr Ala Ile Pro Glu Val Leu Lys Arg
305                 310                 315                 320

Thr Gly Leu Thr Val Asp Asp Ile Asp Val Phe Glu Ile Asn Glu Ala
                325                 330                 335

Phe Ala Ala Gln Cys Leu Tyr Ser Ala Glu Gln Val Asn Val Pro Glu
                340                 345                 350

Glu Lys Leu Asn Ile Asn Gly Gly Ala Ile Ala Leu Gly His Pro Leu
            355                 360                 365

Gly Glu Thr Gly Ala Arg Gln Tyr Ala Thr Ile Ile Pro Leu Leu Lys
        370                 375                 380

Pro Gly Gln Ile Gly Leu Thr Ser Met Cys Ile Gly Ser Gly Met Gly
385                 390                 395                 400

Ser Ala Ser Ile Leu Val Arg Glu
                405

<210> SEQ ID NO 105
<211> LENGTH: 392
<212> TYPE: PRT
<213> ORGANISM: Chromobacterium violaceum
<220> FEATURE:
<221> NAME/KEY: MISC_FEATURE
<223> OTHER INFORMATION: Uniprot name: THIL_CHRVO.  Acetyl-CoA
      acetyltransferase

<400> SEQUENCE: 105

Met Glu Val Ala Ile Val Ala Ala Gln Arg Thr Ala Ile Gly Ser Phe
1               5                   10                  15

Gly Gly Gly Leu Ala Lys Ile Pro Ala Pro Glu Leu Gly Ala Thr Val
                20                  25                  30

Ile Lys Ala Leu Leu Glu Lys Thr Gly Val Lys Pro Glu Asp Val Ser
            35                  40                  45

Glu Val Ile Leu Gly Gln Val Leu Thr Ala Gly Ser Gly Gln Asn Pro
        50                  55                  60

Ala Arg Gln Ala Leu Ile Lys Ala Gly Leu Pro Val Thr Thr Pro Ala
65                  70                  75                  80

Thr Thr Leu Asn Val Cys Gly Ser Gly Leu Arg Ala Val His Leu
                85                  90                  95

Ala Ala Gln Ala Ile Leu Ala Gly Asp Ala Asp Ile Val Ile Ala Gly
                100                 105                 110

Gly Gln Glu Ser Met Ser Leu Ser Pro His Ile Leu Pro Gly Ser Arg

```
                    115                 120                 125
Asp Gly Phe Arg Met Gly Asn Ala Gln Leu Val Asp Thr Met Val Asn
    130                 135                 140

Asp Gly Leu Thr Asp Ala Tyr Asn Ala Tyr His Met Gly Ile Thr Ala
145                 150                 155                 160

Glu Asn Val Ala Ala Lys Tyr Gly Ile Gly Arg Glu Glu Gln Asp Ala
                165                 170                 175

Phe Ser Leu Gln Ser Gln Gln Arg Ala Ala Ala Gln Lys Ala Gly
            180                 185                 190

Lys Phe Arg Asp Glu Ile Val Pro Val Leu Val Pro Gln Arg Lys Gly
            195                 200                 205

Asp Pro Leu Ala Phe Asp Ala Asp Glu Phe Ile Lys His Asp Ala Ser
    210                 215                 220

Ala Asp Gly Leu Ala Lys Leu Arg Pro Ala Phe Lys Lys Asp Gly Thr
225                 230                 235                 240

Val Thr Ala Gly Asn Ala Ser Gly Ile Asn Asp Gly Ala Ala Ala Val
                245                 250                 255

Leu Leu Met Ser Thr Gln Lys Ala Asp Gln Leu Gly Leu Lys Pro Leu
            260                 265                 270

Ala Ile Ile Lys Gly Tyr Ala Leu Thr Gly Cys Glu Pro Glu Ile Met
            275                 280                 285

Gly Ile Gly Pro Val Ser Ala Thr Arg Lys Ala Leu Ser Lys Ala Gly
            290                 295                 300

Trp Thr Val Glu Asp Leu Asp Leu Val Glu Ala Asn Glu Ala Phe Ala
305                 310                 315                 320

Ala Gln Ala Leu Gly Val Ala Lys Glu Leu Gly Trp Gly Ser Asp Lys
                325                 330                 335

Val Asn Val Asn Gly Gly Ala Ile Ala Leu Gly His Pro Ile Gly Ala
            340                 345                 350

Ser Gly Cys Arg Val Leu Val Thr Leu Leu His Glu Met Gln Arg Arg
            355                 360                 365

Gly Ala Lys Lys Gly Leu Ala Thr Leu Cys Ile Gly Gly Gly Met Gly
            370                 375                 380

Val Ala Leu Ala Val Glu Arg Pro
385                 390

<210> SEQ ID NO 106
<211> LENGTH: 392
<212> TYPE: PRT
<213> ORGANISM: Chromohalobacter salexigens
<220> FEATURE:
<221> NAME/KEY: MISC_FEATURE
<223> OTHER INFORMATION: Uniprot name: FADA_CHRSD. 3-ketoacyl-CoA
      thiolase

<400> SEQUENCE: 106

Met Ser Leu Asn Pro Arg Asp Ile Val Val Asp Ala Val Arg Thr
1               5                   10                  15

Ala Met Ala Lys Ala Lys His Gly Ala Phe Arg Asn Val Arg Ala Glu
                20                  25                  30

Asn Leu Ser Ala Ala Val Met Gln Ala Leu Phe Asp Arg Asn Ala Asn
            35                  40                  45

Leu Val Pro Ala Glu Val Asp Asp Val Ile Trp Gly Cys Val Asn Gln
    50                  55                  60

Thr Leu Glu Gln Ser Met Asn Ile Ala Arg Asn Ala Ala Ile Met Thr
65                  70                  75                  80
```

```
Gly Ile Pro Arg Thr Val Pro Ala Gln Thr Val Asn Arg Leu Cys Gly
                85                  90                  95

Ser Ser Met Ser Ala Leu His Ile Ala Thr Ala Asn Ile Lys Ala Gly
            100                 105                 110

Met Gly Asp Phe Tyr Ile Ile Gly Val Glu His Met Glu His Val
        115                 120                 125

Pro Met Thr His Gly Val Asp Val Asn Pro Ala Ser Lys Tyr Ala
    130                 135                 140

Ala Lys Ala Ala Met Met Gly Leu Thr Ala Glu Leu Leu Gly Lys
145                 150                 155                 160

Met His Gly Val Gly Arg Glu Glu Gln Asp Ala Phe Gly Val Arg Ser
                165                 170                 175

His Gln Arg Ala Gln Ala Ala Asn Glu Asn Gly Tyr Phe Asp Asn Glu
            180                 185                 190

Ile Val Gly Val Glu Gly His Asp Ala Asp Gly Phe Leu Arg Leu Ile
        195                 200                 205

Asp Arg Asp Glu Val Ile Arg Gln Asp Ala Asn Leu Glu Asp Met Gly
    210                 215                 220

Lys Leu Lys Pro Val Phe Asp Pro Lys Gly Gly Thr Val Thr Ala Gly
225                 230                 235                 240

Thr Ser Ser Ala Leu Ser Val Gly Ala Ser Ala Leu Ala Val Met Ser
                245                 250                 255

Tyr Glu Arg Ala Gln Ala Leu Gly Leu Glu Pro Leu Ala Arg Val Val
            260                 265                 270

Ser Thr Gly Val Ala Gly Cys Asp Ala Ser Ile Met Gly Tyr Gly Pro
        275                 280                 285

Val Pro Ala Thr Gln Lys Ala Leu Lys Ser Ala Gly Leu Ala Ile Asp
    290                 295                 300

Asp Ile Gln Thr Val Glu Leu Asn Glu Ala Phe Ala Ala Gln Ser Ile
305                 310                 315                 320

Pro Val Leu Lys Asp Leu Gly Leu Arg Glu Arg Met Asp Asp Ala Val
                325                 330                 335

Asn Leu His Gly Gly Ala Ile Ala Leu Gly His Pro Leu Gly Cys Ser
            340                 345                 350

Gly Ala Arg Ile Cys Thr Thr Leu Leu Asn Val Met Arg Gln Gln Asp
        355                 360                 365

Thr Thr Leu Gly Leu Ala Thr Met Cys Ile Gly Met Gly Gln Gly Val
    370                 375                 380

Ala Thr Val Phe Glu Arg Leu Lys
385                 390

<210> SEQ ID NO 107
<211> LENGTH: 389
<212> TYPE: PRT
<213> ORGANISM: Citrobacter koseri
<220> FEATURE:
<221> NAME/KEY: MISC_FEATURE
<223> OTHER INFORMATION: Uniprot name: FADA_CITK8.  3-ketoacyl-CoA
      thiolase

<400> SEQUENCE: 107

Met Glu Gln Val Val Ile Val Asp Ala Ile Arg Thr Pro Met Gly Arg
1               5                   10                  15

Ser Lys Gly Gly Ala Phe Arg Asn Val Arg Ala Glu Asp Leu Ser Ala
            20                  25                  30
```

His Leu Met Arg Ser Leu Leu Ala Arg Asn Pro Ala Leu Glu Ala Thr
            35                  40                  45

Ala Ile Asp Asp Ile Tyr Trp Gly Cys Val Gln Gln Thr Leu Glu Gln
 50                  55                  60

Gly Phe Asn Ile Ala Arg Asn Ala Ala Leu Leu Ala Glu Ile Pro His
 65                  70                  75                  80

Ser Val Pro Ala Val Thr Val Asn Arg Leu Cys Gly Ser Ser Met Gln
                 85                  90                  95

Ala Leu His Asp Ala Ala Arg Met Ile Met Thr Gly Asp Ala Gln Thr
            100                 105                 110

Cys Leu Ile Gly Gly Val Glu His Met Gly His Val Pro Met Ser His
            115                 120                 125

Gly Val Asp Phe His Pro Gly Leu Ser Arg Asn Val Ala Lys Ala Ala
130                 135                 140

Gly Met Met Gly Leu Thr Ala Glu Met Leu Ser Arg Met His Gly Ile
145                 150                 155                 160

Ser Arg Glu Met Gln Asp Ala Phe Ala Ala Arg Ser His Ala Arg Ala
                165                 170                 175

Trp Ala Ala Thr Gln Ser Gly Ala Phe Lys Asn Glu Ile Ile Pro Thr
            180                 185                 190

Gly Gly His Asp Ala Asp Gly Val Leu Lys Gln Phe Ser Tyr Asp Glu
            195                 200                 205

Val Ile Arg Pro Glu Thr Thr Val Glu Ala Leu Ser Thr Leu Arg Pro
210                 215                 220

Ala Phe Asp Pro Val Ser Gly Thr Val Thr Ala Gly Thr Ser Ser Ala
225                 230                 235                 240

Leu Ser Asp Gly Ala Ala Ala Met Leu Val Met Ser Glu Ser Arg Ala
                245                 250                 255

Arg Glu Leu Gly Leu Gln Pro Arg Ala Arg Ile Arg Ser Met Ala Val
            260                 265                 270

Val Gly Cys Asp Pro Ser Ile Met Gly Tyr Gly Pro Val Pro Ala Ser
            275                 280                 285

Lys Leu Ala Leu Lys Lys Ala Gly Leu Ala Ala Ser Asp Ile Asp Leu
290                 295                 300

Phe Glu Met Asn Glu Ala Phe Ala Ala Gln Ile Leu Pro Cys Ile Lys
305                 310                 315                 320

Asp Leu Gly Leu Met Glu Gln Ile Asp Glu Lys Ile Asn Leu Asn Gly
                325                 330                 335

Gly Ala Ile Ala Leu Gly His Pro Leu Gly Cys Ser Gly Ala Arg Ile
            340                 345                 350

Ser Thr Thr Leu Leu Asn Leu Met Glu Arg Lys Asp Ala Gln Phe Gly
            355                 360                 365

Leu Ala Thr Met Cys Ile Gly Leu Gly Gln Gly Ile Ala Thr Val Phe
370                 375                 380

Glu Arg Val Gln Ser
385

<210> SEQ ID NO 108
<211> LENGTH: 436
<212> TYPE: PRT
<213> ORGANISM: Citrobacter koseri
<220> FEATURE:
<221> NAME/KEY: MISC_FEATURE
<223> OTHER INFORMATION: Uniprot name: FADI_CITK8.  3-ketoacyl-CoA
      thiolase

<400> SEQUENCE: 108

```
Met Ser Gln Ala Leu Pro Leu Val Thr Arg Gln Gly Asp Arg Ile Ala
1               5                   10                  15

Ile Val Ser Gly Leu Arg Thr Pro Phe Ala Arg Gln Ala Thr Ala Phe
            20                  25                  30

His Gly Ile Pro Ala Val Glu Leu Gly Lys Met Val Val Gly Glu Leu
        35                  40                  45

Leu Ala Arg Ser Glu Ile Pro Ala Glu Val Ile Glu Gln Leu Val Phe
    50                  55                  60

Gly Gln Val Val Gln Met Pro Glu Ala Pro Asn Ile Ala Arg Glu Ile
65                  70                  75                  80

Val Leu Gly Thr Gly Met Asn Val His Thr Asp Ala Tyr Ser Val Ser
                85                  90                  95

Arg Ala Cys Ala Thr Ser Phe Gln Ala Val Ala Asn Val Ala Glu Ser
            100                 105                 110

Leu Met Ala Gly Thr Ile Arg Ala Gly Ile Ala Gly Ala Asp Ser
        115                 120                 125

Ser Ser Val Leu Pro Ile Gly Val Ser Lys Lys Leu Ala Arg Ile Leu
130                 135                 140

Val Asp Val Asn Lys Ala Arg Thr Thr Gly Gln Lys Leu Lys Leu Phe
145                 150                 155                 160

Ser Arg Leu Arg Leu Arg Asp Leu Met Pro Val Pro Pro Ala Val Ala
                165                 170                 175

Glu Tyr Ser Thr Gly Leu Arg Met Gly Asp Thr Ala Glu Gln Met Ala
            180                 185                 190

Lys Thr Tyr Gly Ile Thr Arg Glu Gln Gln Asp Ala Leu Ala His Arg
        195                 200                 205

Ser His Gln Arg Ala Ala Gln Ala Trp Ala Glu Gly Lys Leu Ala Asp
    210                 215                 220

Glu Val Met Thr Thr Tyr Ala Pro Pro Tyr Lys Glu Pro Phe Ser Glu
225                 230                 235                 240

Asp Asn Asn Ile Arg Gly Asn Ser Thr Leu Ala Asp Tyr Ala Lys Leu
                245                 250                 255

Arg Pro Ala Phe Asp Arg Gln His Gly Thr Val Thr Ala Ala Asn Ser
            260                 265                 270

Thr Pro Leu Thr Asp Gly Ala Ala Ala Val Ile Leu Met Thr Glu Ser
        275                 280                 285

Arg Ala Lys Glu Leu Gly Leu Ala Pro Leu Gly Tyr Leu Arg Ser Tyr
    290                 295                 300

Ala Phe Thr Ala Ile Asp Val Trp Gln Asp Met Leu Leu Gly Pro Ala
305                 310                 315                 320

Trp Ser Thr Pro Leu Ala Leu Glu Arg Ala Gly Leu Thr Leu Ala Asp
                325                 330                 335

Leu Ser Leu Ile Asp Met His Glu Ala Phe Ala Ala Gln Thr Leu Ala
            340                 345                 350

Asn Ile Gln Leu Leu Gly Ser Glu Arg Phe Ala Arg Asp Val Leu Gly
        355                 360                 365

Arg Ala His Ala Thr Gly Glu Val Asp Asp Ser Lys Phe Asn Val Leu
    370                 375                 380

Gly Gly Ser Ile Ala Tyr Gly His Pro Phe Ala Ala Thr Gly Ala Arg
385                 390                 395                 400

Met Ile Thr Gln Thr Leu His Glu Leu Arg Arg Arg Gly Gly Gly Phe
                405                 410                 415
```

Gly Leu Val Thr Ala Cys Ala Ala Gly Gly Leu Gly Ala Ala Met Val
            420                 425                 430

Leu Glu Ala Glu
        435

<210> SEQ ID NO 109
<211> LENGTH: 392
<212> TYPE: PRT
<213> ORGANISM: Clostridium acetobutylicum
<220> FEATURE:
<221> NAME/KEY: MISC_FEATURE
<223> OTHER INFORMATION: Uniprot name: THLA_CLOAB.  Acetyl-CoA
      acetyltransferase

<400> SEQUENCE: 109

Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Val Ile Lys Gly Arg Lys
        195                 200                 205

Gly Glu Thr Val Val Asp Thr Asp Glu His Pro Arg Phe Gly Ser Thr
    210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
    290                 295                 300

Trp Thr Val Asp Glu Leu Asp Leu Ile Glu Ser Asn Glu Ala Phe Ala
305                 310                 315                 320

```
Ala Gln Ser Leu Ala Val Lys Asp Leu Lys Phe Asp Met Asn Lys
            325                 330                 335

Val Asn Val Asn Gly Gly Ala Ile Ala Leu Gly His Pro Ile Gly Ala
            340                 345                 350

Ser Gly Ala Arg Ile Leu Val Thr Leu Val His Ala Met Gln Lys Arg
            355                 360                 365

Asp Ala Lys Lys Gly Leu Ala Thr Leu Cys Ile Gly Gly Gly Gln Gly
            370                 375                 380

Thr Ala Ile Leu Leu Glu Lys Cys
385                 390

<210> SEQ ID NO 110
<211> LENGTH: 393
<212> TYPE: PRT
<213> ORGANISM: Cupriavidus necator (Ralstonia eutropha)
<220> FEATURE:
<221> NAME/KEY: MISC_FEATURE
<223> OTHER INFORMATION: Uniprot name: THIL_CUPNH.  Acetyl-CoA
      acetyltransferase

<400> SEQUENCE: 110

Met Thr Asp Val Val Ile Val Ser Ala Ala Arg Thr Ala Val Gly Lys
1               5                   10                  15

Phe Gly Gly Ser Leu Ala Lys Ile Pro Ala Pro Glu Leu Gly Ala Val
            20                  25                  30

Val Ile Lys Ala Ala Leu Glu Arg Ala Gly Val Lys Pro Glu Gln Val
            35                  40                  45

Ser Glu Val Ile Met Gly Gln Val Leu Thr Ala Gly Ser Gly Gln Asn
50                  55                  60

Pro Ala Arg Gln Ala Ala Ile Lys Ala Gly Leu Pro Ala Met Val Pro
65                  70                  75                  80

Ala Met Thr Ile Asn Lys Val Cys Gly Ser Gly Leu Lys Ala Val Met
            85                  90                  95

Leu Ala Ala Asn Ala Ile Met Ala Gly Asp Ala Glu Ile Val Val Ala
            100                 105                 110

Gly Gly Gln Glu Asn Met Ser Ala Ala Pro His Val Leu Pro Gly Ser
            115                 120                 125

Arg Asp Gly Phe Arg Met Gly Asp Ala Lys Leu Val Asp Thr Met Ile
            130                 135                 140

Val Asp Gly Leu Trp Asp Val Tyr Asn Gln Tyr His Met Gly Ile Thr
145                 150                 155                 160

Ala Glu Asn Val Ala Lys Glu Tyr Gly Ile Thr Arg Glu Ala Gln Asp
            165                 170                 175

Glu Phe Ala Val Gly Ser Gln Asn Lys Ala Glu Ala Ala Gln Lys Ala
            180                 185                 190

Gly Lys Phe Asp Glu Glu Ile Val Pro Val Leu Ile Pro Gln Arg Lys
            195                 200                 205

Gly Asp Pro Val Ala Phe Lys Thr Asp Glu Phe Val Arg Gln Gly Ala
            210                 215                 220

Thr Leu Asp Ser Met Ser Gly Leu Lys Pro Ala Phe Asp Lys Ala Gly
225                 230                 235                 240

Thr Val Thr Ala Ala Asn Ala Ser Gly Leu Asn Asp Gly Ala Ala Ala
            245                 250                 255

Val Val Val Met Ser Ala Ala Lys Ala Lys Glu Leu Gly Leu Thr Pro
            260                 265                 270

Leu Ala Thr Ile Lys Ser Tyr Ala Asn Ala Gly Val Asp Pro Lys Val
```

```
                275                 280                 285
Met Gly Met Gly Pro Val Pro Ala Ser Lys Arg Ala Leu Ser Arg Ala
        290                 295                 300

Glu Trp Thr Pro Gln Asp Leu Asp Leu Met Glu Ile Asn Glu Ala Phe
305                 310                 315                 320

Ala Ala Gln Ala Leu Ala Val His Gln Gln Met Gly Trp Asp Thr Ser
                325                 330                 335

Lys Val Asn Val Asn Gly Gly Ala Ile Ala Ile Gly His Pro Ile Gly
            340                 345                 350

Ala Ser Gly Cys Arg Ile Leu Val Thr Leu Leu His Glu Met Lys Arg
        355                 360                 365

Arg Asp Ala Lys Lys Gly Leu Ala Ser Leu Cys Ile Gly Gly Gly Met
    370                 375                 380

Gly Val Ala Leu Ala Val Glu Arg Lys
385                 390

<210> SEQ ID NO 111
<211> LENGTH: 387
<212> TYPE: PRT
<213> ORGANISM: Enterobacter cloacae
<220> FEATURE:
<221> NAME/KEY: MISC_FEATURE
<223> OTHER INFORMATION: Uniprot name: FADA_ENTCL. 3-ketoacyl-CoA
      thiolase

<400> SEQUENCE: 111

Met Glu Lys Val Val Ile Val Asp Ala Ile Arg Thr Pro Met Gly Arg
1               5                   10                  15

Ser Lys Gly Gly Ala Phe Arg Asn Val Arg Ala Glu Asp Leu Ser Ala
            20                  25                  30

His Leu Met Arg Ser Leu Leu Ala Arg Asn Pro Ala Leu Asp Pro Ala
        35                  40                  45

Ala Leu Asp Asp Ile Tyr Trp Gly Cys Leu His Gln Thr Leu Glu Gln
    50                  55                  60

Gly Phe Asn Leu Ala Arg Asn Ala Ser Leu Leu Ala Glu Ile Pro His
65                  70                  75                  80

Ser Val Pro Ala Val Thr Val Asn Arg Leu Cys Gly Ser Ser Met Gln
                85                  90                  95

Ala Leu His Asp Ala Ala Arg Met Ile Met Thr Gly Asp Ala Gln Ala
            100                 105                 110

Cys Leu Val Gly Gly Val Glu His Met Gly His Val Pro Met Ser His
        115                 120                 125

Gly Val His Phe His Pro Gly Met Ser Arg Asn Val Ala Lys Ala Ala
    130                 135                 140

Gly Met Met Gly Leu Thr Ala Glu Met Leu Ser Arg Leu His Gly Ile
145                 150                 155                 160

Ser Arg Glu Met Gln Asp Ala Phe Ala Ala Arg Ser His Ala Arg Ala
                165                 170                 175

Trp Ala Ala Thr Gln Ser Gly Ala Phe Lys Asn Glu Ile Ile Pro Thr
            180                 185                 190

Gly Gly His Asp Ala Asp Gly Val Leu Lys Gln Phe Ser Tyr Asp Glu
        195                 200                 205

Val Ile Arg Pro Glu Thr Thr Val Glu Ala Leu Ser Thr Leu Arg Pro
    210                 215                 220

Ala Phe Asp Pro Val Thr Gly Thr Val Thr Ala Gly Thr Ser Ser Ala
225                 230                 235                 240
```

```
Leu Ser Asp Gly Ala Ala Met Leu Val Met Ser Glu Ser Arg Ala
            245                 250                 255

Arg Glu Leu Gly Leu Thr Pro Arg Ala Arg Val Arg Ser Met Ala Val
        260                 265                 270

Val Gly Cys Asp Pro Ser Ile Met Gly Tyr Gly Pro Val Pro Ala Ser
        275                 280                 285

Lys Leu Ala Leu Lys Ala Gly Leu Thr Ala Ser Asp Ile Asp Leu
        290                 295                 300

Phe Glu Met Asn Glu Ala Phe Ala Ala Gln Ile Leu Pro Cys Ile Lys
305                 310                 315                 320

Asp Leu Gly Leu Met Gly Gln Ile Asp Glu Lys Ile Asn Leu Asn Gly
            325                 330                 335

Gly Ala Ile Ala Leu Gly His Pro Leu Gly Cys Ser Gly Ala Arg Ile
            340                 345                 350

Ser Thr Thr Leu Ile Asn Leu Met Glu Gly Lys Asp Ala Gln Phe Gly
            355                 360                 365

Leu Ala Thr Met Cys Ile Gly Leu Gly Gln Gly Ile Ala Thr Val Phe
    370                 375                 380

Glu Arg Val
385

<210> SEQ ID NO 112
<211> LENGTH: 387
<212> TYPE: PRT
<213> ORGANISM: Erwinia tasmaniensis
<220> FEATURE:
<221> NAME/KEY: MISC_FEATURE
<223> OTHER INFORMATION: Uniprot name: FADA_ERWT9. 3-ketoacyl-CoA
      thiolase

<400> SEQUENCE: 112

Met Glu Lys Val Val Ile Val Asp Ala Ile Arg Thr Pro Met Gly Arg
1               5                   10                  15

Ser Lys Gly Gly Ala Phe Arg His Val Arg Ala Glu Asp Leu Ser Ala
            20                  25                  30

His Leu Met Arg Ser Leu Leu Ser Arg Asn Pro Ser Val Asp Pro Ala
        35                  40                  45

Thr Leu Asp Asp Ile Tyr Trp Gly Cys Val Gln Gln Thr Leu Glu Gln
    50                  55                  60

Gly Phe Asn Ile Ala Arg Asn Ala Ala Leu Leu Ala Glu Ile Pro His
65                  70                  75                  80

Ser Val Pro Ala Thr Thr Val Asn Arg Leu Cys Gly Ser Ser Met Gln
                85                  90                  95

Ala Leu His Asp Ala Ala Arg Ala Ile Met Val Gly Asp Ala Arg Thr
            100                 105                 110

Cys Leu Ile Gly Gly Val Glu His Met Gly His Val Pro Met Ser His
        115                 120                 125

Gly Val Asp Phe His Pro Gly Leu Ser Arg Asn Val Ala Lys Ala Ala
    130                 135                 140

Gly Met Met Gly Leu Thr Ala Glu Met Leu Ala Arg Met His Gly Ile
145                 150                 155                 160

Ser Arg Glu Met Gln Asp Arg Phe Ala Ala Arg Ser His Gln Arg Ala
                165                 170                 175

Ala Ala Ala Thr Gln Ala Gly His Phe Ala Ala Glu Ile Val Ala Val
            180                 185                 190
```

```
Cys Gly His Asp Ala Asp Gly Val Leu Lys Arg Tyr Asp Ala Asp Glu
            195                 200                 205

Val Ile Arg Pro Glu Thr Thr Val Glu Ser Leu Met Ala Leu Arg Pro
    210                 215                 220

Ala Phe Asp Pro Val Asp Gly Thr Val Thr Ala Gly Ser Ser Ser Ala
225                 230                 235                 240

Leu Ser Asp Gly Ala Ala Met Leu Ile Met Ser Gly Ser Gln Ala
            245                 250                 255

Arg Gln Gln Gly Leu Lys Ala Arg Arg Ile Arg Ser Met Ala Val
            260                 265                 270

Val Gly Cys Asp Pro Ser Ile Met Gly Tyr Gly Pro Val Pro Ala Ser
        275                 280                 285

Gln Leu Ala Leu Lys Arg Ala Gly Leu Ser Ile Ala Asp Ile Gly Val
    290                 295                 300

Phe Glu Leu Asn Glu Ala Phe Ala Ala Gln Thr Leu Pro Cys Ile Lys
305                 310                 315                 320

Asp Leu Gly Leu Met Asp Lys Leu Asp Glu Lys Val Asn Leu Asn Gly
                325                 330                 335

Gly Ala Ile Ala Leu Gly His Pro Leu Gly Cys Ser Gly Ala Arg Ile
            340                 345                 350

Ser Thr Thr Leu Leu Asn Leu Met Glu Arg Arg Asp Ala Gln Phe Gly
            355                 360                 365

Leu Ala Thr Met Cys Ile Gly Leu Gly Gln Gly Ile Ala Thr Val Phe
    370                 375                 380

Glu Arg Ile
385

<210> SEQ ID NO 113
<211> LENGTH: 437
<212> TYPE: PRT
<213> ORGANISM: Erwinia tasmaniensis
<220> FEATURE:
<221> NAME/KEY: MISC_FEATURE
<223> OTHER INFORMATION: Uniprot name: FADI_ERWT9. 3-ketoacyl-CoA
      thiolase

<400> SEQUENCE: 113

Met Ser Lys Ala Leu Pro Leu Leu Thr Arg Gln Gly Glu Arg Ile Ala
1               5                   10                  15

Ile Thr His Gly Leu Arg Thr Pro Phe Ala Arg Gln Ala Thr Ala Phe
            20                  25                  30

His Gly Ile Pro Ala Leu Glu Leu Gly Arg Met Val Val Ser Glu Leu
        35                  40                  45

Leu Ala Arg Ser Glu Ile Ser Pro Asp Val Ile Glu Gln Leu Val Phe
    50                  55                  60

Gly Gln Val Val Gln Met Pro Glu Ala Pro Asn Ile Ala Arg Glu Ile
65                  70                  75                  80

Val Leu Ala Ser Ala Leu Ser Val His Thr Asp Ala Trp Ser Val Ser
                85                  90                  95

Arg Ala Cys Ala Thr Ser Phe Gln Ala Val Ala Asn Val Ala Glu Ser
            100                 105                 110

Leu Met Ile Gly His Ile Gln Ala Gly Ile Ala Gly Gly Ala Asp Ser
        115                 120                 125

Ser Ser Val Leu Pro Ile Gly Val Ser Lys Lys Leu Ala Arg Leu Leu
    130                 135                 140

Val Asp Ala Ser Lys Thr Arg Ser Leu Ala Gln Lys Leu Lys Leu Phe
```

```
145                 150                 155                 160
Ser Gly Leu Arg Pro Arg Asp Leu Leu Pro Val Ala Pro Ala Val Ala
            165                 170                 175

Glu Tyr Ser Thr Gly Leu Arg Met Gly Asp Ser Ala Glu Gln Met Ala
            180                 185                 190

Lys Asn His Gly Ile Thr Arg Glu Gln Gln Asp Ala Leu Ala Leu Arg
            195                 200                 205

Ser His Gln Arg Ala Ala His Ala Trp Gln Gln Gly Leu Leu Asn Asp
        210                 215                 220

Glu Val Met Thr Ala Cys Val Pro Pro Trp Glu Gln Pro Phe Glu Gln
225                 230                 235                 240

Asp Asn Asn Val Arg Ala Glu Ser Lys Met Gln Asp Tyr Ala Arg Leu
                245                 250                 255

Arg Pro Ala Phe Asp Arg Arg His Gly Thr Val Thr Ala Ala Asn Ser
            260                 265                 270

Thr Pro Leu Thr Asp Gly Ala Ala Val Ile Leu Met Thr Ala Ser
            275                 280                 285

Arg Ala Arg Glu Leu Gly Ile Ala Pro Leu Gly Phe Leu Arg Ser Tyr
        290                 295                 300

Ala Phe Ser Ala Ile Asp Val Arg Gln Asp Met Leu Leu Gly Pro Ser
305                 310                 315                 320

Tyr Ala Ser Pro Leu Ala Leu Asp Arg Ala Gly Ile Thr Leu Ala Asp
                325                 330                 335

Leu Ser Leu Ile Asp Met His Glu Ala Phe Ala Ala Gln Thr Leu Ala
            340                 345                 350

Asn Leu Lys Met Phe Ala Asp Glu Arg Phe Ala Arg Glu Val Leu Asp
        355                 360                 365

Arg Pro Arg Ala Leu Gly Glu Val Asp Met Glu Arg Phe Asn Val Leu
    370                 375                 380

Gly Gly Ser Ile Ala Tyr Gly His Pro Phe Ala Ala Thr Gly Ala Arg
385                 390                 395                 400

Met Ile Thr Gln Thr Leu Asn Glu Leu Arg Arg Arg Gly Gly Gly Leu
                405                 410                 415

Gly Leu Val Thr Ala Cys Ala Ala Gly Gly Leu Gly Ala Ala Met Val
            420                 425                 430

Leu Glu Val Asp Ser
        435

<210> SEQ ID NO 114
<211> LENGTH: 387
<212> TYPE: PRT
<213> ORGANISM: Escherichia coli
<220> FEATURE:
<221> NAME/KEY: MISC_FEATURE
<223> OTHER INFORMATION: Uniprot name: FADA_ECOLI.  3-ketoacyl-CoA
      thiolase

<400> SEQUENCE: 114

Met Glu Gln Val Val Ile Val Asp Ala Ile Arg Thr Pro Met Gly Arg
1               5                   10                  15

Ser Lys Gly Gly Ala Phe Arg Asn Val Arg Ala Glu Asp Leu Ser Ala
            20                  25                  30

His Leu Met Arg Ser Leu Leu Ala Arg Asn Pro Ala Leu Glu Ala Ala
        35                  40                  45

Ala Leu Asp Asp Ile Tyr Trp Gly Cys Val Gln Gln Thr Leu Glu Gln
    50                  55                  60
```

Gly Phe Asn Ile Ala Arg Asn Ala Ala Leu Leu Ala Glu Val Pro His
65                  70                  75                  80

Ser Val Pro Ala Val Thr Val Asn Arg Leu Cys Gly Ser Ser Met Gln
                85                  90                  95

Ala Leu His Asp Ala Ala Arg Met Ile Met Thr Gly Asp Ala Gln Ala
            100                 105                 110

Cys Leu Val Gly Gly Val Glu His Met Gly His Val Pro Met Ser His
            115                 120                 125

Gly Val Asp Phe His Pro Gly Leu Ser Arg Asn Val Ala Lys Ala Ala
        130                 135                 140

Gly Met Met Gly Leu Thr Ala Glu Met Leu Ala Arg Met His Gly Ile
145                 150                 155                 160

Ser Arg Glu Met Gln Asp Ala Phe Ala Ala Arg Ser His Ala Arg Ala
                165                 170                 175

Trp Ala Ala Thr Gln Ser Ala Ala Phe Lys Asn Glu Ile Ile Pro Thr
            180                 185                 190

Gly Gly His Asp Ala Asp Gly Val Leu Lys Gln Phe Asn Tyr Asp Glu
        195                 200                 205

Val Ile Arg Pro Glu Thr Thr Val Glu Ala Leu Ala Thr Leu Arg Pro
210                 215                 220

Ala Phe Asp Pro Val Asn Gly Met Val Thr Ala Gly Thr Ser Ser Ala
225                 230                 235                 240

Leu Ser Asp Gly Ala Ala Ala Met Leu Val Met Ser Glu Ser Arg Ala
                245                 250                 255

His Glu Leu Gly Leu Lys Pro Arg Ala Arg Val Arg Ser Met Ala Val
            260                 265                 270

Val Gly Cys Asp Pro Ser Ile Met Gly Tyr Gly Pro Val Pro Ala Ser
        275                 280                 285

Lys Leu Ala Leu Lys Lys Ala Gly Leu Ser Ala Ser Asp Ile Gly Val
290                 295                 300

Phe Glu Met Asn Glu Ala Phe Ala Ala Gln Ile Leu Pro Cys Ile Lys
305                 310                 315                 320

Asp Leu Gly Leu Ile Glu Gln Ile Asp Glu Lys Ile Asn Leu Asn Gly
                325                 330                 335

Gly Ala Ile Ala Leu Gly His Pro Leu Gly Cys Ser Gly Ala Arg Ile
            340                 345                 350

Ser Thr Thr Leu Leu Asn Leu Met Glu Arg Lys Asp Val Gln Phe Gly
        355                 360                 365

Leu Ala Thr Met Cys Ile Gly Leu Gly Gln Gly Ile Ala Thr Val Phe
370                 375                 380

Glu Arg Val
385

<210> SEQ ID NO 115
<211> LENGTH: 436
<212> TYPE: PRT
<213> ORGANISM: Escherichia coli
<220> FEATURE:
<221> NAME/KEY: MISC_FEATURE
<223> OTHER INFORMATION: Uniprot name: FADI_ECOLI. 3-ketoacyl-CoA
      thiolase

<400> SEQUENCE: 115

Met Gly Gln Val Leu Pro Leu Val Thr Arg Gln Gly Asp Arg Ile Ala
1               5                   10                  15

-continued

```
Ile Val Ser Gly Leu Arg Thr Pro Phe Ala Arg Gln Ala Thr Ala Phe
             20                  25                  30

His Gly Ile Pro Ala Val Asp Leu Gly Lys Met Val Val Gly Glu Leu
         35                  40                  45

Leu Ala Arg Ser Glu Ile Pro Ala Glu Val Ile Glu Gln Leu Val Phe
     50                  55                  60

Gly Gln Val Val Gln Met Pro Glu Ala Pro Asn Ile Ala Arg Glu Ile
 65                  70                  75                  80

Val Leu Gly Thr Gly Met Asn Val His Thr Asp Ala Tyr Ser Val Ser
                 85                  90                  95

Arg Ala Cys Ala Thr Ser Phe Gln Ala Val Ala Asn Val Ala Glu Ser
            100                 105                 110

Leu Met Ala Gly Thr Ile Arg Ala Gly Ile Ala Gly Gly Ala Asp Ser
        115                 120                 125

Ser Ser Val Leu Pro Ile Gly Val Ser Lys Lys Leu Ala Arg Val Leu
    130                 135                 140

Val Asp Val Asn Lys Ala Arg Thr Met Ser Gln Arg Leu Lys Leu Phe
145                 150                 155                 160

Ser Arg Leu Arg Leu Arg Asp Leu Met Pro Val Pro Pro Ala Val Ala
                165                 170                 175

Glu Tyr Ser Thr Gly Leu Arg Met Gly Asp Thr Ala Glu Gln Met Ala
            180                 185                 190

Lys Thr Tyr Gly Ile Thr Arg Glu Gln Gln Asp Ala Leu Ala His Arg
        195                 200                 205

Ser His Gln Arg Ala Ala Gln Ala Trp Ser Asp Gly Lys Leu Lys Glu
    210                 215                 220

Glu Val Met Thr Ala Phe Ile Pro Pro Tyr Lys Gln Pro Leu Val Glu
225                 230                 235                 240

Asp Asn Asn Ile Arg Gly Asn Ser Ser Leu Ala Asp Tyr Ala Lys Leu
                245                 250                 255

Arg Pro Ala Phe Asp Arg Lys His Gly Thr Val Thr Ala Ala Asn Ser
            260                 265                 270

Thr Pro Leu Thr Asp Gly Ala Ala Val Ile Leu Met Thr Glu Ser
        275                 280                 285

Arg Ala Lys Glu Leu Gly Leu Val Pro Leu Gly Tyr Leu Arg Ser Tyr
    290                 295                 300

Ala Phe Thr Ala Ile Asp Val Trp Gln Asp Met Leu Leu Gly Pro Ala
305                 310                 315                 320

Trp Ser Thr Pro Leu Ala Leu Glu Arg Ala Gly Leu Thr Met Ser Asp
                325                 330                 335

Leu Thr Leu Ile Asp Met His Glu Ala Phe Ala Ala Gln Thr Leu Ala
            340                 345                 350

Asn Ile Gln Leu Leu Gly Ser Glu Arg Phe Ala Arg Glu Ala Leu Gly
        355                 360                 365

Arg Ala His Ala Thr Gly Glu Val Asp Asp Ser Lys Phe Asn Val Leu
    370                 375                 380

Gly Gly Ser Ile Ala Tyr Gly His Pro Phe Ala Ala Thr Gly Ala Arg
385                 390                 395                 400

Met Ile Thr Gln Thr Leu His Glu Leu Arg Arg Arg Gly Gly Phe
                405                 410                 415

Gly Leu Val Thr Ala Cys Ala Ala Gly Gly Leu Gly Ala Ala Met Val
            420                 425                 430

Leu Glu Ala Glu
```

<210> SEQ ID NO 116
<211> LENGTH: 394
<212> TYPE: PRT
<213> ORGANISM: Escherichia coli
<220> FEATURE:
<221> NAME/KEY: MISC_FEATURE
<223> OTHER INFORMATION: Uniprot name: ATOB_ECOLI. Acetyl-CoA acetyltransferase

<400> SEQUENCE: 116

```
Met Lys Asn Cys Val Ile Val Ser Ala Val Arg Thr Ala Ile Gly Ser
1               5                   10                  15

Phe Asn Gly Ser Leu Ala Ser Thr Ser Ala Ile Asp Leu Gly Ala Thr
            20                  25                  30

Val Ile Lys Ala Ala Ile Glu Arg Ala Lys Ile Asp Ser Gln His Val
        35                  40                  45

Asp Glu Val Ile Met Gly Asn Val Leu Gln Ala Gly Leu Gly Gln Asn
    50                  55                  60

Pro Ala Arg Gln Ala Leu Leu Lys Ser Gly Leu Ala Glu Thr Val Cys
65                  70                  75                  80

Gly Phe Thr Val Asn Lys Val Cys Gly Ser Gly Leu Lys Ser Val Ala
                85                  90                  95

Leu Ala Ala Gln Ala Ile Gln Ala Gly Gln Ala Gln Ser Ile Val Ala
            100                 105                 110

Gly Gly Met Glu Asn Met Ser Leu Ala Pro Tyr Leu Leu Asp Ala Lys
        115                 120                 125

Ala Arg Ser Gly Tyr Arg Leu Gly Asp Gly Gln Val Tyr Asp Val Ile
    130                 135                 140

Leu Arg Asp Gly Leu Met Cys Ala Thr His Gly Tyr His Met Gly Ile
145                 150                 155                 160

Thr Ala Glu Asn Val Ala Lys Glu Tyr Gly Ile Thr Arg Glu Met Gln
                165                 170                 175

Asp Glu Leu Ala Leu His Ser Gln Arg Lys Ala Ala Ala Ala Ile Glu
            180                 185                 190

Ser Gly Ala Phe Thr Ala Glu Ile Val Pro Val Asn Val Val Thr Arg
        195                 200                 205

Lys Lys Thr Phe Val Phe Ser Gln Asp Glu Phe Pro Lys Ala Asn Ser
    210                 215                 220

Thr Ala Glu Ala Leu Gly Ala Leu Arg Pro Ala Phe Asp Lys Ala Gly
225                 230                 235                 240

Thr Val Thr Ala Gly Asn Ala Ser Gly Ile Asn Asp Gly Ala Ala Ala
                245                 250                 255

Leu Val Ile Met Glu Glu Ser Ala Leu Ala Ala Gly Leu Thr Pro
            260                 265                 270

Leu Ala Arg Ile Lys Ser Tyr Ala Ser Gly Gly Val Pro Pro Ala Leu
        275                 280                 285

Met Gly Met Gly Pro Val Pro Ala Thr Gln Lys Ala Leu Gln Leu Ala
    290                 295                 300

Gly Leu Gln Leu Ala Asp Ile Asp Leu Ile Glu Ala Asn Glu Ala Phe
305                 310                 315                 320

Ala Ala Gln Phe Leu Ala Val Gly Lys Asn Leu Gly Phe Asp Ser Glu
                325                 330                 335

Lys Val Asn Val Asn Gly Gly Ala Ile Ala Leu Gly His Pro Ile Gly
            340                 345                 350
```

Ala Ser Gly Ala Arg Ile Leu Val Thr Leu Leu His Ala Met Gln Ala
        355                 360                 365

Arg Asp Lys Thr Leu Gly Leu Ala Thr Leu Cys Ile Gly Gly Gly Gln
370                 375                 380

Gly Ile Ala Met Val Ile Glu Arg Leu Asn
385                 390

<210> SEQ ID NO 117
<211> LENGTH: 393
<212> TYPE: PRT
<213> ORGANISM: Escherichia coli
<220> FEATURE:
<221> NAME/KEY: MISC_FEATURE
<223> OTHER INFORMATION: Uniprot name: YQEF_ECOLI.  Probable acetyl-CoA
      acetyltransferase

<400> SEQUENCE: 117

Met Lys Asp Val Val Ile Val Gly Ala Leu Arg Thr Pro Ile Gly Cys
1               5                   10                  15

Phe Arg Gly Ala Leu Ala Gly His Ser Ala Val Glu Leu Gly Ser Leu
                20                  25                  30

Val Val Lys Ala Leu Ile Glu Arg Thr Gly Val Pro Ala Tyr Ala Val
            35                  40                  45

Asp Glu Val Ile Leu Gly Gln Val Leu Thr Ala Gly Ala Gly Gln Asn
        50                  55                  60

Pro Ala Arg Gln Ser Ala Ile Lys Gly Gly Leu Pro Asn Ser Val Ser
65                  70                  75                  80

Ala Ile Thr Ile Asn Asp Val Cys Gly Ser Gly Leu Lys Ala Leu His
                85                  90                  95

Leu Ala Thr Gln Ala Ile Gln Cys Gly Glu Ala Asp Ile Val Ile Ala
            100                 105                 110

Gly Gly Gln Glu Asn Met Ser Arg Ala Pro His Val Leu Thr Asp Ser
        115                 120                 125

Arg Thr Gly Ala Gln Leu Gly Asn Ser Gln Leu Val Asp Ser Leu Val
130                 135                 140

His Asp Gly Leu Trp Asp Ala Phe Asn Asp Tyr His Ile Gly Val Thr
145                 150                 155                 160

Ala Glu Asn Leu Ala Arg Glu Tyr Gly Ile Ser Arg Gln Leu Gln Asp
                165                 170                 175

Ala Tyr Ala Leu Ser Ser Gln Gln Lys Ala Arg Ala Ala Ile Asp Ala
            180                 185                 190

Gly Arg Phe Lys Asp Glu Ile Val Pro Val Met Thr Gln Ser Asn Gly
        195                 200                 205

Gln Thr Leu Val Val Asp Thr Asp Glu Gln Pro Arg Thr Asp Ala Ser
210                 215                 220

Ala Glu Gly Leu Ala Arg Leu Asn Pro Ser Phe Asp Ser Leu Gly Ser
225                 230                 235                 240

Val Thr Ala Gly Asn Ala Ser Ser Ile Asn Asp Gly Ala Ala Ala Val
                245                 250                 255

Met Met Met Ser Glu Ala Lys Ala Arg Ala Leu Asn Leu Pro Val Leu
            260                 265                 270

Ala Arg Ile Arg Ala Phe Ala Ser Val Gly Val Asp Pro Ala Leu Met
        275                 280                 285

Gly Ile Ala Pro Val Tyr Ala Thr Arg Arg Cys Leu Glu Arg Val Gly
290                 295                 300

```
Trp Gln Leu Ala Glu Val Asp Leu Ile Glu Ala Asn Glu Ala Phe Ala
305                 310                 315                 320

Ala Gln Ala Leu Ser Val Gly Lys Met Leu Glu Trp Asp Glu Arg Arg
            325                 330                 335

Val Asn Val Asn Gly Gly Ala Ile Ala Leu Gly His Pro Ile Gly Ala
                340                 345                 350

Ser Gly Cys Arg Ile Leu Val Ser Leu Val His Glu Met Val Lys Arg
            355                 360                 365

Asn Ala Arg Lys Gly Leu Ala Thr Leu Cys Ile Gly Gly Gln Gly
            370                 375                 380

Val Ala Leu Thr Ile Glu Arg Asp Glu
385                 390
```

<210> SEQ ID NO 118
<211> LENGTH: 401
<212> TYPE: PRT
<213> ORGANISM: Escherichia coli
<220> FEATURE:
<221> NAME/KEY: MISC_FEATURE
<223> OTHER INFORMATION: Uniprot name: PAAJ_ECOLI.
    3-oxoadipyl-CoA/3-oxo-5,6-dehydrosuberyl-CoA thiolase

<400> SEQUENCE: 118

```
Met Arg Glu Ala Phe Ile Cys Asp Gly Ile Arg Thr Pro Ile Gly Arg
1               5                   10                  15

Tyr Gly Gly Ala Leu Ser Ser Val Arg Ala Asp Asp Leu Ala Ala Ile
                20                  25                  30

Pro Leu Arg Glu Leu Leu Val Arg Asn Pro Arg Leu Asp Ala Glu Cys
            35                  40                  45

Ile Asp Asp Val Ile Leu Gly Cys Ala Asn Gln Ala Gly Glu Asp Asn
50                  55                  60

Arg Asn Val Ala Arg Met Ala Thr Leu Leu Ala Gly Leu Pro Gln Ser
65                  70                  75                  80

Val Ser Gly Thr Thr Ile Asn Arg Leu Cys Gly Ser Gly Leu Asp Ala
                85                  90                  95

Leu Gly Phe Ala Ala Arg Ala Ile Lys Ala Gly Asp Gly Asp Leu Leu
            100                 105                 110

Ile Ala Gly Gly Val Glu Ser Met Ser Arg Ala Pro Phe Val Met Gly
            115                 120                 125

Lys Ala Ala Ser Ala Phe Ser Arg Gln Ala Glu Met Phe Asp Thr Thr
            130                 135                 140

Ile Gly Trp Arg Phe Val Asn Pro Leu Met Ala Gln Gln Phe Gly Thr
145                 150                 155                 160

Asp Ser Met Pro Glu Thr Ala Glu Asn Val Ala Glu Leu Leu Lys Ile
                165                 170                 175

Ser Arg Glu Asp Gln Asp Ser Phe Ala Leu Arg Ser Gln Gln Arg Thr
            180                 185                 190

Ala Lys Ala Gln Ser Ser Gly Ile Leu Ala Glu Ile Val Pro Val
            195                 200                 205

Val Leu Lys Asn Lys Lys Gly Val Val Thr Glu Ile Gln His Asp Glu
            210                 215                 220

His Leu Arg Pro Glu Thr Thr Leu Glu Gln Leu Arg Gly Leu Lys Ala
225                 230                 235                 240

Pro Phe Arg Ala Asn Gly Val Ile Thr Ala Gly Asn Ala Ser Gly Val
                245                 250                 255

Asn Asp Gly Ala Ala Ala Leu Ile Ile Ala Ser Glu Gln Met Ala Ala
```

```
            260                 265                 270
Ala Gln Gly Leu Thr Pro Arg Ala Arg Ile Val Ala Met Ala Thr Ala
            275                 280                 285

Gly Val Glu Pro Arg Leu Met Gly Leu Gly Pro Val Pro Ala Thr Arg
            290                 295                 300

Arg Val Leu Glu Arg Ala Gly Leu Ser Ile His Asp Met Asp Val Ile
305                 310                 315                 320

Glu Leu Asn Glu Ala Phe Ala Ala Gln Ala Leu Gly Val Leu Arg Glu
                325                 330                 335

Leu Gly Leu Pro Asp Asp Ala Pro His Val Asn Pro Asn Gly Gly Ala
            340                 345                 350

Ile Ala Leu Gly His Pro Leu Gly Met Ser Gly Ala Arg Leu Ala Leu
            355                 360                 365

Ala Ala Ser His Glu Leu His Arg Arg Asn Gly Arg Tyr Ala Leu Cys
            370                 375                 380

Thr Met Cys Ile Gly Val Gly Gln Gly Ile Ala Met Ile Leu Glu Arg
385                 390                 395                 400

Val
```

```
<210> SEQ ID NO 119
<211> LENGTH: 393
<212> TYPE: PRT
<213> ORGANISM: Haemophilus influenzae
<220> FEATURE:
<221> NAME/KEY: MISC_FEATURE
<223> OTHER INFORMATION: Uniprot name: ATOB_HAEIN.  Acetyl-CoA
      acetyltransferase

<400> SEQUENCE: 119
```

```
Met Glu Asn Val Val Ile Val Ser Ala Val Arg Thr Pro Ile Gly Ser
1               5                   10                  15

Phe Asn Gly Ala Leu Ser Ser Val Ser Ala Val Asp Leu Gly Ala Ile
                20                  25                  30

Val Ile Gln Glu Ala Ile Lys Arg Ala Asn Ile Glu Ser Ala Leu Val
            35                  40                  45

Asn Glu Val Ile Met Gly Asn Val Leu Gln Ala Gly Leu Gly Gln Asn
        50                  55                  60

Pro Ala Arg Gln Ala Ala Leu Lys Ala Gly Ile Glu Lys Glu Ile Pro
65                  70                  75                  80

Ser Leu Thr Ile Asn Lys Val Cys Gly Ser Gly Leu Lys Ser Val Ala
                85                  90                  95

Leu Gly Ala Gln Ser Ile Ile Ser Gly Asp Ala Asp Ile Val Val Val
            100                 105                 110

Gly Gly Met Glu Asn Met Ser Gln Ala Pro Tyr Leu Leu Asp Ser Lys
        115                 120                 125

Val Arg Gln Gly Val Lys Met Gly Asn Leu Thr Leu Arg Asp Thr Met
130                 135                 140

Ile Glu Asp Gly Leu Thr Cys Ala Ser Asn His Tyr His Met Gly Ile
145                 150                 155                 160

Thr Ala Glu Asn Ile Ala Glu Gln Tyr Gly Ile Ser Arg Gln Ala Gln
                165                 170                 175

Asp Glu Leu Ala Leu Arg Ser Gln Thr Leu Ala Ser Gln Ala Val Gln
            180                 185                 190

Leu Gly Val Phe Asp Lys Glu Ile Val Pro Val Met Val Lys Thr Arg
        195                 200                 205
```

```
Lys Gly Asp Ile Ile Val Ser Arg Asp Glu Tyr Pro Lys Ala Asp Thr
210                 215                 220

Thr Ala Glu Gly Leu Ala Lys Leu Lys Pro Ala Phe Lys Lys Glu Gly
225                 230                 235                 240

Thr Val Thr Ala Gly Asn Ala Ser Gly Ile Asn Asp Gly Ala Ala Ala
                245                 250                 255

Leu Ile Leu Val Ser Glu Ser Lys Ala His Ala Leu Gly Leu Lys Ala
                260                 265                 270

Ile Ala Lys Ile Arg Ser Tyr Ala Ser Gly Gly Val Asp Pro Ser Val
                275                 280                 285

Met Gly Leu Gly Pro Val Pro Ala Thr Gln Lys Ala Leu Lys Lys Ala
290                 295                 300

Gly Ile Asn Leu Asp Asp Ile Asp Leu Ile Glu Ala Asn Glu Ala Phe
305                 310                 315                 320

Ala Ser Gln Phe Leu Gly Val Gly Lys Asp Leu Asn Leu Asp Met Asn
                325                 330                 335

Lys Thr Asn Ile His Gly Gly Ala Ile Ala Leu Gly His Pro Ile Gly
                340                 345                 350

Ala Ser Gly Ala Arg Ile Leu Val Thr Leu Leu His Asn Leu Ile Glu
                355                 360                 365

Lys Asp Lys Lys Leu Gly Leu Ala Thr Leu Cys Ile Gly Gly Gly Gln
                370                 375                 380

Gly Ile Ser Met Ile Val Glu Arg Leu
385                 390

<210> SEQ ID NO 120
<211> LENGTH: 391
<212> TYPE: PRT
<213> ORGANISM: Hahella chejuensis
<220> FEATURE:
<221> NAME/KEY: MISC_FEATURE
<223> OTHER INFORMATION: Uniprot name: FADA_HAHCH.  3-ketoacyl-CoA
      thiolase

<400> SEQUENCE: 120

Met Ser Leu Asn Pro Arg Asp Val Val Ile Asp Cys Val Arg Ser
1               5                   10                  15

Pro Met Gly Arg Ala Lys Ala Gly Cys Phe Arg Asn Val Arg Ala Glu
                20                  25                  30

Thr Leu Ser Ala Thr Leu Ile Asp Ala Leu Phe Asp Arg Asn Asp Lys
                35                  40                  45

Val Asp Pro Ala Glu Val Glu Asp Leu Ile Trp Gly Cys Val Asn Gln
50                  55                  60

Thr Leu Glu Gln Gly Phe Asn Val Ala Arg Gln Ile Ser Leu Leu Thr
65                  70                  75                  80

Arg Ile Pro His Thr Ser Ser Ala Gln Thr Val Asn Arg Leu Cys Gly
                85                  90                  95

Ser Ala Met Ser Ala Ile His Thr Ala Ala Gln Ala Ile Met Thr Gly
                100                 105                 110

Asn Gly Asp Val Phe Val Val Gly Gly Val Glu His Met Gly His Val
                115                 120                 125

Pro Met Thr Gln Gly Phe Asp His Asn Pro Ala Ala Ser Lys Tyr Ser
                130                 135                 140

Ala Lys Ala Ser Asn Met Met Gly Leu Thr Ala Glu Met Leu Ala Lys
145                 150                 155                 160

Met His Gly Ile Ser Arg Gln Gln Gln Asp Glu Phe Gly Ala Arg Ser
```

```
                      165                 170                 175

His Arg Leu Ala His Glu Ala Thr Leu Glu Gly Arg Phe Arg Asn Glu
                180                 185                 190

Ile Ile Ser Ile Gln Gly His Asp Asp Gly Phe Pro Ala Leu Ile
            195                 200                 205

Glu Asn Asp Glu Thr Ile Arg Pro Glu Thr Thr Ala Glu Ser Leu Ala
            210                 215                 220

Gln Leu Arg Pro Ala Phe Asp Pro Lys Ser Gly Thr Val Thr Ala Gly
225                 230                 235                 240

Gln Ser Ser Gln Leu Thr Asp Gly Ala Ser Ala Met Leu Leu Met Ser
                245                 250                 255

Ala Glu Arg Ala Gln Ala Leu Gly Leu Thr Pro Met Ala Lys Ile Arg
                260                 265                 270

Ser Met Ala Thr Ala Gly Cys Asp Pro Ala Ile Met Gly Tyr Gly Pro
                275                 280                 285

Val Pro Ala Thr Lys Lys Ala Leu Lys Arg Ala Gly Leu Lys Val Glu
            290                 295                 300

Asp Ile Asp Phe Trp Glu Leu Asn Glu Ala Phe Ala Ala Gln Ser Leu
305                 310                 315                 320

Pro Val Ile Lys Asp Leu Lys Leu Met Gly Val Val Asp Gln Lys Val
                325                 330                 335

Asn Leu Asn Gly Gly Ala Ile Ala Leu Gly His Pro Leu Gly Cys Ser
                340                 345                 350

Gly Ala Arg Ile Ser Thr Thr Leu Leu Asn Val Met Ala Ala Lys Gly
                355                 360                 365

Gly Thr Leu Gly Val Ser Thr Met Cys Ile Gly Leu Gly Gln Gly Ile
            370                 375                 380

Ala Thr Val Trp Glu Arg Ile
385                 390

<210> SEQ ID NO 121
<211> LENGTH: 387
<212> TYPE: PRT
<213> ORGANISM: Klebsiella pneumoniae subsp. pneumoniae
<220> FEATURE:
<221> NAME/KEY: MISC_FEATURE
<223> OTHER INFORMATION: Uniprot name: FADA_KLEP7. 3-ketoacyl-CoA
      thiolase

<400> SEQUENCE: 121

Met Glu Gln Val Val Ile Val Asp Ala Ile Arg Thr Pro Met Gly Arg
1               5                   10                  15

Ser Lys Gly Gly Ala Phe Arg His Val Arg Ala Glu Asp Leu Ser Ala
            20                  25                  30

His Leu Met Arg Ser Leu Leu Ser Arg Asn Pro Ser Leu Glu Ala Ser
        35                  40                  45

Ala Ile Asp Asp Ile Tyr Trp Gly Cys Val Gln Gln Thr Leu Glu Gln
    50                  55                  60

Gly Phe Asn Ile Ala Arg Asn Ala Ala Leu Leu Ala Glu Ile Pro His
65                  70                  75                  80

Ser Val Pro Ala Asn Thr Val Asn Arg Leu Cys Gly Ser Ser Met Gln
                85                  90                  95

Ala Leu His Asp Ala Ala Arg Met Ile Met Thr Gly Asp Ala Gly Val
            100                 105                 110

Cys Leu Ile Gly Gly Val Glu His Met Gly His Val Pro Met Ser His
        115                 120                 125
```

```
Gly Val Asp Phe His Pro Gly Leu Ser Arg Asn Val Ala Lys Ala Ala
            130                 135                 140

Gly Met Met Gly Leu Thr Ala Glu Met Leu Ala Arg Leu His Gly Ile
145                 150                 155                 160

Ser Arg Glu Met Gln Asp Gln Phe Ala Ala Arg Ser His Ala Arg Ala
                165                 170                 175

Trp Ala Ala Thr Gln Ser Gly Ala Phe Lys Ala Glu Ile Ile Pro Thr
                180                 185                 190

Gly Gly His Asp Ala Asp Gly Val Leu Lys Ser Phe Asn Tyr Asp Glu
            195                 200                 205

Val Ile Arg Pro Glu Thr Thr Val Glu Thr Leu Ser Thr Leu Lys Pro
210                 215                 220

Ala Phe Asp Pro Val Thr Gly Thr Val Thr Ala Gly Thr Ser Ser Ala
225                 230                 235                 240

Leu Ser Asp Gly Ala Ala Ala Met Leu Leu Met Ser Glu Ser Arg Ala
                245                 250                 255

Arg Glu Leu Gly Leu Lys Pro Arg Ala Arg Val Arg Ser Met Ala Val
                260                 265                 270

Val Gly Cys Asp Pro Ser Ile Met Gly Tyr Gly Pro Val Pro Ala Ser
            275                 280                 285

Lys Leu Ala Leu Lys Lys Ala Gly Leu Ser Thr Ser Asp Ile Asp Val
290                 295                 300

Phe Glu Met Asn Glu Ala Phe Ala Ala Gln Ile Leu Pro Cys Ile Lys
305                 310                 315                 320

Asp Leu Gly Leu Met Glu Gln Ile Asp Glu Lys Ile Asn Leu Asn Gly
                325                 330                 335

Gly Ala Ile Ala Leu Gly His Pro Leu Gly Cys Ser Gly Ala Arg Ile
            340                 345                 350

Ser Thr Thr Leu Ile Asn Gln Met Glu Arg Lys Asp Ala Gln Phe Gly
                355                 360                 365

Leu Ala Thr Met Cys Ile Gly Leu Gly Gln Gly Ile Ala Thr Val Phe
            370                 375                 380

Glu Arg Val
385

<210> SEQ ID NO 122
<211> LENGTH: 436
<212> TYPE: PRT
<213> ORGANISM: Klebsiella pneumoniae subsp. pneumoniae
<220> FEATURE:
<221> NAME/KEY: MISC_FEATURE
<223> OTHER INFORMATION: Uniprot name: FADI_KLEP7. 3-ketoacyl-CoA
      thiolase

<400> SEQUENCE: 122

Met Ser Gln Ala Leu Pro Leu Ile Thr Arg Gln Gly Asp Arg Ile Ala
1               5                   10                  15

Ile Val Thr Gly Leu Arg Thr Pro Phe Ala Arg Gln Ala Thr Ala Phe
                20                  25                  30

His Gly Val Pro Ala Ile Asp Leu Gly Lys Met Val Val Gly Glu Met
            35                  40                  45

Leu Ala Arg Ser Asp Ile Pro Ala Glu Val Ile Glu Gln Leu Val Phe
        50                  55                  60

Gly Gln Val Val Gln Met Pro Glu Ala Pro Asn Ile Ala Arg Glu Ile
65                  70                  75                  80
```

```
Val Leu Gly Thr Gly Met Ser Val His Thr Asp Ala Tyr Ser Val Ser
            85                  90                  95

Arg Ala Cys Ala Thr Ser Phe Gln Ala Val Ala Asn Val Ala Glu Ser
           100                 105                 110

Leu Met Ala Gly Thr Ile Arg Ala Gly Ile Ala Gly Gly Ala Asp Ser
           115                 120                 125

Ser Ser Val Leu Pro Ile Gly Val Ser Lys Thr Leu Ala Arg Thr Leu
130                 135                 140

Val Asp Ala Asn Lys Ala Arg Thr Leu Ser Gln Lys Leu Lys Leu Phe
145                 150                 155                 160

Ser Arg Leu Arg Pro Arg Asp Leu Leu Pro Val Pro Pro Ala Val Ala
                165                 170                 175

Glu Tyr Ser Thr Gly Leu Arg Met Gly Asp Thr Ala Glu Gln Met Ala
           180                 185                 190

Lys Ser Trp Gly Ile Ser Arg Glu Gln Gln Asp Ala Leu Ala His Arg
           195                 200                 205

Ser His Gln Leu Ala Ala Lys Ala Trp Glu Glu Gly Lys Leu Ser Ala
210                 215                 220

Glu Val Met Thr Ala Tyr Ala Pro Pro Phe Arg Glu Pro Leu Glu Gln
225                 230                 235                 240

Asp Asn Asn Ile Arg Lys Asn Ser Thr Leu Ala Asp Tyr Gln Lys Leu
                245                 250                 255

Arg Pro Ala Phe Asp Arg Lys His Gly Thr Val Thr Ala Ala Asn Ser
           260                 265                 270

Thr Pro Leu Thr Asp Gly Ala Ala Ala Val Ile Leu Met Thr Glu Ser
           275                 280                 285

Arg Ala Lys Glu Leu Gly Leu Arg Pro Leu Gly Tyr Leu Arg Ser Tyr
290                 295                 300

Ala Phe Thr Ala Ile Asp Val Trp Gln Asp Met Leu Leu Gly Pro Ala
305                 310                 315                 320

Trp Ser Thr Pro Leu Ala Leu Glu Arg Ala Gly Leu Thr Leu Ala Asp
                325                 330                 335

Leu Thr Leu Ile Asp Met His Glu Ala Phe Ala Ala Gln Thr Leu Ala
           340                 345                 350

Asn Leu Gln Cys Leu Ala Ser Asp Arg Phe Ala Arg Glu Val Leu Gly
           355                 360                 365

Arg Ser Gln Ala Thr Gly Glu Val Asp Glu Ser Lys Phe Asn Val Leu
370                 375                 380

Gly Gly Ser Ile Ala Tyr Gly His Pro Phe Ala Ala Thr Gly Ala Arg
385                 390                 395                 400

Met Ile Thr Gln Thr Leu His Glu Val Arg Arg Gly Gly Phe
                405                 410                 415

Gly Leu Val Thr Ala Cys Ala Ala Gly Gly Leu Gly Ala Ala Met Ile
           420                 425                 430

Val Glu Ala Glu
        435

<210> SEQ ID NO 123
<211> LENGTH: 391
<212> TYPE: PRT
<213> ORGANISM: Marinobacter hydrocarbonoclasticus
<220> FEATURE:
<221> NAME/KEY: MISC_FEATURE
<223> OTHER INFORMATION: Uniprot name: FADA_MARHV.  3-ketoacyl-CoA
      thiolase
```

<400> SEQUENCE: 123

```
Met Ser Leu Asn Pro Arg Asp Val Val Val Asp Cys Val Arg Thr
1               5                   10                  15

Pro Met Gly Arg Ala Lys Asn Gly Cys Phe Arg Asn Val Arg Ala Glu
            20                  25                  30

Thr Leu Ser Ala Ala Leu Ile Glu Ala Leu Phe Glu Arg Asn Pro Lys
        35                  40                  45

Leu Asp Pro Lys Glu Val Glu Asp Val Ile Trp Gly Cys Val Asn Gln
50                  55                  60

Thr Lys Glu Gln Gly Phe Asn Val Ala Arg Gln Ile Ser Leu Leu Thr
65                  70                  75                  80

Arg Ile Pro His Glu Ser Ala Ala Gln Thr Val Asn Arg Leu Cys Gly
                85                  90                  95

Ser Ala Met Ser Ala Ile His Thr Ala Ala Gln Ala Ile Gln Thr Gly
            100                 105                 110

Asn Gly Asp Val Phe Leu Val Gly Gly Val Glu His Met Gly His Val
        115                 120                 125

Pro Met Thr Glu Gly Phe Asp His Asn Pro Ala Ala Ser Lys Tyr Ser
130                 135                 140

Ala Lys Ala Ser Asn Met Met Gly Leu Thr Ala Glu Met Leu Ala Lys
145                 150                 155                 160

Met His Gly Ile Thr Arg Glu Gln Gln Asp Glu Phe Gly Ala Arg Ser
                165                 170                 175

His Arg Leu Ala His Glu Ala Thr Gln Glu Gly Arg Phe Lys Asn Glu
            180                 185                 190

Ile Val Pro Ile Glu Gly His Asp Glu Asn Gly Phe Val Lys Leu Ile
        195                 200                 205

Glu Glu Asp Glu Thr Ile Arg Pro Glu Thr Thr Ala Glu Ser Leu Gly
210                 215                 220

Gln Leu Arg Pro Ala Phe Asp Pro Lys Asn Gly Thr Val Thr Ala Gly
225                 230                 235                 240

Thr Ser Ser Gln Leu Thr Asp Gly Ala Ser Ala Met Val Leu Met Ser
                245                 250                 255

Ala Glu Arg Ala Glu Ala Leu Gly Leu Thr Pro Ile Ala Lys Ile Arg
            260                 265                 270

Ser Met Ala Val Ala Gly Cys Asp Pro Ala Ile Met Gly Tyr Gly Pro
        275                 280                 285

Val Pro Ala Thr Lys Lys Ala Leu Lys Arg Ala Gly Leu Lys Val Glu
290                 295                 300

Asp Ile Asp Phe Trp Glu Leu Asn Glu Ala Phe Ala Gly Gln Ser Leu
305                 310                 315                 320

Pro Val Leu Lys Asp Leu Lys Leu Leu Gly Val Met Glu Glu Lys Val
                325                 330                 335

Asn Leu Asn Gly Gly Ala Ile Ala Leu Gly His Pro Leu Gly Cys Ser
            340                 345                 350

Gly Ala Arg Ile Ser Thr Thr Leu Leu Asn Ile Met Gln Ala Lys Gly
        355                 360                 365

Gly Lys Leu Gly Val Ser Thr Met Cys Ile Gly Leu Gly Gln Gly Ile
370                 375                 380

Ala Thr Val Trp Glu Arg Ile
385                 390
```

<210> SEQ ID NO 124

```
<211> LENGTH: 389
<212> TYPE: PRT
<213> ORGANISM: Mycobacterium tuberculosis
<220> FEATURE:
<221> NAME/KEY: MISC_FEATURE
<223> OTHER INFORMATION: Uniprot name: FADA4_MYCTO. Probable acetyl-CoA
      acetyltransferase

<400> SEQUENCE: 124

Met Ile Val Ala Gly Ala Arg Thr Pro Ile Gly Lys Leu Met Gly Ser
1               5                   10                  15

Leu Lys Asp Phe Ser Ala Ser Glu Leu Gly Ala Ile Ala Ile Lys Gly
            20                  25                  30

Ala Leu Glu Lys Ala Asn Val Pro Ala Ser Leu Val Glu Tyr Val Ile
        35                  40                  45

Met Gly Gln Val Leu Thr Ala Gly Ala Gly Gln Met Pro Ala Arg Gln
    50                  55                  60

Ala Ala Val Ala Ala Gly Ile Gly Trp Asp Val Pro Ala Leu Thr Ile
65                  70                  75                  80

Asn Lys Met Cys Leu Ser Gly Ile Asp Ala Ile Ala Leu Ala Asp Gln
                85                  90                  95

Leu Ile Arg Ala Arg Glu Phe Asp Val Val Val Ala Gly Gly Gln Glu
            100                 105                 110

Ser Met Thr Lys Ala Pro His Leu Leu Met Asn Ser Arg Ser Gly Tyr
        115                 120                 125

Lys Tyr Gly Asp Val Thr Val Leu Asp His Met Ala Tyr Asp Gly Leu
    130                 135                 140

His Asp Val Phe Thr Asp Gln Pro Met Gly Ala Leu Thr Glu Gln Arg
145                 150                 155                 160

Asn Asp Val Asp Met Phe Thr Arg Ser Glu Gln Asp Glu Tyr Ala Ala
                165                 170                 175

Ala Ser His Gln Lys Ala Ala Ala Ala Trp Lys Asp Gly Val Phe Ala
            180                 185                 190

Asp Glu Val Ile Pro Val Asn Ile Pro Gln Arg Thr Gly Asp Pro Leu
        195                 200                 205

Gln Phe Thr Glu Asp Glu Gly Ile Arg Ala Asn Thr Thr Ala Ala Ala
    210                 215                 220

Leu Ala Gly Leu Lys Pro Ala Phe Arg Gly Asp Gly Thr Ile Thr Ala
225                 230                 235                 240

Gly Ser Ala Ser Gln Ile Ser Asp Gly Ala Ala Ala Val Val Val Met
                245                 250                 255

Asn Gln Glu Lys Ala Gln Glu Leu Gly Leu Thr Trp Leu Ala Glu Ile
            260                 265                 270

Gly Ala His Gly Val Val Ala Gly Pro Asp Ser Thr Leu Gln Ser Gln
        275                 280                 285

Pro Ala Asn Ala Ile Asn Lys Ala Leu Asp Arg Glu Gly Ile Ser Val
    290                 295                 300

Asp Gln Leu Asp Val Val Glu Ile Asn Glu Ala Phe Ala Ala Val Ala
305                 310                 315                 320

Leu Ala Ser Ile Arg Glu Leu Gly Leu Asn Pro Gln Ile Val Asn Val
                325                 330                 335

Asn Gly Gly Ala Ile Ala Val Gly His Pro Leu Gly Met Ser Gly Thr
            340                 345                 350

Arg Ile Thr Leu His Ala Ala Leu Gln Leu Ala Arg Arg Gly Ser Gly
        355                 360                 365
```

```
Val Gly Val Ala Ala Leu Cys Gly Ala Gly Gly Gln Gly Asp Ala Leu
    370                 375                 380

Ile Leu Arg Ala Gly
385
```

<210> SEQ ID NO 125
<211> LENGTH: 391
<212> TYPE: PRT
<213> ORGANISM: Paracoccus denitrificans
<220> FEATURE:
<221> NAME/KEY: MISC_FEATURE
<223> OTHER INFORMATION: Uniprot name: THIL_PARDE.  Acetyl-CoA
      acetyltransferase

<400> SEQUENCE: 125

```
Met Thr Lys Ala Val Ile Val Ser Ala Ala Arg Thr Pro Val Gly Ser
1               5                   10                  15

Phe Leu Gly Ser Phe Ala Asn Leu Pro Ala His Glu Leu Gly Ala Ile
            20                  25                  30

Val Leu Lys Ala Val Val Glu Arg Ala Gly Ile Asp Pro Ser Glu Val
        35                  40                  45

Ser Glu Thr Ile Leu Gly Gln Val Leu Thr Ala Ala Gln Gly Gln Asn
50                  55                  60

Pro Ala Arg Gln Ala His Ile Lys Val Gly Leu Pro Arg Glu Ser Ala
65                  70                  75                  80

Ala Trp Val Ile Asn Gln Val Cys Gly Ser Gly Leu Arg Thr Val Ala
                85                  90                  95

Leu Ala Ala Gln Gln Val Leu Leu Gly Asp Ala Arg Ile Val Val Ala
            100                 105                 110

Gly Gly Gln Glu Ser Met Ser Leu Ala Pro His Ala Ala Tyr Ile Ala
        115                 120                 125

Pro Gly Gln Lys Met Gly Asp Met Lys Met Leu Asp Thr Met Ile Lys
130                 135                 140

Asp Gly Leu Trp Asp Ala Phe Asn Asp Tyr His Met Gly Thr Thr Ala
145                 150                 155                 160

Glu Asn Val Ala Gly Lys Trp Glu Ile Ser Arg Ala Glu Gln Asp Gln
                165                 170                 175

Phe Ala Val Ala Ser Gln Asn Lys Ala Glu Ala Ala Gln Lys Ala Gly
            180                 185                 190

Lys Phe Ala Asp Glu Ile Val Pro Val Thr Ile Lys Ser Arg Lys Gly
        195                 200                 205

Glu Thr Val Val Asp Ala Asp Glu Tyr Ile Arg His Gly Ala Thr Leu
210                 215                 220

Glu Ala Met Glu Asn Val Arg Pro Ala Phe Ser Lys Glu Gly Thr Val
225                 230                 235                 240

Thr Ala Gly Asn Ala Ser Gly Leu Asn Asp Gly Ala Ala Ala Val Leu
                245                 250                 255

Val Met Thr Glu Asp Glu Ala Ala Arg Arg Gly Leu Thr Pro Leu Ala
            260                 265                 270

Arg Ile Ala Ser Tyr Ala Thr Ala Gly Val Asp Pro Gln Ile Met Gly
        275                 280                 285

Thr Gly Pro Ile Pro Ala Ser Arg Lys Ala Leu Glu Lys Ala Gly Trp
    290                 295                 300

Ser Val Gly Asp Leu Asp Leu Val Glu Ala Asn Glu Ala Phe Ala Ala
305                 310                 315                 320

Gln Ala Ile Ala Val Asn Arg Asp Met Gly Trp Asp Pro Ser Ile Val
```

```
                    325                 330                 335
Asn Val Asn Gly Gly Ala Ile Ala Ile Gly His Pro Ile Gly Ala Ser
            340                 345                 350

Gly Cys Arg Ile Leu Asn Thr Leu Leu Phe Glu Met Gln Arg Arg Asp
            355                 360                 365

Ala Lys Lys Gly Leu Ala Thr Leu Cys Ile Gly Gly Met Gly Val
            370                 375                 380

Ala Leu Cys Leu Glu Arg Pro
385                 390

<210> SEQ ID NO 126
<211> LENGTH: 387
<212> TYPE: PRT
<213> ORGANISM: Pectobacterium atrosepticum (Erwinia carotovora subsp.
      atroseptica)
<220> FEATURE:
<221> NAME/KEY: MISC_FEATURE
<223> OTHER INFORMATION: Uniprot name: FADA_PECAS.  3-ketoacyl-CoA
      thiolase

<400> SEQUENCE: 126

Met Glu Lys Val Val Ile Val Asp Ala Val Arg Thr Pro Met Gly Arg
1               5                   10                  15

Ser Lys Gly Gly Ala Phe Arg Gln Val Arg Ala Glu Asp Leu Ser Ala
            20                  25                  30

His Leu Met Arg Ser Leu Leu Ser Arg Asn Thr Ala Leu Asp Ala Arg
        35                  40                  45

Glu Ile Asp Asp Ile Tyr Trp Gly Cys Val Gln Gln Ala Leu Glu Gln
    50                  55                  60

Gly Phe Asn Val Ala Arg Asn Ala Ala Leu Leu Ala Glu Ile Pro Val
65                  70                  75                  80

Ser Val Pro Ala Thr Thr Val Asn Arg Leu Cys Gly Ser Ser Met Gln
                85                  90                  95

Ala Leu His Asp Ala Ala Arg Ala Ile Met Val Gly Asp Ala Asn Val
            100                 105                 110

Cys Leu Ile Gly Gly Val Glu His Met Gly His Val Pro Met Asn His
        115                 120                 125

Gly Val Asp Phe His Pro Gly Leu Ser Arg Thr Ile Ala Lys Ala Ala
    130                 135                 140

Gly Met Met Gly Leu Thr Ala Glu Met Leu Ala Arg Met His Asn Ile
145                 150                 155                 160

Ser Arg Glu Met Gln Asp Gln Phe Ala Ala Arg Ser His Gln Arg Ala
                165                 170                 175

Tyr His Ala Thr Gln Ser Gly Ala Phe Arg His Glu Ile Val Pro Thr
            180                 185                 190

Ala Gly His Asp Ala Asp Gly Ala Leu Gln Arg Phe Asp Tyr Asp Glu
        195                 200                 205

Val Ile Arg Pro Asp Thr Thr Ile Asp Ser Leu Ala Ala Leu Lys Pro
    210                 215                 220

Ala Phe Asp Pro Val Asn Gly Thr Val Thr Ala Gly Ser Ser Ser Ala
225                 230                 235                 240

Leu Ser Asp Gly Ala Ser Ala Met Leu Ile Met Ser Glu Ser Arg Ala
                245                 250                 255

Ala Ser Leu Gly Leu Pro Val Arg Ala Arg Ile Arg Ala Met Ala Val
            260                 265                 270

Val Gly Cys Asp Pro Ser Ile Met Gly Tyr Gly Pro Val Pro Ala Thr
```

275                 280                 285
Lys Leu Ala Leu Lys Arg Ala Gly Leu Ser Leu Ala Asp Ile Gly Ile
            290                 295                 300

Phe Glu Leu Asn Glu Ala Phe Ala Ala Gln Thr Leu Pro Cys Ile Lys
305                 310                 315                 320

Asp Leu Gly Leu Leu Glu Gln Leu Asp Glu Lys Val Asn Leu Asn Gly
            325                 330                 335

Gly Ala Ile Ala Leu Gly His Pro Leu Gly Cys Ser Gly Ala Arg Ile
            340                 345                 350

Ser Thr Thr Leu Ile Asn Leu Met Glu Ser Arg Asp Ala Gln Phe Gly
            355                 360                 365

Val Ala Thr Met Cys Ile Gly Leu Gly Gln Gly Ile Ala Thr Val Phe
            370                 375                 380

Glu Arg Ala
385

<210> SEQ ID NO 127
<211> LENGTH: 437
<212> TYPE: PRT
<213> ORGANISM: Pectobacterium atrosepticum (Erwinia carotovora subsp.
      atroseptica)
<220> FEATURE:
<221> NAME/KEY: MISC_FEATURE
<223> OTHER INFORMATION: Uniprot name: FADI_PECAS.  3-ketoacyl-CoA
      thiolase

<400> SEQUENCE: 127

Met Ser Glu Val Leu Pro Leu Ile Thr Arg Arg Gly Asp Arg Ile Ala
1               5                   10                  15

Phe Val Ser Gly Leu Arg Thr Pro Phe Ala Arg Gln Ala Thr Ala Tyr
            20                  25                  30

His Gly Val Pro Ala Ile Glu Leu Gly Lys Leu Val Thr Ser Glu Leu
        35                  40                  45

Leu Val Arg Thr Gly Ile Asp Pro Glu Leu Ile Glu Leu Leu Val Phe
    50                  55                  60

Gly Gln Val Val Gln Met Pro Glu Ala Pro Asn Ile Ala Arg Glu Ile
65                  70                  75                  80

Val Leu Gly Thr Gly Met Ser Val His Thr Asp Ala Tyr Ser Val Ser
                85                  90                  95

Arg Ala Cys Ala Thr Ser Phe Gln Ala Val Ala Asn Val Ala Glu Ser
            100                 105                 110

Ile Met Ala Gly Thr Val Glu Val Gly Ile Ala Gly Gly Ala Asp Ser
        115                 120                 125

Ser Ser Val Leu Pro Ile Gly Val Ser Lys Ala Leu Ala Arg Thr Leu
    130                 135                 140

Val Asp Met Asn Lys Ala Arg Thr Leu Gly Gln Lys Leu Arg Leu Leu
145                 150                 155                 160

Ser Gly Leu Arg Pro Lys Asp Leu Leu Pro Val Ala Pro Ala Val Ala
                165                 170                 175

Glu Tyr Ser Thr Gly Leu Arg Met Gly Asp Thr Ala Glu Gln Met Ala
            180                 185                 190

Lys Thr Tyr Gly Ile Thr Arg Glu Glu Gln Asp Glu Leu Ala His Arg
        195                 200                 205

Ser His Lys Leu Ala Ala Gln Ala Trp Glu Ser Gly Val Leu Arg Asp
    210                 215                 220

Glu Val Met Thr Ala Tyr Val Pro Pro Tyr Glu Lys Ala Leu Ser Glu

```
                225                 230                 235                 240

Asp Asn Asn Val Arg His Asp Ser Ala Ile Glu Gln Tyr Ser Arg Leu
                245                 250                 255

Arg Pro Ala Phe Asp Arg Arg His Gly Thr Val Thr Ala Ala Asn Ser
                260                 265                 270

Thr Pro Leu Thr Asp Gly Ala Ala Ala Val Leu Met Met Ser Glu Ser
                275                 280                 285

Lys Ala Lys Ser Leu Gly Leu Thr Pro Leu Gly Tyr Leu Arg Ser Tyr
                290                 295                 300

Ala Phe Ser Ala Ile Gly Val Gln Arg Asp Met Leu Leu Gly Pro Ala
305                 310                 315                 320

Tyr Ala Ser Pro Leu Ala Leu Ala Arg Ala Gly Val Ala Leu Ala Asp
                325                 330                 335

Leu Thr Leu Ile Asp Met His Glu Ala Phe Ala Ala Gln Thr Leu Ala
                340                 345                 350

Asn Leu Lys Leu Phe Ala Ser Asp Glu Phe Ala Arg Asn Gln Leu Gly
                355                 360                 365

Arg Asn Ala Ala Leu Gly Glu Val Asp Arg Ala Lys Phe Asn Val Leu
                370                 375                 380

Gly Gly Ser Ile Ala Tyr Gly His Pro Phe Ala Ala Thr Gly Ala Arg
385                 390                 395                 400

Met Ile Thr Gln Thr Leu Asn Glu Leu Arg Arg Arg Gly Gly Gly Leu
                405                 410                 415

Gly Leu Thr Thr Ala Cys Ala Ala Gly Gly Leu Gly Ala Ala Met Val
                420                 425                 430

Leu Glu Val Thr Pro
        435

<210> SEQ ID NO 128
<211> LENGTH: 387
<212> TYPE: PRT
<213> ORGANISM: Photobacterium profundum (Photobacterium sp.)
<220> FEATURE:
<221> NAME/KEY: MISC_FEATURE
<223> OTHER INFORMATION: Uniprot name: FADA_PHOPR. 3-ketoacyl-CoA
      thiolase

<400> SEQUENCE: 128

Met Asn Asn Val Val Ile Val Asp Cys Ile Arg Thr Pro Met Gly Arg
1               5                   10                  15

Ser Lys Ala Gly Ala Phe Arg Asn Val Arg Ala Glu Asp Leu Ser Ala
                20                  25                  30

His Leu Met Lys Gly Leu Ile Ser Arg Asn Pro Gln Leu Asp Pro Asn
                35                  40                  45

Ser Ile Glu Asp Ile Tyr Trp Gly Cys Val Gln Gln Thr Leu Glu Gln
            50                  55                  60

Gly Phe Asn Val Ala Arg Asn Ala Ser Leu Leu Ala Gly Ile Pro His
65                  70                  75                  80

Thr Val Ala Ala Thr Thr Val Asn Arg Leu Cys Gly Ser Ser Met Gln
                85                  90                  95

Ala Leu His Asp Ala Thr Arg Ala Ile Met Val Gly Asp Ala Glu Thr
                100                 105                 110

Cys Ile Ile Gly Gly Val Glu His Met Gly His Val Pro Met Asn His
                115                 120                 125

Gly Val Asp Phe His Pro Gly Met Ser Lys Ser Val Ala Lys Ala Ala
                130                 135                 140
```

```
Gly Met Met Gly Leu Thr Ala Glu Met Leu Gly Arg Met His Gly Ile
145                 150                 155                 160

Ser Arg Gln Met Gln Asp Glu Phe Ala Ala Arg Ser His Gln Arg Ala
                165                 170                 175

His Ala Ala Thr Ile Glu Gly Arg Phe Lys Asn Glu Ile Leu Pro Ile
            180                 185                 190

Glu Gly His Asp Glu Asn Gly Ile Leu Lys Leu Tyr Asp Tyr Asp Glu
        195                 200                 205

Val Ile Arg Pro Glu Thr Thr Val Glu Gly Leu Ser Asn Leu Arg Pro
210                 215                 220

Ala Phe Asp Pro Val Asn Gly Thr Val Thr Ala Gly Ser Ser Ser Ala
225                 230                 235                 240

Leu Ser Asp Gly Ala Ser Ala Met Leu Val Met Ser Glu His Arg Ala
                245                 250                 255

Lys Glu Leu Gly Leu Thr Ile Arg Ala Arg Val Lys Ser Met Ala Val
                260                 265                 270

Ala Gly Cys Asp Pro Ser Ile Met Gly Tyr Gly Pro Val Pro Ala Thr
            275                 280                 285

Gln Lys Ala Leu Lys Arg Ala Gly Leu Ser Ile Asp Asp Ile Gly Met
        290                 295                 300

Val Glu Leu Asn Glu Ala Phe Ala Ala Gln Ser Leu Pro Cys Ala Lys
305                 310                 315                 320

Asp Leu Gly Leu Leu Asp Lys Ile Asp Glu Lys Val Asn Leu Asn Gly
                325                 330                 335

Gly Ala Ile Ala Leu Gly His Pro Leu Gly Cys Ser Gly Ser Arg Ile
                340                 345                 350

Ser Thr Thr Leu Ile Asn Gln Met Glu His His Asp Val Gln Phe Gly
            355                 360                 365

Leu Ala Thr Met Cys Ile Gly Leu Gly Gln Gly Ile Ala Thr Val Phe
        370                 375                 380

Glu Arg Val
385

<210> SEQ ID NO 129
<211> LENGTH: 436
<212> TYPE: PRT
<213> ORGANISM: Photobacterium profundum (Photobacterium sp.)
<220> FEATURE:
<221> NAME/KEY: MISC_FEATURE
<223> OTHER INFORMATION: Uniprot name: FADI_PHOPR. 3-ketoacyl-CoA
      thiolase

<400> SEQUENCE: 129

Met Thr Arg Leu Gln Asn Leu Thr Thr Arg Gln Gly Glu Arg Ile Ala
1               5                   10                  15

Val Val Ser Gly Leu Arg Thr Pro Phe Ala Arg Gln Ala Thr Ala Phe
                20                  25                  30

Asn Gly Val Pro Ala Leu Asp Met Gly Lys Met Val Val Asn Glu Met
            35                  40                  45

Leu Gln Glu Leu Asp Phe Asp Pro Lys Leu Ile Glu Gln Val Val Phe
        50                  55                  60

Gly Gln Val Val Gln Met Pro Glu Ala Pro Asn Ile Ala Arg Glu Ile
65                  70                  75                  80

Val Leu Gly Thr Gly Met His Ile Gly Thr Asp Ala Tyr Ser Val Thr
                85                  90                  95
```

Arg Ala Cys Ala Thr Ser Phe Gln Ala Ala Asn Val Ala Glu Ser
            100                 105                 110

Ile Ile Ser Gly Thr Ile Asp Ile Gly Ile Ala Gly Gly Ala Asp Ser
        115                 120                 125

Ser Ser Val Leu Pro Ile Gly Val Ser Lys Lys Leu Ala Ala Thr Leu
    130                 135                 140

Leu Ala Leu Ser Lys Ala Arg Thr Met Ser Lys Arg Leu Lys Leu Leu
145                 150                 155                 160

Ser Thr Leu Ser Val Lys Asp Leu Met Pro Val Pro Pro Ala Val Ala
                165                 170                 175

Glu Tyr Ser Thr Gly Ile Ser Met Gly Gln Thr Ala Glu Gln Met Ala
            180                 185                 190

Lys Ser His Gly Ile Thr Arg Gln Glu Gln Asp Ala Leu Ala Tyr Arg
        195                 200                 205

Ser His Thr Leu Ala Ala Lys Ala Trp Lys Asp Gly Leu Ile Arg Gly
    210                 215                 220

Glu Val Met Thr Ala Phe Pro Glu Pro Tyr Gly Gln Trp Ile Asp Lys
225                 230                 235                 240

Asp Asn Asn Ile Arg Glu Asp Ser Thr Leu Glu Ser Tyr Ala Lys Leu
                245                 250                 255

Arg Pro Ala Phe Asp Arg Lys Phe Gly Thr Val Thr Ala Ala Asn Ser
            260                 265                 270

Thr Pro Leu Thr Asp Gly Ala Ala Ala Ile Leu Leu Met Arg Glu Gly
        275                 280                 285

Arg Ala Lys Glu Leu Gly Leu Lys Pro Leu Gly Tyr Ile Arg Ser Tyr
    290                 295                 300

Ala Phe Ser Ala Ile Gly Val Glu Gln Asp Met Leu Met Gly Pro Ser
305                 310                 315                 320

Tyr Ala Thr Pro Met Ala Leu Asp Arg Ala Gly Ile Ser Leu Ser Asp
                325                 330                 335

Leu Thr Leu Ile Asp Met His Glu Ala Phe Ala Ala Gln Thr Leu Ala
            340                 345                 350

Asn Val Lys Met Phe Gly Ser Lys Lys Phe Ala Gln Glu Asn Leu Gly
        355                 360                 365

Arg Ser Gln Ala Ile Gly Glu Ile Asp Met Asp Lys Phe Asn Val Leu
    370                 375                 380

Gly Gly Ser Leu Ala Tyr Gly His Pro Phe Ala Ala Thr Gly Ala Arg
385                 390                 395                 400

Met Ile Thr Gln Thr Leu Arg Glu Leu Gln Arg Arg Gly Gly Phe
                405                 410                 415

Ala Leu Asn Thr Ala Cys Ala Ala Gly Gly Leu Gly Ala Ala Met Ile
            420                 425                 430

Leu Glu Ala Glu
        435

<210> SEQ ID NO 130
<211> LENGTH: 386
<212> TYPE: PRT
<213> ORGANISM: Pseudoalteromonas atlantica
<220> FEATURE:
<221> NAME/KEY: MISC_FEATURE
<223> OTHER INFORMATION: Uniprot name: FADA_PSEA6. 3-ketoacyl-CoA
      thiolase

<400> SEQUENCE: 130

Met Lys Glu Val Val Val Val Asp Cys Ile Arg Thr Pro Met Gly Arg

|   |   |   |   |   |   |   |   |   |   |   |   |   |   |   |   |
|---|---|---|---|---|---|---|---|---|---|---|---|---|---|---|---|
| 1 |   |   |   | 5 |   |   |   |   | 10 |   |   |   |   | 15 |   |

Ser Lys Gly Gly Ile Phe Arg Asn Val Arg Ala Glu Thr Leu Ser Ala
            20                  25              30

His Leu Met Ser Lys Leu Ile Glu Arg Asn Pro Asn Leu Asp Pro Asn
            35                  40              45

Glu Ile Glu Asp Ile Ile Trp Gly Cys Val Gln Gln Thr Lys Glu Gln
50                      55                  60

Gly Phe Asn Ile Ala Arg Asn Ala Gln Leu Leu Thr Asp Ile Pro Arg
65                      70                  75                  80

Ser Val Ala Ala Val Thr Val Asn Arg Leu Cys Gly Ser Ser Met Gln
                85                  90                  95

Ala Leu His Asp Ala Thr Ser Gly Ile Met Ser Gly Arg Gly Asp Val
            100                 105             110

Tyr Met Ile Gly Gly Val Glu His Met Gly His Val Pro Met Asp Phe
            115                 120             125

Asn Ile Asp Phe His Pro Gly Ile Ala Lys Thr Ala Ala Arg Ala Ser
130                     135                 140

Gly Ser Met Gly Met Thr Ala Glu Leu Leu Gly Arg Gln Asn Gly Ile
145                     150                 155                 160

Ser Arg Glu Met Gln Asp Ala Phe Gly Ala Arg Ser His Gln Lys Ala
                165                 170                 175

His Ala Ala Ala Val Glu Gly Arg Trp Asn Glu Ile Val Ala Thr Glu
            180                 185             190

Gly His Asp Ala Asp Gly Ile Leu Lys Leu Ile Asp Ala Asp Glu Thr
            195                 200             205

Ile Arg Pro Asp Ser Thr Thr Glu Ser Met Ser Gly Leu Arg Pro Val
210                     215                 220

Phe Asp Pro Val Asn Gly Thr Val Thr Ala Gly Thr Ser Ser Ala Leu
225                     230                 235                 240

Ser Asp Gly Ala Ser Ala Met Leu Ile Met Ser Ala Asp Lys Ala Lys
                245                 250                 255

Ala Leu Gly Leu Thr Pro Arg Ala Lys Ile Arg Ala Met Ala Val Ala
            260                 265             270

Gly Cys Asp Ala Ala Ile Met Gly Phe Gly Pro Val Pro Ala Thr Gln
            275                 280             285

Lys Ala Leu Lys Arg Ala Gly Met Thr Met Ala Asp Ile Glu Leu Ala
            290                 295             300

Glu Phe Asn Glu Ala Phe Ala Ala Gln Ala Leu Ser Cys Ile Lys Gln
305                     310                 315                 320

Leu Gly Trp Leu Asp Thr Tyr Glu Asp Lys Val Asn Leu Asn Gly Gly
                325                 330                 335

Ala Ile Ala Leu Gly His Pro Leu Gly Cys Ser Gly Ser Arg Ile Ser
            340                 345             350

Thr Thr Leu Ile Asn Leu Met Glu Ala Asn Asp Lys Ser Ile Gly Leu
            355                 360             365

Ala Thr Met Cys Ile Gly Leu Gly Gln Gly Ile Ala Thr Val Phe Glu
            370                 375             380

Arg Val
385

<210> SEQ ID NO 131
<211> LENGTH: 436
<212> TYPE: PRT
<213> ORGANISM: Pseudoalteromonas atlantica
<220> FEATURE:
<221> NAME/KEY: MISC_FEATURE
<223> OTHER INFORMATION: Uniprot name: FADI_PSEA6. 3-ketoacyl-CoA thiolase

<400> SEQUENCE: 131

```
Met Thr Ala Lys Gln Thr Val Thr Thr Arg Asp Gly Glu Arg Ile Ala
1               5                   10                  15

Ile Val Ala Gly Leu Arg Thr Pro Phe Ala Lys Met Ala Thr Asn Phe
            20                  25                  30

His Gly Val Pro Ala Val Asp Leu Gly Lys Met Val Val Asn Glu Met
        35                  40                  45

Leu Val Lys His Asn Val Asp Pro Leu Leu Ile Glu Gln Leu Val Tyr
    50                  55                  60

Gly Gln Val Val Gln Met Pro Glu Ala Pro Asn Ile Ala Arg Glu Ile
65                  70                  75                  80

Val Leu Gly Thr Gly Met Ser Val His Thr Asp Ala Tyr Ser Val Ser
                85                  90                  95

Arg Ala Cys Ala Thr Ser Phe Gln Ser Thr Val Asn Ile Ala Glu Ser
            100                 105                 110

Met Met Leu Gly Asn Ile Ser Val Gly Ile Ala Gly Ala Asp Ser
        115                 120                 125

Thr Ser Val Ser Pro Ile Gly Val Ser Lys Asn Leu Ala Arg Ala Leu
    130                 135                 140

Thr Asp Leu Gln Lys Thr Lys Thr Leu Gly Gln Lys Phe Asn Val Leu
145                 150                 155                 160

Lys Lys Leu Gly Leu Lys Asp Leu Leu Pro Val Pro Pro Ala Val Ala
                165                 170                 175

Glu Tyr Ser Thr Gly Leu Ser Met Gly Gln Thr Ala Glu Gln Met Ala
            180                 185                 190

Lys Ser His Ser Ile Ser Arg Ala Asp Gln Asp Lys Leu Ala His Arg
        195                 200                 205

Ser His Ser Leu Ala Ala Gln Ser Trp Asn Glu Gly Lys Leu Ala Gly
    210                 215                 220

Glu Val Met Thr Ala Tyr Pro Ala Pro Tyr Lys Ser Ala Phe Glu Lys
225                 230                 235                 240

Asp Asn Asn Ile Arg Phe Asp Ser Lys Leu Glu Gly Tyr Ala Lys Leu
                245                 250                 255

Arg Pro Val Phe Asp Lys Lys His Gly Thr Val Thr Ala Ala Asn Ala
            260                 265                 270

Thr Pro Leu Thr Asp Gly Ala Ser Ala Val Leu Met Met Thr Glu Ser
        275                 280                 285

Arg Ala Lys Ala Leu Gly Tyr Thr Pro Leu Gly Tyr Ile Lys Ser Tyr
    290                 295                 300

Ala Phe Ala Ala Ile Asp Val Trp Glu Asp Met Leu Met Gly Pro Ser
305                 310                 315                 320

Tyr Ala Thr Pro Met Ala Leu Asp Arg Ala Gly Met Thr Leu Asn Asp
                325                 330                 335

Leu Thr Leu Ile Glu Met His Glu Ala Phe Ala Ala Gln Thr Leu Ala
            340                 345                 350

Asn Ile Lys Met Phe Ala Ser Asp Lys Phe Ala Gln Glu Lys Leu Gly
        355                 360                 365

Arg Ser Lys Ala Thr Gly Glu Ile Asp Met Ala Lys Phe Asn Val Met
    370                 375                 380
```

```
Gly Ser Ser Leu Ala Tyr Gly His Pro Phe Ala Thr Gly Thr Arg
385                 390                 395                 400

Met Ile Thr Gln Met Leu Asn Glu Leu Asn Arg Arg Gly Gly Ser
                405                 410                 415

Gly Leu Leu Thr Ala Cys Ala Ala Gly Gly Leu Ala Ala Met Ile
                420                 425                 430

Val Glu Thr Glu
        435
```

<210> SEQ ID NO 132
<211> LENGTH: 393
<212> TYPE: PRT
<213> ORGANISM: Pseudomonas aeruginosa
<220> FEATURE:
<221> NAME/KEY: MISC_FEATURE
<223> OTHER INFORMATION: Uniprot name: ATOB_PSEAE. Acetyl-CoA
      acetyltransferase

<400> SEQUENCE: 132

```
Met Gln Asp Val Val Ile Val Ala Ala Thr Arg Thr Ala Val Gly Ser
1               5                   10                  15

Phe Gln Gly Ser Leu Ala Gly Ile Pro Ala Pro Glu Leu Gly Ala Ala
                20                  25                  30

Val Ile Arg Arg Leu Leu Glu Gln Thr Gly Leu Asp Ala Gly Gln Val
            35                  40                  45

Asp Glu Val Ile Leu Gly Gln Val Leu Thr Ala Gly Ser Gly Gln Asn
        50                  55                  60

Pro Ala Arg Gln Ala Ala Ile Lys Ala Gly Leu Pro Val Gly Val Pro
65                  70                  75                  80

Ala Met Thr Leu Asn Lys Val Cys Gly Ser Gly Leu Lys Ala Leu His
                85                  90                  95

Leu Gly Ala Gln Ala Ile Arg Cys Gly Asp Ala Glu Val Ile Val Ala
            100                 105                 110

Gly Gly Gln Glu Asn Met Ser Leu Ala Pro Tyr Val Met Pro Gly Ala
        115                 120                 125

Arg Thr Gly Leu Arg Met Gly His Ala Lys Leu Val Asp Ser Met Ile
130                 135                 140

Glu Asp Gly Leu Trp Asp Ala Phe Asn Asp Tyr His Met Gly Ile Thr
145                 150                 155                 160

Ala Glu Asn Leu Ala Glu Lys Tyr Gly Leu Thr Arg Glu Glu Gln Asp
                165                 170                 175

Ala Phe Ala Ala Ser Gln Gln Lys Ala Ile Ala Ala Ile Glu Gly Gly
            180                 185                 190

Gly Arg Phe Arg Asp Glu Ile Thr Pro Ile Gln Val Pro Gln Arg Lys
        195                 200                 205

Gly Glu Pro Leu Gly Phe Asp Thr Asp Glu Gln Pro Arg Ala Gly Thr
210                 215                 220

Thr Val Glu Ala Leu Ala Lys Leu Lys Pro Ala Phe Arg Lys Asp Gly
225                 230                 235                 240

Ser Val Thr Ala Gly Asn Ala Ser Ser Leu Asn Asp Gly Ala Ala Ala
                245                 250                 255

Val Leu Leu Met Ser Ala Ala Lys Ala Lys Ala Leu Gly Leu Pro Val
            260                 265                 270

Leu Ala Arg Ile Ala Ser Tyr Ala Ser Ala Gly Val Asp Pro Ala Ile
        275                 280                 285

Met Gly Ile Gly Pro Val Ser Ala Thr Arg Arg Ala Leu Asp Lys Ala
```

```
                290                 295                 300
Gly Trp Ser Leu Glu Gln Leu Asp Leu Ile Glu Ala Asn Glu Ala Phe
305                 310                 315                 320

Ala Ala Gln Ser Leu Ala Val Gly Arg Glu Leu Gly Trp Asp Ala Ala
                325                 330                 335

Arg Val Asn Val Asn Gly Gly Ala Ile Ala Leu Gly His Pro Ile Gly
                340                 345                 350

Ala Ser Gly Cys Arg Val Leu Val Thr Leu Leu His Glu Met Ile Arg
                355                 360                 365

Arg Asp Ala Lys Lys Gly Leu Ala Thr Leu Cys Ile Gly Gly Gly Gln
                370                 375                 380

Gly Val Ala Leu Thr Leu Ala Arg Asp
385                 390

<210> SEQ ID NO 133
<211> LENGTH: 391
<212> TYPE: PRT
<213> ORGANISM: Pseudomonas aeruginosa
<220> FEATURE:
<221> NAME/KEY: MISC_FEATURE
<223> OTHER INFORMATION: Uniprot name: FADA_PSEAE. 3-ketoacyl-CoA
      thiolase

<400> SEQUENCE: 133

Met Ser Leu Asn Pro Arg Asp Val Val Ile Val Asp Phe Gly Arg Thr
1               5                   10                  15

Pro Met Gly Arg Ser Lys Gly Gly Met His Arg Asn Thr Arg Ala Glu
                20                  25                  30

Thr Met Ser Ala His Leu Ile Ser Lys Leu Leu Glu Arg Asn Pro Lys
            35                  40                  45

Val Asp Pro Ala Glu Val Glu Asp Val Ile Trp Gly Cys Val Asn Gln
        50                  55                  60

Thr Leu Glu Gln Gly Trp Asn Ile Ala Arg Met Ala Ser Leu Met Thr
65                  70                  75                  80

Gln Ile Pro His Thr Ser Ala Ala Gln Thr Val Ser Arg Leu Cys Gly
                85                  90                  95

Ser Ser Met Ser Ala Leu His Thr Ala Ala Gln Ala Ile Gln Thr Gly
                100                 105                 110

Asn Gly Asp Val Phe Val Ile Gly Gly Val Glu His Met Gly His Val
            115                 120                 125

Gly Met Met His Gly Val Asp Pro Asn Pro His Leu Ser Leu Tyr Ala
        130                 135                 140

Ala Lys Ala Ser Gly Met Met Gly Leu Thr Ala Glu Met Leu Gly Lys
145                 150                 155                 160

Met His Gly Ile Ser Arg Glu Ala Gln Asp Lys Phe Gly Ala Arg Ser
                165                 170                 175

His Gln Leu Ala Trp Lys Ala Thr Gln Glu Gly Lys Phe Lys Asp Glu
                180                 185                 190

Ile Ile Pro Met Glu Gly Tyr Asp Glu Asn Gly Phe Leu Lys Val Phe
            195                 200                 205

Asp Phe Asp Glu Thr Ile Arg Pro Glu Thr Thr Val Glu Thr Leu Ala
        210                 215                 220

Glu Leu Lys Pro Ala Phe Asn Pro Lys Gly Gly Thr Val Thr Ala Gly
225                 230                 235                 240

Thr Ser Ser Gln Ile Thr Asp Gly Ala Ser Cys Met Ile Val Met Ser
                245                 250                 255
```

```
Ala Gln Arg Ala Gln Asp Leu Gly Ile Gln Pro Met Ala Val Ile Arg
            260                 265                 270

Ser Met Ala Val Ala Gly Val Asp Pro Ala Ile Met Gly Tyr Gly Pro
            275                 280                 285

Val Pro Ser Thr Asn Lys Ala Leu Lys Arg Ala Gly Leu Thr Ile Ala
290                 295                 300

Asp Ile Asp Phe Val Glu Leu Asn Glu Ala Phe Ala Ala Gln Ala Leu
305                 310                 315                 320

Pro Val Leu Lys Asp Leu Lys Leu Leu Asp Lys Met Asp Glu Lys Val
            325                 330                 335

Asn Leu His Gly Gly Ala Ile Ala Leu Gly His Pro Phe Gly Cys Ser
            340                 345                 350

Gly Ala Arg Ile Ser Gly Thr Leu Leu Asn Val Met Lys Gln Asn Gly
            355                 360                 365

Gly Thr Leu Gly Val Ser Thr Met Cys Val Gly Leu Gly Gln Gly Ile
            370                 375                 380

Thr Thr Val Phe Glu Arg Ile
385                 390

<210> SEQ ID NO 134
<211> LENGTH: 391
<212> TYPE: PRT
<213> ORGANISM: Pseudomonas putida
<220> FEATURE:
<221> NAME/KEY: MISC_FEATURE
<223> OTHER INFORMATION: Uniprot name: FADA_PSEPK. 3-ketoacyl-CoA
      thiolase

<400> SEQUENCE: 134

Met Ser Leu Asn Pro Arg Asp Val Val Ile Val Asp Phe Gly Arg Thr
1               5                   10                  15

Pro Met Gly Arg Ser Lys Gly Gly Met His Arg Asn Thr Arg Ala Glu
            20                  25                  30

Asp Met Ser Ala His Leu Ile Ser Lys Leu Leu Glu Arg Asn Gly Lys
        35                  40                  45

Val Asp Pro Lys Glu Val Glu Asp Val Ile Trp Gly Cys Val Asn Gln
    50                  55                  60

Thr Leu Glu Gln Gly Trp Asn Ile Ala Arg Met Ala Ser Leu Met Thr
65                  70                  75                  80

Pro Ile Pro His Thr Ser Ala Ala Gln Thr Val Ser Arg Leu Cys Gly
                85                  90                  95

Ser Ser Met Ser Ala Leu His Thr Ala Ala Gln Ala Ile Met Thr Gly
            100                 105                 110

Asn Gly Asp Val Phe Val Val Gly Gly Val Glu His Met Gly His Val
        115                 120                 125

Ser Met Met His Gly Val Asp Pro Asn Pro His Leu Ser Leu His Ala
    130                 135                 140

Ala Lys Ala Ser Gly Met Met Gly Leu Thr Ala Glu Met Leu Gly Lys
145                 150                 155                 160

Met His Gly Ile Thr Arg Glu Gln Gln Asp Leu Phe Gly Leu Arg Ser
                165                 170                 175

His Gln Leu Ala His Lys Ala Thr Val Glu Gly Lys Phe Lys Asp Glu
            180                 185                 190

Ile Ile Pro Met Gln Gly Tyr Asp Glu Asn Gly Phe Leu Lys Val Phe
        195                 200                 205
```

```
Asp Phe Asp Glu Thr Ile Arg Pro Glu Thr Thr Leu Glu Gly Leu Ala
    210                 215                 220

Ser Leu Lys Pro Ala Phe Asn Pro Lys Gly Gly Thr Val Thr Ala Gly
225                 230                 235                 240

Thr Ser Ser Gln Ile Thr Asp Gly Ala Ser Cys Met Ile Val Met Ser
                245                 250                 255

Gly Gln Arg Ala Met Asp Leu Gly Ile Gln Pro Leu Ala Val Ile Arg
            260                 265                 270

Ser Met Ala Val Ala Gly Val Asp Pro Ala Ile Met Gly Tyr Gly Pro
            275                 280                 285

Val Pro Ser Thr Gln Lys Ala Leu Lys Arg Ala Gly Leu Thr Met Ala
    290                 295                 300

Asp Ile Asp Phe Ile Glu Leu Asn Glu Ala Phe Ala Ala Gln Ala Leu
305                 310                 315                 320

Pro Val Leu Lys Asp Leu Lys Val Leu Asp Lys Met Asp Glu Lys Val
                325                 330                 335

Asn Leu His Gly Gly Ala Ile Ala Leu Gly His Pro Phe Gly Cys Ser
            340                 345                 350

Gly Ala Arg Ile Ser Gly Thr Leu Leu Asn Val Met Lys Gln Asn Gly
            355                 360                 365

Gly Thr Leu Gly Val Ala Thr Met Cys Val Gly Leu Gly Gln Gly Ile
    370                 375                 380

Thr Thr Val Phe Glu Arg Val
385                 390

<210> SEQ ID NO 135
<211> LENGTH: 400
<212> TYPE: PRT
<213> ORGANISM: Pseudomonas putida (Arthrobacter siderocapsulatus)
<220> FEATURE:
<221> NAME/KEY: MISC_FEATURE
<223> OTHER INFORMATION: Uniprot name: PCAF_PSEPU. Beta-ketoadipyl-CoA
      thiolase

<400> SEQUENCE: 135

Met Arg Asp Val Phe Ile Cys Asp Ala Ile Arg Thr Pro Ile Gly Arg
1               5                   10                  15

Phe Gly Gly Ala Leu Ala Gly Val Arg Ala Asp Asp Leu Ala Ala Val
            20                  25                  30

Pro Leu Lys Ala Leu Ile Glu Pro Asn Pro Ala Val Gln Trp Asp Gln
        35                  40                  45

Val Asp Glu Val Phe Phe Gly Cys Ala Asn Gln Ala Gly Glu Asp Asn
    50                  55                  60

Arg Asn Val Ala Arg Met Ala Leu Leu Leu Ala Gly Leu Pro Glu Ser
65                  70                  75                  80

Ile Pro Gly Val Thr Leu Asn Arg Leu Cys Ala Ser Gly Met Asp Ala
                85                  90                  95

Ile Gly Thr Ala Phe Arg Ala Ile Ala Ser Gly Glu Met Glu Leu Ala
            100                 105                 110

Ile Ala Gly Gly Val Glu Ser Met Ser Arg Ala Pro Phe Val Met Gly
        115                 120                 125

Lys Ala Glu Ser Gly Tyr Ser Arg Asn Met Lys Leu Glu Asp Thr Thr
    130                 135                 140

Ile Gly Trp Arg Phe Ile Asn Pro Leu Met Lys Ser Gln Tyr Gly Val
145                 150                 155                 160

Asp Ser Met Pro Glu Thr Ala Asp Asn Val Ala Asp Asp Tyr Gln Val
```

165                 170                 175

Ser Arg Ala Asp Gln Asp Ala Phe Ala Leu Arg Ser Gln Gln Lys Ala
                180                 185                 190

Ala Ala Ala Gln Ala Ala Gly Phe Phe Ala Glu Glu Ile Val Pro Val
            195                 200                 205

Arg Ile Ala His Lys Lys Gly Glu Thr Ile Val Glu Arg Asp Glu His
        210                 215                 220

Leu Arg Pro Glu Thr Thr Leu Glu Ala Leu Thr Lys Leu Lys Pro Val
225                 230                 235                 240

Asn Gly Pro Asp Lys Thr Val Thr Ala Gly Asn Ala Ser Gly Val Asn
                245                 250                 255

Asp Gly Ala Ala Ala Leu Ile Leu Ala Ser Ala Glu Ala Val Lys Lys
            260                 265                 270

His Gly Leu Thr Pro Arg Ala Arg Val Leu Gly Met Ala Ser Gly Gly
        275                 280                 285

Val Ala Pro Arg Val Met Gly Ile Gly Pro Val Pro Ala Val Arg Lys
290                 295                 300

Leu Thr Glu Arg Leu Gly Val Ala Val Ser Asp Phe Asp Val Ile Glu
305                 310                 315                 320

Leu Asn Glu Ala Phe Ala Ser Gln Gly Leu Ala Val Leu Arg Glu Leu
                325                 330                 335

Gly Val Ala Asp Asp Ala Pro Gln Val Asn Pro Asn Gly Gly Ala Ile
            340                 345                 350

Ala Leu Gly His Pro Leu Gly Met Ser Gly Ala Arg Leu Val Leu Thr
        355                 360                 365

Ala Leu His Gln Leu Glu Lys Ser Gly Gly Arg Lys Gly Leu Ala Thr
    370                 375                 380

Met Cys Val Gly Val Gly Gln Gly Leu Ala Leu Ala Ile Glu Arg Val
385                 390                 395                 400

<210> SEQ ID NO 136
<211> LENGTH: 390
<212> TYPE: PRT
<213> ORGANISM: Psychrobacter arcticus
<220> FEATURE:
<221> NAME/KEY: MISC_FEATURE
<223> OTHER INFORMATION: Uniprot name: FADA_PSYA2.  3-ketoacyl-CoA
      thiolase

<400> SEQUENCE: 136

Met Thr Ile Leu Ser Pro Lys Asp Val Ile Val Asp Gly Val Arg
1               5                   10                  15

Ser Ala Met Gly Lys Thr Lys Asn Gly Met Phe Arg His Val Arg Ala
                20                  25                  30

Asp Ser Met Ser Ala Glu Leu Val Arg Ala Leu Val Glu Arg Asn Asp
            35                  40                  45

Phe Asp Pro Arg Asp Val Glu Asp Ile Ile Trp Gly Cys Val Asn Gln
        50                  55                  60

Thr Leu Glu Gln Gly Leu Asn Ile Gly Arg Asn Ile Gly Leu Leu Ala
65                  70                  75                  80

Gly Ile Pro Lys Thr Ala Gly Gly Gln Thr Val Asn Arg Leu Cys Gly
                85                  90                  95

Ser Ser Met Gln Ala Leu His Thr Ala Ala Gln Ile Met Thr Gly
            100                 105                 110

Gln Gly Asp Val Phe Ile Ile Gly Gly Val Glu His Met Gly His Val
        115                 120                 125

Gly Met Met His Gly Ile Asp Leu Asn Pro Glu Ala Ser Lys His Tyr
    130                 135                 140

Ala Lys Ala Ser Asn Met Met Gly Leu Thr Ala Glu Met Leu Gly Arg
145                 150                 155                 160

Met Asn Asn Ile Thr Arg Glu Glu Gln Asp Ala Phe Gly Leu Glu Ser
                165                 170                 175

His Arg Arg Ala Trp Ala Ala Thr Thr Glu Gly Arg Phe Asp Asn Glu
            180                 185                 190

Ile Ile Gly Ile Glu Gly His Asp Ala Ala Gly Arg Leu Gln Leu Cys
        195                 200                 205

Thr Val Asp Glu Val Ile Arg Pro Asp Ala Thr Met Glu Gln Met Gln
210                 215                 220

Lys Leu Arg Pro Ala Phe Asp Pro Val Ser Gly Thr Val Thr Ala Ala
225                 230                 235                 240

Thr Ser Ser Ala Leu Ser Asp Gly Ala Ser Ala Met Leu Ile Met Ser
                245                 250                 255

Ala Gln Lys Ala Lys Glu Leu Gly Leu Lys Pro Arg Ala Arg Ile Arg
            260                 265                 270

Ser Met Ala Val Ala Gly Cys Asp Ala Ala Ile Met Gly Tyr Gly Pro
        275                 280                 285

Val Pro Ala Thr Gln Lys Ala Leu Lys Arg Ala Gly Met Ser Ile Glu
290                 295                 300

Asp Met Gln Thr Ile Glu Leu Asn Glu Ala Phe Ala Ala Gln Gly Leu
305                 310                 315                 320

Ser Val Leu Lys Ala Leu Asn Leu Thr Asp Lys Gln Asp Ile Val Asn
                325                 330                 335

Ile Asn Gly Gly Ala Ile Ala Leu Gly His Pro Leu Gly Cys Ser Gly
            340                 345                 350

Ala Arg Ile Thr Val Thr Leu Leu Asn Ala Met Glu Gln Ser Asp Thr
        355                 360                 365

Glu Ile Gly Leu Ala Thr Met Cys Ile Gly Leu Gly Gln Gly Ile Ser
370                 375                 380

Thr Ile Ile Glu Arg Val
385                 390

<210> SEQ ID NO 137
<211> LENGTH: 393
<212> TYPE: PRT
<213> ORGANISM: Rhizobium meliloti (Ensifer meliloti) (Sinorhizobium
      meliloti)
<220> FEATURE:
<221> NAME/KEY: MISC_FEATURE
<223> OTHER INFORMATION: Uniprot name: THIL_RHIME . Acetyl-CoA
      acetyltransferase

<400> SEQUENCE: 137

Met Ser Asn Pro Ser Ile Val Ile Ala Ser Ala Arg Thr Ala Val
1               5                   10                  15

Gly Ser Phe Asn Gly Ala Phe Gly Asn Thr Leu Ala His Glu Leu Gly
            20                  25                  30

Ala Ala Ala Ile Lys Ala Val Leu Glu Arg Ala Gly Val Glu Ala Gly
        35                  40                  45

Glu Val Asp Glu Val Ile Leu Gly Gln Val Leu Pro Ala Gly Glu Gly
50                  55                  60

Gln Asn Pro Ala Arg Gln Ala Ala Met Lys Ala Gly Leu Pro Gln Glu
65                  70                  75                  80

```
Lys Thr Ala Trp Gly Met Asn Gln Leu Cys Gly Ser Gly Leu Arg Ala
                85                  90                  95

Val Ala Leu Gly Met Gln Gln Ile Ala Thr Gly Asp Ala Lys Val Ile
            100                 105                 110

Val Ala Gly Gly Met Glu Ser Met Ser Met Ala Pro His Cys Ala His
            115                 120                 125

Leu Arg Gly Gly Val Lys Met Gly Asp Tyr Lys Met Ile Asp Thr Met
130                 135                 140

Ile Lys Asp Gly Leu Thr Asp Ala Phe Tyr Gly Tyr His Met Gly Ile
145                 150                 155                 160

Thr Ala Glu Asn Val Ala Arg Lys Trp Gln Leu Thr Arg Glu Glu Gln
                165                 170                 175

Asp Glu Phe Ala Leu Ala Ser Gln Asn Lys Ala Glu Ala Ala Gln Lys
            180                 185                 190

Ala Gly Arg Phe Ala Asp Glu Ile Val Pro Phe Val Val Lys Thr Arg
        195                 200                 205

Lys Gly Asp Val Asn Val Asp Gln Asp Glu Tyr Ile Arg His Gly Ala
    210                 215                 220

Thr Leu Asp Ser Ile Ala Lys Leu Arg Pro Ala Phe Asp Lys Glu Gly
225                 230                 235                 240

Thr Val Thr Ala Gly Asn Ala Ser Gly Leu Asn Asp Gly Ala Ala Ala
                245                 250                 255

Ala Leu Leu Met Thr Glu Ala Glu Ala Arg Arg Gly Ile Gln Pro
            260                 265                 270

Leu Ala Arg Ile Val Ser Trp Ala Thr Ala Gly Val Asp Pro Gln Ile
        275                 280                 285

Met Gly Thr Gly Pro Ile Pro Ala Ser Arg Lys Ala Leu Glu Lys Ala
    290                 295                 300

Gly Trp Ser Val Ala Asp Ile Glu Leu Val Glu Ala Asn Glu Ala Phe
305                 310                 315                 320

Ala Ala Gln Ala Cys Ala Val Asn Lys Asp Leu Gly Trp Asp Pro Ser
                325                 330                 335

Ile Val Asn Val Asn Gly Gly Ala Ile Ala Ile Gly His Pro Ile Gly
            340                 345                 350

Ala Ser Gly Ala Arg Val Leu Asn Thr Leu Leu Phe Glu Met Lys Arg
        355                 360                 365

Arg Gly Val Ser Lys Gly Leu Ala Thr Leu Cys Ile Gly Gly Gly Met
    370                 375                 380

Gly Val Ala Met Cys Val Glu Arg Leu
385                 390

<210> SEQ ID NO 138
<211> LENGTH: 417
<212> TYPE: PRT
<213> ORGANISM: Saccharomyces cerevisiae
<220> FEATURE:
<221> NAME/KEY: MISC_FEATURE
<223> OTHER INFORMATION: Uniprot name: THIK_YEAST. 3-ketoacyl-CoA
      thiolase

<400> SEQUENCE: 138

Met Ser Gln Arg Leu Gln Ser Ile Lys Asp His Leu Val Glu Ser Ala
1               5                   10                  15

Met Gly Lys Gly Glu Ser Lys Arg Lys Asn Ser Leu Leu Glu Lys Arg
            20                  25                  30
```

-continued

Pro Glu Asp Val Val Ile Val Ala Ala Asn Arg Ser Ala Ile Gly Lys
            35                  40                  45

Gly Phe Lys Gly Ala Phe Lys Asp Val Asn Thr Asp Tyr Leu Leu Tyr
 50                  55                  60

Asn Phe Leu Asn Glu Phe Ile Gly Arg Phe Pro Glu Pro Leu Arg Ala
 65                  70                  75                  80

Asp Leu Asn Leu Ile Glu Val Ala Cys Gly Asn Val Leu Asn Val
                 85                  90                  95

Gly Ala Gly Ala Thr Glu His Arg Ala Ala Cys Leu Ala Ser Gly Ile
                100                 105                 110

Pro Tyr Ser Thr Pro Phe Val Ala Leu Asn Arg Gln Cys Ser Ser Gly
            115                 120                 125

Leu Thr Ala Val Asn Asp Ile Ala Asn Lys Ile Lys Val Gly Gln Ile
130                 135                 140

Asp Ile Gly Leu Ala Leu Gly Val Glu Ser Met Thr Asn Asn Tyr Lys
145                 150                 155                 160

Asn Val Asn Pro Leu Gly Met Ile Ser Ser Glu Leu Gln Lys Asn
                165                 170                 175

Arg Glu Ala Lys Lys Cys Leu Ile Pro Met Gly Ile Thr Asn Glu Asn
                180                 185                 190

Val Ala Ala Asn Phe Lys Ile Ser Arg Lys Asp Gln Asp Glu Phe Ala
195                 200                 205

Ala Asn Ser Tyr Gln Lys Ala Tyr Lys Ala Lys Asn Glu Gly Leu Phe
        210                 215                 220

Glu Asp Glu Ile Leu Pro Ile Lys Leu Pro Asp Gly Ser Ile Cys Gln
225                 230                 235                 240

Ser Asp Glu Gly Pro Arg Pro Asn Val Thr Ala Glu Ser Leu Ser Ser
                245                 250                 255

Ile Arg Pro Ala Phe Ile Lys Asp Arg Gly Thr Thr Ala Gly Asn
                260                 265                 270

Ala Ser Gln Val Ser Asp Gly Val Ala Gly Val Leu Leu Ala Arg Arg
        275                 280                 285

Ser Val Ala Asn Gln Leu Asn Leu Pro Val Leu Gly Arg Tyr Ile Asp
290                 295                 300

Phe Gln Thr Val Gly Val Pro Pro Glu Ile Met Gly Val Gly Pro Ala
305                 310                 315                 320

Tyr Ala Ile Pro Lys Val Leu Glu Ala Thr Gly Leu Gln Val Gln Asp
                325                 330                 335

Ile Asp Ile Phe Glu Ile Asn Glu Ala Phe Ala Ala Gln Ala Leu Tyr
            340                 345                 350

Cys Ile His Lys Leu Gly Ile Asp Leu Asn Lys Val Asn Pro Arg Gly
            355                 360                 365

Gly Ala Ile Ala Leu Gly His Pro Leu Gly Cys Thr Gly Ala Arg Gln
370                 375                 380

Val Ala Thr Ile Leu Arg Glu Leu Lys Lys Asp Gln Ile Gly Val Val
385                 390                 395                 400

Ser Met Cys Ile Gly Thr Gly Met Gly Ala Ala Ala Ile Phe Ile Lys
                405                 410                 415

Glu

<210> SEQ ID NO 139
<211> LENGTH: 398
<212> TYPE: PRT
<213> ORGANISM: Saccharomyces cerevisiae

```
<220> FEATURE:
<221> NAME/KEY: MISC_FEATURE
<223> OTHER INFORMATION: Uniprot name: THIL_YEAST. Acetyl-CoA
      acetyltransferase

<400> SEQUENCE: 139

Met Ser Gln Asn Val Tyr Ile Val Ser Thr Ala Arg Thr Pro Ile Gly
1               5                   10                  15

Ser Phe Gln Gly Ser Leu Ser Ser Lys Thr Ala Val Glu Leu Gly Ala
            20                  25                  30

Val Ala Leu Lys Gly Ala Leu Ala Lys Val Pro Glu Leu Asp Ala Ser
        35                  40                  45

Lys Asp Phe Asp Glu Ile Ile Phe Gly Asn Val Leu Ser Ala Asn Leu
50                  55                  60

Gly Gln Ala Pro Ala Arg Gln Val Ala Leu Ala Ala Gly Leu Ser Asn
65                  70                  75                  80

His Ile Val Ala Ser Thr Val Asn Lys Val Cys Ala Ser Ala Met Lys
                85                  90                  95

Ala Ile Ile Leu Gly Ala Gln Ser Ile Lys Cys Gly Asn Ala Asp Val
            100                 105                 110

Val Val Ala Gly Gly Cys Glu Ser Met Thr Asn Ala Pro Tyr Tyr Met
        115                 120                 125

Pro Ala Ala Arg Ala Gly Ala Lys Phe Gly Gln Thr Val Leu Val Asp
130                 135                 140

Gly Val Glu Arg Asp Gly Leu Asn Asp Ala Tyr Asp Gly Leu Ala Met
145                 150                 155                 160

Gly Val His Ala Glu Lys Cys Ala Arg Asp Trp Asp Ile Thr Arg Glu
                165                 170                 175

Gln Gln Asp Asn Phe Ala Ile Glu Ser Tyr Gln Lys Ser Gln Lys Ser
            180                 185                 190

Gln Lys Glu Gly Lys Phe Asp Asn Glu Ile Val Pro Val Thr Ile Lys
        195                 200                 205

Gly Phe Arg Gly Lys Pro Asp Thr Gln Val Thr Lys Asp Glu Glu Pro
210                 215                 220

Ala Arg Leu His Val Glu Lys Leu Arg Ser Ala Arg Thr Val Phe Gln
225                 230                 235                 240

Lys Glu Asn Gly Thr Val Thr Ala Ala Asn Ala Ser Pro Ile Asn Asp
                245                 250                 255

Gly Ala Ala Ala Val Ile Leu Val Ser Glu Lys Val Leu Lys Glu Lys
            260                 265                 270

Asn Leu Lys Pro Leu Ala Ile Ile Lys Gly Trp Gly Glu Ala Ala His
        275                 280                 285

Gln Pro Ala Asp Phe Thr Trp Ala Pro Ser Leu Ala Val Pro Lys Ala
290                 295                 300

Leu Lys His Ala Gly Ile Glu Asp Ile Asn Ser Val Asp Tyr Phe Glu
305                 310                 315                 320

Phe Asn Glu Ala Phe Ser Val Val Gly Leu Val Asn Thr Lys Ile Leu
                325                 330                 335

Lys Leu Asp Pro Ser Lys Val Asn Val Tyr Gly Gly Ala Val Ala Leu
            340                 345                 350

Gly His Pro Leu Gly Cys Ser Gly Ala Arg Val Val Thr Leu Leu
        355                 360                 365

Ser Ile Leu Gln Gln Glu Gly Gly Lys Ile Gly Val Ala Ala Ile Cys
370                 375                 380
```

```
Asn Gly Gly Gly Gly Ala Ser Ser Ile Val Ile Glu Lys Ile
385                 390                 395
```

<210> SEQ ID NO 140
<211> LENGTH: 387
<212> TYPE: PRT
<213> ORGANISM: Salmonella typhimurium
<220> FEATURE:
<221> NAME/KEY: MISC_FEATURE
<223> OTHER INFORMATION: Uniprot name: FADA_SALTY. 3-ketoacyl-CoA
      thiolase

<400> SEQUENCE: 140

```
Met Glu Gln Val Val Ile Val Asp Ala Ile Arg Thr Pro Met Gly Arg
1               5                   10                  15

Ser Lys Gly Gly Ala Phe Arg Asn Val Arg Ala Glu Asp Leu Ser Ala
            20                  25                  30

His Leu Met Arg Ser Leu Leu Ala Arg Asn Pro Ser Leu Thr Ala Ala
        35                  40                  45

Thr Leu Asp Asp Ile Tyr Trp Gly Cys Val Gln Gln Thr Leu Glu Gln
    50                  55                  60

Gly Phe Asn Ile Ala Arg Asn Ala Ala Leu Leu Ala Glu Ile Pro His
65                  70                  75                  80

Ser Val Pro Ala Val Thr Val Asn Arg Leu Cys Gly Ser Ser Met Gln
                85                  90                  95

Ala Leu His Asp Ala Ala Arg Met Ile Met Thr Gly Asp Ala Gln Val
            100                 105                 110

Cys Leu Val Gly Gly Val Glu His Met Gly His Val Pro Met Ser His
        115                 120                 125

Gly Val Asp Phe His Pro Gly Leu Ser Arg Asn Val Ala Lys Ala Ala
    130                 135                 140

Gly Met Met Gly Leu Thr Ala Glu Met Leu Ser Arg Leu His Gly Ile
145                 150                 155                 160

Ser Arg Glu Met Gln Asp Gln Phe Ala Ala Arg Ser His Ala Arg Ala
                165                 170                 175

Trp Ala Ala Thr Gln Ser Gly Ala Phe Lys Thr Glu Ile Ile Pro Thr
            180                 185                 190

Gly Gly His Asp Ala Asp Gly Val Leu Lys Gln Phe Asn Tyr Asp Glu
        195                 200                 205

Val Ile Arg Pro Glu Thr Thr Val Glu Ala Leu Ser Thr Leu Arg Pro
    210                 215                 220

Ala Phe Asp Pro Val Ser Gly Thr Val Thr Ala Gly Thr Ser Ser Ala
225                 230                 235                 240

Leu Ser Asp Gly Ala Ala Ala Met Leu Val Met Ser Glu Ser Arg Ala
                245                 250                 255

Arg Glu Leu Gly Leu Lys Pro Arg Ala Arg Ile Arg Ser Met Ala Val
            260                 265                 270

Val Gly Cys Asp Pro Ser Ile Met Gly Tyr Gly Pro Val Pro Ala Ser
        275                 280                 285

Lys Leu Ala Leu Lys Lys Ala Gly Leu Ser Ala Ser Asp Ile Asp Val
    290                 295                 300

Phe Glu Met Asn Glu Ala Phe Ala Ala Gln Ile Leu Pro Cys Ile Lys
305                 310                 315                 320

Asp Leu Gly Leu Met Glu Gln Ile Asp Glu Lys Ile Asn Leu Asn Gly
                325                 330                 335

Gly Ala Ile Ala Leu Gly His Pro Leu Gly Cys Ser Gly Ala Arg Ile
```

```
            340             345             350
Ser Thr Thr Leu Ile Asn Leu Met Glu Arg Lys Asp Ala Gln Phe Gly
            355             360             365

Leu Ala Thr Met Cys Ile Gly Leu Gly Gln Gly Ile Ala Thr Val Phe
            370             375             380

Glu Arg Val
385

<210> SEQ ID NO 141
<211> LENGTH: 436
<212> TYPE: PRT
<213> ORGANISM: Salmonella typhimurium
<220> FEATURE:
<221> NAME/KEY: MISC_FEATURE
<223> OTHER INFORMATION: Uniprot name: FADI_SALTY.  3-ketoacyl-CoA
      thiolase

<400> SEQUENCE: 141

Met Arg Gln Ala Leu Pro Leu Val Thr Arg Gln Gly Asp Arg Ile Ala
1               5                   10                  15

Ile Val Ser Gly Leu Arg Thr Pro Phe Ala Arg Gln Ala Thr Ala Phe
            20                  25                  30

His Gly Ile Pro Ala Val Asp Leu Gly Lys Met Val Val Gly Glu Leu
        35                  40                  45

Leu Ala Arg Ser Glu Ile Pro Ala Asp Ala Ile Glu Gln Leu Val Phe
    50                  55                  60

Gly Gln Val Val Gln Met Pro Glu Ala Pro Asn Ile Ala Arg Glu Ile
65                  70                  75                  80

Val Leu Gly Thr Gly Met Asn Val His Thr Asp Ala Tyr Ser Val Ser
                85                  90                  95

Arg Ala Cys Ala Thr Ser Phe Gln Ala Val Ala Asn Val Ala Glu Ser
            100                 105                 110

Leu Met Ala Gly Thr Ile Arg Ala Gly Ile Ala Gly Gly Ala Asp Ser
        115                 120                 125

Ser Ser Val Leu Pro Ile Gly Val Ser Lys Ala Leu Ala Arg Val Leu
    130                 135                 140

Val Asp Val Asn Lys Ala Arg Thr Thr Arg Gln Arg Leu Thr Leu Phe
145                 150                 155                 160

Ser Arg Leu Arg Leu Arg Asp Leu Leu Pro Val Pro Pro Ala Val Ala
                165                 170                 175

Glu Tyr Ser Thr Gly Leu Arg Met Gly Asp Thr Ala Glu Gln Met Ala
            180                 185                 190

Lys Thr Tyr Gly Ile Thr Arg Glu Gln Gln Asp Ala Leu Ala His Arg
        195                 200                 205

Ser His Gln Arg Ala Ala Gln Ala Trp Ala Glu Gly Lys Leu Ala Glu
    210                 215                 220

Glu Val Met Thr Thr Tyr Val Pro Pro Tyr Lys Asn Pro Phe Ala Glu
225                 230                 235                 240

Asp Asn Asn Ile Arg Gly Ala Ser Thr Leu Ala Asp Tyr Ala Lys Leu
                245                 250                 255

Arg Pro Ala Phe Asp Arg Lys His Gly Ser Val Thr Ala Ala Asn Ser
            260                 265                 270

Thr Pro Leu Thr Asp Gly Ala Ala Ala Val Ile Leu Met Thr Glu Ser
        275                 280                 285

Arg Ala Lys Glu Leu Gly Leu Arg Pro Leu Gly Tyr Leu Arg Thr Tyr
    290                 295                 300
```

```
Ala Phe Thr Ala Ile Asp Val Trp Gln Asp Met Leu Leu Gly Pro Ala
305                 310                 315                 320

Trp Ser Thr Pro Leu Ala Leu Glu Arg Ala Gly Leu Thr Met Ala Asp
                325                 330                 335

Leu Thr Leu Phe Asp Met His Glu Ala Phe Ala Ala Gln Thr Leu Ala
            340                 345                 350

Asn Leu Gln Leu Leu Gly Ser Glu Arg Phe Ala Arg Glu Val Leu Gly
        355                 360                 365

Cys Ala Gln Ala Thr Gly Glu Val Asp Asp Ala Lys Phe Asn Val Leu
    370                 375                 380

Gly Gly Ser Ile Ala Tyr Gly His Pro Phe Ala Ala Thr Gly Ala Arg
385                 390                 395                 400

Met Ile Thr Gln Thr Leu His Glu Leu Arg Arg Arg Gly Gly Phe
                405                 410                 415

Gly Leu Val Thr Ala Cys Ala Ala Gly Gly Leu Gly Ala Ala Met Val
            420                 425                 430

Leu Glu Ala Glu
        435

<210> SEQ ID NO 142
<211> LENGTH: 395
<212> TYPE: PRT
<213> ORGANISM: Schizosaccharomyces pombe
<220> FEATURE:
<221> NAME/KEY: MISC_FEATURE
<223> OTHER INFORMATION: Uniprot name: THIL_SCHPO.  Acetyl-CoA
      acetyltransferase

<400> SEQUENCE: 142

Met Val Asn Thr Glu Val Tyr Ile Val Ser Ala Val Arg Thr Pro Met
1               5                   10                  15

Gly Ser Phe Gly Gly Ser Phe Ala Ser Leu Pro Ala Thr Lys Leu Gly
                20                  25                  30

Ser Ile Ala Ile Lys Gly Ala Leu Glu Arg Val Asn Ile Lys Pro Ser
            35                  40                  45

Asp Val Asp Glu Val Phe Met Gly Asn Val Val Ser Ala Asn Leu Gly
        50                  55                  60

Gln Asn Pro Ala Arg Gln Cys Ala Leu Gly Ala Gly Leu Pro Arg Ser
65                  70                  75                  80

Ile Val Cys Thr Thr Val Asn Lys Val Cys Ala Ser Gly Met Lys Ala
                85                  90                  95

Thr Ile Leu Gly Ala Gln Thr Ile Met Thr Gly Asn Ala Glu Ile Val
            100                 105                 110

Val Ala Gly Gly Thr Glu Ser Met Ser Asn Ala Pro Tyr Tyr Ala Pro
        115                 120                 125

Lys Asn Arg Phe Gly Ala Lys Tyr Gly Asn Val Glu Leu Val Asp Gly
130                 135                 140

Leu Leu Arg Asp Gly Leu Ser Asp Ala Tyr Asp Gly Leu Pro Met Gly
145                 150                 155                 160

Asn Ala Ala Glu Leu Cys Ala Glu Glu His Ser Ile Asp Arg Ala Ser
                165                 170                 175

Gln Asp Ala Phe Ala Ile Ser Ser Tyr Lys Arg Ala Gln Asn Ala Gln
            180                 185                 190

Ala Thr Lys Ala Phe Glu Gln Glu Ile Val Pro Val Glu Val Pro Val
        195                 200                 205
```

```
Gly Arg Gly Lys Pro Asn Lys Leu Val Thr Glu Asp Glu Pro Lys
    210                 215                 220

Asn Leu Asn Glu Asp Lys Leu Lys Ser Val Arg Ala Val Phe Lys Ser
225                 230                 235                 240

Asn Gly Thr Val Thr Ala Ala Asn Ala Ser Thr Leu Asn Asp Gly Ala
                245                 250                 255

Ser Ala Leu Val Leu Met Ser Ala Ala Lys Val Lys Glu Leu Gly Leu
                260                 265                 270

Lys Pro Leu Ala Lys Ile Ile Gly Trp Gly Ala Ala Gln Asp Pro
                275                 280                 285

Glu Arg Phe Thr Thr Ser Pro Ser Leu Ala Ile Pro Lys Ala Leu Lys
290                 295                 300

His Ala Gly Ile Glu Ala Ser Gln Val Asp Tyr Tyr Glu Ile Asn Glu
305                 310                 315                 320

Ala Phe Ser Val Val Ala Val Ala Asn Thr Lys Ile Leu Gly Leu Asp
                325                 330                 335

Pro Glu Arg Val Asn Ile Asn Gly Gly Val Ala Met Gly His Pro
                340                 345                 350

Leu Gly Ser Ser Gly Ser Arg Ile Ile Cys Thr Leu Ala Tyr Ile Leu
                355                 360                 365

Ala Gln Lys Asp Ala Lys Ile Gly Val Ala Ala Val Cys Asn Gly Gly
370                 375                 380

Gly Gly Ala Ser Ser Ile Val Ile Glu Arg Val
385                 390                 395

<210> SEQ ID NO 143
<211> LENGTH: 387
<212> TYPE: PRT
<213> ORGANISM: Serratia proteamaculans
<220> FEATURE:
<221> NAME/KEY: MISC_FEATURE
<223> OTHER INFORMATION: Uniprot name: FADA_SERP5. 3-ketoacyl-CoA
      thiolase

<400> SEQUENCE: 143

Met Glu Asn Val Val Ile Val Asp Ala Val Arg Thr Pro Met Gly Arg
1               5                   10                  15

Ser Lys Gly Gly Ala Phe Arg Gln Val Arg Ala Glu Asp Leu Ser Ala
                20                  25                  30

His Leu Met Arg Ala Val Leu Ser Arg Asn Pro Ser Leu Asp Ala Ala
            35                  40                  45

Glu Ile Asp Asp Ile Tyr Trp Gly Cys Val Gln Gln Thr Leu Glu Gln
50                  55                  60

Gly Phe Asn Ile Ala Arg Asn Ala Ser Leu Leu Ala Glu Ile Pro His
65              70                  75                  80

Ser Val Pro Ala Val Thr Val Asn Arg Leu Cys Gly Ser Ser Met Gln
                85                  90                  95

Ala Leu His Asp Ala Ala Arg Ala Ile Met Val Gly Asp Ala His Val
            100                 105                 110

Ser Leu Ile Gly Gly Val Glu His Met Gly His Val Pro Met Asn His
            115                 120                 125

Gly Val Asp Phe His Pro Gly Leu Ser Arg Ser Val Ala Lys Ala Ala
            130                 135                 140

Gly Met Met Gly Leu Thr Ala Glu Met Leu Ala Lys Met His Asn Ile
145                 150                 155                 160

Ser Arg Gln Met Gln Asp Glu Phe Ala Ala Arg Ser His Gln Arg Ala
```

```
                    165                 170                 175
His Ala Ala Thr Leu Ala Gly Tyr Phe Lys Asn Glu Ile Ile Pro Thr
            180                 185                 190

Thr Gly His Asp Ala Asp Gly Val Leu Thr Arg Tyr Asp Phe Asp Glu
        195                 200                 205

Val Ile Arg Pro Glu Thr Thr Val Ala Ser Leu Ala Ala Leu Arg Pro
210                 215                 220

Ala Phe Asp Pro Val Asn Gly Thr Val Thr Ala Gly Thr Ser Ser Ala
225                 230                 235                 240

Leu Ser Asp Gly Ala Ser Ala Met Leu Leu Met Ser Glu Ser Arg Ala
                245                 250                 255

Lys Ala Leu Gly Leu Lys Ala Arg Ala Arg Ile Arg Ser Met Ala Val
            260                 265                 270

Val Gly Cys Asp Pro Ser Ile Met Gly Tyr Gly Pro Val Pro Ala Ser
        275                 280                 285

Lys Leu Ala Leu Lys Arg Ala Gly Leu Ser Val Gln Asp Ile Asp Leu
    290                 295                 300

Phe Glu Leu Asn Glu Ala Phe Ala Ala Gln Ser Leu Pro Cys Ile Lys
305                 310                 315                 320

Asp Leu Gly Leu Leu Asp Ser Ile Asp Asp Lys Ile Asn Leu Asn Gly
                325                 330                 335

Gly Ala Ile Ala Leu Gly His Pro Leu Gly Cys Ser Gly Ser Arg Ile
            340                 345                 350

Ser Thr Thr Leu Leu Asn Asn Met Glu Arg Arg Asp Val Gln Phe Gly
        355                 360                 365

Leu Ala Thr Met Cys Ile Gly Leu Gly Gln Gly Ile Ala Thr Val Phe
    370                 375                 380

Glu Arg Val
385

<210> SEQ ID NO 144
<211> LENGTH: 436
<212> TYPE: PRT
<213> ORGANISM: Serratia proteamaculans
<220> FEATURE:
<221> NAME/KEY: MISC_FEATURE
<223> OTHER INFORMATION: Uniprot name: FADI_SERP5. 3-ketoacyl-CoA
      thiolase

<400> SEQUENCE: 144

Met Ser Lys Ala Leu Pro Leu Val Thr Arg His Gly Asp Arg Ile Ala
1               5                   10                  15

Ile Val Asn Gly Leu Arg Thr Pro Phe Ala Lys Gln Ala Thr Ala Tyr
            20                  25                  30

His Gly Ile Pro Ala Val Asp Leu Gly Lys Thr Ala Val Ser Glu Leu
        35                  40                  45

Leu Ala Arg Thr Gly Ile Asp Pro Ala Leu Ile Glu Gln Leu Val Phe
    50                  55                  60

Gly Gln Val Val Gln Met Pro Glu Ala Pro Asn Ile Ala Arg Glu Ile
65                  70                  75                  80

Val Leu Gly Thr Gly Met Ser Val His Thr Asp Ala Tyr Ser Val Ser
                85                  90                  95

Arg Ala Cys Ala Thr Ser Phe Gln Ala Ile Ala Asn Val Ala Glu Ser
            100                 105                 110

Ile Met Ala Gly Ser Ile Ser Ile Gly Ile Ala Gly Gly Ala Asp Ser
        115                 120                 125
```

Ser Ser Val Leu Pro Ile Gly Val Ser Lys Ala Leu Ala Arg Thr Leu
130                 135                 140

Val Asp Val Asn Lys Ala Arg Thr Leu Ser Gln Arg Leu Lys Leu Phe
145                 150                 155                 160

Ser Arg Leu Lys Phe Arg Asp Leu Met Pro Val Pro Pro Ala Val Ala
                165                 170                 175

Glu Tyr Ser Thr Gly Leu Arg Met Gly Asp Thr Ala Glu Gln Met Ala
                180                 185                 190

Lys Ser His Gly Ile Thr Arg Glu Glu Gln Asp Ala Leu Ala His Arg
                195                 200                 205

Ser His Gln Leu Ala Ala Lys Ala Trp Glu Gln Gly Leu Leu His Asp
                210                 215                 220

Glu Val Met Thr Ala Tyr Val Pro Pro Tyr Arg Thr Gln Ile Ser Glu
225                 230                 235                 240

Asp Asn Asn Val Arg Lys Asp Ser Ser Leu Ala Ser Tyr Ala Lys Leu
                245                 250                 255

Lys Pro Ala Phe Asp Arg Lys His Gly Ser Val Thr Ala Ala Asn Ser
                260                 265                 270

Thr Pro Leu Thr Asp Gly Ala Ala Ala Val Leu Met Met Ser Glu Ser
                275                 280                 285

Arg Ala Lys Glu Leu Gly Leu Gln Pro Leu Gly Tyr Leu Arg Ser Phe
290                 295                 300

Ala Phe Ser Ala Ile Asp Val Trp Glu Asp Met Leu Leu Gly Pro Ser
305                 310                 315                 320

Tyr Ala Thr Pro Leu Ala Leu Asp Arg Ala Gly Ile Gly Leu Ala Asp
                325                 330                 335

Leu Thr Leu Ile Asp Met His Glu Ala Phe Ala Ala Gln Thr Leu Ala
                340                 345                 350

Asn Leu Lys Met Phe Ala Ser Asp Glu Phe Ala Gln Gln Lys Leu Gly
                355                 360                 365

Arg Ser Arg Ala Ile Gly Glu Val Asp Met Asp Lys Phe Asn Val Leu
370                 375                 380

Gly Gly Ser Ile Ala Tyr Gly His Pro Phe Ala Ala Thr Gly Ala Arg
385                 390                 395                 400

Met Ile Thr Gln Thr Leu His Glu Leu Lys Arg Arg Gly Gly Gly Leu
                405                 410                 415

Gly Leu Thr Thr Ala Cys Ala Ala Gly Gly Leu Gly Ala Ala Met Ile
                420                 425                 430

Val Glu Val Glu
435

<210> SEQ ID NO 145
<211> LENGTH: 387
<212> TYPE: PRT
<213> ORGANISM: Shewanella denitrificans
<220> FEATURE:
<221> NAME/KEY: MISC_FEATURE
<223> OTHER INFORMATION: Uniprot name: FADA_SHEDO. 3-ketoacyl-CoA
      thiolase

<400> SEQUENCE: 145

Met Lys Gln Ala Val Ile Val Asp Cys Ile Arg Thr Pro Met Gly Arg
1               5                   10                  15

Ser Lys Ala Gly Val Phe Arg Asn Val Arg Ala Glu Thr Leu Ser Ala
                20                  25                  30

```
Glu Leu Met Lys Ala Leu Leu Ile Arg Asn Pro Gln Leu Asp Pro Ser
             35                  40                  45

Leu Ile Glu Asp Val Ile Trp Gly Cys Val Gln Gln Thr Leu Glu Gln
 50                  55                  60

Gly Phe Asn Ile Ala Arg Asn Ala Ser Leu Leu Ala Gly Ile Pro Lys
 65                  70                  75                  80

Thr Ala Gly Ala Val Thr Val Asn Arg Leu Cys Gly Ser Ser Met Asp
                 85                  90                  95

Ala Ile His Gln Ala Ala Arg Ala Ile Met Thr Gly Met Gly Asp Thr
            100                 105                 110

Phe Ile Ile Gly Gly Val Glu His Met Gly His Val Pro Met Asn His
            115                 120                 125

Gly Val Asp Phe His Pro Gly Leu Ala Asn Arg Val Ala Lys Ala Ser
130                 135                 140

Gly Met Met Gly Leu Thr Ala Glu Met Leu Gly Lys Met His Gly Ile
145                 150                 155                 160

Ser Arg Glu Gln Gln Asp Ala Phe Ala Val Arg Ser His Gln Arg Ala
                165                 170                 175

His Ala Ala Thr Val Glu Gly Arg Phe Ala Lys Glu Ile Trp Ala Met
            180                 185                 190

Glu Gly His Asp Ala Asn Gly Ala Leu Ile Lys Val Met His Asp Glu
            195                 200                 205

Val Ile Arg Pro Glu Thr Thr Met Glu Ser Leu Ala Gly Leu Arg Pro
210                 215                 220

Val Phe Asp Pro Ala Asn Gly Thr Val Thr Ala Gly Thr Ser Ser Ala
225                 230                 235                 240

Leu Ser Asp Gly Ala Ser Ala Met Leu Val Met Glu Glu Ser Lys Ala
                245                 250                 255

Arg Ala Leu Gly Leu Pro Ile Arg Ala Arg Ile Arg Ser Met Ala Val
            260                 265                 270

Ala Gly Cys Asp Ala Ala Ile Met Gly Tyr Gly Pro Val Pro Ala Thr
            275                 280                 285

Gln Lys Ala Leu Ala Arg Ala Gly Leu Thr Val Ala Asp Leu Asp Val
290                 295                 300

Ile Glu Leu Asn Glu Ala Phe Ala Ala Gln Ser Leu Pro Cys Val Lys
305                 310                 315                 320

Asp Leu Gly Leu Gln Asp Val Val Glu Lys Ile Asn Leu Asn Gly
                325                 330                 335

Gly Ala Ile Ala Leu Gly His Pro Leu Gly Cys Ser Gly Ala Arg Ile
            340                 345                 350

Ser Thr Thr Leu Ile Asn Leu Met Glu Glu Lys Asp Ala Thr Ile Gly
                355                 360                 365

Leu Ala Thr Met Cys Ile Gly Leu Gly Gln Gly Ile Ala Thr Val Phe
370                 375                 380

Glu Arg Val
385

<210> SEQ ID NO 146
<211> LENGTH: 436
<212> TYPE: PRT
<213> ORGANISM: Shewanella denitrificans
<220> FEATURE:
<221> NAME/KEY: MISC_FEATURE
<223> OTHER INFORMATION: Uniprot name: FADI_SHEDO. 3-ketoacyl-CoA
      thiolase
```

<400> SEQUENCE: 146

```
Met Ser Asp Arg Gln Gln Val Lys Asn Ala Arg Gly Glu Arg Ile Ala
1               5                   10                  15
Ile Val Ala Gly Leu Arg Thr Pro Phe Ala Lys Gln Ala Thr Ala Phe
            20                  25                  30
His Gly Val Ser Ala Leu Asp Met Gly Lys Met Val Val Asn Glu Leu
        35                  40                  45
Ile Ser Arg Ser Glu Leu Asp Pro Lys Leu Ile Glu Gln Leu Val Tyr
    50                  55                  60
Gly Gln Val Val Leu Met Pro Ala Ala Pro Asn Ile Ala Arg Glu Ile
65                  70                  75                  80
Val Leu Gly Thr Gly Met Asn Val Ser Thr Asp Ala Tyr Ser Val Thr
                85                  90                  95
Arg Ala Cys Ala Thr Ser Phe Gln Ser Ala Val Asn Val Ala Glu Ser
            100                 105                 110
Ile Met Thr Gly Asn Val Glu Ile Gly Ile Ala Gly Gly Ala Asp Ser
        115                 120                 125
Ser Ser Val Leu Pro Ile Thr Val Ser Lys Lys Leu Ala His Ala Leu
    130                 135                 140
Val Asp Leu Asn Lys Ala Arg Thr Leu Gly Gln Lys Phe Ala Ile Met
145                 150                 155                 160
Arg Arg Leu Gly Leu Lys Asp Leu Met Pro Val Pro Pro Ala Val Ala
                165                 170                 175
Glu Tyr Ser Thr Gly Leu Ser Met Gly Gln Thr Ala Glu Gln Met Ala
            180                 185                 190
Lys Thr Tyr Gly Ile Ser Arg Ala Asp Gln Asp Ala Leu Ala His Arg
        195                 200                 205
Ser His Thr Leu Ala Thr Glu Thr Trp Asn Ser Gly Asn Leu Arg Asp
    210                 215                 220
Glu Val Met Thr Ala His Val Ala Pro Tyr Lys Gln Phe Ile Asp Arg
225                 230                 235                 240
Asp Asn Asn Ile Arg Glu Asn Ser Val Leu Glu Ser Tyr Ala Lys Leu
                245                 250                 255
Arg Pro Ala Phe Asp Arg Lys His Gly Ser Val Thr Ala Ala Asn Ser
            260                 265                 270
Thr Pro Leu Thr Asp Gly Ala Ser Ala Ile Ile Leu Met Ser Glu Gly
        275                 280                 285
Arg Ala Lys Ala Leu Gly Tyr Gln Pro Ile Gly Tyr Ile Lys Ser Tyr
    290                 295                 300
Ala Phe Thr Ala Ile Asp Val Trp Gln Asp Met Leu Met Gly Pro Ser
305                 310                 315                 320
Tyr Ala Thr Pro Leu Ala Leu Lys Arg Ala Gly Met Glu Leu Glu Asp
                325                 330                 335
Leu Thr Leu Ile Glu Met His Glu Ala Phe Ala Ala Gln Thr Leu Ala
            340                 345                 350
Asn Met Gln Met Phe Gly Ser Lys Lys Phe Ala Ala Glu Lys Leu Gly
        355                 360                 365
Arg Asn Arg Ala Ile Gly Asp Ile Asp Met Ser Lys Phe Asn Val Leu
    370                 375                 380
Gly Gly Ser Leu Ala Tyr Gly His Pro Phe Ala Ala Thr Gly Thr Arg
385                 390                 395                 400
Leu Ile Thr Gln Val Cys Arg Glu Leu Lys Arg Arg Gly Gly Gly Thr
                405                 410                 415
```

```
Gly Leu Ala Thr Ala Cys Ala Ala Gly Gly Leu Gly Ala Ala Met Ile
                420                 425                 430

Val Glu Val Glu
        435

<210> SEQ ID NO 147
<211> LENGTH: 387
<212> TYPE: PRT
<213> ORGANISM: Shigella flexneri
<220> FEATURE:
<221> NAME/KEY: MISC_FEATURE
<223> OTHER INFORMATION: Uniprot name: FADA_SHIFL.  3-ketoacyl-CoA
      thiolase

<400> SEQUENCE: 147

Met Glu Gln Val Val Ile Val Asp Ala Ile Arg Thr Pro Met Gly Arg
1               5                   10                  15

Ser Lys Gly Gly Ala Phe Arg Asn Val Arg Ala Glu Asp Leu Ser Ala
            20                  25                  30

His Leu Met Arg Ser Leu Leu Ala Arg Asn Pro Ala Leu Glu Ala Ala
        35                  40                  45

Ala Leu Asp Asp Ile Tyr Trp Gly Cys Val Gln Gln Thr Leu Glu Gln
    50                  55                  60

Gly Phe Asn Ile Ala Arg Asn Ala Ala Leu Leu Ala Glu Val Pro His
65                  70                  75                  80

Ser Val Pro Ala Val Thr Val Asn Arg Leu Cys Gly Ser Ser Met Gln
                85                  90                  95

Ala Leu His Asp Ala Ala Arg Met Ile Met Thr Gly Asp Ala Gln Ala
            100                 105                 110

Cys Leu Val Gly Gly Val Glu His Ile Gly His Val Pro Met Ser His
        115                 120                 125

Gly Val Asp Phe His Pro Gly Leu Ser Arg Asn Val Ala Lys Ala Ala
    130                 135                 140

Gly Met Met Gly Leu Thr Ala Glu Met Leu Ala Arg Met His Gly Ile
145                 150                 155                 160

Ser Arg Glu Met Gln Asp Ala Phe Ala Ala Arg Ser His Ala Arg Ala
                165                 170                 175

Trp Ala Ala Thr Gln Ser Ala Ala Phe Lys Asn Glu Ile Ile Pro Thr
            180                 185                 190

Gly Gly His Asp Ala Asp Gly Val Leu Lys Gln Phe Asn Tyr Asp Glu
        195                 200                 205

Val Ile Arg Pro Glu Thr Thr Val Glu Ala Leu Ala Thr Leu Arg Pro
    210                 215                 220

Ala Phe Asp Pro Val Asn Gly Thr Val Thr Ala Gly Thr Ser Ser Ala
225                 230                 235                 240

Leu Ser Asp Gly Ala Ala Ala Met Leu Val Met Ser Glu Ser Arg Ala
                245                 250                 255

His Glu Leu Gly Leu Lys Pro Arg Ala Arg Val Arg Ser Met Ala Val
            260                 265                 270

Val Gly Cys Asp Pro Ser Ile Met Gly Tyr Gly Pro Val Pro Ala Ser
        275                 280                 285

Lys Leu Ala Leu Lys Lys Ala Gly Leu Ser Ala Ser Asp Ile Gly Val
    290                 295                 300

Phe Glu Met Asn Glu Ala Phe Ala Ala Gln Ile Leu Pro Cys Ile Lys
305                 310                 315                 320
```

```
Asp Leu Gly Leu Met Glu Gln Ile Asp Glu Lys Ile Asn Leu Asn Gly
                325                 330                 335

Gly Ala Ile Ala Leu Gly His Pro Leu Gly Cys Ser Gly Ala Arg Ile
            340                 345                 350

Ser Thr Thr Leu Leu Asn Leu Met Glu Arg Lys Asp Val Gln Phe Gly
        355                 360                 365

Leu Ala Thr Met Cys Ile Gly Leu Gly Gln Gly Ile Ala Thr Val Phe
    370                 375                 380

Glu Arg Val
385

<210> SEQ ID NO 148
<211> LENGTH: 436
<212> TYPE: PRT
<213> ORGANISM: Shigella flexneri
<220> FEATURE:
<221> NAME/KEY: MISC_FEATURE
<223> OTHER INFORMATION: Uniprot name: FADI_SHIFL.  3-ketoacyl-CoA
      thiolase

<400> SEQUENCE: 148

Met Gly Gln Val Leu Pro Leu Val Thr Arg Gln Gly Asp Arg Ile Ala
1               5                   10                  15

Ile Val Ser Gly Leu Arg Thr Pro Phe Ala Arg Gln Ala Thr Ala Phe
            20                  25                  30

His Gly Ile Pro Thr Val Asp Leu Gly Lys Met Val Val Gly Glu Leu
        35                  40                  45

Leu Ala Arg Ser Glu Ile Pro Ala Glu Val Ile Glu Gln Leu Val Phe
    50                  55                  60

Gly Gln Val Val Gln Met Pro Glu Ala Pro Asn Ile Ala Arg Glu Ile
65                  70                  75                  80

Val Leu Gly Thr Gly Met Asn Val His Thr Asp Ala Tyr Ser Val Ser
                85                  90                  95

Arg Ala Cys Ala Thr Ser Phe Gln Ala Val Ala Asn Val Ala Glu Ser
            100                 105                 110

Leu Met Ala Gly Thr Ile Arg Ala Gly Ile Ala Gly Gly Ala Asp Ser
        115                 120                 125

Ser Ser Val Leu Pro Ile Gly Val Ser Lys Lys Leu Ala Tyr Val Leu
    130                 135                 140

Val Asp Val Asn Lys Ala Arg Thr Met Ser Gln Arg Leu Lys Leu Phe
145                 150                 155                 160

Ser Arg Leu Arg Leu Arg Asp Leu Met Pro Val Pro Pro Ala Val Ala
                165                 170                 175

Glu Tyr Ser Thr Gly Leu Arg Met Gly Asp Thr Ala Glu Gln Met Ala
            180                 185                 190

Lys Thr Tyr Gly Ile Thr Arg Glu Gln Gln Asp Ala Leu Ala His Arg
        195                 200                 205

Ser His Gln Arg Ala Ala Gln Ala Trp Ser Asp Gly Lys Leu Lys Glu
    210                 215                 220

Glu Val Met Thr Ala Phe Ile Pro Pro Tyr Lys Gln Pro Leu Val Glu
225                 230                 235                 240

Asp Asn Asn Ile Arg Gly Asn Ser Ser Leu Ala Asp Tyr Ala Lys Leu
                245                 250                 255

Arg Pro Ala Phe Asp Arg Lys His Gly Thr Val Thr Ala Ala Asn Ser
            260                 265                 270

Thr Pro Leu Thr Asp Gly Ala Thr Ala Val Ile Leu Met Thr Glu Ser
```

-continued

```
                275                 280                 285

Arg Ala Lys Glu Leu Gly Leu Val Pro Leu Gly Tyr Leu Arg Ser Tyr
    290                 295                 300

Ala Phe Thr Ala Ile Asp Val Trp Gln Asp Met Leu Leu Gly Pro Ala
305                 310                 315                 320

Trp Ser Thr Pro Leu Ala Leu Glu Arg Ala Gly Leu Thr Met Ser Glu
                325                 330                 335

Leu Thr Leu Ile Asp Met His Glu Ala Phe Ala Ala Gln Thr Leu Ala
                340                 345                 350

Asn Ile Gln Leu Leu Gly Ser Glu Arg Phe Ala Arg Glu Val Leu Gly
                355                 360                 365

Arg Ala His Ala Thr Gly Glu Val Asp Asp Ser Lys Phe Asn Val Leu
                370                 375                 380

Gly Gly Ser Ile Ala Tyr Gly His Pro Phe Ala Ala Thr Gly Ala Arg
385                 390                 395                 400

Met Ile Thr Gln Thr Leu His Glu Leu Arg Arg Arg Gly Gly Phe
                405                 410                 415

Gly Leu Val Thr Ala Cys Ala Ala Gly Gly Leu Gly Ala Ala Met Val
                420                 425                 430

Leu Glu Ala Glu
        435

<210> SEQ ID NO 149
<211> LENGTH: 393
<212> TYPE: PRT
<213> ORGANISM: Staphylococcus aureus
<220> FEATURE:
<221> NAME/KEY: MISC_FEATURE
<223> OTHER INFORMATION: Uniprot name: THLA_STAAM. Probable acetyl-CoA
      acyltransferase

<400> SEQUENCE: 149

Met Thr Arg Val Val Leu Ala Ala Ala Tyr Arg Thr Pro Ile Gly Val
1               5                   10                  15

Phe Gly Gly Ala Phe Lys Asp Val Pro Ala Tyr Asp Leu Gly Ala Thr
                20                  25                  30

Leu Ile Glu His Ile Ile Lys Glu Thr Gly Leu Asn Pro Ser Glu Ile
            35                  40                  45

Asp Glu Val Ile Ile Gly Asn Val Leu Gln Ala Gly Gln Gly Gln Asn
        50                  55                  60

Pro Ala Arg Ile Ala Ala Met Lys Gly Gly Leu Pro Glu Thr Val Pro
65                  70                  75                  80

Ala Phe Thr Val Asn Lys Val Cys Gly Ser Gly Leu Lys Ser Ile Gln
                85                  90                  95

Leu Ala Tyr Gln Ser Ile Val Thr Gly Glu Asn Asp Ile Val Leu Ala
            100                 105                 110

Gly Gly Met Glu Asn Met Ser Gln Ser Pro Met Leu Val Asn Asn Ser
        115                 120                 125

Arg Phe Gly Phe Lys Met Gly His Gln Ser Met Val Asp Ser Met Val
130                 135                 140

Tyr Asp Gly Leu Thr Asp Val Phe Asn Gln Tyr His Met Gly Ile Thr
145                 150                 155                 160

Ala Glu Asn Leu Val Glu Gln Tyr Gly Ile Ser Arg Glu Glu Gln Asp
                165                 170                 175

Thr Phe Ala Val Asn Ser Gln His Lys Ala Val Arg Ala Gln Gln Asn
            180                 185                 190
```

```
Gly Glu Phe Asp Ser Glu Ile Val Pro Val Ser Ile Pro Gln Arg Lys
            195                 200                 205

Gly Glu Pro Ile Leu Val Thr Lys Asp Glu Gly Val Arg Glu Asn Val
        210                 215                 220

Ser Val Glu Lys Leu Ser Arg Leu Arg Pro Ala Phe Lys Lys Asp Gly
225                 230                 235                 240

Thr Val Thr Ala Gly Asn Ala Ser Gly Ile Asn Asp Gly Ala Ala Met
                245                 250                 255

Met Leu Val Met Ser Glu Asp Lys Ala Lys Glu Leu Asn Ile Glu Pro
            260                 265                 270

Leu Ala Val Leu Asp Gly Phe Gly Ser His Gly Val Asp Pro Ser Ile
        275                 280                 285

Met Gly Ile Ala Pro Val Gly Ala Val Glu Lys Ala Leu Lys Arg Ser
    290                 295                 300

Lys Lys Glu Leu Ser Asp Ile Asp Val Phe Glu Leu Asn Glu Ala Phe
305                 310                 315                 320

Ala Ala Gln Leu Leu Ala Val Asp Arg Glu Leu Lys Leu Pro Pro Glu
                325                 330                 335

Lys Val Asn Val Lys Gly Gly Ala Ile Ala Leu Gly His Pro Ile Gly
            340                 345                 350

Ala Ser Gly Ala Arg Val Leu Val Thr Leu Leu His Gln Leu Asn Asp
        355                 360                 365

Glu Val Glu Thr Gly Leu Thr Ser Leu Cys Ile Gly Gly Gly Gln Ala
    370                 375                 380

Ile Ala Ala Val Val Ser Lys Tyr Lys
385                 390

<210> SEQ ID NO 150
<211> LENGTH: 394
<212> TYPE: PRT
<213> ORGANISM: Staphylococcus epidermidis
<220> FEATURE:
<221> NAME/KEY: MISC_FEATURE
<223> OTHER INFORMATION: Uniprot name: THLA_STAES.  Probable acetyl-CoA
      acyltransferase

<400> SEQUENCE: 150

Met Ser Arg Ile Val Leu Ala Glu Ala Tyr Arg Thr Pro Ile Gly Val
1               5                   10                  15

Phe Gly Gly Val Phe Lys Asp Ile Pro Ala Tyr Glu Leu Gly Ala Thr
            20                  25                  30

Val Ile Arg Gln Ile Leu Glu His Ser Gln Ile Asp Pro Asn Glu Ile
        35                  40                  45

Asn Glu Val Ile Leu Gly Asn Val Leu Gln Ala Gly Gln Gly Gln Asn
    50                  55                  60

Pro Ala Arg Ile Ala Ala Ile His Gly Gly Val Pro Glu Ala Val Pro
65                  70                  75                  80

Ser Phe Thr Val Asn Lys Val Cys Gly Ser Gly Leu Lys Ala Ile Gln
                85                  90                  95

Leu Ala Tyr Gln Ser Ile Val Ala Gly Asp Asn Glu Ile Val Ile Ala
            100                 105                 110

Gly Gly Met Glu Ser Met Ser Gln Ser Pro Met Leu Leu Lys Asn Ser
        115                 120                 125

Arg Phe Gly Phe Lys Met Gly Asn Gln Thr Leu Glu Asp Ser Met Ile
    130                 135                 140
```

```
Ala Asp Gly Leu Thr Asp Lys Phe Asn Asp Tyr His Met Gly Ile Thr
145                 150                 155                 160

Ala Glu Asn Leu Val Glu Gln Tyr Gln Ile Ser Arg Lys Glu Gln Asp
            165                 170                 175

Gln Phe Ala Phe Asp Ser Gln Gln Lys Ala Ser Arg Ala Gln Gln Ala
        180                 185                 190

Gly Val Phe Asp Ala Glu Ile Val Pro Val Glu Val Pro Gln Arg Lys
    195                 200                 205

Gly Asp Pro Leu Ile Ile Ser Gln Asp Glu Gly Ile Arg Pro Gln Thr
210                 215                 220

Thr Ile Asp Lys Leu Ala Gln Leu Arg Pro Ala Phe Lys Lys Asp Gly
225                 230                 235                 240

Ser Val Thr Ala Gly Asn Ala Ser Gly Ile Asn Asp Gly Ala Ala Ala
            245                 250                 255

Met Leu Val Met Thr Glu Asp Lys Ala Lys Ala Leu Gly Leu Gln Pro
            260                 265                 270

Ile Ala Val Leu Asp Ser Phe Gly Ala Ser Gly Val Ala Pro Ser Ile
            275                 280                 285

Met Gly Ile Gly Pro Val Glu Ala Ile His Lys Ala Leu Lys Arg Ser
290                 295                 300

Asn Lys Val Ile Asn Asp Val Asp Ile Phe Glu Leu Asn Glu Ala Phe
305                 310                 315                 320

Ala Ala Gln Ser Ile Ala Val Asn Arg Glu Leu Gln Leu Pro Gln Asp
            325                 330                 335

Lys Val Asn Val Asn Gly Gly Ala Ile Ala Leu Gly His Pro Ile Gly
            340                 345                 350

Ala Ser Gly Ala Arg Thr Leu Val Ser Leu Leu His Gln Leu Ser Asp
            355                 360                 365

Ala Lys Pro Thr Gly Val Ala Ser Leu Cys Ile Gly Gly Gln Gly
            370                 375                 380

Ile Ala Thr Val Val Ser Lys Tyr Glu Val
385                 390

<210> SEQ ID NO 151
<211> LENGTH: 394
<212> TYPE: PRT
<213> ORGANISM: Thiocystis violacea
<220> FEATURE:
<221> NAME/KEY: MISC_FEATURE
<223> OTHER INFORMATION: Uniprot name: THIL_THIVI. Acetyl-CoA
      acetyltransferase

<400> SEQUENCE: 151

Met Ser Asp Thr Ile Val Ile Val Asp Ala Gly Arg Thr Ala Ile Gly
1               5                   10                  15

Thr Phe Gly Gly Ala Leu Ser Ala Leu Gln Ala Thr Asp Ile Gly Thr
            20                  25                  30

Thr Val Leu Lys Ala Leu Ile Glu Arg Thr Gly Ile Ala Pro Glu Gln
        35                  40                  45

Val Ser Glu Val Ile Leu Gly Gln Val Leu Thr Ala Gly Cys Gly Gln
    50                  55                  60

Asn Pro Ala Arg Gln Thr Thr Leu Met Ala Gly Leu Pro His Thr Val
65                  70                  75                  80

Pro Ala Met Thr Ile Asn Lys Val Cys Gly Ser Gly Leu Lys Ala Val
            85                  90                  95

His Leu Ala Met Gln Ala Val Ala Cys Gly Asp Ala Glu Ile Val Ile
```

```
                    100                 105                 110
Ala Gly Gly Gln Glu Ser Met Ser Gln Ser His Val Leu Pro Arg
            115                 120                 125

Ser Arg Glu Gly Gln Arg Met Gly Asp Trp Pro Met Lys Asp Thr Met
        130                 135                 140

Ile Val Asp Gly Leu Trp Asp Ala Phe Asn Gln Cys His Met Gly Val
145                 150                 155                 160

Thr Ala Glu Asn Ile Ala Lys Lys Tyr Ala Phe Thr Arg Glu Ala Gln
                165                 170                 175

Asp Ala Phe Ala Ala Ser Gln Gln Lys Ala Glu Ala Ala Ile Gln
            180                 185                 190

Ser Gly Arg Phe Ala Asp Glu Ile Ile Pro Val Ser Ile Pro Gln Arg
        195                 200                 205

Lys Gly Asp Pro Leu Val Phe Asp Thr Asp Glu Phe Pro Arg Pro Gly
210                 215                 220

Thr Thr Ala Glu Thr Leu Gly Arg Leu Arg Pro Ala Phe Asp Lys Gln
225                 230                 235                 240

Gly Thr Val Thr Ala Gly Asn Ala Ser Gly Ile Asn Asp Gly Ala Ala
                245                 250                 255

Met Val Val Val Met Lys Glu Ser Lys Ala Lys Glu Leu Gly Leu Thr
            260                 265                 270

Pro Met Ala Arg Leu Val Ala Phe Ser Ser Ala Gly Val Asp Pro Ala
        275                 280                 285

Ile Met Gly Thr Gly Pro Ile Pro Ala Ser Thr Asp Cys Leu Lys Lys
        290                 295                 300

Ala Gly Trp Ala Pro Ala Asp Leu Asp Leu Val Glu Ala Asn Glu Ala
305                 310                 315                 320

Phe Ala Ala Gln Ala Met Ser Val Asn Gln Glu Met Gly Trp Asp Leu
                325                 330                 335

Ser Lys Val Asn Val Asn Gly Gly Ala Ile Ala Ile Gly His Pro Ile
            340                 345                 350

Gly Ala Ser Gly Ala Arg Val Leu Val Thr Leu Leu Tyr Glu Met Gln
        355                 360                 365

Lys Arg Asp Ala Lys Lys Gly Leu Ala Thr Leu Cys Ile Gly Gly Gly
        370                 375                 380

Gln Gly Val Ala Leu Ala Val Glu Arg Leu
385                 390

<210> SEQ ID NO 152
<211> LENGTH: 387
<212> TYPE: PRT
<213> ORGANISM: Vibrio fischeri
<220> FEATURE:
<221> NAME/KEY: MISC_FEATURE
<223> OTHER INFORMATION: Uniprot name: FADA_VIBF1. 3-ketoacyl-CoA
      thiolase

<400> SEQUENCE: 152

Met Lys Asn Val Val Ile Val Asp Cys Ile Arg Thr Pro Met Gly Arg
1               5                   10                  15

Ser Lys Asn Gly Val Phe Arg His Thr Arg Ala Glu Asp Leu Ser Ala
            20                  25                  30

His Leu Met Lys Gly Leu Leu Lys Arg Asn Pro Ser Val Asp Pro Asn
        35                  40                  45

Asp Ile Glu Asp Ile Tyr Trp Gly Cys Val Gln Gln Thr Leu Glu Gln
    50                  55                  60
```

Gly Phe Asn Ile Ala Arg Asn Ser Ala Leu Leu Ala Gly Leu Pro Gln
65                  70                  75                  80

Ser Ile Ala Ala Thr Thr Val Asn Arg Leu Cys Gly Ser Ser Met Gln
            85                  90                  95

Ala Leu His Asp Ala Ser Arg Ala Ile Met Val Gly Asp Ala Glu Ile
        100                 105                 110

Cys Ile Ile Gly Gly Val Glu His Met Gly His Val Pro Met Asn His
        115                 120                 125

Gly Val Asp Phe His Ser Gly Leu Ser Lys Ser Val Ala Lys Ala Ser
    130                 135                 140

Gly Met Met Gly Leu Thr Ala Glu Met Leu Gly Lys Met His Gly Ile
145                 150                 155                 160

Ser Arg Glu Gln Gln Asp Ala Phe Ala Leu Ala Ser His Gln Lys Ala
                165                 170                 175

His Lys Ala Thr Ile Glu Gly Tyr Phe Asp Ser Glu Ile Leu Pro Met
        180                 185                 190

Glu Gly His Asp Glu Asn Gly Ala Leu Thr Leu Val Thr His Asp Glu
    195                 200                 205

Val Ile Arg Pro Glu Thr Thr Leu Glu Gly Leu Ala Ala Leu Arg Pro
    210                 215                 220

Ala Phe Asp Pro Ala Asn Gly Thr Val Thr Ala Gly Ser Ser Ser Ala
225                 230                 235                 240

Leu Ser Asp Gly Ala Ser Ala Met Leu Val Met Ser Glu Glu Lys Ala
                245                 250                 255

Asn Glu Leu Gly Leu Pro Ile Arg Ala Lys Val Arg Ser Met Ala Val
                260                 265                 270

Ser Gly Cys Asp Pro Ser Ile Met Gly Tyr Gly Pro Val Pro Ala Thr
    275                 280                 285

Lys Lys Ala Leu Lys Arg Ala Gly Leu Ser Leu Asp Asp Ile Glu Leu
    290                 295                 300

Phe Glu Leu Asn Glu Ala Phe Ala Ala Gln Ser Leu Pro Cys Ile Lys
305                 310                 315                 320

Asp Leu Gly Leu Leu Asp Val Met Asp Glu Lys Val Asn Leu Asn Gly
                325                 330                 335

Gly Ala Ile Ala Leu Gly His Pro Leu Gly Cys Ser Gly Ser Arg Ile
            340                 345                 350

Ala Thr Thr Leu Ile Asn Asn Met Glu Arg Thr Gly Ala Lys Leu Gly
            355                 360                 365

Val Ala Thr Met Cys Ile Gly Leu Gly Gln Gly Ile Ala Thr Val Phe
    370                 375                 380

Glu Arg Pro
385

<210> SEQ ID NO 153
<211> LENGTH: 442
<212> TYPE: PRT
<213> ORGANISM: Vibrio fischeri
<220> FEATURE:
<221> NAME/KEY: MISC_FEATURE
<223> OTHER INFORMATION: Uniprot name: FADI_VIBF1. 3-ketoacyl-CoA
      thiolase

<400> SEQUENCE: 153

Met Ser Asn Ser Val Asn Ser Ser Lys Tyr Gln Pro Leu Thr Thr Arg
1               5                   10                  15

```
Gln Gly Asp Arg Ile Ala Val Val Ser Gly Ile Arg Thr Pro Phe Ala
             20                  25                  30
Lys Gln Ser Thr Ala Phe Ser Thr Thr Pro Ala Val Asp Leu Gly Lys
         35                  40                  45
Leu Ala Val Lys Ala Leu Met Asp Lys Thr Asp Ile Asp Pro Lys Leu
     50                  55                  60
Ile Asp Gln Val Val Phe Gly Gln Val Val Gln Met Pro Glu Ala Pro
 65                  70                  75                  80
Asn Ile Ala Arg Glu Ile Val Leu Gly Thr Gly Met Asn Ile Gly Thr
                 85                  90                  95
Asp Ala Tyr Ser Val Thr Arg Ala Cys Ala Thr Ser Phe Gln Thr Thr
             100                 105                 110
Ala Asn Val Val Glu Ser Ile Met Ala Gly Thr Ile Asp Ile Gly Ile
         115                 120                 125
Ala Gly Gly Ala Asp Ser Ser Ser Val Leu Pro Ile Gly Val Ser Lys
     130                 135                 140
Lys Leu Ala Ser Thr Leu Leu Ala Leu Ser Lys Thr Lys Thr Val Tyr
145                 150                 155                 160
Gln Lys Leu Ser Leu Leu Arg Thr Leu Ser Leu Lys Asp Ile Ala Pro
                 165                 170                 175
Val Pro Pro Ala Val Ala Glu Tyr Ser Thr Gly Ile Ser Met Gly Gln
             180                 185                 190
Thr Ala Glu Gln Met Ala Lys Ser His Gly Ile Thr Arg Glu Glu Gln
         195                 200                 205
Asp Ala Leu Ala His Arg Ser His Thr Leu Ala Ala Lys Ala Trp Lys
     210                 215                 220
Asp Gly Leu Ile Gln Asp Glu Val Met Thr Ala Phe Pro Glu Pro Tyr
225                 230                 235                 240
Thr Ala Trp Leu Asp His Asp Asn Asn Ile Arg His Asp Ser Asp Leu
                 245                 250                 255
Ala Ser Tyr Ala Lys Leu Arg Pro Ala Phe Asp His Lys Tyr Gly Ser
             260                 265                 270
Val Thr Ala Ala Asn Ser Thr Pro Leu Thr Asp Gly Gly Ala Ala Leu
         275                 280                 285
Leu Leu Met Ser Glu Lys Arg Ala Lys Glu Leu Gly Tyr Glu Pro Leu
     290                 295                 300
Gly Tyr Ile Arg Ser Phe Ala Phe Ser Ala Ile Asp Val His His Asp
305                 310                 315                 320
Met Leu Met Gly Pro Ser Tyr Ala Thr Pro Met Ala Leu Asp Lys Ala
                 325                 330                 335
Gly Ile Ser Leu Ser Asp Leu Thr Leu Ile Asp Met His Glu Ala Phe
             340                 345                 350
Ala Ala Gln Thr Leu Ser Asn Val Lys Met Phe Ala Ser Asn Lys Phe
         355                 360                 365
Ala Lys Glu Tyr Leu Gly Arg Asp Lys Ala Ile Gly Glu Ile Asp Met
     370                 375                 380
Glu Lys Phe Asn Val Leu Gly Gly Ser Ile Ala Tyr Gly His Pro Phe
385                 390                 395                 400
Ala Ala Thr Gly Ala Arg Met Ile Ile Gln Thr Leu Arg Glu Leu Lys
                 405                 410                 415
Arg Arg Gly Gly Gly Leu Gly Leu Asn Thr Ala Cys Ala Ala Gly Gly
             420                 425                 430
Leu Gly Ala Ala Met Val Leu Glu Val Glu
```

```
                       435                 440

<210> SEQ ID NO 154
<211> LENGTH: 414
<212> TYPE: PRT
<213> ORGANISM: Yarrowia lipolytica (Candida lipolytica)
<220> FEATURE:
<221> NAME/KEY: MISC_FEATURE
<223> OTHER INFORMATION: Uniprot name: THIK_YARLI.  3-ketoacyl-CoA
      thiolase

<400> SEQUENCE: 154

Met Asp Arg Leu Asn Asn Leu Ala Thr Gln Leu Glu Gln Asn Pro Ala
1               5                   10                  15

Lys Gly Leu Asp Ala Ile Thr Ser Lys Asn Pro Asp Asp Val Val Ile
            20                  25                  30

Thr Ala Ala Tyr Arg Thr Ala His Thr Lys Gly Gly Lys Gly Leu Phe
        35                  40                  45

Lys Asp Thr Ser Ser Ser Glu Leu Leu Ala Ser Leu Leu Glu Gly Leu
    50                  55                  60

Val Lys Glu Ser Lys Ile Asp Pro Lys Leu Ile Gly Asp Val Val Cys
65                  70                  75                  80

Gly Asn Val Leu Ala Ala Gly Ala Gly Ala Thr Glu His Arg Ala Ala
                85                  90                  95

Cys Leu Val Ala Gly Ile Pro Glu Thr Val Pro Phe Val Ala Leu Asn
            100                 105                 110

Arg Gln Cys Ser Ser Gly Leu Met Ala Val Asn Asp Val Ala Asn Lys
        115                 120                 125

Ile Arg Ala Gly Gln Ile Asp Ile Gly Ile Gly Cys Gly Val Glu Ser
    130                 135                 140

Met Ser Asn Gln Tyr Gly Pro Asn Ser Val Thr Pro Phe Ser Asn Lys
145                 150                 155                 160

Phe Gln Asn Asn Glu Glu Ala Lys Lys Cys Leu Ile Pro Met Gly Ile
                165                 170                 175

Thr Ser Glu Asn Val Ala Ala Lys Tyr Asn Val Ser Arg Lys Ala Gln
            180                 185                 190

Asp Ala Phe Ala Ala Lys Ser Tyr Glu Lys Ala Ala Ala Gln Ala
        195                 200                 205

Ala Gly Lys Phe Asp Gln Glu Ile Leu Pro Ile Lys Thr Thr Val Leu
    210                 215                 220

Asp Asp Asp Asp Asn Glu Lys Glu Val Thr Val Asn Lys Asp Asp Gly
225                 230                 235                 240

Ile Arg Pro Gly Val Thr Ala Glu Lys Leu Gly Lys Leu Lys Pro Ala
                245                 250                 255

Phe Ser Ala Glu Gly Thr Thr His Ala Gly Asn Ala Ser Gln Ile Ser
            260                 265                 270

Asp Gly Ala Gly Ala Val Leu Leu Met Arg Arg Ser Val Ala Glu Lys
        275                 280                 285

Leu Gly Gln Pro Ile Leu Ala Lys Phe Val His Cys Lys Thr Val Gly
    290                 295                 300

Val Pro Pro Glu Leu Met Gly Ile Gly Pro Ala Tyr Ala Ile Pro Ala
305                 310                 315                 320

Val Leu Glu Asp Leu Gly Leu Thr Val Asn Asp Val Asp Val Phe Glu
                325                 330                 335

Ile Asn Glu Ala Phe Ala Ser Gln Ala Leu Phe Ser Ile Gln His Cys
            340                 345                 350
```

Gly Ile Asp Glu Ser Lys Val Asn Pro Arg Gly Gly Ala Ile Ala Ile
            355                 360                 365

Gly His Pro Leu Gly Ala Thr Gly Ala Arg Gln Phe Ala Thr Leu Leu
        370                 375                 380

Ser Glu Leu Lys Glu Ser Gly Lys Lys Val Gly Val Thr Ser Met Cys
385                 390                 395                 400

Ile Gly Thr Gly Met Gly Ala Ala Ser Leu Val Val Ala Glu
                405                 410

<210> SEQ ID NO 155
<211> LENGTH: 397
<212> TYPE: PRT
<213> ORGANISM: Yarrowia lipolytica (Candida lipolytica)
<220> FEATURE:
<221> NAME/KEY: MISC_FEATURE
<223> OTHER INFORMATION: Uniprot name: THIL_YARLI. Acetyl-CoA
      acetyltransferase

<400> SEQUENCE: 155

Met Arg Leu Thr Leu Pro Arg Leu Asn Ala Ala Tyr Ile Val Gly Ala
1               5                   10                  15

Ala Arg Thr Pro Val Gly Lys Phe Asn Gly Ala Leu Lys Ser Val Ser
            20                  25                  30

Ala Ile Asp Leu Gly Ile Thr Ala Ala Lys Ala Val Gln Arg Ser
        35                  40                  45

Lys Val Pro Ala Asp Gln Ile Asp Glu Phe Leu Phe Gly Gln Val Leu
    50                  55                  60

Thr Ala Asn Ser Gly Gln Ala Pro Ala Arg Gln Val Val Ile Lys Gly
65                  70                  75                  80

Gly Phe Pro Glu Ser Val Glu Ala Thr Thr Ile Asn Lys Val Cys Ser
                85                  90                  95

Ser Gly Leu Lys Thr Val Ala Leu Ala Ala Gln Ala Ile Lys Ala Gly
            100                 105                 110

Asp Arg Asn Val Ile Val Ala Gly Gly Met Glu Ser Met Ser Asn Thr
        115                 120                 125

Pro Tyr Tyr Ser Gly Arg Gly Leu Val Phe Gly Asn Gln Lys Leu Glu
    130                 135                 140

Asp Ser Ile Val Lys Asp Gly Leu Trp Asp Pro Tyr Asn Asn Ile His
145                 150                 155                 160

Met Gly Asn Cys Cys Glu Asn Thr Asn Lys Arg Asp Gly Ile Thr Arg
                165                 170                 175

Glu Gln Gln Asp Glu Tyr Ala Ile Glu Ser Tyr Arg Arg Ala Asn Glu
            180                 185                 190

Ser Ile Lys Asn Gly Ala Phe Lys Asp Glu Ile Val Pro Val Glu Ile
        195                 200                 205

Lys Thr Arg Lys Gly Thr Val Thr Val Ser Glu Asp Glu Pro Lys
    210                 215                 220

Gly Ala Asn Ala Glu Lys Leu Lys Gly Leu Lys Pro Val Phe Asp Lys
225                 230                 235                 240

Gln Gly Ser Val Thr Ala Gly Asn Ala Ser Pro Ile Asn Asp Gly Ala
                245                 250                 255

Ser Ala Val Val Val Ala Ser Gly Thr Lys Ala Lys Glu Leu Gly Thr
            260                 265                 270

Pro Val Leu Ala Lys Ile Val Ser Tyr Ala Asp Ala Ala Thr Ala Pro
        275                 280                 285

```
Ile Asp Phe Thr Ile Ala Pro Ser Leu Ala Ile Pro Ala Ala Leu Lys
290                 295                 300

Lys Ala Gly Leu Thr Lys Asp Asp Ile Ala Leu Trp Glu Ile Asn Glu
305                 310                 315                 320

Ala Phe Ser Gly Val Ala Leu Ala Asn Leu Met Arg Leu Gly Ile Asp
                325                 330                 335

Lys Ser Lys Val Asn Val Lys Gly Ala Val Ala Leu Gly His Pro
                340                 345                 350

Ile Gly Ala Ser Gly Asn Arg Ile Phe Val Thr Leu Val Asn Ala Leu
                355                 360                 365

Lys Glu Gly Glu Tyr Gly Val Ala Ala Ile Cys Asn Gly Gly Ala
370                 375                 380

Ser Thr Ala Ile Val Ile Lys Lys Val Ser Ser Val Glu
385                 390                 395

<210> SEQ ID NO 156
<211> LENGTH: 387
<212> TYPE: PRT
<213> ORGANISM: Yersinia pestis
<220> FEATURE:
<221> NAME/KEY: MISC_FEATURE
<223> OTHER INFORMATION: Uniprot name: FADA_YERPE.  3-ketoacyl-CoA
      thiolase

<400> SEQUENCE: 156

Met Glu Asn Val Val Ile Ile Asp Ala Val Arg Thr Pro Met Gly Arg
1               5                   10                  15

Ser Lys Gly Gly Ala Phe Arg His Val Arg Ala Glu Asp Leu Ser Ala
                20                  25                  30

His Leu Met Arg Ala Val Ile Ser Arg Asn Pro Gly Leu Asn Ala Ala
                35                  40                  45

Glu Ile Asp Asp Ile Tyr Trp Gly Cys Val Gln Gln Thr Leu Glu Gln
            50                  55                  60

Gly Phe Asn Ile Ala Arg Asn Ala Ser Leu Leu Ala Glu Ile Pro His
65                  70                  75                  80

Ser Val Pro Ala Val Thr Val Asn Arg Leu Cys Gly Ser Ser Met Gln
                85                  90                  95

Ala Leu His Asp Gly Ala Arg Ala Ile Met Val Gly Asp Ala Lys Ile
                100                 105                 110

Ser Leu Ile Gly Gly Val Glu His Met Gly His Val Pro Met Asn His
            115                 120                 125

Gly Val Asp Phe His Pro Gly Met Gly Arg Thr Val Ala Lys Ala Ala
130                 135                 140

Gly Met Met Gly Leu Thr Ala Glu Met Leu Ala Lys Ile His Asn Ile
145                 150                 155                 160

Ser Arg Gln Ser Gln Asp Glu Phe Ala Phe Arg Ser His Gln Arg Ala
                165                 170                 175

Tyr Ala Ala Thr Gln Ala Gly His Phe Ala Lys Glu Ile Val Ala Thr
                180                 185                 190

Asn Gly His Asp Ala Glu Gly Val Leu Lys Arg Phe Asp Phe Asp Glu
            195                 200                 205

Val Ile Arg Pro Glu Thr Asn Leu Ser Gly Leu Ala Ala Leu Arg Pro
210                 215                 220

Ala Phe Asp Pro Val Asn Gly Thr Val Thr Ala Gly Thr Ser Ser Ala
225                 230                 235                 240

Leu Ser Asp Gly Ala Ser Ala Met Leu Ile Met Ser Glu Ser Arg Ala
```

-continued

```
                  245                 250                 255
    Lys Ser Leu Gly Leu Thr Pro Arg Ala Arg Ile Arg Ser Met Ala Val
                260                 265                 270

Val Gly Cys Asp Pro Ser Ile Met Gly Tyr Gly Pro Val Pro Ala Ser
                275                 280                 285

Gln Leu Ala Leu Lys Arg Ala Gly Leu Glu Leu Ala Asp Ile Gly Leu
                290                 295                 300

Phe Glu Leu Asn Glu Ala Phe Ala Ala Gln Ser Leu Ala Cys Leu Lys
    305                 310                 315                 320

Gly Leu Gly Leu Leu Glu Ser Met Asp Asp Lys Val Asn Leu Asn Gly
                325                 330                 335

Gly Ala Ile Ala Leu Gly His Pro Leu Gly Cys Ser Gly Ala Arg Ile
                340                 345                 350

Ser Thr Thr Leu Leu Asn Leu Met Glu Arg Arg Asp Val Gln Phe Gly
                355                 360                 365

Leu Ala Thr Met Cys Ile Gly Leu Gly Gln Gly Ile Ala Thr Val Phe
                370                 375                 380

Glu Arg Leu
    385

<210> SEQ ID NO 157
<211> LENGTH: 436
<212> TYPE: PRT
<213> ORGANISM: Yersinia pestis
<220> FEATURE:
<221> NAME/KEY: MISC_FEATURE
<223> OTHER INFORMATION: Uniprot name: FADI_YERPE.  3-ketoacyl-CoA
      thiolase

<400> SEQUENCE: 157

Met Ser Lys Pro Leu Pro Leu Val Thr Arg Gln Gly Asp Arg Ile Val
    1               5                   10                  15

Ile Val Asn Gly Leu Arg Thr Pro Phe Ala Lys Gln Ala Thr Ala Tyr
                20                  25                  30

His Gly Val Pro Ala Val Asp Leu Gly Lys Ile Val Val Ser Glu Leu
                35                  40                  45

Leu Ala Arg Ser Gly Ile Ser Ser Glu Leu Ile Asp Gln Leu Val Phe
                50                  55                  60

Gly Gln Val Val Gln Met Pro Glu Ala Pro Asn Ile Ala Arg Glu Ile
    65                  70                  75                  80

Val Leu Gly Thr Gly Met Ser Val His Thr Asp Ala Tyr Ser Val Ser
                85                  90                  95

Arg Ala Cys Ala Thr Ser Phe Gln Ala Val Ala Asn Val Ala Glu Ser
                100                 105                 110

Ile Ile Ala Gly Ser Val Asp Ile Ala Ile Ala Gly Gly Ala Asp Ser
                115                 120                 125

Ser Ser Val Leu Pro Ile Gly Val Ser Lys Ala Leu Ala Arg Thr Leu
                130                 135                 140

Val Asp Ala Asn Lys Ala Arg Ser Leu Ser Gln Lys Leu Lys Leu Phe
    145                 150                 155                 160

Ser Arg Leu Arg Leu Arg Asp Leu Leu Pro Val Ala Pro Ala Val Ala
                165                 170                 175

Glu Tyr Ser Thr Gly Leu Arg Met Gly Asp Thr Ala Glu Gln Met Ala
                180                 185                 190

Lys Thr Tyr Gly Ile Ser Arg Glu Asp Gln Asp Ala Leu Ala Leu Arg
                195                 200                 205
```

-continued

```
Ser His Gln Leu Ala Ala Glu Ala Trp Gln Gly Trp Leu His Asp
    210                 215                 220

Glu Val Met Thr Ala Tyr Ile Pro Pro Tyr Arg Gly Ala Ile Ile Glu
225                 230                 235                 240

Asp Asn Asn Ile Arg Lys Asp Ser Thr Leu Ala Gln Tyr Ala Lys Leu
                245                 250                 255

Arg Pro Ala Phe Asp Arg Gln His Gly Ser Val Thr Ala Ala Asn Ser
            260                 265                 270

Thr Pro Leu Thr Asp Gly Ala Ala Val Leu Met Met Ser Glu Ser
        275                 280                 285

Lys Ala Lys Ala Leu Gly Leu Pro Pro Leu Gly Tyr Leu Arg Ser Phe
290                 295                 300

Ala Phe Ser Ala Ile Asp Val Trp Gln Asp Met Leu Leu Gly Pro Ser
305                 310                 315                 320

Tyr Ala Thr Pro Leu Ala Leu Asp Arg Ala Gly Ile Thr Leu Ala Asp
                325                 330                 335

Leu Thr Leu Ile Asp Met His Glu Ala Phe Ala Ala Gln Thr Leu Ala
                340                 345                 350

Asn Leu Lys Met Phe Ala Ser Asp Thr Phe Ala Arg Glu Lys Leu Gly
            355                 360                 365

Arg Ser Gln Ala Ile Gly Glu Val Asp Met Ser Lys Phe Asn Val Leu
370                 375                 380

Gly Gly Ser Ile Ala Tyr Gly His Pro Phe Ala Ala Thr Gly Ala Arg
385                 390                 395                 400

Met Ile Thr Gln Thr Leu Asn Glu Leu Arg Arg Gly Gly Leu
                405                 410                 415

Gly Leu Thr Thr Ala Cys Ala Ala Gly Gly Leu Gly Ala Ala Met Ile
            420                 425                 430

Leu Glu Val Glu
        435

<210> SEQ ID NO 158
<211> LENGTH: 346
<212> TYPE: PRT
<213> ORGANISM: artificial
<220> FEATURE:
<223> OTHER INFORMATION: cd05917 : FACL_like_2 : Uncharacterized
      subfamily of fatty acid CoA ligase (FACL)

<400> SEQUENCE: 158

Asp Asp Pro Ala Leu Ile Gln Tyr Thr Ser Gly Thr Thr Gly Arg Pro
1               5                   10                  15

Lys Gly Ala Met Leu Thr His Arg Asn Val Leu Asn Asn Gly Tyr Ser
            20                  25                  30

Ile Ala Arg Arg Leu Gly Leu Thr Glu Gly Asp Arg Thr Leu Val Pro
        35                  40                  45

Val Pro Leu Phe His Val Phe Gly Leu Val Leu Gly Val Leu Ala Ser
    50                  55                  60

Leu Thr Ala Gly Ala Thr Leu Val Leu Met Glu Lys Phe Asp Pro Gly
65                  70                  75                  80

Ala Ala Leu Arg Leu Ile Glu Arg Glu Arg Ile Thr Ala Leu His Gly
                85                  90                  95

Val Pro Thr Met Phe Ile Ala Leu Leu Glu His Pro Asp Phe Asp Lys
            100                 105                 110

Phe Asp Leu Ser Ser Leu Arg Thr Gly Ile Ser Gly Gly Ala Pro Val
```

```
               115                 120                 125
Pro Pro Glu Leu Val Arg Arg Ile Arg Glu Glu Phe Pro Met Ala Glu
            130                 135                 140

Ile Thr Thr Gly Tyr Gly Met Thr Glu Thr Ser Gly Val Gly Thr Gln
145                 150                 155                 160

Thr Ser Gly Asp Asp Pro Tyr Glu Asp Arg Pro Gly Thr Val Gly Arg
                165                 170                 175

Pro Leu Pro Gly Val Glu Val Lys Ile Val Asp Pro Asp Gly Gly Glu
            180                 185                 190

Val Pro Pro Gly Glu Val Gly Glu Ile Cys Val Arg Gly Tyr Ser Val
            195                 200                 205

Met Lys Gly Tyr Tyr Asn Asp Pro Glu Ala Thr Ala Glu Ala Ile Asp
            210                 215                 220

Ala Asp Gly Trp Leu His Thr Gly Asp Leu Gly Tyr Met Asp Glu Asp
225                 230                 235                 240

Gly Tyr Leu Arg Ile Val Gly Arg Ile Lys Asp Met Ile Ile Arg Gly
                245                 250                 255

Gly Glu Asn Ile Tyr Pro Ala Glu Ile Glu Glu Ala Leu Leu Thr His
                260                 265                 270

Pro Ala Val Ala Glu Ala Ala Val Val Gly Val Pro Asp Glu Arg Leu
            275                 280                 285

Gly Glu Val Val Ala Ala Phe Val Val Leu Lys Pro Gly Ala Thr Leu
            290                 295                 300

Thr Glu Glu Glu Leu Ile Ala Phe Cys Arg Gly Arg Leu Ala Arg Phe
305                 310                 315                 320

Lys Val Pro Arg Tyr Val Arg Phe Val Asp Glu Leu Pro Arg Thr Ala
                325                 330                 335

Ser Gly Lys Ile Gln Lys Phe Lys Leu Arg
                340                 345
```

The invention claimed is:

1. A method for the fermentative conversion of levulinic acid into propionyl-CoA and acetyl-CoA, comprising the step of culturing, under fermentation conditions, a genetically modified microorganism, in a culture medium comprising as a source of carbon at least levulinic acid,
wherein said genetically modified microorganism overexpresses relative to a corresponding non-genetically modified microorganism:
at least one enzyme converting levulinic acid into levulinyl-CoA selected from acyl CoA: 3-ketoacid CoA/acetate CoA transferases (EC 2.8.3.5/EC 2.8.3.8) and combinations thereof, wherein said at least one enzyme comprises the amino acid sequence of SEQ ID NO: 3 or SEQ ID NO: 5, and
at least one enzyme converting said levulinyl-CoA into propionyl-CoA and acetyl-CoA, selected from acetyl-CoA C-acetyltransferases (EC 2.3.1.9/EC 2.3.1.16) and combinations thereof, wherein said at least one enzyme comprises the amino acid sequence of SEQ ID NO: 9.

2. A method for the fermentative production of 1,2-propanediol, said method comprising the steps of:
a) culturing, under fermentation conditions, a genetically modified microorganism, in a culture medium comprising as a source of carbon at least levulinic acid, and
b) recovering said 1,2-propanediol,
wherein said genetically modified microorganism overexpresses relative to a corresponding non-genetically modified microorganism:
at least one enzyme converting levulinic acid into levulinyl-CoA selected from acyl CoA: 3-ketoacid CoA/acetate CoA transferases (EC 2.8.3.5/EC 2.8.3.8) and combinations thereof, wherein said at least one enzyme comprises the amino acid sequence of SEQ ID NO: 3 or SEQ ID NO: 5, and
at least one enzyme converting said levulinyl-CoA into propionyl-CoA and acetyl-CoA, selected from acetyl-CoA C-acetyltransferases (EC 2.3.1.9/EC 2.3.1.16) and combinations thereof, wherein said at least one enzyme comprises the amino acid sequence of SEQ ID NO: 9.

3. The method according to claim 2, wherein said source of carbon is a lignocellulosic substrate.

4. The method according to claim 1, wherein said source of carbon further comprises at least one carbohydrate substrate.

5. The method according to claim 2, wherein said source of carbon further comprises at least one carbohydrate substrate.

6. The method according to claim 5, wherein said carbohydrate substrate is selected from xylose, glycerol, glucose, galactose, fructose, lactose, maltose, sucrose, and combinations thereof.

7. The method according to claim 4, wherein said carbohydrate substrate is selected from xylose, glycerol, glucose, galactose, fructose, lactose, maltose, sucrose, and combinations thereof.

8. The method according to claim 1, wherein said microorganism is selected from bacterium, yeast and fungus.

9. The method according to claim 8, wherein said microorganism belongs to the family of the bacteria Enterobacteriaceae, Clostridiaceae, Bacillaceae, Streptomycetaceae, or Corynebacteriaceae, or to the family of yeasts Saccharomycetaceae.

10. The method according to claim 9, wherein said Enterobacteriaceae bacterium is *Escherichia coli*, said Clostridiaceae bacterium is *Clostridium acetobutylicum*, said Corynebacteriaceae bacterium is *Corynebacterium glutamicum*, or said Saccharomycetaceae yeast is *Saccharomyces cerevisiae*.

11. The method according to claim 2, wherein said microorganism is selected from bacterium, yeast and fungus.

12. The method according to claim 11, wherein said microorganism belongs to the family of the bacteria Enterobacteriaceae, Clostridiaceae, Bacillaceae, Streptomycetaceae, or Corynebacteriaceae, or to the family of yeasts Saccharomycetaceae.

13. The method according to claim 12, wherein said Enterobacteriaceae bacterium is *Escherichia coli*, said Clostridiaceae bacterium is *Clostridium acetobutylicum*, said Corynebacteriaceae bacterium is *Corynebacterium glutamicum*, or said Saccharomycetaceae yeast is *Saccharomyces cerevisiae*.

* * * * *